(12) United States Patent
Krawczyk et al.

(10) Patent No.: US 10,287,558 B2
(45) Date of Patent: May 14, 2019

(54) MICROORGANISMS FOR SUCCINIC ACID PRODUCTION

(71) Applicant: BASF SE, Ludwigshafen (DE)

(72) Inventors: Joanna Martyna Krawczyk, Mannheim (DE); Stefan Haefner, Speyer (DE); Hartwig Schröder, Nußloch (DE); Esther Dantas Costa, Mannheim (DE); Oskar Zelder, Speyer (DE); Gregory Von Abendroth, Tarrytown, NY (US); Christoph Wittmann, Saarlouis (DE); René Stellmacher, Braunschweig (DE); Judith Becker, Kutzhof (DE); Anna Lange, Braunschweig (DE); Benjamin J. Lyons, Gainesville, FL (US); Thomas J. Lyons, Gainesville, FL (US); Eudes De Crecy, Gainesville, FL (US); Ewa Hughes, Gainesville, FL (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/116,669

(22) PCT Filed: Feb. 2, 2015

(86) PCT No.: PCT/EP2015/052048
§ 371 (c)(1),
(2) Date: Aug. 4, 2016

(87) PCT Pub. No.: WO2015/117916
PCT Pub. Date: Aug. 13, 2015

(65) Prior Publication Data
US 2016/0348082 A1    Dec. 1, 2016

(30) Foreign Application Priority Data

Feb. 7, 2014  (EP) .................................... 14154302
Jul. 10, 2014 (EP) .................................... 14176517

(51) Int. Cl.
*C12N 9/12*       (2006.01)
*C12P 7/46*       (2006.01)
*C12N 15/52*      (2006.01)

(52) U.S. Cl.
CPC ........... *C12N 9/1205* (2013.01); *C12N 15/52* (2013.01); *C12P 7/46* (2013.01); *C12Y 207/0104* (2013.01)

(58) Field of Classification Search
None
See application file for complete search history.

(56) References Cited

U.S. PATENT DOCUMENTS

2010/0159543 A1   6/2010  Scholten et al.

FOREIGN PATENT DOCUMENTS

| EP | 1005562 A1 | 6/2000 |
|---|---|---|
| EP | 2360137 A1 | 8/2011 |
| WO | WO-2005/030973 A1 | 4/2005 |
| WO | WO-2005/052135 A1 | 6/2005 |
| WO | WO-2008/010373 A1 | 1/2008 |
| WO | WO2009008574 * | 1/2009 |
| WO | WO-2009/024294 A1 | 2/2009 |
| WO | WO-2010/092155 A1 | 8/2010 |
| WO | WO-2011/043443 A1 | 4/2011 |
| WO | WO-2011/064151 A1 | 6/2011 |
| WO | WO-2011/082378 A2 | 7/2011 |
| WO | WO-2011/123268 A1 | 10/2011 |

OTHER PUBLICATIONS

Soellner et al. J Appl Microbiol. Dec. 2013;115(6):1368-78. Epub Sep. 6, 2013.*
Chica et al. Curr Opin Biotechnol. Aug. 2005;16(4):378-84.*
Singh et al. Curr Protein Pept Sci. 2017, 18, 1-11.*
Accession Q65TA6. Oct. 25, 2004.*
Becker et al. Biotechnol. Bioeng., 110 (2013), pp. 3013-3023.*
Asanuma et al., Effects of pH and energy supply on activity and amount of pyruvate formate-lyase in Streptococcus bovis, Appl. Environ. Microbiol., 66(9):3773-7 (2000).
Bergmeyer et al. (eds.), Methods of Enzymatic Analysis, Third Edition, vol. III, pp. 126-33, Weinheim: Verlag Chemie (1983).
Bergmeyer et al. (eds.) Methods of Enzymatic Analysis, Second Edition, vol. I, pp. 509-511, New York, NY: Academic Press, Inc. (1974).
European Search Report, European patent application No. EP 14154302, dated Jul. 3, 2014.
Hong, Systems approaches to succinic acid-producing microorganisms, Biotechnology and Bioprocess Engineering, 12:73-9 (2007).
Hong et al., The genome sequence of the capnophilic rumen bacterium Mannheimia succiniciproducens, Nat. Biotechnol., 22(10):1275-81 (2004).
International Preliminary Report on Patentability, International Application No. PCT/EP2015/052048, dated Feb. 1, 2016.
International Search Report and Written Opinion, International Application No. PCT/EP2015/052048, dated Jun. 23, 2015.
Lee et al., Genome-based metabolic engineering of Mannheimia succiniciproducens for succinic acid production, Appl. Environ. Microbiol., 72(3):1939-48 (2006).
Lee et al., Metabolic engineering of Escherichia coli for enhanced production of succinic acid, based on genome comparison and in silico gene knockout simulation, Appl. Env. Microbiol., 71(12):7880-7 (2005).
Leenhouts et al., Campbell-like integration of heterologous plasmid DNA into the chromosome of Lactococcus lactis subsp. *lactis*, App. Environ. Microbiol., 55(2):394-400 (1989).
UniProt:Q65TA6 RecName: Full=Pyruvate kinase, EC=2.7.1.40 (Oct. 25, 2004).

(Continued)

*Primary Examiner* — Christian L Fronda

(74) *Attorney, Agent, or Firm* — Marshall, Gerstein & Borun LLP

(57) ABSTRACT

The present invention relates to a modified microorganism having, compared to its wild-type, a reduced activity of the enzyme that is encoded by the pykA-gene. The present invention also relates to a method for producing an organic compound and to the use of modified microorganisms.

11 Claims, 11 Drawing Sheets

Specification includes a Sequence Listing.

(56) References Cited

OTHER PUBLICATIONS

Using DNA Fragments as Probes, Units 6.3.1-6.3.6, Current Protocols in Molecular Biology, New York, NY: John Wiley & Sons (1989).

* cited by examiner

```
                      1                                                50
PykA wild type   (1)  MSRRLRRTKIVCTMGPATDKGNNLEKIIAAGANVVRMNFSHGTPEDHIGR
       PykA2     (1)  MSRRLRRTKIVCTMGPATDKGNNLEKIIAAGANVVRMNFSHGTPEDHIGR
       PykA6     (1)  MSRRLRRTKIVCTMGPATDKGNNLEKIIAAGANVVRMNFSHGTPEDHIGR
       PykA4     (1)  MSRRLRRTKIVCTMGPATDKGNNLEKIIAAGANVVRMNFSHGTPEDHIGR
       PykA5     (1)  MSRRLRRTKIVCTMGPATDKGNNLEKIIAAGANVVRMNFSHGTPEDHIGR
    Consensus    (1)  MSRRLRRTKIVCTMGPATDKGNNLEKIIAAGANVVRMNFSHGTPEDHIGR
                      51                                               100
PykA wild type  (51)  AEKVREIAHKLGKHVAILGDLQGPKIRVSTFKEGKIFLNIGDKFILDAEM
       PykA2    (51)  AEKVREIAHKLGKHVAILGDLQGPKIRVSTFKEGKIFLNIGDKFILDAEM
       PykA6    (51)  AEKVREIAHKLGKHVAILGDLQGPKIRVSTFKEGKIFLNIGDKFILDAEM
       PykA4    (51)  AEKVREIAHKLGKHVAILGDLQGPKIRVSTFKEGKIFLNIGDKFILDAEM
       PykA5    (51)  AEKVREIAHKLGKHVAILGDLQGPKIRVSTFKEGKIFLNIGDKFILDAEM
    Consensus   (51)  AEKVREIAHKLGKHVAILGDLQGPKIRVSTFKEGKIFLNIGDKFILDAEM
                      101                                              150
PykA wild type (101)  PKGEGNQEAVGLDYKTLPQDVVPGDILLLDDGRVQLKVLATEGAKVFTEV
       PykA2   (101)  PKGEGNQEAVGLDYKTLPQDVVPGDILLLDDGRVQLKVLATEGAKVFTEV
       PykA6   (101)  PKGEGNQEAVGLDYKTLPQDVVPGDILLLDDGRVQLKVLATEGAKVFTEV
       PykA4   (101)  PKGEGNQEAVGLDYKTLPQDVVPGDILLLDDGRVQLKVLATEGAKVFTEV
       PykA5   (101)  PKGEGNQEAVGLDYKTLPQDVVPGDILLLDDGRVQLKVLATEGAKVFTEV
    Consensus  (101)  PKGEGNQEAVGLDYKTLPQDVVPGDILLLDDGRVQLKVLATEGAKVFTEV
                      151                                              200
PykA wild type (151)  TVGGPLSNNKGINKLGGGLSADALTEKDKADIITAARIGVDYLAVSFPRS
       PykA2   (151)  TVGGPLSNNKGINKLGCGLSADALTEKDKADIITAARIGVDYLAVSFPRS
       PykA6   (151)  TVGGPLSNNKGINKLGCGLSADALTEKDKADIITAARIGVDYLAVSFPRS
       PykA4   (151)  TVGGPLSNNKGINKLGGGLSADALTEKDKADIITAARIGVDYLAVSFPRS
       PykA5   (151)  TVGGPLSNNKGINKLGGGLSGDALTEKDKADIITAARIGVDYLAVSFPRS
    Consensus  (151)  TVGGPLSNNKGINKLGGGLSADALTEKDKADIITAARIGVDYLAVSFPRS
                      201                                              250
PykA wild type (201)  SADLNYARQLAKDAGLDAKIVAKVERAETVETDEAMDDIINAADVIMVAR
       PykA2   (201)  SADLNYARQLAKDAGLDAKIVAKVERAETVETDEAMDDIINAADVIMVAR
       PykA6   (201)  SADLNYARQLAKDAGLDAKIVAKVERAETVETDEAMDDIINAADVIMVAR
       PykA4   (201)  SADLNYARQLAKDAGLDAKIVAKVERAETVETDEAMDDIINAADVIMVAR
       PykA5   (201)  SADLNYARQLAKDAGLDAKIVAKVERAETVETDEAMDDIINAADVIMVAR
    Consensus  (201)  SADLNYARQLAKDAGLDAKIVAKVERAETVETDEAMDDIINAADVIMVAR
                      251                                              300
PykA wild type (251)  GDLGVEIGDPELVGVQKKLIRRSRQLNRVVITATQMMESMISNPMPTRAE
       PykA2   (251)  GDLGVEIGDPELVGVQKKLIRRSRQLNRVVITATQMMESMISNPMPTRAE
       PykA6   (251)  GDLGVEIGDPELVGVQKKLIRRSRQLNRVVITATQMMESMISNPMPTRAE
       PykA4   (251)  GDLGVEIGDPELVGVQKKLIRRSRQLNRVVITATQMMESMISNPMPTRAE
       PykA5   (251)  GDLGVEIGDPELVGVQKKLIRRSRQLNRVVITATQMMESMISNPMPTRAE
    Consensus  (251)  GDLGVEIGDPELVGVQKKLIRRSRQLNRVVITATQMMESMISNPMPTRAE
                      301                                              350
PykA wild type (301)  VMDVANAVLDGTDAVMLSAETAAGQYPAETVAAMAKVALGAEKMPSINVS
       PykA2   (301)  VMDVANAVLDGTDAVMLSAETAAGQYPAETVAAMAKVALGAEKMPSINVS
       PykA6   (301)  VMDVANAVLDGTDAVMLSAETAAGQYPAETVAAMAKVALGAEKMPSINVS
       PykA4   (301)  VMDVANAVLDGTDAVMLSAETAAGQYPAETVAAMAKVALGAEKMPSINVS
       PykA5   (301)  VMDVANAVLDGTDAVMLSAETAAGQYPAETVAAMAKVALGAEKMPSINVS
    Consensus  (301)  VMDVANAVLDGTDAVMLSAETAAGQYPAETVAAMAKVALGAEKMPSINVS
                      351                                              400
PykA wild type (351)  KHRMNVQFESIEESVAMSAMYAANHMRGVAAIITLTSSGRTARLMSRISS
       PykA2   (351)  KHRMNVQFESIEESVAMSAMYAANHMRGVAAIITLTSSGRTARLMSRISS
       PykA6   (351)  KHRMNVQFESIEESVAMSAMYAANHMRGVAAIITLTSSGRTARLMSRISS
       PykA4   (351)  KHRMNVQFESIEESVAMSAMYAANHMRGVAAIITLTSSGRTARLMSRISS
       PykA5   (351)  KHRMNVQFESIEESVAMSAMYAANHMRGVAAIITLTSSGRTARLMSRISS
    Consensus  (351)  KHRMNVQFESIEESVAMSAMYAANHMRGVAAIITLTSSGRTARLMSRISS
                      401                                              450
PykA wild type (401)  GLPIFALSRNESTLNLCALYRGVTPVHFDKDSRTSEGATAAVQLLKDEGF
       PykA2   (401)  GLPIFALSRNESTLNLCALYRGVTPVHFDKDSRTSEGATAAVQLLKDEGF
       PykA6   (401)  GLPIFALSRNESTLNLCALYRGVTPVHFDKDSRTSEGATAAVQLLKDEGF
       PykA4   (401)  GLPIFALSRNESTLNLYALYRGVTPVHFDKDSRTSEGATAAVQLLKDEGF
       PykA5   (401)  GLPIFALSRNESTLNLCALYRGVTPVHFDKDSRTSEGATAAVQLLKDEGF
    Consensus  (401)  GLPIFALSRNESTLNLCALYRGVTPVHFDKDSRTSEGATAAVQLLKDEGF
                      451                      480
PykA wild type (451)  LVSGDLVLLTQGDASSSSGTNLCRTLIVE-
       PykA2   (451)  LVSGDLVLLTQGDASSSSGTNLCRTLIVE-
       PykA6   (451)  LVSGDLVLLTQGDASSSSGTNLCRTLIVE-
       PykA4   (451)  LVSGDLVLLTQGDASSSSGTNLCRTLIVE-
       PykA5   (451)  LVSGDLVLLTQGDASSSSGTNLCRTLIVE-
    Consensus  (451)  LVSGDLVLLTQGDASSSSGTNLCRTLIVE
```

Fig. 11

MICROORGANISMS FOR SUCCINIC ACID PRODUCTION

This application is a National Stage application of International Application No. PCT/EP2015/052048, filed Feb. 2, 2015, which claims priority under 35 U.S.C. § 119 to European Patent Application Nos. 14154302.5, filed Feb. 7, 2014 and 14176517.2, filed Jul. 10, 2014.

INCORPORATION BE REFERENCE OF MATERIAL SUBMITTED ELECTRONICALLY

This application incorporates by reference in its entirety a computer-readable nucleotide/amino acid sequence listing identified as one 135,309 byte ASCII (text) file named "H75273_SubSeqListing.txt," created Jul. 27, 2016.

The present invention relates to a modified microorganism, to a method for producing organic compounds and to the use of modified microorganisms.

Organic compounds such as small dicarboxylic acids having 6 or fewer carbons are commercially significant chemicals with many uses. For example, the small diacids include 1,4-diacids, such as succinic acid, malic acid and tartaric acid, and the 5-carbon molecule itaconic acid. Other diacids include the two carbon oxalic acid, three carbon malonic acid, five carbon glutaric acid and the 6 carbon adipic acid and there are many derivatives of such diacids as well.

As a group the small diacids have some chemical similarity and their uses in polymer production can provide specialized properties to the resin. Such versatility enables them to fit into the downstream chemical infrastructure markets easily. For example, the 1,4-diacid molecules fulfill many of the uses of the large scale chemical maleic anhydride in that they are converted to a variety of industrial chemicals (tetrahydrofuran, butyrolactone, 1,4-butanediol, 2-pyrrolidone) and the succinate derivatives succindiamide, succinonitrile, diaminobutane and esters of succinate. Tartaric acid has a number of uses in the food, leather, metal and printing industries. Itaconic acid forms the starting material for production of 3-methylpyrrolidone, methyl-BDO, methyl-THF and others.

In particular, succinic acid or succinate—these terms are used interchangeably herein—has drawn considerable interest because it has been used as a precursor of many industrially important chemicals in the food, chemical and pharmaceutical industries. In fact, a report from the U.S. Department of Energy reports that succinic acid is one of 12 top chemical building blocks manufactured from biomass. Thus, the ability to make diacids in bacteria would be of significant commercial importance.

WO-A-2009/024294 discloses a succinic acid producing bacterial strain, being a member of the family of Pasteurellaceae, originally isolated from rumen, and capable of utilizing glycerol as a carbon source and variant and mutant strains derived there from retaining said capability, in particular, a bacterial strain designated DD1 as deposited with DSMZ (Deutsche Sammlung von Mikroorganismen and Zellkulturen GmbH, Inhoffenstr. 7B, D-38124 Braunschweig, Germany) having the deposit number DSM 18541 (ID 06-614) and having the ability to produce succinic acid. The DD1-strain belongs to the species *Basfia succiniciproducens* and the family of Pasteurellaceae as classified by Kuhnert et al., 2010. Mutations of these strains, in which the ldhA-gene and/or the pflD- or the pflA-gene have been disrupted, are disclosed in WO-A2010/092155, these mutant strains being characterized by a significantly increased production of succinic acid from carbon sources such as glycerol or mixtures of glycerol and carbohydrates such as maltose, under anaerobic conditions compared to the DD1-wild-type disclosed in WO-A-2009/024294.

However, when using bacterial strains such as those disclosed in WO-A-2009/024294 or WO-A2010/092155 for the production or organic compounds such as succinic acid, the selectivity in which the carbon sources are converted into the desired organic compounds and also the yield of the desired organic compound is still improvable.

Furthermore, it has been observed that when using the bacterial strains of the prior art for the production of organic compounds such as succinic acid under anaerobic conditions, the growth rate of the microorganisms is also improvable in order to make the microorganisms more suitable for the production of organic compounds such as succinic acid in an industrial scale.

It was therefore an object of the present invention to overcome the disadvantages of the prior art.

In particular, it was an object of the present invention to provide microorganisms which can be used for the fermentative production of organic compounds such as succinic acid and which not only produce the desired organic products, such as succinic acid, from assimilable carbon sources such as glycerol, glucose, sucrose, xylose, lactose, fructose or maltose in large amounts, preferably with only low amounts of side products, but which are also characterized by a fast growth under anaerobic conditions.

A contribution to achieving the abovementioned aims is provided by a modified microorganism having, compared to its wild-type, a reduced activity of the enzyme that is encoded by the pykA-gene, wherein the wild-type from which the modified microorganism has been derived belongs to the family of Pasteurellaceae. A contribution to achieving the above mentioned aims is in particular provided by a modified microorganism in which mutations have been introduced into the wild-type pykA-gene, wherein the wild-type from which the modified microorganism has been derived belongs to the family of Pasteurellaceae.

Surprisingly, it has been discovered that a reduction of the activity of the enzyme that is encoded by the pykA-gene (this enzyme PykA is a pyruvate kinase catalyzing the conversion of phosphoenolpyruvate (PEP) to pyruvate (EC 2.7.1.40)), preferably by introducing at least one mutation into the wild-type-pykA-gene, results in a recombinant Pasteurellaceae-strain that, compared to the corresponding microorganism in which the activity of this enzyme has not been decreased, is characterized by an increased yield of organic compounds such as succinic acid and also by a faster growth under anaerobic conditions.

In context with the expression "a modified microorganism having, compared to its wild-type, a reduced activity of the enzyme that is encoded by the x-gene", wherein the x-gene is the pykA-gene and optionally, as described later, the ldhA-gene, the pflA-gene and/or the pflD-gene, the term "wild-type" refers to a microorganism in which the activity of the enzyme that is encoded by the x-gene has not been decreased, i. e. to a microorganism whose genome is present in a state as before the introduction of a genetic modification of the x-gene (in particular of the pykA-gene and optionally the ldhA-gene, the pflA-gene and/or the pflD-gene). Preferably, the expression "wild-type" refers to a microorganism whose genome, in particular whose x-gene, is present in a state as generated naturally as the result of evolution. The term may be used both for the entire microorganism but preferably for individual genes, e.g. the pykA-gene, the ldhA-gene, the pflA-gene and/or the pflD-gene. The term "modified microorganism" thus includes a microorganism which has been genetically altered, modified or engineered (e.g., genetically engineered) such that it exhibits an altered, modified or different genotype and/or phenotype (e. g., when the genetic modification affects coding nucleic acid sequences of the microorganism) as compared to the naturally-occurring wild-type microorganism from which it was derived. According to a particular preferred embodiment of the modified microorganism according to the present invention the modified microorganism is a recombinant microorganism, which means that the microorganism has been obtained using recombinant DNA. The expression "recombinant DNA" as used herein refers to DNA sequences that result from the use of laboratory methods (molecular cloning) to bring together genetic material from multiple sources, creating sequences that would not otherwise be found in biological organisms. An example of such a recombinant DNA is a plasmid into which a heterologous DNA-sequence has been inserted.

The wild-type from which the microorganisms according to the present invention are derived belongs to the family of Pasteurellaceae. Pasteurellaceae comprise a large family of Gramnegative Proteobacteria with members ranging from bacteria such as *Haemophilus influenzae* to commensals of the animal and human mucosa. Most members live as commensals on mucosal surfaces of birds and mammals, especially in the upper respiratory tract. Pasteurellaceae are typically rod-shaped, and are a notable group of facultative anaerobes. They can be distinguished from the related Enterobacteriaceae by the presence of oxidase, and from most other similar bacteria by the absence of flagella. Bacteria in the family Pasteurellaceae have been classified into a number of genera based on metabolic properties and their sequences of the 16S RNA and 23S RNA. Many of the Pasteurellaceae contain pyruvate-formate-lyase genes and are capable of anaerobically fermenting carbon sources to organic acids.

According to a particular preferred embodiment of the modified microorganism according to the present invention the wild-type from which the modified microorganism has been derived belongs to the genus *Basfia* and it is particularly preferred that the wild-type from which the modified microorganism has been derived belongs to the species *Basfia succiniciproducens*.

Most preferably, the wild-type from which the modified microorganism according to the present invention as been derived is *Basfia succiniciproducens*-strain DD1 deposited on Aug. 11, 2006 under the Budapest Treaty with DSMZ (Deutsche Sammlung von Mikroorganismen und Zellkulturen, GmbH), Germany, having the deposit number DSM 18541. This strain has been originally isolated from the rumen of a cow of German origin. *Pasteurella* bacteria can be isolated from the gastrointestinal tract of animals and, preferably, mammals. The bacterial strain DD1, in particular, can be isolated from bovine rumen and is capable of utilizing glycerol (including crude glycerol) as a carbon source. Further strains of the genus *Basfia* that can be used for preparing the modified microorganism according to the present invention are the *Basfia*-strain that has been deposited under the deposit number DSM 22022 with DSZM or the *Basfia*-strains that have been deposited with the Culture Collection of the University of Goteborg (CCUG), Sweden, having the deposit numbers CCUG 57335, CCUG 57762, CCUG 57763, CCUG 57764, CCUG 57765 or CCUG 57766. Said strains have been originally isolated from the rumen of cows of German or Swiss origin.

In this context it is particularly preferred that the wild-type from which the modified microorganism according to the present invention has been derived has a 16S rDNA of SEQ ID NO: 1 or a sequence, which shows a sequence homology of at least 96%, at least 97%, at least 98%, at least 99% or at least 99.9% with SEQ ID NO: 1. It is also preferred that the wild-type from which the modified microorganism according to the present invention has been derived has a 23S rDNA of SEQ ID NO: 2 or a sequence, which shows a sequence homology of at least 96%, at least 97%, at least 98%, at least 99% or at least 99.9% with SEQ ID NO: 2.

The identity in percentage values referred to in connection with the various polypeptides or polynucleotides to be used for the modified microorganism according to the present invention is, preferably, calculated as identity of the residues over the complete length of the aligned sequences, such as, for example, the identity calculated (for rather similar sequences) with the aid of the program needle from the bioinformatics software package EMBOSS (Version 5.0.0, http://emboss.source-forge.net/what/) with the default parameters which are, i.e. gap open (penalty to open a gap): 10.0, gap extend (penalty to extend a gap): 0.5, and data file (scoring matrix file included in package): EDNAFUL.

It should be noted that the modified microorganism according to the present invention can not only be derived from the above mentioned wild-type-microorganisms, especially from *Basfia succiniciproducens*-strain DD1, but also from variants of these strains. In this context the expression "a variant of a strain" comprises every strain having the same or essentially the same characteristics as the wild-type-strain. In this context it is particularly preferred that the 16 S rDNA of the variant has an identity of at least 90%, preferably at least 95%, more preferably at least 99%, more preferably at least 99.5%, more preferably at least 99.6%, more preferably at least 99.7%, more preferably at least 99.8% and most preferably at least 99.9% with the wild-type from which the variant has been derived. It is also particularly preferred that the 23 S rDNA of the variant has an identity of at least 90%, preferably at least 95%, more preferably at least 99%, more preferably at least 99.5%, more preferably at least 99.6%, more preferably at least 99.7%, more preferably at least 99.8% and most preferably at least 99.9% with the wild-type from which the variant has been derived. A variant of a strain in the sense of this definition can, for example, be obtained by treating the wild-type-strain with a mutagenizing chemical agent, X-rays, or UV light.

The modified microorganism according to the present invention is characterized in that, compared to its wild-type, the activity of the enzyme that is encoded by the pykA-gene is reduced.

The reduction of the enzyme activity ($\Delta_{activity}$) is preferably defined as follows:

$$\Delta_{activity} = 100\% - \left(\frac{\text{activity of the modified microorganism}}{\text{activity of the wildtype}} \times 100\%\right)$$

wherein, when determining $\Delta_{activity}$, the activity in the wild-type and the activity in the modified microorganism are determined under exactly the same conditions. Methods for the detection and determination of the activity of the enzyme that is encoded by the pykA-gene can be found, for example, in Bergmeyer, H. U., Gawehn, K., and Grassi, M. (1974):

"*Methods of Enzymatic Analysis*", Second Edition, Volume I, pages 509-511, Academic Press, Inc., New York, N.Y.

The reduced activity of the enzymes disclosed herein, in particular the reduced activity of the enzyme encoded by the pykA-gene, the lactate dehydrogenase and/or the pyruvate formate lyase, can be a reduction of the enzymatic activity by 0.1 to 99%, compared to the activity of said enzyme in the wild-type of the microorganism, or a reduction of the enzymatic activity by at least 15%, or at least 25%, or at least 35%, or at least 45%, or at least 55%, or at least 65%, or at least 75% or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%. Preferably, the reduction of the activity of the enzyme encoded by the pykA-gene is in the range of 15 to 99%, more preferably in the range of 50 to 95% and even more preferably in the range of 90 to 99%. The term "reduced activity of the enzyme that is encoded by the pykA-gene" or—as described below—"a reduced lactate dehydrogenase activity" or "a reduced pyruvate formate lyase activity", also encompasses a modified microorganism which has no detectable activity of these enzymes.

The term "reduced activity of an enzyme" includes, for example, the expression of the enzyme by said genetically modified (e.g., genetically engineered) microorganism at a lower level than that expressed by the wild-type of said microorganism. Genetic manipulations for reducing the expression of an enzyme can include, but are not limited to, deleting the gene or parts thereof encoding for the enzyme, altering or modifying regulatory sequences or sites associated with expression of the gene encoding the enzyme (e.g., by removing strong promoters or repressible promoters), modifying proteins (e.g., regulatory proteins, suppressors, enhancers, transcriptional activators and the like) involved in transcription of the gene encoding the enzyme and/or the translation of the gene product, or any other conventional means of decreasing expression of a particular gene routine in the art (including, but not limited to, the use of antisense nucleic acid molecules or other methods to knock-out or block expression of the target protein). Further on, one may introduce destabilizing elements into the mRNA or introduce genetic modifications leading to deterioration of ribosomal binding sites (RBS) of the RNA. It is also possible to change the codon usage of the gene in a way, that the translation efficiency and speed is decreased.

A reduced activity of an enzyme can also be obtained by introducing one or more gene mutations which lead to a reduced activity of the enzyme. Furthermore, a reduction of the activity of an enzyme may also include an inactivation (or the reduced expression) of activating enzymes which are necessary in order to activate the enzyme the activity of which is to be reduced. By the latter approach the enzyme the activity of which is to be reduced is preferably kept in an inactivated state.

Microorganisms having a reduced activity of the enzyme encoded by the pykA-gene may occur naturally, i.e. due to spontaneous mutations. A microorganism can be modified to lack or to have significantly reduced activity of the enzyme that is encoded by the pykA-gene by various techniques, such as chemical treatment or radiation. To this end, microorganisms will be treated by, e.g., a mutagenizing chemical agent, X-rays, or UV light. In a subsequent step, those microorganisms which have a reduced activity of the enzyme that is encoded by the pykA-gene will be selected. Modified microorganisms are also obtainable by homologous recombination techniques which aim to mutate, disrupt or excise the pykA-gene in the genome of the microorganism or to substitute the gene with a corresponding gene that encodes for an enzyme which, compared to the enzyme encoded by the wild-type-gene, has a reduced activity.

According to a preferred embodiment of the modified microorganism according to the present invention, the activity of the enzyme encoded by the pykA-gene is reduced by introducing at least one mutation into the pykA-gene, preferably into the wild-type-pykA-gene. In this context it is particularly preferred that the at least one mutation leads to a modification of the nucleic acid sequence of the pykA-gene, such that the amino acid sequence of the enzyme encoded by the modified gene differs from the amino acid sequence of the enzyme encoded by the wild-type pykA-gene in at least one amino acid.

A mutation into the pykA-gene can be introduced, for example, by site-directed or random mutagenesis, followed by an introduction of the modified gene into the genome of the microorganism by recombination. Variants of the pykA-gene can be are generated by mutating the gene sequence SEQ ID NO: 3 by means of PCR. The "Quickchange Site-directed Mutagenesis Kit" (Stratagene) can be used to carry out a directed mutagenesis. A random mutagenesis over the entire coding sequence, or else only part thereof, of SEQ ID NO: 3 can be performed with the aid of the "GeneMorph II Random Mutagenesis Kit" (Stratagene). The mutagenesis rate is set to the desired amount of mutations via the amount of the template DNA used. Multiple mutations are generated by the targeted combination of individual mutations or by the sequential performance of several mutagenesis cycles.

In the following, a suitable technique for recombination, in particular for introducing the modified pykA-gene into the microorgansim, is described.

This technique is also sometimes referred to as the "Campbell recombination" herein (Leenhouts et al., *Appl Env Microbiol*. (1989), Vol. 55, pages 394-400). "Campbell in", as used herein, refers to a transformant of an original host cell in which an entire circular double stranded DNA molecule (for example a plasmid) has integrated into a chromosome by a single homologous recombination event (a cross in event), and that effectively results in the insertion of a linearized version of said circular DNA molecule into a first DNA sequence of the chromosome that is homologous to a first DNA sequence of the said circular DNA molecule. "Campbelled in" refers to the linearized DNA sequence that has been integrated into the chromosome of a "Campbell in" transformant. A "Campbell in" contains a duplication of the first homologous DNA sequence, each copy of which includes and surrounds a copy of the homologous recombination crossover point.

"Campbell out", as used herein, refers to a cell descending from a "Campbell in" transformant, in which a second homologous recombination event (a cross out event) has occurred between a second DNA sequence that is contained on the linearized inserted DNA of the "Campbelled in" DNA, and a second DNA sequence of chromosomal origin, which is homologous to the second DNA sequence of said linearized insert, the second recombination event resulting in the deletion (jettisoning) of a portion of the integrated DNA sequence, but, importantly, also resulting in a portion (this can be as little as a single base) of the integrated Campbelled in DNA remaining in the chromosome, such that compared to the original host cell, the "Campbell out" cell contains one or more intentional changes in the chromosome (for example, a single base substitution, multiple base substitutions, insertion of a heterologous gene or DNA sequence, insertion of an additional copy or copies of a homologous gene or a modified homologous gene, or insertion of a DNA sequence comprising more than one of these aforementioned examples listed above). A "Campbell out" cell is, preferably, obtained by a counter-selection against a gene that is contained in a portion (the portion that is desired to be jettisoned) of the "Campbelled in" DNA sequence, for example the *Bacillus subtilis* sacB-gene, which is lethal when expressed in a cell that is grown in the presence of about 5% to 10% sucrose. Either with or without a counter-selection, a desired "Campbell out" cell can be obtained or identified by screening for the desired cell, using any screenable phenotype, such as, but not limited to, colony morphology, colony color, presence or absence of antibiotic resistance, presence or absence of a given DNA sequence by polymerase chain reaction, presence or absence of an auxotrophy, presence or absence of an enzyme, colony nucleic acid hybridization, antibody screening, etc. The term "Campbell in" and "Campbell out" can also be used as verbs in various tenses to refer to the method or process described above.

It is understood that the homologous recombination events that leads to a "Campbell in" or "Campbell out" can occur over a range of DNA bases within the homologous DNA sequence, and since the homologous sequences will be identical to each other for at least part of this range, it is not usually possible to specify exactly where the crossover event occurred. In other words, it is not possible to specify precisely which sequence was originally from the inserted DNA, and which was originally from the chromosomal DNA. Moreover, the first homologous DNA sequence and the second homologous DNA sequence are usually separated by a region of partial non-homology, and it is this region of non-homology that remains deposited in a chromosome of the "Campbell out" cell.

Preferably, first and second homologous DNA sequence are at least about 200 base pairs in length, and can be up to several thousand base pairs in length. However, the procedure can be made to work with shorter or longer sequences. For example, a length for the first and second homologous sequences can range from about 500 to 2000 bases, and the obtaining of a "Campbell out" from a "Campbell in" is facilitated by arranging the first and second homologous sequences to be approximately the same length, preferably with a difference of less than 200 base pairs and most preferably with the shorter of the two being at least 70% of the length of the longer in base pairs.

The pykA-gene the activity of which is reduced in the modified microorganism according to the present invention preferably comprises a nucleic acid selected from the group consisting of:
a) nucleic acids having the nucleotide sequence of SEQ ID NO: 3;
b) nucleic acids encoding the amino acid sequence of SEQ ID NO: 4;
c) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of a) or b), the identity being the identity over the total length of the nucleic acids of a) or b);
d) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of a) or b), the identity being the identity over the total length of amino acid sequence encoded by the nucleic acids of a) or b);
e) nucleic acids capable of hybridizing under stringent conditions with a complementary sequence of any of the nucleic acids according to a) or b); and
f) nucleic acids encoding the same protein as any of the nucleic acids of a) or b), but differing from the nucleic acids of a) or b) above due to the degeneracy of the genetic code.

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature". The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl (see e.g., Anderson and Young, Quantitative Filter Hybridization, in Nucleic Acid Hybridization (1985)). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contiguous nucleotides or more, 150 contiguous nucleotides or more, 200 contiguous nucleotides or more or 250 contiguous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ss RNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. Preferably, the complementary nucleotides hybridize with a fragment or the whole pykA nucleic acids. Alternatively, preferred hybridization conditions encompass hybridization at 65° C. in 1×SSC or at 42° C. in 1×SSC and 50% formamide, followed by washing at 65° C. in 0.3×SSC or hybridization at 50° C. in 4×SSC or at 40° C. in 6×SSC and 50% formamide, followed by washing at 50° C. in 2×SSC. Further preferred hybridization conditions are 0.1% SDS, 0.1 SSD and 65° C.

The pykA-gene in which at last one mutation is introduced by the above mentioned combination of side-directed mutagenesis and "Campbell recombination" preferably comprises a nucleic acid as defined above.

Nucleic acid having the nucleotide sequence of SEQ ID NO: 3 corresponds to the pykA-gene of *Basfia succiniciproducens*-strain DD1.

According to a preferred embodiment of the modified microorganism according to the present invention, the modified microorganism does not have, compared to its wild-type, an increased level of the activity of phosphoenol pyruvate carboxykinase (EC 4.1.1.49), which is encoded by the pcK-gene. In this context it is particularly preferred that in the modified microorganism the level of the of phosphoenol pyruvate carboxykinase activity is not increased as a result from the replacement of native regulatory sequences of the pck-gene with altered regulatory sequences that increases phosphoenol pyruvate carboxykinase activity.

According to a further preferred embodiment of the modified microorganism according to the present invention, this microorganism is not only characterized by a reduced activity of the enzyme encoded by the pykA-gene, but also, compared to its wild-type, by
i) a reduced pyruvate formate lyase activity,
ii) a reduced lactate dehydrogenase activity, or
iii) a reduced pyruvate formate lyase activity and a reduced lactate dehydrogenase activity.

Modified microorganisms being deficient in lactate dehydrogenase and/or being deficient in pyruvate formate lyase activity are disclosed in WO-A-2010/092155, US 2010/0159543 and WO-A-2005/052135, the disclosure of which with respect to the different approaches of reducing the activity of lactate dehydrogenase and/or pyruvate formate lyase in a microorganism, preferably in a bacterial cell of the genus *Pasteurella*, particular preferred in *Basfia succiniciproducens* strain DD1, is incorporated herein by reference. Methods for determining the pyruvate formate lyase activity are, for example, disclosed by Asanuma N. and Hino T. in "*Effects of pH and Energy Supply on Activity and Amount of Pyruvate-Formate-Lyase in Streptococcus bovis*", Appl. Environ. Microbiol. (2000), Vol. 66, pages 3773-3777" and methods for determining the lactate dehydrogenase activity are, for example, disclosed by Bergmeyer, H. U., Bergmeyer J. and Grassi, M. (1983-1986) in "*Methods of Enzymatic Analysis*", 3$^{rd}$ Edition, Volume III, pages 126-133, Verlag Chemie, Weinheim.

In this context it is preferred that the reduction of the activity of lactate dehydrogenase is achieved by an inactivation of the IdhA-gene (which encodes the lactate dehydrogenase LdhA; EC 1.1.1.27 or EC 1.1.1.28) and the reduction of the pyruvate formate lyase is achieved by an inactivation of the pflA-gene (which encodes for an activator of pyruvate formate lyase PflA; EC 1.97.1.4) or the pflD-gene (which encodes the pyruvate formate lyase PflD; EC 2.3.1.54), wherein the inactivation of these genes (i. e. IdhA, pflA and pflD) is preferably achieved by a deletion of theses genes or parts thereof, by a deletion of a regulatory element of these genes or at least a part thereof or by an introduction of at least one mutation into these genes, wherein these modifications are preferably performed by means of the "Campbell recombination" as described above.

The IdhA-gene the activity of which is reduced in the modified microorganism according to the present invention preferably comprises a nucleic acid selected from the group consisting of:

α1) nucleic acids having the nucleotide sequence of SEQ ID NO: 27;
α2) nucleic acids encoding the amino acid sequence of SEQ ID NO: 28;
α3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of α1) or α2), the identity being the identity over the total length of the nucleic acids of α1) or α2);
α4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of α1) or α2), the identity being the identity over the total length of amino acid sequence encoded by the nucleic acids of α1) or α2)
α5) nucleic acids capable of hybridizing under stringent conditions with a complementary sequence of any of the nucleic acids according to α1) or α2); and
α6) nucleic acids encoding the same protein as any of the nucleic acids of α1) or α2), but differing from the nucleic acids of α1) or α2) above due to the degeneracy of the genetic code.

The pflA-gene the activity of which is reduced in the modified microorganism according to the present invention preferably comprises a nucleic acid selected from the group consisting of:

β1) nucleic acids having the nucleotide sequence of SEQ ID NO: 29;
β2) nucleic acids encoding the amino acid sequence of SEQ ID NO: 30;
β3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of β1) or β2), the identity being the identity over the total length of the nucleic acids of β1) or β2);
β4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of β1) or β2), the identity being the identity over the total length of amino acid sequence encoded by the nucleic acids of β1) or β2);
β5) nucleic acids capable of hybridizing under stringent conditions with a complementary sequence of any of the nucleic acids according to β1) or β2); and
β6) nucleic acids encoding the same protein as any of the nucleic acids of β1) or β2), but differing from the nucleic acids of β1) or β2) above due to the degeneracy of the genetic code.

The pflD-gene the activity of which is reduced in the modified microorganism according to the present invention preferably comprises a nucleic acid selected from the group consisting of:

γ1) nucleic acids having the nucleotide sequence of SEQ ID NO: 31;
γ2) nucleic acids encoding the amino acid sequence of SEQ ID NO: 32;

γ3) nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the nucleic acid of γ1) or γ2), the identity being the identity over the total length of the nucleic acids of γ1) or γ2);

γ4) nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence encoded by the nucleic acid of γ1) or γ2), the identity being the identity over the total length of amino acid sequence encoded by the nucleic acids of γ1) or γ2);

γ5) nucleic acids capable of hybridizing under stringent conditions with a complementary sequence of any of the nucleic acids according to γ1) or γ2); and γ6) nucleic acids encoding the same protein as any of the nucleic acids of γ1) or γ2), but differing from the nucleic acids of γ1) or γ2) above due to the degeneracy of the genetic code.

In this context it is preferred that the modified microorganism according to the present invention further comprises:
A) a deletion of the IdhA-gene or at least a part thereof, a deletion of a regulatory element of the IdhA-gene or at least a part thereof or an introduction of at least one mutation into the IdhA-gene;
B) a deletion of the pflD-gene or at least a part thereof, a deletion of a regulatory element of the pflD-gene or at least a part thereof or an introduction of at least one mutation into the pflD-gene;
C) a deletion of the pflA-gene or at least a part thereof, a deletion of a regulatory element of the pflA-gene or at least a part thereof or an introduction of at least one mutation into the pflA-gene;
D) a deletion of the IdhA-gene or at least a part thereof, a deletion of a regulatory element of the IdhA-gene or at least a part thereof or an introduction of at least one mutation into the IdhA-gene
and
a deletion of the pflD-gene or at least a part thereof, a deletion of a regulatory element of the pflD-gene or at least a part thereof or an introduction of at least one mutation into the pflD-gene;
or
E) a deletion of the IdhA-gene or at least a part thereof, a deletion of a regulatory element of the IdhA-gene or at least a part thereof or an introduction of at least one mutation into the IdhA-gene
and
a deletion of the pflA-gene or at least a part thereof, a deletion of a regulatory element of the pflA-gene or at least a part thereof or an introduction of at least one mutation into the pflA-gene.

Particular preferred embodiments of the modified microorganisms according to the present invention are:
modified bacterial cells of the genus *Basfia* and particular preferred of the species *Basfia succiniciproducens*, in which at least one mutation has been introduced in the pykA-gene, preferably at least one mutation the results in the substitution of at least one amino acid in the enzyme encoded by the pykA-gene, most preferred a mutation that results at least in a substitution of glycine by cysteine a position 167, or a substitution of cysteine by tyrosine at position 417 or a substitution of alanine by glycine at position 171, or a substitution glycine by cysteine a position 167 and a substitution of cysteine by tyrosine at position 417, or a substitution of glycine by cysteine a position 167 and a substitution of alanine by glycine at position 171, or a substitution of cysteine by tyrosine at position 417 and a substitution of alanine by glycine at position 171, or a substitution glycine by cysteine a position 167, a substitution of cysteine by tyrosine at position 417 and a substitution of alanine by glycine at position 171 in the enzyme encoded by the pykA-gene, and wherein it is further preferred that the modified bacterial cell does not have, compared to the wild-type, an increased activity of the enzyme that is encoded by the pck-gene;

modified bacterial cells of the genus *Basfia* and particular preferred of the species *Basfia succiniciproducens*, in which at least one mutation has been introduced in the pykA-gene, preferably at least one mutation the results in the substitution of at least one amino acid in the enzyme encoded by the pykA-gene, most preferred a mutation that results at least in a substitution glycine by cysteine a position 167, or a substitution of cysteine by tyrosine at position 417 or a substitution of alanine by glycine at position 171, or a substitution glycine by cysteine a position 167 and a substitution of cysteine by tyrosine at position 417, or a substitution of glycine by cysteine a position 167 and a substitution of alanine by glycine at position 171, or a substitution of cysteine by tyrosine at position 417 and a substitution of alanine by glycine at position 171, or a substitution glycine by cysteine a position 167, a substitution of cysteine by tyrosine at position 417 and a substitution of alanine by glycine at position 171 in the enzyme encoded by the pykA-gene, and in which, compared to the wild-type, the activity of the lactate dehydrogenase is reduced, preferably by a modification of the IdhA-gene, in particular by a modification of the IdhA-gene having the nucleic acid sequence according to SEQ ID NO: 27 and encoding for LdhA having the amino acid sequence according to SEQ ID NO: 28, and wherein it is further preferred that the modified bacterial cell does not have, compared to the wild-type, an increased activity of the enzyme that is encoded by the pck-gene;

modified bacterial cells of the genus *Basfia* and particular preferred of the species *Basfia succiniciproducens*, in which at least one mutation has been introduced in the pykA-gene, preferably at least one mutation the results in the substitution of at least one amino acid in the enzyme encoded by the pykA-gene, most preferred a mutation that results at least in a substitution glycine by cysteine a position 167, or a substitution of cysteine by tyrosine at position 417 or a substitution of alanine by glycine at position 171, or a substitution glycine by cysteine a position 167 and a substitution of cysteine by tyrosine at position 417, or a substitution of glycine by cysteine a position 167 and a substitution of alanine by glycine at position 171, or a substitution of cysteine by tyrosine at position 417 and a substitution of alanine by glycine at position 171, or a substitution glycine by cysteine a position 167, a substitution of cysteine by tyrosine at position 417 and a substitution of alanine by glycine at position 171 in the enzyme encoded by the pykA-gene, and in which, compared to the wild-type, the activity of the pyruvate formate lyase is reduced, preferably by a modification of the pflA-gene or the pflD-gene, in particular by a modification of the pflA-gene having the nucleic acid sequence according to SEQ ID NO: 29 and encoding for PflA having the amino acid sequence according to SEQ ID NO: 30 or by a modification of the pflD-gene having the nucleic acid sequence according to SEQ ID NO: 31 and encoding for PflD having the amino acid sequence according to SEQ ID NO: 32, and wherein it is further preferred that the modified bacterial cell does not have, compared to the wild-type, an increased activity of the enzyme that is encoded by the pck-gene;
or modified bacterial cells of the genus *Basfia* and particular preferred of the species *Basfia succiniciproducens*, in which at least one mutation has been introduced in the pykA-gene, preferably at least one mutation the results in the substitution of at least one amino acid in the enzyme encoded by the pykA-gene, most preferred a mutation that results at least in a substitution glycine by cysteine a position 167, or a substitution of cysteine by tyrosine at position 417 or a substitution of alanine by glycine at position 171, or a substitution glycine by cysteine a position 167 and a substitution of cysteine by tyrosine at position 417, or a substitution of glycine by cysteine a position 167 and a substitution of alanine by glycine at position 171, or a substitution of cysteine by tyrosine at position 417 and a substitution of alanine by glycine at position 171, or a substitution glycine by cysteine a position 167, a substitution of cysteine by tyrosine at position 417 and a substitution of alanine by glycine at position 171 in the enzyme encoded by the pykA-gene, and in which, compared to the wild-type, the activity of the lactate dehydrogenase and the pyruvate formate lyase are reduced, preferably by a modification of the IdhA-gene and the pflA-gene, in particular by a modification of the IdhA-gene having the nucleic acid sequence according to SEQ ID NO: 27 and encoding for LdhA having the amino acid sequence according to SEQ ID NO: 28 or by a modification of the pflA-gene having the nucleic acid sequence according to SEQ ID NO: 29 and encoding for PflA having the amino acid sequence according to SEQ ID NO: 30, or a modification of the IdhA-geneand the pflD-gene, in particular by a modification of the IdhA-gene having the nucleic acid sequence according to SEQ ID NO: 27 and encoding for LdhA having the amino acid sequence according to SEQ ID NO: 28 or by a modification of the pflD-gene having the nucleic acid sequence according to SEQ ID NO: 31 and encoding for PflD having the amino acid sequence according to SEQ ID NO: 32, and wherein it is further preferred that the modified bacterial cell does not have, compared to the wild-type, an increased activity of the enzyme that is encoded by the pck-gene.

A contribution to solving the problems mentioned at the outset is furthermore provided by a method of producing an organic compound comprising:

I) cultivating the modified microorganism according to the present invention in a culture medium comprising at least one assimilable carbon source to allow the modified microorganism to produce the organic compound, thereby obtaining a fermentation broth comprising the organic compound;

II) recovering the organic compound from the fermentation broth obtained in process step I).

In process step I) the modified microorganism according to the present invention is cultured in a culture medium comprising at least one assimilable carbon source to allow the modified microorganism to produce the organic compound, thereby obtaining a fermentation broth comprising the organic compound. Preferred organic compounds that can be produced by the process according to the present invention comprise carboxylic acids such as formic acid, lactic acid, propionic acid, 2-hydroxypropionic acid, 3-hydroxypropionic acid, 3-hydroxybutyric acid, acrylic acid, pyruvic acid or salts of these carboxylic acids, dicarboxylic acids such as malonic acid, succinic acid, malic acid, tartaric acid, glutaric acid, itaconic acid, adipic acid or salts thereof, tricarboxylic acids such as citric acid or salts thereof, alcohols such as methanol or ethanol, amino acids such as L-asparagine, L-aspartic acid, L-arginine, L-isoleucine, L-glycine, Lglutamine, L-glutamic acid, L-cysteine, L-serine, L-tyrosine, L-tryptophan, L-threonine, L-valine, L-histidine, L-proline, L-methionine, L-lysine, L-leucine, etc.

According to a preferred embodiment of the process according to the present invention the organic compound is succinic acid. The term "succinic acid", as used in the context of the present invention, has to be understood in its broadest sense and also encompasses salts thereof (i. e. succinate), as for example alkali metal salts, like $Na^+$ and $K^+$-salts, or earth alkali salts, like $Mg^{2+}$ and $Ca^{2+}$-salts, or ammonium salts or anhydrides of succinic acid.

The modified microorganism according to the present invention is preferably incubated in the culture medium at a temperature in the range of about 10 to 60° C. or 20 to 50° C. or 30 to 45° C. at a pH of 5.0 to 9.0 or 5.5 to 8.0 or 6.0 to 7.0.

Preferably, the organic compound, especially succinic acid, is produced under anaerobic conditions. Anaerobic conditions may be established by means of conventional techniques, as for example by degassing the constituents of the reaction medium and maintaining anaerobic conditions by introducing carbon dioxide or nitrogen or mixtures thereof and optionally hydrogen at a flow rate of, for example, 0.1 to 1 or 0.2 to 0.5 vvm. Aerobic conditions may be established by means of conventional techniques, as for example by introducing air or oxygen at a flow rate of, for example, 0.1 to 1 or 0.2 to 0.5 vvm. If appropriate, a slight over pressure of 0.1 to 1.5 bar may be applied in the process.

The assimilable carbon source is preferably selected from the group consisting of sucrose, maltose, maltotriose, maltotetraose, maltopentaose, maltohexaose, maltoheptaose, D-fructose, D-glucose, D-xylose, L-arabinose, D-galactose, D-mannose, glycerol, mixtures thereof and compositions containing at least one of said compounds, or is selected from decomposition products of starch, cellulose, hemicellulose and/or lignocellulose. Preferably, the assimilable carbon source is selected from the group consisting of D-glucose, maltose, sucrose, glycerol and a mixture of at least two of these compounds, wherein mixtures of glycerol and D-glucose, glycerol and sucrose, glycerol and D-xylose, glycerol and maltose and D-glucose and fructose are particularly preferred.

The initial concentration of the assimilable carbon source is preferably adjusted to a value in a range of 5 to 100 g/l, preferably 5 to 75 g/l and more preferably 5 to 50 g/l and may be maintained in said range during cultivation. The pH of the reaction medium may be controlled by addition of suitable bases as for example, gaseous ammonia, $NH_4HCO_3$, $(NH_4)_2CO_3$, $NaOH$, $Na_2CO_3$, $NaHCO_3$, $KOH$, $K_2CO_3$, $KHCO_3$, $Mg(OH)_2$, $MgCO_3$, $Mg(HCO_3)_2$, $Ca(OH)_2$, $CaCO_3$, $Ca(HCO_3)_2$, $CaO$, $CH_6N_2O_2$, $C_2H_7N$ and/or mixtures thereof. These alkaline neutralization agents are especially required if the organic compounds that are formed in the course of the fermentation process are carboxylic acids or dicarboxylic acids. In the case of succinic acid as the organic compound, Mg(OH)$_2$ and MgCO$_3$ are particular preferred bases.

The fermentation step I) according to the present invention can, for example, be performed in stirred fermenters, bubble columns and loop reactors. A comprehensive overview of the possible method types including stirrer types and geometric designs can be found in Chmiel: "*Bioprozesstechnik: Einführung in die Bioverfahrenstechnik*", Volume 1. In the process according to the present invention, typical variants available are the following variants known to those skilled in the art or explained, for example, in Chmiel, Hammes and Bailey: "*Biochemical Engineering*": such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield (YP/S).

Particularly preferred conditions for producing the organic compound, especially succinic acid, in process step I) are:
Assimilable carbon source: glycerol, sucrose, D-glucose, maltose, glycerol+D-glucose, glycerol+sucrose, glycerol+maltose, glycerol+D-xylose, D-glucose+fructose
Temperature: 30 to 45° C.
pH: 5.5 to 7.0
Supplied gas: CO$_2$ It is furthermore preferred in process step I) that the assimilable carbon source is converted to the organic compound, preferably to succinic acid, with a carbon yield YP/S of at least 0.5 g/g up to about 1.28 g/g; as for example a carbon yield YP/S of at least 0.6 g/g, of at least 0.7 g/g, of at least 0.75 g/g, of at least 0.8 g/g, of at least 0.85 g/g, of at least 0.9 g/g, of at least 0.95 g/g, of at least 1.0 g/g, of at least 1.05 g/g, of at least 1.1 g/g, of at least 1.15 g/g, of at least 1.20 g/g, of at least 1.22 g/g, or of at least 1.24 g/g (organic compound/carbon, preferably succinic acid/carbon).

It is furthermore preferred in process step I) that the assimilable carbon source is converted to the organic compound, preferably to succinic acid, with a specific productivity yield of at least 0.6 g g DCW$^{-1}$h$^{-1}$ organic compound, preferably succinic acid, or of at least of at least 0.65 g g DCW$^{-1}$h$^{-1}$, of at least 0.7 g g DCW$^{-1}$h$^{-1}$, of at least 0.75 g g DCW$^{-1}$h$^{-1}$ or of at least 0.77 g g DCW$^{-1}$h$^{-1}$ organic compound, preferably succinic acid.

It is furthermore preferred in process step I) that the assimilable carbon source is converted to the organic compound, preferably to succinic acid, with a space time yield for the organic compound, preferably for succinic acid, of at least 2.2 g/(L×h) or of at least 2.5 g/(L×h), at least 2.75 g/(L×h), at least 3 g/(L×h), at least 3.25 g/(L×h), at least 3.5 g/(L×h), at least 3.7 g/(L×h), at least 4.0 g/(L×h) at least 4.5 g/(L×h) or at least 5.0 g/(L×h) of the organic compound, preferably succinic acid. According to another preferred embodiment of the process according to the present invention in process step I) the modified microorganism is converting at least 20 g/L, more preferably at least 25 g/l and even more preferably at least 30 g/l of the assimilable carbon source to at least 20 g/l, more preferably to at least 25 g/l and even more preferably at least 30 g/l of the organic compound, preferably succinic acid.

The different yield parameters as described herein ("carbon yield" or "YP/S"; "specific productivity yield"; or "space-time-yield (STY)") are well known in the art and are determined as described for example by Song and Lee, 2006. "Carbon yield" and "YP/S" (each expressed in mass of organic compound produced/mass of assimilable carbon source consumed) are herein used as synonyms. The specific productivity yield describes the amount of a product, like succinic acid, that is produced per h and L fermentation broth per g of dry biomass. The amount of dry cell weight stated as "DCW" describes the quantity of biologically active microorganism in a biochemical reaction. The value is given as g product per g DCW per h (i.e. g g DCW$^{-1}$h$^{-1}$). The space-time-yield (STY) is defined as the ratio of the total amount of organic compound formed in the fermentation process to the volume of the culture, regarded over the entire time of cultivation. The space-time yield is also known as the "volumetric productivity".

In process step II) the organic compound, preferably succinic acid, is recovered from the fermentation broth obtained in process step I).

Usually, the recovery process comprises the step of separating the recombinant microorganisms from the fermentation broth as the so called "biomass". Processes for removing the biomass are known to those skilled in the art, and comprise filtration, sedimentation, flotation or combinations thereof. Consequently, the biomass can be removed, for example, with centrifuges, separators, decanters, filters or in a flotation apparatus. For maximum recovery of the product of value, washing of the biomass is often advisable, for example in the form of a diafiltration. The selection of the method is dependent upon the biomass content in the fermentation broth and the properties of the biomass, and also the interaction of the biomass with the organic compound (e. the product of value). In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

The recovery process may further comprise additional purification steps in which the organic compound, preferably succinic acid, is further purified. If, however, the organic compound is converted into a secondary organic product by chemical reactions as described below, a further purification of the organic compound is, depending on the kind of reaction and the reaction conditions, not necessarily required. For the purification of the organic compound obtained in process step II), preferably for the purification of succinic acid, methods known to the person skilled in the art can be used, as for example crystallization, filtration, electrodialysis and chromatography. In the case of succinic acid as the organic compound, for example, succinic acid may be isolated by precipitating it as a calcium succinate product by using calcium hydroxide, -oxide, -carbonate or hydrogen carbonate for neutralization and filtration of the precipitate. The succinic acid is recovered from the precipitated calcium succinate by acidification with sulfuric acid followed by filtration to remove the calcium sulfate (gypsum) which precipitates. The resulting solution may be further purified by means of ion exchange chromatography in order to remove undesired residual ions. Alternatively, if magnesium hydroxide, magnesium carbonate or mixtures thereof have been used to neutralize the fermentation broth, the fermentation broth obtained in process step I) may be acidified to transform the magnesium succinate contained in the medium into the acid form (i. e. succinic acid), which subsequently can be crystallized by cooling down the acidified medium. Examples of further suitable purification processes are disclosed in EP-A1 005 562, WO-A-2008/010373, WO-A-2011/082378, WO-A-2011/043443, WO-A2005/030973, WO-A-2011/123268 and WO-A-2011/064151 and EP-A-2 360 137.

According to a preferred embodiment of the process according to the present invention the process further comprises the process step:

III) conversion of the organic compound contained in the fermentation broth obtained in process step I) or conversion of the recovered organic compound obtained in process step II) into a secondary organic product being different from the organic compound by at least one chemical reaction.

In case of succinic acid as the organic compound preferred secondary organic products are selected from the group consisting of succinic acid esters and polymers thereof, tetrahydrofuran (THF), 1,4-butanediol (BDO), gamma-butyrolactone (GBL) and pyrrolidones.

According to a preferred embodiment for the production of THF, BDO and/or GBL this process comprises:
b1) either the direct catalytic hydrogenation of the succinic acid obtained in process steps I) or II) to THF and/or BDO and/or GBL or
b2) the chemical esterification of succinic acid and/or succinic acid salts obtained in process steps I) or II) into its corresponding di-lower alkyl ester and subsequent catalytic hydrogenation of said ester to THF and/or BDO and/or GBL.

According to a preferred embodiment for the production of pyrrolidones this process comprises:
b) the chemical conversion of succinic acid ammonium salts obtained in process steps I) or II) to pyrrolidones in a manner known per se.

For details of preparing these compounds reference is made to US-A-2010/0159543 and WO-A-2010/092155.

A contribution to solving the problems mentioned at the outset is furthermore provided by the use of the modified microorganism according to the present invention for the fermentative production of organic compounds. Preferred organic compounds are those compounds that have already been mentioned in connection with the process according to the present invention, succinic acid being the most preferred organic compound. Furthermore, preferred conditions for the fermentative production of organic compounds, preferably of succinic acid, are those conditions that have already been described in connection with process step I) of the process according to the present invention.

The invention is now explained in more detail with the aid of figures and non-limiting examples.

FIG. 11 shows the amino acid sequence alignment of pyruvate kinases (pykA wild-type: amino acid sequence of pyruvate kinase from the wild-type strain *Basfia succiniciproducens* DD1; pykA2: amino acid sequence of pyruvate kinase PykA2 from the DD1 ΔIdhA ΔpflA pykA2-strain; pykA4: amino acid sequence of pyruvate kinase PykA4 from the DD1 ΔIdhA ΔpflD pykA4-strain; pykA5: amino acid sequence of pyruvate kinase PykA5 from the DD1 ΔIdhA ΔpflD pykA5-strain; pykA6: amino acid sequence of pyruvate kinase PykA6 from the DD1 ΔIdhA ΔpflD pykA6-strain).

EXAMPLES

Example 1

General Method for the Transformation of *Basfia Succiniciproducens*

TABLE 1

Nomenclature of the DD1-wild-type and mutants referred to in the examples

| Strain |
| --- |
| Wild-type DD1 (deposit DSM18541) |
| DD1 ΔIdhA |
| DD1 ΔIdhA ΔpflA |
| DD1 ΔIdhA ΔpflA pykA2 |
| DD1 ΔIdhA ΔpflD |
| DD1 ΔIdhA ΔpflD pykA4 |
| DD1 ΔIdhA ΔpflD pykA5 |
| DD1 ΔIdhA ΔpflD pykA5 |

*Basfia succiniciproducens* DD1 (wild-type) was transformed with DNA by electroporation using the following protocol:

For preparing a pre-culture DD1 was inoculated from frozen stock into 40 ml BHI (brain heart infusion; Becton, Dickinson and Company) in 100 ml shake flask. Incubation was performed over night at 37° C.; 200 rpm. For preparing the main-culture 100 ml BHI were placed in a 250 ml shake flask and inoculated to a final OD (600 nm) of 0.2 with the pre-culture. Incubation was performed at 37° C., 200 rpm. The cells were harvested at an OD of approximately 0.5, 0.6 and 0.7, pellet was washed once with 10% cold glycerol at 4° C. and re-suspended in 2 ml 10% glycerol (4° C.).

100 μl of competent cells were the mixed with 2-8 μg Plasmid-DNA and kept on ice for 2 min in an electroporation cuvette with a width of 0.2 cm. Electroporation under the following conditions: 400 Ω; 25 μF; 2.5 kV (Gene Pulser, Bio-Rad). 1 ml of chilled BHI was added immediately after electroporation and incubation was performed for approximately 2 h at 37° C.

Cells were plated on BHI with 5 mg/L chloramphenicol and incubated for 2-5 d at 37° C. until the colonies of the transformants were visible. Clones were isolated and restreaked onto BHI with 5 mg/l chloramphenicol until purity of clones was obtained.

Example 2

Generation of Deletion/Mutation Constructs

1. Generation of Deletions Constructs

Figure 1:
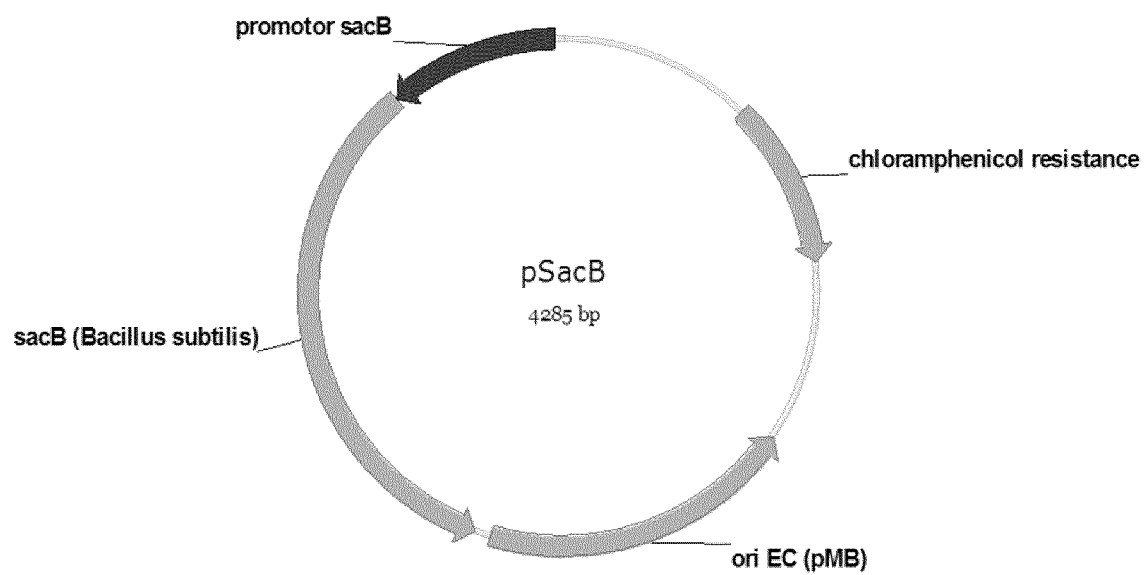
FIG. 1 shows a schematic map of plasmid pSacB (SEQ ID NO: 5).
Figure 2:
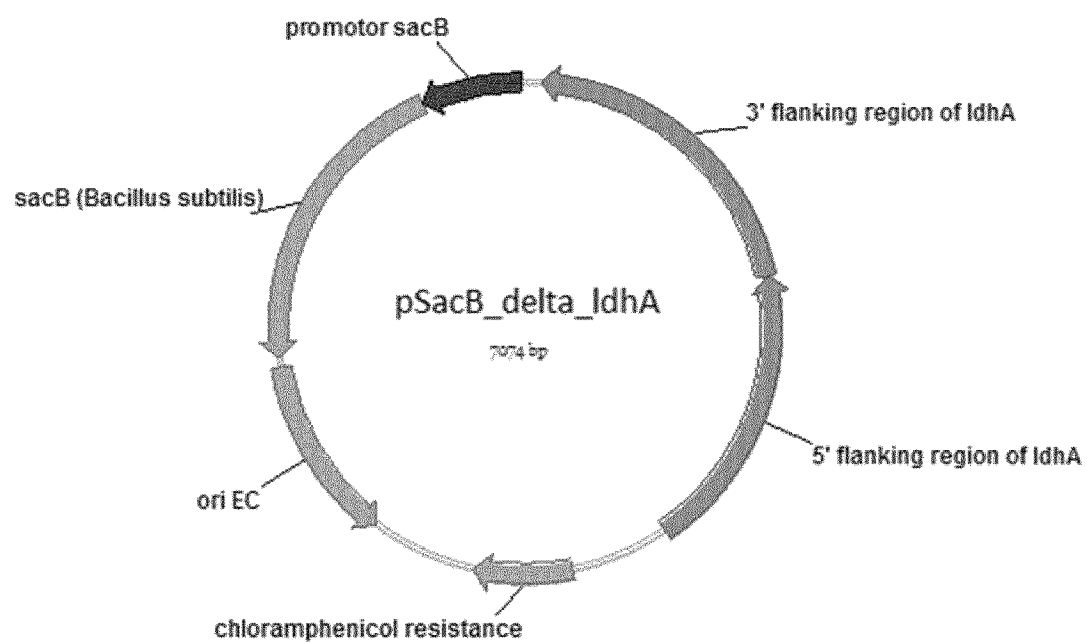
FIG. 2 shows a schematic map of plasmid pSacB ΔIdhA (SEQ ID NO: 6).
Figure 3:
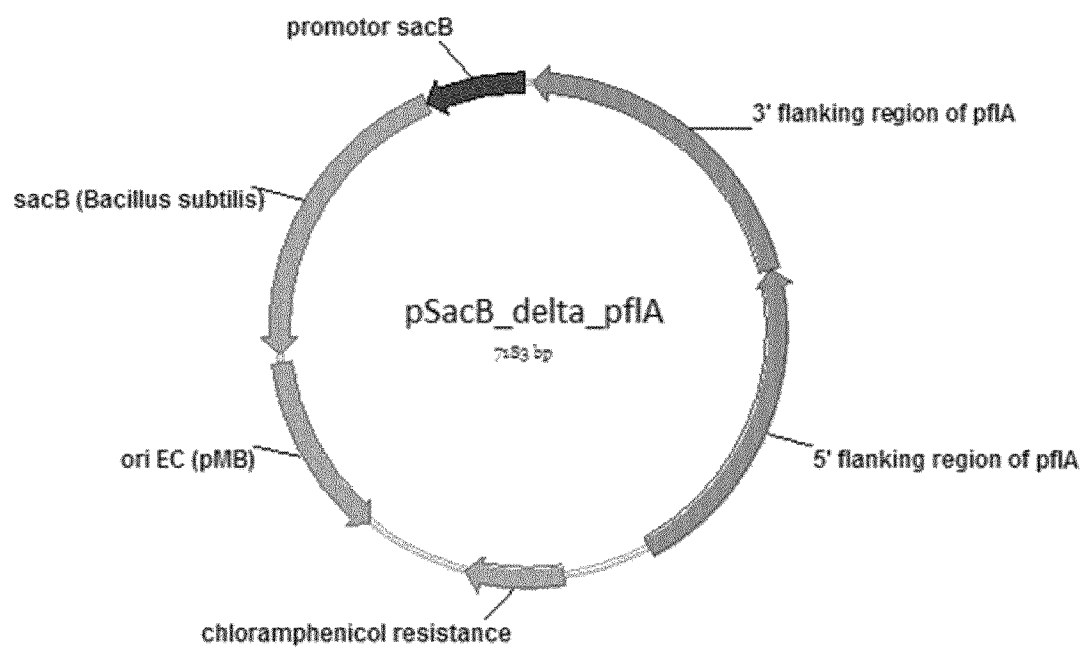
FIG. 3 shows a schematic map of plasmid pSacB ΔpflA (SEQ ID NO: 7).
Figure 4:
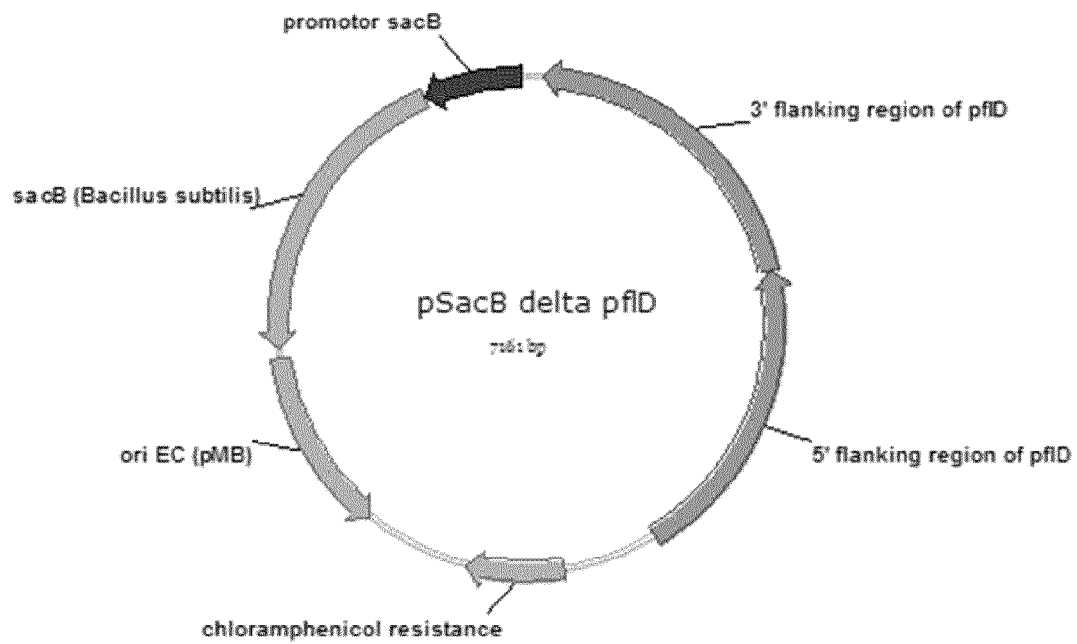
FIG. 4 shows a schematic map of plasmid pSacB ΔpflD (SEQ ID NO: 8).

Deletion plasmids were constructed based on the vector pSacB (SEQ ID NO: 5). FIG. 1 shows a schematic map of plasmid pSacB. 5'- and 3'-flanking regions (approx. 1500 bp each) of the chromosomal fragment, which should be deleted were amplified by PCR from chromosomal DNA of *Basfia succiniciproducens* and introduced into said vector using standard techniques. Normally, at least 80% of the ORF were targeted for a deletion. In such a way, the deletion plasmids for the lactate dehydrogenase IdhA, pSacB_delta_IdhA (SEQ ID NO: 6), the pyruvate formate lyase activating enzyme pflA, pSacB_delta_ pflA (SEQ ID NO: 7) and the pyruvate formate lyase pflD, pSacB_delta_pflD (SEQ ID NO: 8) were constructed. FIGS. 2, 3 and 4 show schematic maps of plasmid pSacB_delta_IdhA, pSacB_delta_pflA and pSacB_delta_pflD, respectively.

In the plasmid sequence of pSacB (SEQ ID NO: 5) the sacB-gene is contained from bases 2380-3801. The sacB-promotor is contained from bases 3802-4264. The chloramphenicol gene is contained from base 526-984. The origin of replication for *E. coli* (ori EC) is contained from base 1477-2337 (see FIG. 1).

In the plasmid sequence of pSacB_delta_IdhA (SEQ ID NO: 6) the 5' flanking region of the IdhA gene, which is homologous to the genome of *Basfia succiniciproducens*, is contained from bases 1519-2850, while the 3' flanking region of the IdhA-gene, which is homologous to the genome of *Basfia succiniciproducens*, is contained from bases 62-1518. The sacBgene is contained from bases 5169-6590. The sacB-promoter is contained from bases 6591-7053. The chloramphenicol gene is contained from base 3315-3773. The origin of replication for *E. coli* (ori EC) is contained from base 4266-5126 (see FIG. 2).

In the plasmid sequence of pSacB_delta_pflA (SEQ ID NO: 7) the 5' flanking region of the pflA-gene, which is homologous to the genome of *Basfia succiniciproducens*, is contained from bases 1506-3005, while the 3' flanking region of the pflA-gene, which is homologous to the genome of *Basfia succiniciproducens*, is contained from bases 6-1505. The sacB-gene is contained from bases 5278-6699. The sacB-promoter is contained from bases 6700-7162. The chloramphenicol gene is contained from base 3424-3882. The origin of replication for *E. coli* (ori EC) is contained from base 4375-5235 (see FIG. 3).

In the plasmid sequence of pSacB_delta_pflD (SEQ ID NO: 8) the 5' flanking region of the pflD-gene, which is homologous to the genome of *Basfia succiniciproducens*, is contained from bases 1533-2955, while the 3' flanking region of the pflD-gene, which is homologous to the genome of *Basfia succiniciproducens*, is contained from bases 62-1532. The sacB-gene is contained from bases 5256-6677. The sacB-promoter is contained from bases 6678-7140. The chloramphenicol gene is contained from base 3402-3860. The origin of replication for *E. coli* (ori EC) is contained from base 4353-5213 (see FIG. 4).

Figure 5:
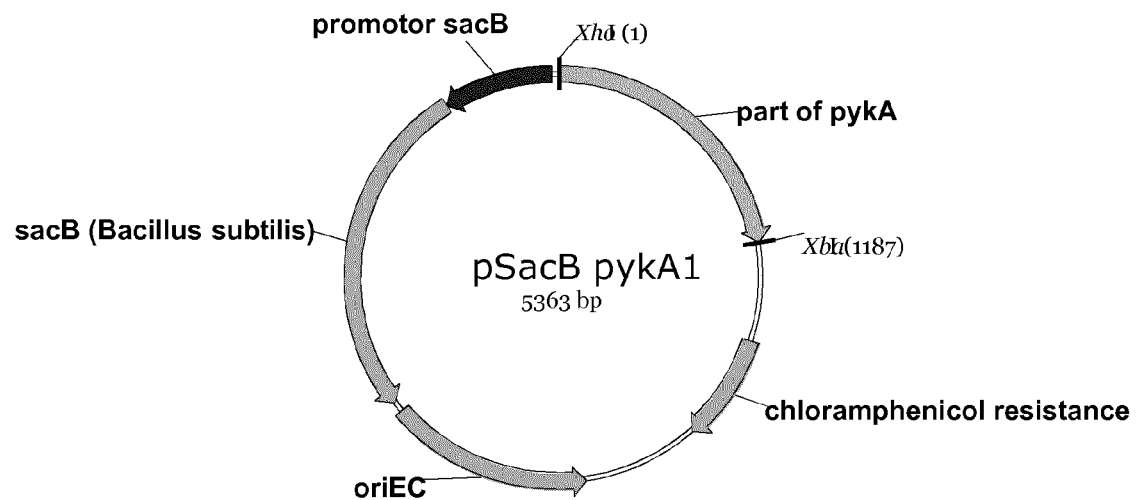
FIG. 5 shows a schematic map of plasmid pSacB pykA1 (SEQ ID NO: 9).

2. Generation of constructs used for introduction of point mutations into the pykA-gene In the plasmid sequence of pSacB_pykA1 (SEQ ID NO: 9) the part of the pykA-gene, which is homologous to the genome of *Basfia succiniciproducens*, is contained from bases 6-1185. The sacB-gene is contained from bases 3458-4879. The sacB-promoter is contained from bases 4880-5342. The chloramphenicol gene is contained from bases 1604-2062. The origin of replication for *E. coli* (ori EC) is contained from bases 2555-3415 (see FIG. 5).

Figure 6:
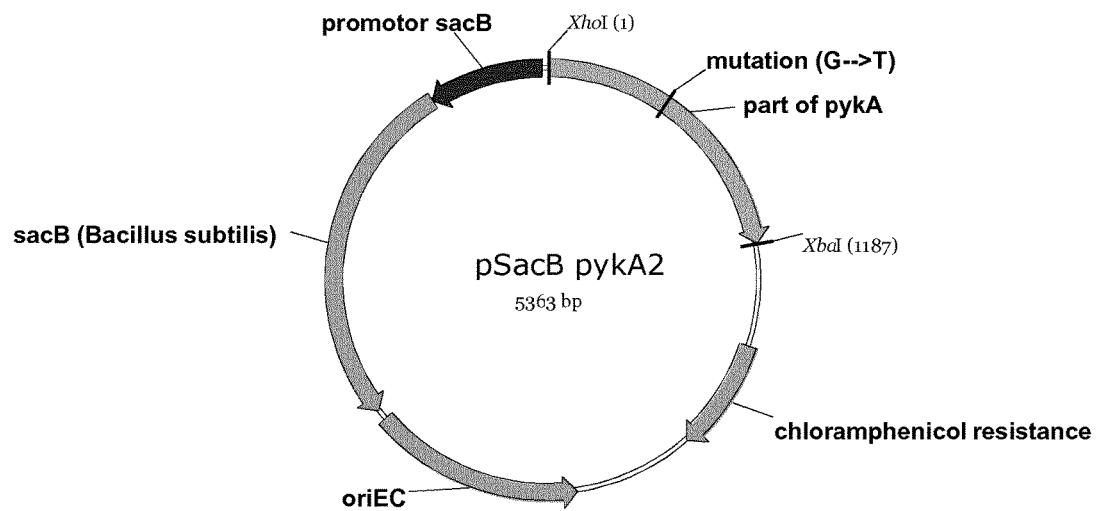
FIG. 6 shows a schematic map of plasmid pSacB pykA2 (SEQ ID NO: 10).

The plasmid pSacB_pykA2 was generated by site-directed mutagenesis from the pSac_pykA1 plasmid. The introduced G to T mutation in the pykA-gene will finally result in exchange of G (glycine) to C (cysteine) at position 167 in the PykA-protein (see FIG. 6). The nucleotide sequence of the pykA-gene in pSacB_pykA2 is shown in SEQ ID NO: 15, the amino acid sequence of the enzyme encoded by this gene in SEQ ID NO: 16.

Figure 7:
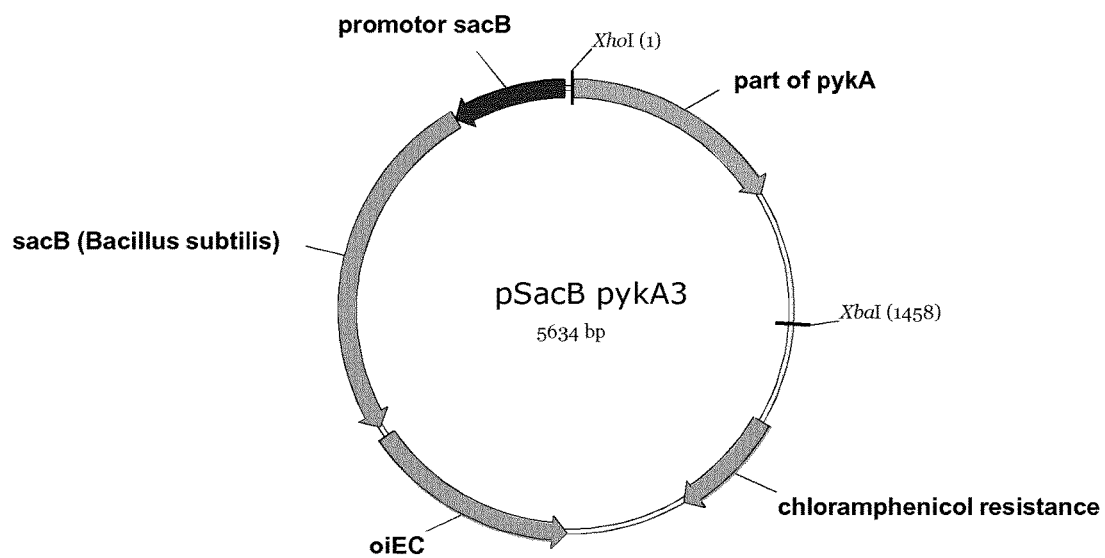
FIG. 7 shows a schematic map of plasmid pSacB pykA3 (SEQ ID NO: 11).

In the plasmid sequence of pSacB_delta_pykA2 (SEQ ID NO: 10) the part of the pykA-gene, which is homologous to the genome of *Basfia succiniciproducens*, is contained from bases 6-1185. The sacB-gene is contained from bases 3458-4879. The sacB-promoter is contained from bases 4880-5342. The chloramphenicol gene is contained from base 1604-2062. The origin of replication for *E. coli* (ori EC) is contained from base 2555-3415 (see FIG. 7).

Figure 8:
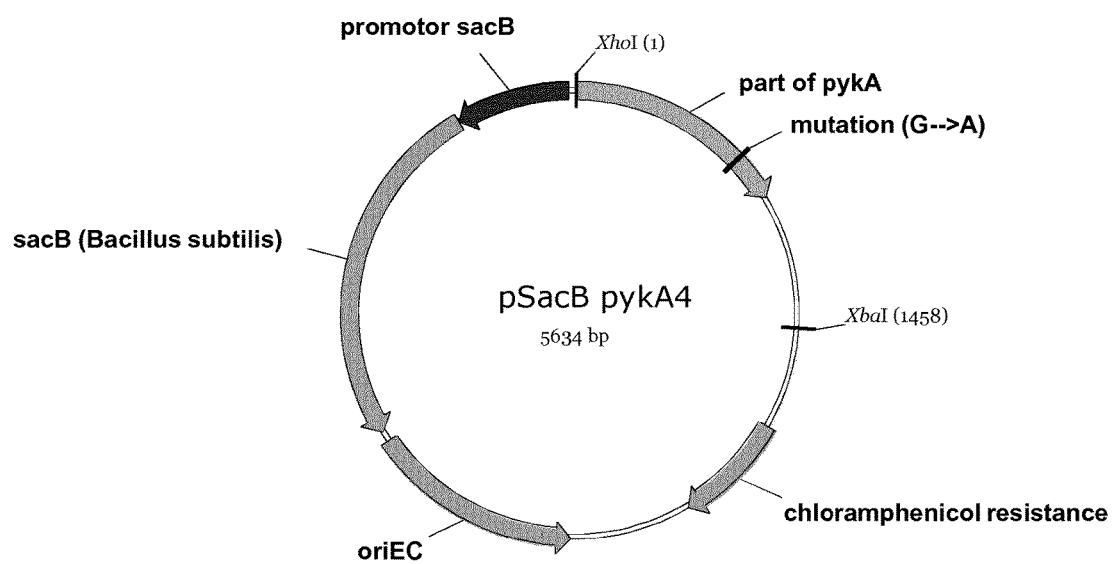
FIG. 8 shows a schematic map of plasmid pSacB pykA4 (SEQ ID NO: 12).

In the plasmid sequence of pSacB_pykA3 (SEQ ID NO: 11) the part of the pykA-gene, which is homologous to the genome of *Basfia succiniciproducens*, is contained from bases 6-909. The sacB-gene is contained from bases 3729-5150. The sacB-promoter is contained from bases 5151-5613. The chloramphenicol gene is contained from bases 1875-2333. The origin of replication for *E. coli* (ori EC) is contained from bases 2826-3686 (see FIG. 8).

Figure 9:
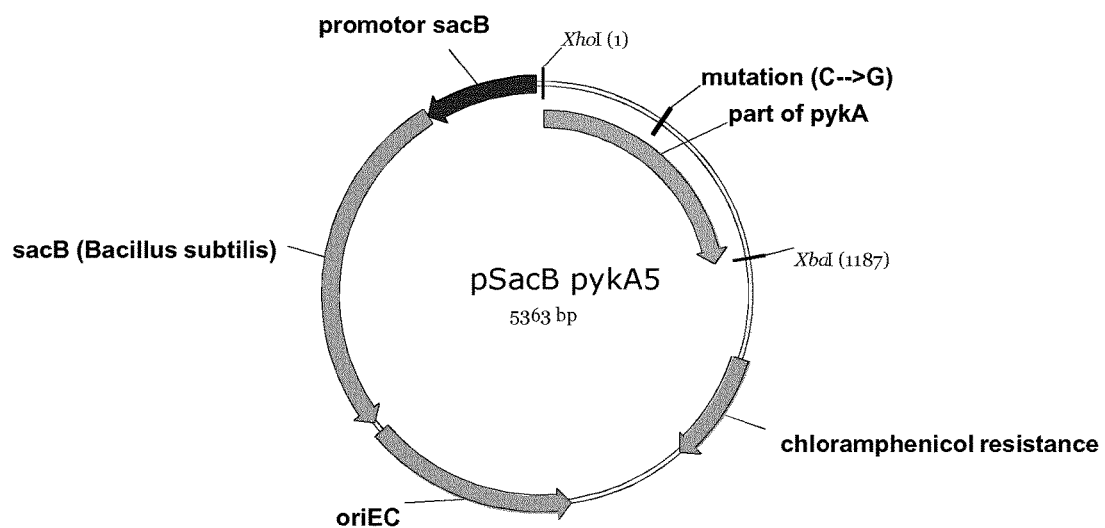
FIG. 9 shows a schematic map of plasmid pSacB pykA5 (SEQ ID NO: 13).

The plasmid pSacB_pykA4 was generated by site-directed mutagenesis from the pSac_pykA3 plasmid. The introduced G to A mutation in the pykA-gene will finally result in exchange of C (cysteine) to Y (tyrosine) at position 417 in the PykA-protein (see FIG. 8). The nucleotide sequence of the pykA-gene in pSacB_pykA4 is shown in SEQ ID NO: 17, the amino acid sequence of the enzyme encoded by this gene in SEQ ID NO: 18. In addition a DraI-restriction site was generated by silent mutation. This restriction site will help to identify correct transformants. In the plasmid sequence of pSacB_delta_pykA4 (SEQ ID NO: 19) the part of the pykA-gene, which is homologous to the genome of *Basfia succiniciproducens*, is contained from bases 6-909. The sacB-gene is contained from bases 3729-5150. The sacB-promoter is contained from bases 5151-5613. The chloramphenicol gene is contained from bases 1875-2333. The origin of replication for *E. coli* (ori EC) is contained from bases 2826-3686 (see FIG. 9).

The plasmid pSacB_pykA5 was generated by site-directed mutagenesis from the pSac_pykA1-plasmid. The introduced C to G mutation in the pykA-gene will finally result in exchange of A (alanine) to G (glycine) at position 171 in the PykA-protein (see FIG. 9). The nucleotide sequence of the pykA-gene in pSacB_pykA5 is shown in SEQ ID NO: 19, the amino acid sequence of the enzyme encoded by this gene in SEQ ID NO: 20. In addition a HpaI-restriction site was generated by silent mutation. This restriction site will help to identify correct transformants. In the plasmid sequence of pSacB_pykA5 (SEQ ID NO: 13) the part of the pykA-gene, which is homologous to the genome of *Basfia succiniciproducens*, is contained from bases 6-1185. The sacB-gene is contained from bases 3458-4879. The sacB-promoter is contained from bases 4880-5342. The chloramphenicol gene is contained from bases 1604-2062. The origin of replication for *E. coli* (ori EC) is contained from bases 2555-3415.

Figure 10:
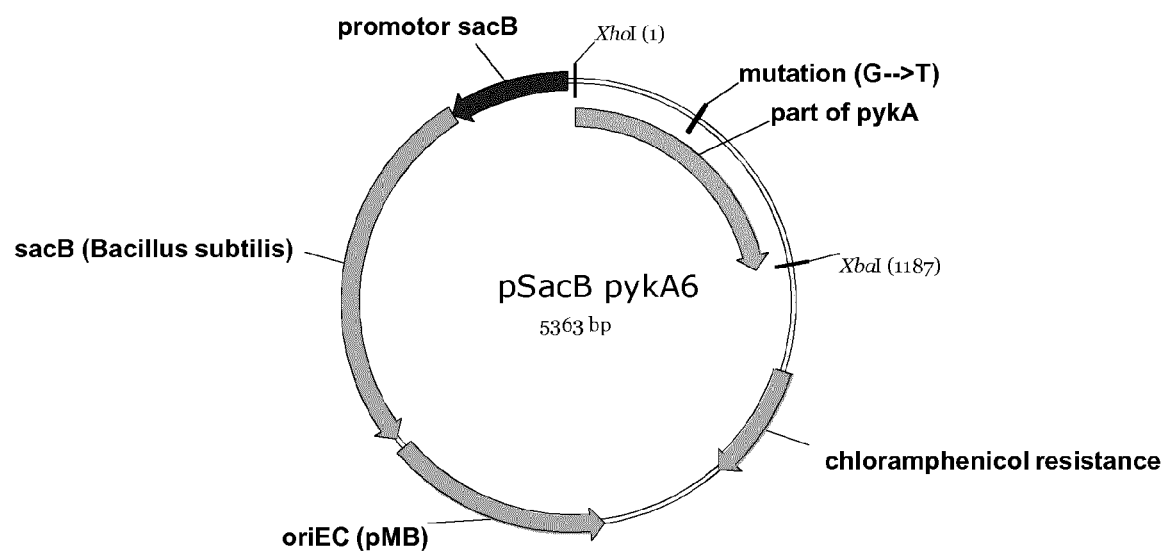
FIG. 10 shows a schematic map of plasmid pSacB pykA6 (SEQ ID NO: 14).

The plasmid pSacB_pykA6 was generated by site-directed mutagenesis from the pSac_pykA1 plasmid. The introduced G to T mutation in the pykA-gene will finally result in exchange of G (glycine) to C (cysteine) at position 167 in the PykA-protein (see FIG. 10). The nucleotide sequence of the pykA-gene in pSacB_pykA6 is shown in SEQ ID NO: 21, the amino acid sequence of the enzyme encoded by this gene in SEQ ID NO: 22. In addition a HpaI-restriction site was generated by silent mutation. This restriction site will help to identify correct transformants. In the plasmid sequence of pSacB_pykA6 (SEQ ID NO: 14) the part of the pykA-gene, which is homologous to the genome of *Basfia succiniciproducens*, is contained from bases 6-1185. The sacB-gene is contained from bases 3458-4879. The sacB-promoter is contained from bases 4880-5342. The chloramphenicol gene is contained from bases 1604-2062. The origin of replication for *E. coli* (ori EC) is contained from bases 2555-3415.

Example 3

Generation of Improved Succinate Producing Strains

1. Generation of Deletion Mutants
   a) *Basfia succiniciproducens* DD1 was transformed as described above with the pSacB_delta_IdhA and "Campbelled in" to yield a "Campbell in" strain. Transformation and integration into the genome of *Basfia succiniciproducens* was confirmed by PCR yielding bands for the integration event of the plasmid into the genome of *Basfia succiniciproducens*.
   The "Campbell in" strain was then "Campbelled out" using agar plates containing sucrose as a counter selection medium, selecting for the loss (of function) of the sacB-gene. Therefore, the "Campbell in" strains were incubated in 25-35 ml of non selective medium (BHI containing no antibiotic) at 37° C., 220 rpm over night. The overnight culture was then streaked onto freshly prepared BHI containing sucrose plates (10%, no antibiotics) and incubated overnight at 37° C. ("first sucrose transfer"). Single colony obtained from first transfer were again streaked onto freshly prepared BHI containing sucrose plates (10%) and incubated overnight at 37° C. ("second sucrose transfer"). This procedure was repeated until a minimal completion of five transfers ("third, forth, fifth sucrose transfer") in sucrose. The term "first to fifth sucrose transfer" refers to the transfer of a strain after chromosomal integration of a vector containing a sacB-levan-sucrase gene onto sucrose and growth medium containing agar plates for the purpose of selecting for strains with the loss of the sacB-gene and the surrounding plasmid sequences. Single colony from the fifth transfer plates were inoculated onto 25-35 ml of non selective medium (BHI containing no antibiotic) and incubated at 37° C., 220 rpm over night. The overnight culture was serially diluted and plated onto BHI plates to obtain isolated single colonies.
   The "Campbelled out" strains containing either the wild-type situation of the IdhAlocus or the mutation/deletion of the IdhA-gene were confirmed by chloramphenicol sensitivity. The mutation/deletion mutants among these strains were identified and confirmed by PCR analysis. This led to the IdhA-deletion mutant *Basfia succiniciproducens* DD1 LIdhA.
   b) *Basfia succiniciproducens* DD1 ΔIdhA was transformed with pSacB_delta_pflA as described above and "Campbelled in" to yield a "Campbell in" strain. Transformation and integration was confirmed by PCR. The "Campbell in" strain was then "Campbelled out" as described previously. The deletion mutants among these strains were identified and confirmed by PCR analysis. This led to the IdhA pflD-double deletion mutant *Basfia succiniciproducens* DD1 ΔIdhA ΔpflA.
   c) *Basfia succiniciproducens* ΔIdhA was transformed with pSacB_delta_pflD as described above and "Campbelled in" to yield a "Campbell in" strain. Transformation and integration was confirmed by PCR. The "Campbell in" strain was then "Campbelled out" as described previously. The deletion mutants among these strains were identified and confirmed by PCR analysis. This led to the IdhA pflD-double deletion mutant *Basfia succiniciproducens* DD1 ΔIdhA ΔpflD.

2. Generation of Mutants Carrying Point Mutations in the pykA-gene
   a) *Basfia succiniciproducens* DD1 ΔIdhA ΔpflA was transformed with pSacB_pykA2 as described above and "Campbelled in" to yield a "Campbell in" strain. The "Campbell in" strain was then "Campbelled out" as described previously. The pykA-coding region was amplified by means of PCR and sequenced to identify the "Campbell out" clones carrying a mutation within the pykA-gene. This led to the mutant *Basfia succiniciproducens* DD1 ΔIdhA ΔpflA pykA2.
   b) *Basfia succiniciproducens* DD1 ΔIdhA ΔpflD was transformed with pSacB_pykA4 as described above and "Campbelled in" to yield a "Campbell in" strain. The "Campbell in" strain was then "Campbelled out" as described previously. To identify the "Campbell out" clones carrying a mutation within the pykA-gene a part of the pykA-locus was amplified by means of PCR with primers pykA4_fw (SEQ ID NO: 23) and pykA4_ry (SEQ ID NO: 24). In the pre-screen resulted DNA fragment was digested with DraI restriction enzyme. Fragments which showed the additional DraI-restriction site were sequenced to confirm the expected point mutation close to the introduced DraI-restriction site within the pykA-gene. This led to the mutant *Basfia succiniciproducens* DD1 ΔIdhA ΔpflD pykA4.
   c) *Basfia succiniciproducens* ΔIdhA ΔpflD was transformed with pSacB_pykA5 as described above and "Campbelled in" to yield a "Campbell in" strain. The "Campbell in" strain was then "Campbelled out" as described previously. To identify the "Campbell out" clones carrying a mutation within the pykA-gene a part of the pykA-locus was amplified by means of PCR with primers pykA5/6_fw (SEQ ID NO: 25) and pykA5/6_rv (SEQ ID NO: 26). In the pre-screen resulted DNA fragment was digested with HpaI-restriction enzyme. Fragments which showed the additional HpaI-restriction site were sequenced to confirm the expected point mutation close to the introduced HpaI-restriction site within the pykA-gene. This led to the mutant *Basfia succiniciproducens* DD1 ΔIdhA ΔpflD pykA5.
   d) *Basfia succiniciproducens* ΔIdhA ΔpflD was transformed with pSacB_pykA6 as described above and "Campbelled in" to yield a "Campbell in" strain. The "Campbell in" strain was then "Campbelled out" as described previously. To identify the "Campbell out" clones carrying a mutation within the pykA-gene a part of the pykA-locus was amplified by means of PCR with primers pykA5/6_fw (SEQ ID NO: 25) and pykA5/6 ry (SEQ ID NO: 26). In the pre-screen resulted DNA fragment was digested with HpaI-restriction enzyme. Fragments which showed the additional HpaI-restriction site were sequenced to confirm the expected point mutation close to the introduced HpaI-restriction site within the pykA-gene. This led to the mutant *Basfia succiniciproducens* DD1 ΔldhA ΔpflD pykA6.

Example 4

Pyruvate Kinase Activity

*Basfia* strains were grown anaerobically in serum bottles in the medium as follows (BHI Medium (Becton Dickinson, containing the following additions MOPS: 9.4 g/l, Mg(OH)$_2$: 0.625 g/l, BISTRIS: 5.8 g/l, NaHCO$_3$: 1.8 g/l) for 18h at 37° C. Cells were harvested by centrifugation and frozen. Pellets of cells were resuspended in 60 mM HEPES-Na, 60 mM KCl, 8.5 mM MgCl$_2$ pH 7.5. Cells were lysed using the Ribolyser (ThermoHybaid) machine and blue matrix tubes. Extracts were centrifuged for 10 minutes at 14000 rpm in an eppedorf centrifufge at 4° C. and kept on ice until the assay was performed. Supernatants were used to assay pyruvate kinase activity using the following assay: Enzyme activity of PykA was determined according to the *Methods of Enzymatic Analysis*, 2nd English ed., Vol. 1, Bergmeyer, H. U., ed., Academic Press (New York, N.Y.: 1974), pp. 509-511. Protein concentrations in cell extracts were determined by the Biorad protein blue assay using IgG as the protein standard for calibration. Enzyme activities are expressed as specific activities (U/mg of protein and min) and relatively as in percent of the activity of the strain DD1 ΔldhA ΔpflD carrying an unmutated pykA-allele. The results are shown in table 2.

TABLE 2

Results of the PykA-enzyme activity test

| Strain | Specific activity [mU/mg protein] | Δ$_{activity}$ [%] |
|---|---|---|
| DD1 ΔldhA ΔpflD | 32.4 | 0 |
| DD1 ΔldhA ΔpflA pykA2 | 2.25 | 93.1 |
| DD1 ΔldhA ΔpflD pykA4 | 2.40 | 92.7 |
| DD1 ΔldhA ΔpflD pykA5 | 9.70 | 90.3 |

Example 5

Cultivation of Various DD1-Strains on Glucose, Sucrose and Maltose/Glycerol

The productivity of the DD1 ΔldhA ΔpflA strain was compared with the productivity of the mutant strain DD1 ΔldhA ΔpflA pykA2 in the presence of glucose, or sucrose, or maltose and glycerol as a carbon source (table 6, 7 and 8).

Productivity was analyzed utilizing media and incubation conditions described below.

1. Medium Preparation

The composition and preparation of the cultivation medium is as described in the following table 3, 4 and 5.

TABLE 3

Medium composition for cultivation on glucose (medium P)

| Compound | Concentration [g/L] |
|---|---|
| Yeast extract (Bio Springer) | 10.0 |
| CaCl$_2$ × 2H$_2$O | 0.2 |
| MgCl$_2$ × 6H$_2$O | 0.2 |

TABLE 3-continued

Medium composition for cultivation on glucose (medium P)

| Compound | Concentration [g/L] |
|---|---|
| (NH$_4$)$_2$SO$_4$ | 2.0 |
| NaCl | 1.0 |
| K$_2$HPO$_4$ | 3.0 |
| MgCO$_3$ | 50.0 |
| NaHCO$_3$ | 8.4 |
| glucose | 52.0 |

TABLE 4

Medium composition for cultivation on sucrose (medium P)

| Compound | Concentration [g/L] |
|---|---|
| Yeast extract (Bio Springer) | 10.0 |
| CaCl$_2$ × 2H$_2$O | 0.2 |
| MgCl$_2$ × 6H$_2$O | 0.2 |
| (NH$_4$)$_2$SO$_4$ | 2.0 |
| NaCl | 1.0 |
| K$_2$HPO$_4$ | 3.0 |
| MgCO$_3$ | 50.0 |
| NaHCO$_3$ | 8.4 |
| sucrose | 50.0 |

TABLE 5

Medium composition for cultivation on maltose/glycerol (medium P)

| Compound | Concentration [g/L] |
|---|---|
| Yeast extract (Bio Springer) | 10.0 |
| CaCl$_2$ × 2H$_2$O | 0.2 |
| MgCl$_2$ × 6H$_2$O | 0.2 |
| (NH$_4$)$_2$SO$_4$ | 2.0 |
| NaCl | 1.0 |
| K$_2$HPO$_4$ | 3.0 |
| MgCO$_3$ | 70.0 |
| NaHCO$_3$ | 8.4 |
| maltose | 22.5 |
| glycerol | 50.0 |

2. Cultivations and Analytics

For growing the main culture bacteria from a freshly grown BHI-agar plate (incubated overnight at 37° C. under anaerobic conditions) was used to inoculate to OD600=0.75 a 100 ml-serum bottle with gas tight butyl rubber stopper containing 50 ml of the liquid medium described in table 3, 4 and 5 with a 002-atmosphere with 0.8 bar overpressure. The bottles were incubated at 37° C. and 160 rpm (shaking diameter: 2.5 cm). Consumption of the C-sources and production of carboxylic acids was quantified via HPLC (HPLC methods are described in tables 9 and 10) after 24h. Cell growth was measured by measuring the absorbance at 600 nm (OD600) using a spectrophotometer (Ultrospec3000, Amersham Biosciences, Uppsala Sweden).

3. Results

The results of the cultivation experiments with for different DD1-strains are shown in tables 6 to 8.

TABLE 6

Cultivation of the DD1 ΔldhA ΔpflA-strain and the DD1 ΔldhA ΔpflA ΔpykA2-strain on glucose

|  | DD1 ΔldhAΔpflA | DD1 ΔldhA ΔpflA pykA2 |
|---|---|---|
| substrate | glucose | glucose |
| tc [h]$^a$ | 24 | 24 |
| ΔC [g/l]$^b$ | 54.00 | 54.00 |
| ΔC$_{SA}$[g/l]$^c$ (succinic acid) | 35.27 | 38.08 |
| ΔC$_{LA}$ [g/L]$^{c,h}$ (lactic acid) | 0.21 | 0.32 |
| ΔC$^{FA}$[g/l]$^{c,h}$ (formic acid) | 0.00 | 0.00 |
| ΔC$_{AA}$[g/l]$^{c,h}$ (acetic acid) | 1.10 | 2.30 |
| ΔC$_{PA}$[g/l]$^{c,h}$ (pyruvic acid) | 2.76 | 2.43 |
| ΔC$_P$[g/l]$^{c,h}$ (propionic acid) | 0.00 | 0.00 |
| ΔC$_E$[g/l]$^c$ (ethanol) | 0.00 | 0.00 |
| Carbon Yield (YP/S) [g/g] | 0.73 | 0.80 |
| SA Yield (SA/S) [g/g]$^g$ | 0.65 | 0.71 |

$^a$cultivation time
$^b$consumption of substrate (glucose)
$^c$formation of succinic acid, lactic acid, formic acid, acetic acid, pyruvic acid and ethanol
$^g$SA yield (ration of SA per consumed substrate)
$^h$detection limits for acetic acid, lactic acid, malic acid, and formic acid were found to be lower than 0.01 g/l in the given HPLC method

TABLE 7

Cultivation of the DD1 ΔldhA ΔpflA-strain and the DD1 ΔldhA, ΔpflA ΔpykA2-strain on sucrose

|  | DD1 ΔldhA ΔpflA | DD1 ΔldhA ΔpflA pykA2 |
|---|---|---|
| substrate | sucrose | sucrose |
| tc [h]$^a$ | 16 | 16 |
| ΔC [g/l]$^b$ | 18.55 | 50.90 |
| ΔC$_{SA}$[g/l]$^c$ (succinic acid) | 10.51 | 32.98 |

$^a$cultivation time
$^b$consumption of substrate (sucrose)
$^c$formation of succinic acid A reduction of the activity of the enzyme encoded by the pykA-gene leads to a faster growth of the cells on sucrose. This gets evident when comparing the values for the sucrose consumption in table 7: within 16 h the DD1 ΔldhA ΔpflA-strain consumed 18.55 g/L of sucrose; during the same time (also 16 h) the DD1 ΔldhA ΔpflA ΔpykA2-strain consumed already 50.90 g/L of sucrose.

TABLE 8

Cultivation of the DD1 ΔldhA ΔpflA-strain and the DD1 ΔldhA ΔpflA ΔpykA2-strain on maltose/glycerol

|  | DD1 ΔldhA ΔpflA | DD1 ΔldhA ΔpflA pykA2 |
|---|---|---|
| substrate | maltose/glycerol | maltose/glycerol |
| tc [h]$^a$ | 16 | 16 |
| ΔC [g/l]$^b$ | 7.50 (maltose) 41.76 (glycerol) | 9.92 (maltose) 53.39 (glycerol) |
| ΔC$_{SA}$[g/l]$^c$ (succinic acid) | 52.58 | 66.04 |

$^a$cultivation time
$^b$consumption of substrate (maltose and glycerol)
$^c$formation of succinic acid

TABLE 9

HPLC method (ZX-THF50) for analysis of glucose, maltose, glycerol, succinic acid, formic acid, lactic acid, acetic acid, pyruvic acid and ethanol

| HPLC column | Aminex HPX-87 H, 300 × 7.8 mm (BioRad) |
|---|---|
| Precolumn | Cation H |
| Temperature | 50° C. |
| Eluent flow rate | 0.50 ml/min |
| Injection volume | 5.0 μl |
| Diode array detector | RI-Detector |
| Runtime | 28 min |
| max. pressure | 140 bar |
| Eluent A | 5 mM $H_2SO_4$ |
| Eluent B | 5 mM $H_2SO_4$ |

| | Time [min] | A [%] | B [%] | Flow [ml/min] |
|---|---|---|---|---|
| Gradient | 0.0 | 50 | 50 | 0.50 |
|  | 28.0 | 50 | 50 | 0.50 |

TABLE 10

HPLC method (Fast-CH) for analysis of glucose and sucrose

| HPLC column | Fast Carbohydrate, 100 × 7.8 mm (Biorad) |
|---|---|
| Precolumn | Deashing Refill Cartridges (30° C.) |
| Temperature | 75° C. |
| Eluent flow rate | 1.00 ml/min |
| Injection volume | 1.0 μl |
| Diode array detector | RI-Detector |
| Runtime | 8 min |
| max. pressure | 150 bar |
| Eluent A | water |
| Eluent B | water |

| | Time [min] | A [%] | B [%] | Flow [ml/min] |
|---|---|---|---|---|
| Gradient | 0.0 | 50 | 50 | 1.00 |
|  | 8.0 | 50 | 50 | 1.00 |

Example 6

Cultivation of DD1 ΔldhA ΔpflD pykA4 in the Presence of Glucose, or Sucrose, or Glycerol and Glucose The productivity of the DD1 ΔldhA ΔpflD strain was compared with the productivity of the mutant strain DD1 ΔldhA ΔpflD pykA4 in the presence of glucose, or sucrose, or glucose and glycerol as a carbon source.

Productivity was analyzed utilizing media and incubation conditions described below.

1. Medium Preparation

The composition and preparation of the cultivation medium CGM is as described in the following table 11.

TABLE 11

The composition of the cultivation medium CGM.
Medium CGM

| Compound | Concentration [g/L] |
|---|---|
| Yeast extract (Bio Springer) | 12.5 |
| Succinic acid | 2.5 |
| $(NH_4)_2SO_4$ | 0.5 |
| $KH_2PO_4$ | 1.0 |
| $MgCO_3$ | 50.0 |
| $Na_2CO_3$ | 2.0 |
| Glucose | 52 |

The composition of the cultivation medium LSM_3_glucose, medium LSM_3_sucrose, and medium LSM_3_glycerol_glucose is as described in the following table 14, 15 and 16.

TABLE 12

Composition of trace element solution 5.
Trace element solution 5

| Compound | Final conc. |
|---|---|
| citric acid | 10 g/L |
| $ZnSO_4 \times 7H_2O$ | 1851 mg/L |
| $CaSO_4 \times 2H_2O$ | 10 mg/L |
| $FeSO_4 \times 7H_2O$ | 2040 mg/L |
| $CaCl_2 \times 2H_2O$ | 12460 mg/L |
| $MnCl_2 \times 4H_2O$ | 1200 mg/L |
| $Na_2MoO_4 \times 2H_2O$ | 38 mg/L |
| $CuCl_2 \times 2H_2O$ | 188 mg/L |
| $NiCl_2 \times 6H_2O$ | 32 mg/L |
| $CoCl_2 \times 6H_2O$ | 101 mg/L |

TABLE 13

Composition of vitamin solution_9.
Vitamin solution 9

| Compound | Final conc. |
|---|---|
| Thiamin HCl (B1) | 1.0 g/L |
| Nicotinic acid (B3) | 1.0 g/L |
| Riboflavin (B2) | 20 mg/L |
| Biotin (B7) | 50 mg/L |
| Pantothenic acid (B5) | 1.0 g/L |
| Pyridoxine (B6) | 1.0 g/L |
| Cyanocobalamin (B12) | 50 mg/L |
| Lipoic acid | 5 mg/L |

TABLE 14

Composition of LSM_3_glucose medium.
Medium LSM_3_glucose

| Compound | Volume/Mass | Stock conc. | Final conc. |
|---|---|---|---|
| Medium 1 | | | |
| $MgCO_3$ | 2.5 g | 100% | 50.00 g/L |
| Water | 38.45 mL | — | — |
| Medium 2 | | | |
| Succinic acid | 2.5 mL | 50 g/L | 2.50 g/L |
| Glucose | 4.00 mL | 650 g/L | 52.00 g/L |
| $(NH_4)_2SO_4$ | 0.5 mL | 500 g/L | 5.00 g/L |
| Betain | 0.5 mL | 23 g/L | 0.23 g/L |
| $KH_2PO_4$ | 0.50 mL | 100 g/L | 1.00 g/L |
| $Na_2CO_3$ | 0.50 mL | 200 g/L | 2.00 g/L |
| vitamin solution 9 (conc. 100x) | 0.50 mL | 4 g/L | 0.04 g/L |
| trace element solution 5 | 0.05 mL | 21 g/L | 0.02 g/L |

TABLE 15

Composition of LSM_3_sucrose medium.
Medium LSM_3_sucrose

| Compound | Volume/Mass | Stock conc. | Final conc. |
|---|---|---|---|
| Medium 1 | | | |
| $MgCO_3$ | 2.5 g | 100% | 50.00 g/L |
| Water | 38.45 mL | — | — |

TABLE 15-continued

Composition of LSM_3_sucrose medium.
Medium LSM_3_sucrose

| Compound | Volume/Mass | Stock conc. | Final conc. |
|---|---|---|---|
| Medium 2 | | | |
| Succinic acid | 2.5 mL | 50 g/L | 2.50 g/L |
| Sucrose | 4.00 mL | 650 g/L | 52.00 g/L |
| $(NH_4)_2SO_4$ | 0.5 mL | 500 g/L | 5.00 g/L |
| Betain | 0.5 mL | 23 g/L | 0.23 g/L |
| $KH_2PO_4$ | 0.50 mL | 100 g/L | 1.00 g/L |
| $Na_2CO_3$ | 0.50 mL | 200 g/L | 2.00 g/L |
| vitamin solution 9 (conc. 100x) | 0.50 mL | 4 g/L | 0.04 g/L |
| trace element solution 5 | 0.05 mL | 21 g/L | 0.02 g/L |

TABLE 16

Composition of LSM_3_glycerol_glucose medium.
Medium LSM_3_glycerol_glucose

| Compound | Volume/Mass | Stock conc. | Final conc. |
|---|---|---|---|
| Medium 1 | | | |
| $MgCO_3$ | 2.5 g | 100% | 50.00 g/L |
| Water | 37.87 mL | — | — |
| Medium 2 | | | |
| Succinic acid | 2.5 mL | 50 g/L | 2.50 g/L |
| Glucose | 3.08 mL | 650 g/L | 40.00 g/L |
| Glycerol | 1.50 mL | 500 g/L | 15.00 g/L |
| $(NH_4)_2SO_4$ | 0.5 mL | 500 g/L | 5.00 g/L |
| Betain | 0.5 mL | 23 g/L | 0.23 g/L |
| $KH_2PO_4$ | 0.50 mL | 100 g/L | 1.00 g/L |
| $Na_2CO_3$ | 0.50 mL | 200 g/L | 2.00 g/L |
| vitamin solution 9 (conc. 100x) | 0.50 mL | 4 g/L | 0.04 g/L |
| trace element solution 5 | 0.05 mL | 21 g/L | 0.02 g/L |

2. Cultivations and Analytics

For growing the pre-culture bacteria from a freshly grown BHI-agar plate (incubated overnight at 37° C. under anaerobic conditions) was used to inoculate a 100 ml-serum bottle with gas tight butyl rubber stopper containing 50 ml of the CGM liquid medium described in table 11 with a $CO_2$-atmosphere. The bottles were incubated at 37° C. and 170 rpm (shaking diameter: 2.5 cm). For growing the main culture 2.5 ml of the bacterial culture in the CGM medium (after 10 hours of incubation) was used to inoculate a 100 ml-serum bottle with gas tight butyl rubber stopper containing 50 ml of the LSM_glucose liquid medium (or the LSM_3_sucrose medium, or the LSM_3_glycerol_glucose medium) described in table 14 (LSM_3_sucrose medium: Table 15, LSM_3_glycerol_glucose medium: Table 16) with a 002-atmosphere. Consumption of C-source and production of carboxylic acids was quantified via HPLC (HPLC methods are described in tables 9 and 10) after 6h and 30h. Cell growth was measured by measuring the absorbance at 600 nm (OD600) using a spectrophotometer (Ultrospec3000, Amersham Biosciences, Uppsala Sweden).

3. Results

The results of the cultivation experiments with the DD1 ΔldhA ΔpflD pykA4 strain on glucose, sucrose and maltose/glycerol are shown in tables 17, 18 and 19.

TABLE 17

Cultivation of the DD1 ΔldhA ΔpflD strain, and the DD1 ΔldhA ΔpflD pykA4 strain on glucose.

|  | DD1 ΔldhA ΔpflD | DD1 ΔldhA ΔpflD pykA4 | DD1 ΔldhA ΔpflD | DD1 ΔldhA ΔpflD pykA4 |
| --- | --- | --- | --- | --- |
| substrate | glucose | glucose | glucose | glucose |
| tc [h]$^a$ | 6 h | 6 h | 30 h | 30 h |
| ΔC [g/L]$^b$ | 25.2 | 28.5 | 51.6 | 51.6 |
| ΔC [g/L]$^c$ (succinic acid) | 19.2 | 20.5 | 38.3 | 38.2 |
| ΔC [g/L]$^c$ (lactic acid) | 0.1 | 0.1 | 0.4 | 0.3 |
| ΔC [g/L]$^c$ (formic acid) | 0.0 | 0.0 | 0.0 | 0.0 |
| ΔC [g/L]$^c$ (acetic acid) | 0.8 | 1.1 | 2.6 | 3.1 |
| ΔC [g/L]$^c$ (pyruvic acid) | 2.1 | 2.1 | 1.3 | 0.5 |

$^a$cultivation time
$^b$consumption of substrate (glucose)
$^c$formation of succinic acid, lactic acid, formic acid, acetic acid, pyruvic acid

TABLE 18

Cultivation of the DD1 ΔldhA ΔpflD strain, and the DD1 ΔldhA ΔpflD pykA4 strain on sucrose.

|  | DD1 ΔldhA ΔpflD | DD1 ΔldhA ΔpflD pykA4 | DD1 ΔldhA ΔpflD | DD1 ΔldhA ΔpflD pykA4 |
| --- | --- | --- | --- | --- |
| substrate | sucrose | sucrose | sucrose | sucrose |
| tc [h]$^a$ | 6 h | 6 h | 30 h | 30 h |
| ΔC [g/L]$^b$ | 13.9 | 34.7 | 32.4 | 50.5 |
| ΔC [g/L]$^c$ (succinic acid) | 10.6 | 25.4 | 19.3 | 37.4 |
| ΔC [g/L]$^c$ (lactic acid) | 0.1 | 0.1 | 0.3 | 0.4 |
| ΔC [g/L]$^c$ (formic acid) | 0.0 | 0.0 | 0.0 | 0.0 |
| ΔC [g/L]$^c$ (acetic acid) | 0.1 | 0.1 | 0.4 | 2.0 |
| ΔC [g/L]$^c$ (pyruvic acid) | 0.0 | 0.0 | 0.0 | 2.2 |

$^a$cultivation time
$^b$consumption of substrate (sucrose)
$^c$formation of succinic acid, lactic acid, formic acid, acetic acid, pyruvic acid

TABLE 19

Cultivation of the DD1 ΔldhA ΔpflD strain, and the DD1 ΔldhA ΔpflD pykA4 strain on glycerol and glucose.

|  | DD1 ΔldhA ΔpflD | DD1 ΔldhA ΔpflD pykA4 | DD1 ΔldhA ΔpflD | DD1 ΔldhA ΔpflD pykA4 |
| --- | --- | --- | --- | --- |
| substrate | glycerol/ glucose | glycerol/ glucose | glycerol/ glucose | glycerol/ glucose |
| tc [h]$^a$ | 6 h | 6 h | 30 h | 30 h |
| ΔC [g/L]$^b$ (glycerol) | 9.8 | 1.6 | 16.0 | 16.0 |
| ΔC [g/L]$^b$ (glucose) | 23.9 | 25.9 | 37.1 | 37.1 |
| ΔC [g/L]$^c$ (succinic acid) | 28.8 | 31.6 | 46.3 | 47.5 |
| ΔC [g/L]$^c$ (lactic acid) | 0.1 | 0.1 | 0.3 | 0.3 |
| ΔC [g/L]$^c$ (formic acid) | 0.0 | 0.0 | 0.0 | 0.0 |
| ΔC [g/L]$^c$ (acetic acid) | 0.5 | 0.8 | 1.9 | 2.1 |
| ΔC [g/L]$^c$ (pyruvic acid) | 2.0 | 1.7 | 0.6 | 0.2 |

$^a$cultivation time
$^b$consumption of substrate (glycerol, glucose)
$^c$formation of succinic acid, lactic acid, formic acid, acetic acid, pyruvic acid A reduction of the activity of the enzyme encoded by the pykA-gene leads to a faster growth of the cells on glucose, sucrose, and also glycerol/glucose mix. This gets evident when comparing the DD1 ΔldhA ΔpflD strain with the DD1 ΔldhA ΔpflD pykA4 strain growing on glucose (Table 17), on sucrose (Table 18), and on glycerol/glucose (Table 19).

```
SEQUENCES
SEQ ID NO: 1 (nucleotide sequence of 16S rDNA of strain DD1)
tttgatcctggctcagattgaacgctggcggcaggcttaacacatgcaagtcgaacggtagcgggaggaaagcttgctttctttgccga cgagtggcggacgggtgagtaatgcttggggatctggcttatggaggggataacgacgggaaactgtcgctaataccgcgtaatat
```

-continued cttcggattaaagggtgggactttcgggccacccgccataagatgagcccaagtgggattaggtagttggtggggtaaaggcctacc aagccgacgatctctagctggtctgagaggatgaccagccacactggaactgagacacggtccagactcctacgggaggcagca gtggggaatattgcacaatggggggaaccctgatgcagccatgccgcgtgaatgaagaaggccttcgggttgtaaagttctttcggtg acgaggaaggtgtttgttttaataggacaagcaattgacgttaatcacagaagaagcaccggctaactccgtgccagcagccgcggt aatacggagggtgcgagcgttaatcggaataactgggcgtaaagggcatgcaggcggacttttaagtgagatgtgaaagccccgg gcttaacctgggaattgcatttcagactgggagtctagagtactttagggaggggtagaattccacgtgtagcggtgaaatgcgtagag atgtggaggaataccgaaggcgaaggcagccccttgggaagatactgacgctcatatgcgaaagcgtggggagcaaacaggatt agataccctggtagtccacgcggtaaacgctgtcgatttgggattgggctttaggcctggtgctcgtagctaacgtgataaatcgacc gcctgggagtacggccgcaaggttaaaactcaaatgaattgacggggccccgcacaagcggtggagcatgtggtttaattcgatg caacgcgaagaaccttacctactcttgacatccagagaatcctgtagagatacgggagtgccttcgggagctctgagacaggtgctg catggctgtcgtcagctcgtgttgtgaaatgttgggttaagtcccgcaacgagcgcaacccttatcctttgttgccagcatgtaaagatgg gaactcaaaggagactgccggtgacaaaccggaggaaggtggggatgacgtcaagtcatcatggcccttacgagtagggctaca cacgtgctacaatggtgcatacagagggcggcgataccgcgaggtagagcgaatctcagaaagtgcatcgtagtccggattggagt ctgcaactcgactccatgaagtcggaatcgctagtaatcgcaaatcagaatgttgcggtgaatacgttcccgggccttgtacacaccg cccgtcacaccatgggagtgggttgtaccagaagtagatagcttaaccttcgggggggcgtttaccacggtatgattcatgactggg gtgaagtcgtaacaaggtaaccgtaggggaacctgcgg SEQ ID NO: 2 (nucleotide sequence of 23S rDNA of strain DD1)
agtaataacgaacgacacaggtataagaatacttgaggttgtatggttaagtgactaagcgtacaaggtggatgccttggcaatcaga ggcgaagaaggacgtgctaatctgcgaaaagcttgggtgagttgataagaagcgtctaacccaagatatccgaatggggcaaccc agtagatgaagaatctactatcaataaccgaatccataggttattgaggcaaaccgggagaactgaaacatctaagtaccccgagg aaaagaaatcaaccgagattacgtcagtagcggcgagcgaaagcgtaagagccggcaagtgatagcatgaggattagaggaat cggctgggaagccgggcggcacagggtgatagccccgtacttgaaaatcattgtgtggtactgagcttgcgagaagtagggcggga cacgagaaatcctgtttgaagaaggggggaccatcctccaaggctaaatactcctgattgaccgatagtgaaccagtactgtgaagg aaaggcgaaaagaaccccggtgaggggagtgaaatagaacctgaaaccttgtacgtacaagcagtgggagcccgcgagggtga ctgcgtaccttttgtataatgggtcagcgacttatattatgtagcgaggttaaccgaatagggggagccgaagggaaaccgagtcttaact gggcgtcgagttgcatgatatagacccgaaacccggtgatctagccatgggcaggttgaaggttgggtaacactaactggaggacc gaaccgactaatgttgaaaaattagcggatgacctgtggctgggggtgaaaggccaatcaaaccgggagatagctggttctccccg aaatctatttaggtagagccttatgtgaataccttcggggtagagcactgtttcggctagggggccatcccggcttaccaacccgatgc aaactgcgaataccgaagagtaatgcataggagacacacggcgggtgctaacgttcgtcgtggagagggaaacaacccagacc gccagctaaggtcccaaagtttatattaagtgggaaacgaagtgggaaggcttagacagctaggatgttggcttagaagcagccatc atttaaagaaagcgtaatagctcactagtcgagtcggcctgcgcggaagatgtaacgggctcaaatatagcaccgaagctgcggc atcaggcgtaagcctgttgggtaggggagcgtcgtgtaagcggaagaaggtggttcgagagggctgctgacgtatcacgagtgcg aatgctgacataagtaacgataaaacgggtgaaaacccgttcgccggaagaccaagggttcctgtccaacgttaatcggggcag ggtgagtcggcccctaaggcgaggctgaagagcgtagtcgatgggaaacgggttaatattcccgtacttgttataattgcgatgtggg gacggagtaggttaggttatcgacctgttggaaaaggtcgtttaagttggtaggtggagcgtttaggcaaatccggacgcttatcaaca ccgagagatgatgacgaggcgctaaggtgccgaagtaaccgataccacacttccaggaaaagccactaagcgtcagattataata aaccgtactataaaccgacacaggtggtcaggtagagaatactcaggcgcttgagagaactcgggtgaaggaactaggcaaaata gcaccgtaacttcgggagaaggtgcgccggcgtagattgtagaggtatacccttgaaggttgaaccggtcgaagtgacccgctggct gcaactgttttattaaaaacacagcactctgcaaacacgaaagtggacgtatagggtgtgatgcctgcccggtgctggaaggttaattg atggcgttatcgcaagagaagcgcctgatcgaagccccagtaaacgcggccgtaactataacggtcctaaggtagcgaaattcctt gtcgggtaagttccgacctgcacgaatggcataatgatggccaggctgtctccacccgagactcagtgaaattgaaatcgccgtgaa -continued gatgcggtgtacccgcggctagacggaaagaccccgtgaacctttactatagcttgacactgaaccttgaattttgatgtgtaggatag gtgggaggctttgaagcggtaacgccagttatcgtggagccatccttgaaataccaccctttaacgtttgatgttctaacgaagtgcccg gaacgggtactcggacagtgtctggtgggtagtttgactggggcggtctcctcccaaagagtaacggaggagcacgaaggtttgcta atgacggtcggacatcgtcaggttagtgcaatggtataagcaagcttaactgcgagacggacaagtcgagcaggtgcgaaagcag gtcatagtgatccggtggttctgaatggaagggccatcgctcaacggataaaaggtactccggggataacaggctgataccgccca agagttcatatcgacgcggtgtttggcacctcgatgtcggctcatcacatcctggggctgaagtaggtcccaagggtatggctgttcgc catttaaagtggtacgcgagctgggtttaaaacgtcgtgagacagtttggtccctatctgccgtgggcgttggagaattgagaggggct gctcctagtacgagaggaccggagtggacgcatcactggtgttccggttgtgtcgcagacgcattgccgggtagctacatgcggaa gagataagtgctgaaagcatctaagcacgaaacttgcctcgagatgagttctcccagtatttaatactgtaagggttgttggagacgac gacgtagataggccgggtgtgtaagcgttgcgagacgttgagctaaccggtactaattgcccgagaggcttagccatacaacgctca agtgtttttggtagtgaaagttattacggaataagtaagtagtcagggaatcggct SEQ ID NO: 3 (nucleotide sequence of pykA-gene from strain DD1)
atgtccagaagattaagaagaacgaaaatcgtatgtacaatggggcctgcaacagacaaaggcaataatttagaaaaaatcattgc tgccggtgcaaacgttgtacgtatgaacttctcccacggtacgcccgaagatcatatcggtcgtgctgaaaaagtacgtgaaatcgctc ataaattaggtaaacacgtagcaatcttaggtgacttacaaggccctaaaatccgtgtttctacttttaaagaaggcaaaattttcttaaat atcggtgataaaattcattttagacgcagagatgcctaaaggtgaaggtaaccaggaagcggttggtttagactataaaacattaccgc aagatgtggttccgggcgatatcttattattagatgacggtcgagttcaattgaaagtattggcaaccgaaggtgcaaaagtattcaccg aagtaacggtcggtggcccactatcaaataataaaggcattaacaaattaggcggcggtttatctgccgatgcattaaccgaaaaag ataaagcggatatcattactgcggcgcgtatcggtgtggattaccttgccgtatctttcccgcgttcaagcgcggatttaaactacgcccg tcaattagcaaaagatgcgggcttggatgcgaaaatcgttgcgaaagtagaacgtgccgaaacagttgaaacggacgaagcaatg gacgatatcatcaatgcggcggacgtaatcatggttgcgcgcggtgacttaggtgttgaaatcggtgatccggaattagtcggtgttcag aaaaaattaatccgtcgttcacgtcagttaaatcgtgttgttattaccgcaactcaaatgatggaatcaatgattagtaatcctatgccgac tcgtgcggaagtaatggacgtagctaacgcagtattggacgtaccgatgcggtaatgctttctgctgaaaccgcggctggtcaatatc cggcggaaactgttgcggcgatggcgaaagttgcgttaggtgcggagaaaatgccaagcattaatgtgtctaaacaccgtatgaacg ttcaattcgagtctattgaagaatctgttgcgatgtctgcaatgtatgcggcaaaccacatgagaggcgtagcggcgattatcacattaa caagtagcggtcgtactgctcgtttaatgtctcgcattagttccggtttaccaatctttgcattgtcacgtaacgaatctacattaaacttatgc gcattatatcgtggtgtgacaccggttcattttgataaagacagccgtacctcagaaggtgcgacagcggcggttcaattattaaaaga cgaaggtttcttagtgtctggcgatttagtgttattaactcagggcgacgcaagcagttctagcggtactaacctttgccgtacattgattgtt gaataa SEQ ID NO: 4 (amino acid sequence of PykA from strain DD1)
MSRRLRRTKIVCTMGPATDKGNNLEKIIAAGANVVRMNFSHGTPEDHIGR

AEKVREIAHKLGKHVAILGDLQGPKIRVSTFKEGKIFLNIGDKFILDAEMPK

GEGNQEAVGLDYKTLPQDVVPGDILLLDDGRVQLKVLATEGAKVFTEVTV

GGPLSNNKGINKLGGGLSADALTEKDKADIITAARIGVDYLAVSFPRSSAD

LNYARQLAKDAGLDAKIVAKVERAETVETDEAMDDIINAADVIMVARGDL

GVEIGDPELVGVQKKLIRRSRQLNRVVITATQMMESMISNPMPTRAEVMD

VANAVLDGTDAVMLSAETAAGQYPAETVAAMAKVALGAEKMPSINVSKH

RMNVQFESIEESVAMSAMYAANHMRGVAAIITLTSSGRTARLMSRISSGL

PIFALSRNESTLNLCALYRGVTPVHFDKDSRTSEGATAAVQLLKDEGFLV

SGDLVLLTQGDASSSSGTNLCRTLIVE

SEQ ID NO: 5 (complete nucleotide sequence of plasmid pSacB)
tcgagaggcctgacgtcgggcccggtaccacgcgtcatatgactagttcggacctagggatatcgtcgacatcgatgctcttctgcgtt aattaacaattgggatcctctagactccataggccgctttcctggctttgcttccagatgtatgctctcctccggagagtaccgtgactttatt ttcggcacaaatacaggggtcgatggataaatacggcgatagtttcctgacggatgatccgtatgtaccggcggaagacaagctgca aacctgtcagatggagattgatttaatggcggatgtgctgagagcaccgccccgtgaatccgcagaactgatccgctatgtgtttgcgg atgattggccggaataaataaagccgggcttaatacagattaagcccgtataggqtattattactgaataccaaacagcttacggagg acggaatgttacccattgagacaaccagactgccttctgattattaatattttcactattaatcagaaggaataaccatgaattttacccg gattgacctgaatacctggaatcgcagggaacactttgcctttatcgtcagcagattaaatgcggattcagcctgaccaccaaactcg atattaccgctttgcgtaccgcactggcggagacaggttataagttttatccgctgatgatttacctgatctcccgggctgttaatcagtttcc ggagttccggatggcactgaaagacaatgaacttatttactgggaccagtcagaccggtctttactgtctttcataaagaaaccgaaa cattctctgcactgtcctgccgttattttccggatctcagtgagtttatggcaggttataatgcggtaacggcagaatatcagcatgatacca gattgtttccgcagggaaatttaccggagaatcacctgaatatatcatcattaccgtgggtgagttttgacgggatttaacctgaacatca ccggaaatgatgattattttgccccggttttacgatggcaaagtttcagcaggaaggtgaccgcgtattattacctgtttctgtacaggttc atcatgcagtctgtgatggctttcatgcagcacggtttattaatacacttcagctgatgtgtgataacatactgaaataaattaattaattctg tatttaagccaccgtatccggcaggaatggtggcttttttttttatattttaaccgtaatctgtaatttcgtttcagactggttcaggatgagctcg cttggactcctgttgatagatccagtaatgacctcagaactccatctggatttgttcagaacgctcggttgccgccgggcgttttttattggtg agaatccaagcactagcggcgcgccggccggccggtgtgaaataccgcacagatgcgtaaggagaaaataccgcatcaggcg ctcttccgcttcctcgctcactgactcgctgcgctcggtcgttcggctgcggcgagcggtatcagctcactcaaaggcggtaatacggtt atccacagaatcaggggataacgcaggaaagaacatgtgagcaaaaggccagcaaaaggccaggaaccgtaaaaaggccgc gttgctggcgtttttccataggctccgcccccctgacgagcatcacaaaaatcgacgctcaagtcagaggtggcgaaacccgacagg actataaagataccaggcgtttccccctggaagctccctcgtgcgctctcctgttccgaccctgccgcttaccggatacctgtccgccttc tcccttcgggaagcgtggcgctttctcatagctcacgctgtaggtatctcagttcggtgtaggtcgttcgctccaagctgggctgtgtgcac gaaccccccgttcagcccgaccgctgcgccttatccggtaactatcgtcttgagtccaacccggtaagacacgacttatcgccactgg cagcagccactggtaacaggattagcagagcgaggtatgtaggcggtgctacagagttcttgaagtggtggcctaactacggctaca ctagaaggacagtatttggtatctgcgctctgctgaagccagttaccttcggaaaaagagttggtagctcttgatccggcaaacaaacc accgctggtagcggtggtttttttgtttgcaagcagcagattacgcgcagaaaaaaaggatctcaagaagatcctttgatcttttctacgg ggtctgacgctcagtggaacgaaaactcacgttaagggattttggtcatgagattatcaaaaaggatcttcacctagatccttttaaagg ccggccgcggccgccatcggcatttcttttgcgtttttatttgttaactgttaattgtccttgttcaaggatgctgtctttgacaacagatgttttct tgcctttgatgttcagcaggaagctcggcgcaaacgttgattgtttgtctgcgtagaatcctctgtttgtcatatagcttgtaatcacgacatt gtttccttcgcttgaggtacagcgaagtgtgagtaagtaaaggttacatcgttaggatcaagatccatttttaacacaaggccagttttgtt cagcggcttgtatgggccagttaaagaattagaaacataaccaagcatgtaaatatcgttagacgtaatgccgtcaatcgtcattttgat ccgcgggagtcagtgaacaggtaccatttgccgttcattttaaagacgttcgcgcgttcaatttcatctgttactgtgttagatgcaatcagc ggtttcatcactttttttcagtgtgtaatcatcgtttagctcaatcataccgagagcgccgtttgctaactcagccgtgcgttttttatcgctttgca gaagttttgactttcttgacggaagaatgatgtgcttttgccatagtatgctttgttaaataaagattcttcgccttggtagccatcttcagttcc agtgtttgcttcaaatactaagtatttgtggcctttatcttctacgtagtgaggatctctcagcgtatggttgtcgcctgagctgtagttgccttc atcgatgaactgctgtacattttgatacgttttccgtcaccgtcaaagattgatttataatcctctacaccgttgatgttcaaagagctgtctg atgctgatacgttaacttgtgcagttgtcagtgtttgtttgccgtaatgtttaccggagaaatcagtgtagaataaacggattttccgtcaga tgtaaatgtggctgaacctgaccattcttgtgtttggtcttttaggatagaatcattgcatcgaatttgtcgctgtctttaaagacgcggccag cgttttccagctgtcaatagaagtttcgccgacttttgatagaacatgtaaatcgatgtgtcatccgcatttttaggatctccggctaatgc aaagacgatgtggtagccgtgatagtttgcgacagtgccgtcagcgttttgtaatggccagctgtcccaaacgtccaggccttttgcaga agagatattttttaattgtggacgaatcaaattcagaaacttgatatttttcattttttttgctgttcagggatttgcagcatatcatggcgtgtaata -continued

```
tgggaaatgccgtatgtttccttatatggcttttggttcgtttcttcgcaaacgcttgagttgcgcctcctgccagcagtgcggtagtaaagg ttaatactgttgcttgttttgcaaacttttttgatgttcatcgttcatgtctcctttttttatgtactgtgttagcggtctgcttcttccagccctcctgtttga agatggcaagttagttacgcacaataaaaaaagacctaaaatatgtaaggggtgacgccaaagtatacactttgcccttttacacatttt aggtcttgcctgctttatcagtaacaaacccgcgcgatttacttttcgacctcattctattagactctcgtttggattgcaactggtctatttttcct cttttgtttgatagaaaatcataaaaggatttgcagactacgggcctaaagaactaaaaaatctatctgtttcttttcattctctgtattttttata gtttctgttgcatgggcataaagttgccttttaatcacaattcagaaaatatcataatatctcatttcactaaataatagtgaacggcaggt atatgtgatgggttaaaaaggatcggcggccgctcgatttaaatc
```

SEQ ID NO: 6 (complete nucleotide sequence of plasmid pSacB_delta_ldhA)

```
tcgagaggcctgacgtcgggcccggtaccacgcgtcatatgactagttcggacctagggatgggtcagcctgaacgaaccgcactt gtatgtaggtagttttgaccgcccgaatattcgttataccttggtggaaaaattcaaaccgatggagcaattatacaattttgtggcggcgc aaaaaggtaaaagcggtatcgtctattgcaacagccgtagcaaagtggagcgcattgcggaagccctgaagaaaagaggcatttc cgcagccgcttatcatgcgggcatggagccgtcgcagcgggaagcggtgcaacaggcgtttcaacgggataatattcaagtggtgg tggcgaccattgcttttggtatggggatcaacaaatctaatgtgcgttttgtggcgcattttgatttatctcgcagcattgaggcgtattatcag gaaaccgggcgcgggcgggacgacctgccggcggaagcggtactgttttacgagccggcggattatgcctggttgcataaaat tttattggaagagccggaaagcccgcaacgggatattaaacggcataagctggaagccatcggcgaatttgccgaaagccagacc tgccgtcgtttagtgctgttaaattatttcggcgaaaaccgccaaacgccatgtaataactgtgatatctgcctcgatccgccgaaaaaat atgacggattattagacgcgcagaaaatcctttcgaccatttatcgcaccgggcaacgtttcggcacgcaatacgtaatcggcgtaatg cgcggtttgcagaatcagaaaataaaagaaaatcaacatgatgagttgaaagtctacggaattggcaaagataaaagcaaagaat actggcaatcggtaattcgtcagctgattcatttgggctttgtgcaacaaatcatcagcgatttcggcatggggaccagattacagctcac cgaaagcgcgcgtcccgtgctgcgcggcgaagtgtctttggaactggccatgccgagattatcttccattaccatggtacaggctccgc aacgcaatgcggtaaccaactacgacaaagatttatttgcccgcctgcgtttcctgcgcaaacagattgccgacaaagaaaacattc cgccttatattgtgttcagtgacgcgaccttgcaggaaatgtcgttgtatcagccgaccagcaaagtggaaatgctgcaaatcaacggt gtcggcgccatcaaatggcagcgcttcggacagccttttatggcgattattaaagaacatcaggctttgcgtaaagcgggtaagaatc cgttggaattgcaatcttaaaattttttaacttttttgaccgcacttttaaggttagcaaattccaataaaaagtgcggtgggttttcgggaattttt aacgcgctgatttcctcgtcttttcaattttyttcgyctccatttgttcggyggttgccggatcctttcttgactgagatccataagagagtagaa tagcgccgcttatatttttaatagcgtacctaatcgggtacgcttttttttatgcggaaaatccatatttttctaccgcacttttttctttaaagatttat acttaagtctgtttgattcaattttatttggaggttttatgcaacacattcaactggctcccgatttaacattcagtcgcttaattcaaggattctg gcggttaaaaagctggcggaaatcgccgcaggaattgcttacattcgttaagcaaggattagaattaggcgttgatacgctggatcat gccgcttgttacggggcttttacttccgaggcggaattcggacgggcgctggcgctggataaatccttgcgcgcacagcttactttggtg accaaatgcgggattttgtatcctaatgaagaattacccgatataaaatcccatcactatgacaacagctaccgccatattatgtggtcg gcgcaacgttccattgaaaaactgcaatgcgactattttagatgtattgctgattcaccgwctttctccctgtgcggatcccgaacaaatcg cgcgggcttttgatgaactttatcaaaccgggraaagtacgttatttcggggtatctaactatacgccggctaagttcgccatgttgcaatctt atgtgaatcagccgttaatcactaatcaaattgagatttcgcctcttcatcgtcaggcttttgatgacggtaccctggatttttttactggaaaa acgtattcaaccgatggcatggtcgccacttgccggcggtcgtttattcaatcaggatgagaacagtcgggcggtgcaaaaaacatta ctcgaaatcggtgaaacgaaaggagaaacccgtttagatacattggcttatgcctggttattggcgcatccggcaaaaattatgccggt tatggggtccggtaaaattgaacgggtaaaaagcgcggcggatgcgttacgaatttccttcactgaggaagaatggattaaggtttatg ttgccgcacagggacgggatattccgtaacatcatccgtctaatcctgcgtatctggggaaagatgcgtcatcgtaagaggtctataat attcgtcgttttgataagggtgccatatccggcacccgttaaaatcacattgcgttcgcaacaaaattattccttacgaatagcattcacct cttttaacagatgttgaatatccgtatcggcaaaaatatcctctatatttgcggttaaacggcgccgccagttagcatattgagtgctggttc ccggaatattgacgggtcggtcataccgagccagtcttcaggttggaatccccatcgtcgacatcgatgctcttctgcgttaattaacaa ttgggatcctctagactccataggccgctttcctggctttgcttccagatgtatgctctcctccggagagtaccgtgactttattttcggcaca
```

-continued

```
aatacaggggtcgatggataaatacggcgatagtttcctgacggatgatccgtatgtaccggcggaagacaagctgcaaacctgtca gatggagattgatttaatggcggatgtgctgagagcaccgccccgtgaatccgcagaactgatccgctatgtgtttgcggatgattggc cggaataaataaagccgggcttaatacagattaagcccgtatagggtattattactgaataccaaacagcttacggaggacggaatg ttacccattgagacaaccagactgccttctgattattaatattttttcactattaatcagaaggaataaccatgaattttacccggattgacct gaatacctggaatcgcagggaacactttgcccttatccgtcagcagattaaatgcggattcagcctgaccaccaaactcgatattaccg ctttgcgtaccgcactggcggagacaggttataagttttatccgctgatgatttacctgatctcccgggctgttaatcagtttccggagttcc ggatggcactgaaagacaatgaacttatttactgggaccagtcagacccggtctttactgtctttcataaagaaaccgaaacattctctg cactgtcctgccgttattttccggatctcagtgagtttatggcaggttataatgcggtaacggcagaatatcagcatgataccagattgtttc cgcagggaaatttaccggagaatcacctgaatatatcatcattaccgtgggtgagttttgacgggatttaacctgaacatcaccggaaa tgatgattattttgccccggttttttacgatggcaaagtttcagcaggaaggtgaccgcgtattattacctgtttctgtacaggttcatcatgca gtctgtgatggctttcatgcagcacggtttattaatacacttcagctgatgtgtgataacatactgaaataaattaattaattctgtatttaagc caccgtatccgcaggaatggtggcttttttttttatattttaaccgtaatctgtaatttcgtttcagactggttcaggatgagctcgcttggactc ctgttgatagatccagtaatgacctcagaactccatctggatttgttcagaacgctcggttgccgccgggcgttttttattggtgagaatcca agcactagcggcgccggccggcccggtgtgaaataccgcacagatgcgtaaggagaaaataccgcatcaggcgctcttccgct tcctcgctcactgactcgctgcgctcggtcgttcggctgcggcgagcggtatcagctcactcaaaggcggtaatacggttatccacaga atcagggataacgcaggaaagaacatgtgagcaaaaggccagcaaaaggccaggaaccgtaaaaaggccgcgttgctggcg ttttccataggctccgcccccctgacgagcatcacaaaaatcgacgctcaagtcagaggtggcgaaacccgacaggactataaag ataccaggcgtttccccctggaagctccctcgtgcgctctcctgttccgaccctgccgcttaccggatacctgtccgcctttctcccttcgg gaagcgtggcgctttctcatagctcacgctgtaggtatctcagttcggtgtaggtcgttcgctccaagctgggctgtgtgcacgaaccccc cgttcagcccgaccgctgcgccttatccggtaactatcgtcttgagtccaacccggtaagacacgacttatcgccactggcagcagcc actggtaacaggattagcagagcgaggtatgtaggcggtgctacagagttcttgaagtggtggcctaactacggctacactagaagg acagtatttggtatctgcgctctgctgaagccagttaccttcggaaaaagagttggtagctcttgatccggcaaacaaaccaccgctggt agcggtggtttttttgtttgcaagcagcagattacgcgcagaaaaaaaggatctcaagaagatcctttgatcttttctacggggtctgacg ctcagtggaacgaaaactcacgttaagggattttggtcatgagattatcaaaaaggatcttcacctagatccttttaaaggccggccgc ggccgccatcggcattttcttttgcgtttttatttgttaactgttaattgtccttgttcaaggatgctgtctttgacaacagatgttttcttgcctttgat gttcagcaggaagctcggcgcaaacgttgattgtttgtctgcgtagaatcctctgtttgtcatatagcttgtaatcacgacattgtttcctttcg cttgaggtacagcgaagtgtgagtaagtaaaggttacatcgttaggatcaagatccattttaacacaaggccagttttgttcagcggctt gtatgggccagttaaagaattagaaacataaccaagcatgtaaatatcgttagacgtaatgccgtcaatcgtcattttgatccgcggga gtcagtgaacaggtaccatttgccgttcatttaaagacgttcgcgcgttcaatttcatctgttactgtgttagatgcaatcagcggtttcatc acttttttcagtgtgtaatcatcgtttagctcaatcataccgagagcgccgtttgctaactcagccgtgcgttttttatcgctttgcagaagttttt gactttcttgacggaagaatgatgtgcttttgccatagtatgctttgttaaataaagattcttcgccttggtagccatcttcagttccagtgtttg cttcaaatactaagtatttgtggcctttatcttctacgtagtgaggatctctcagcgtatggttgtcgcctgagctgtagttgccttcatcgatg aactgctgtacattttgatacgttttccgtcaccgtcaaagattgatttataatcctctacaccgttgatgttcaaagagctgtctgatgctga tacgttaacttgtgcagttgtcagtgtttgtttgccgtaatgtttaccggagaaatcagtgtagaataaacggattttttccgtcagatgtaaat gtggctgaacctgaccattcttgtgtttggtcttttaggatagaatcatttgcatcgaatttgtcgctgtctttaaagacgcggccagcgttttttc cagctgtcaatagaagtttcgccgactttttgatagaacatgtaaatcgatgtgtcatccgcattttaggatctccggctaatgcaaagac gatgtggtagccgtgatagtttgcgacagtgccgtcagcgttttgtaatggccagctgtcccaaacgtccaggccttttgcagaagagat attttttaattgtggacgaatcaaattcagaaacttgatattttcatttttttgctgttcagggatttgcagcatatcatggcgtgtaatatgggaa atgccgtatgtttccttatatggcttttggttcgtttctttcgcaaacgcttgagttgcgcctcctgccagcagtgcggtagtaaaggttaatact gttgcttgttttgcaaacttttttgatgttcatcgttcatgtctccttttttatgtactgtgttagcggtctgcttcttccagccctcctgtttgaagatgg
```

-continued caagttagttacgcacaataaaaaaagacctaaaatatgtaaggggtgacgccaaagtatacactttgccctttacacattttaggtctt gcctgctttatcagtaacaaacccgcgcgattttacttttcgacctcattctattagactctcgtttggattgcaactggtctattttcctcttttgttt gatagaaaatcataaaaggatttgcagactacgggcctaaagaactaaaaaatctatctgtttcttttcattctctgtattttttatagtttctgt tgcatgggcataaagttgccttttaatcacaattcagaaaatatcataatatctcatttcactaaataatagtgaacggcaggtatatgtg atgggttaaaaaggatcggcggccgctcgatttaaatc SEQ ID NO: 7 (complete nucleotide sequence of plasmid pSacB_delta_pflA)
tcgagtcaatgcggatttgacttatgatgtggcaaacaaccgatttccgattattactacacgtaaaagttattggaaagcggcgattgcg gagtttctggttatatccgcggctacgataatgcggcggatttccgtaaattaggagcaaaaacctgggatgccaacgctaatgaaa atcaggtatggctgaataaccctcatcgcaaaggcaccgacgacatggggcgcgtttacggcgtacagggcagagcctggcgtaa gcctaacggcgaaaccgttgatcaattacgcaaaattgtcaacaatttaagtcgcggcattgatgatcgcggcgaaattctgaccttttt aaacccgggcgaattcgatctcggttgtctgcgcccttgtatgtacaatcacacgttttcttgctgggcgatacgctttatttaaccagttat caacgctcctgtgacgtacctttaggcttgaatttcaatcaaattcaagtatttacattcttagctttaatggcgcagattaccggtaaaaaa gccggtcaggcatatcacaaaatcgtcaatgcgcatatttacgaagaccagctggaactaatgcgcgacgtgcagttaaaacgcga accgttcccgtcgccaaaactggaaattaatccggacattaaaacccttgaagatttagaaacctgggtaaccatggatgatttcaacg tcgttggttaccaatgccacgaaccgataaaatatccgttctcggtataaaccgacaaaagtgcggtcaaaaatttaatattttcatctgtt atagaaaatattttttcaacataaaatctagggatgcctgtttggcgtccgtaaatacgcagaaaaatattaaattttttgaccgcacttttttc atctcaattaacagcctgataattcttatggatcaacaaattagctttgacgaaaaaatgatgaatcgagctcttttccttgccgacaagg cggaagctttaggggaaattcccgtaggtgccgtattggtggatgaacggggcaatatcattggtgaaggctggaacctctctattgtg aactcggatcccaccgccatgccgaaattattgcgttgcgtaacgccgcgcagaaaatccaaaattaccgcctgctcaataccactt tatacgtgactttagaaccctgcaccatgtgcgccggcgcgattttacacagccgaatcaaacgcttggtattcggggcgtccgattac aaaaccggtgcggtgggttccagatttcatttttttgaggattataaaatgaatcatgggggttgagatcacaagcggtgtcttacaggatc aatgcagtcagaagttaagccgcttttccaaaagcgcagggaacagaaaaaacaacaaaaagctaccgcacttttacaacaccc ccggcttaactcctctgaaaaatagtgacaaaaaaccgtcataatgtttacgacggttttttatttcttaatatgcccttaaataatcaac aaaatatagcaagaagattatagcaaagaatttcgttttttcagagaatagtcaaatcttcgcaaaaaactaccgcacttttatccgcttt aatcaggggaattaaaacaaaaaaattccgcctattgaggcggaatttattaagcaataagacaaactctcaattacattgattgtgta aacgtacgagtgatgacgtcttgttgttgctcttagttaatgagttgaaacgaaccgcgtaacctgaaacacgaatggttaattgcgggt atttttccggattttccatcgcgtctaacaacatttcacggttaagaacgttaacattcaagtgttgaccgccttccactgtcgcttcatgatg gaaataaccgtccattaaaccggcaaggttgcgttttgcgcttcgtcatctttacctaatgcgttcggtacgatagagaaggtatatgaa ataccgtctttcgcgtaagcgaacggaagtttagccacagaagtaagtgaagcaaccgcaccttttggtcacgaccgtgcattgggttt gcacccggtccgaatgcgcgcctgctcgacgaccgtccggagtattaccggttttcttaccgtataccacgttagaagtgatagtcag gatagattgtgtcggagttgcgttgcggtaagttttgtgttttttgaactttttttcatgaaacgttcaactaagtctaccgctaaatcatcaacac gcggatcattgttaccgaattgcggatattcgccttcaatttcgaagtcgatagcaacattcgaggccacgacattaccgtctttatctttga tgtcgccgcgaatcggtttaactttcgcatatttgattgcggataatgagtccgcagccacggaaagacccgcgataccgcaagccatt gtacggaatacgtcgcgatcgtggaacgccatcaatgccgcttcatatgcatatttatcgtgcatgaagtggatgatgttcaatgcggtta catattgagtcgccaaccagtccatgaaactgtccatacgttcgattacggtatcgaaattcaatacttcgtctgtaatcggcgcagtttta ggaccgacttgcataccattttctctcatcgataccgccgttaattgcgtataacatagttttagctaagtttgcgcgcgcaccgaagaattg catttgtttacctacgaccatcggtgatacgcagcatgcgattgcatagtcatcgttgttgaagtcaggacgcattaagtcatcattttcgta ttgtacggaggaagtatcaatagatactttcgcacagaaacgtttgaacgcttcaggtaattgttcggaccaaagaatagttaagtttggt tccggagaagtacccatagtgtataaagtatgtaatacgcggaagctgtttttagttaccaacggacgaccgtctaagcccataccggc gatagtttcggttgccctctagactccataggccgctttcctggctttgcttccagatgtatgctctcctccggagagtaccgtgactttattttc ggcacaaatacaggggtcgatggataaaatacggcgatagtttcctgacggatgatccgtatgtaccggcggaagacaagctgcaaa -continued

```
cctgtcagatggagattgatttaatggcggatgtgctgagagcaccgccccgtgaatccgcagaactgatccgctatgtgtttgcggat gattggccggaataaataaagccgggcttaatacagattaagcccgtatagggtattattactgaataccaaacagcttacggaggac ggaatgttacccattgagacaaccagactgccttctgattattaatattttcactattaatcagaaggaataaccatgaattttacccggat tgacctgaatacctggaatcgcagggaacactttgcccttatcgtcagcagattaaatgcggattcagcctgaccaccaaactcgata ttaccgctttgcgtaccgcactggcggagacaggttataagttttatccgctgatgatttacctgatctcccgggctgttaatcagtttccgg agttccggatggcactgaaagacaatgaacttatttactgggaccagtcagacccggtctttactgtctttcataaagaaaccgaaaca ttctctgcactgtcctgccgttattttccggatctcagtgagtttatggcaggttataatgcggtaacggcagaatatcagcatgataccag attgtttccgcaggaaatttaccggagaatcacctgaatatatcatcattaccgtgggtgagttttgacgggatttaacctgaacatcac cggaaatgatgattattttgccccggttttacgatggcaaagtttcagcaggaaggtgaccgcgtattattacctgtttctgtacaggttcat catgcagtctgtgatggctttcatgcagcacggtttattaatacacttcagctgatgtgtgataacactgaaataaattaattaattctgta tttaagccaccgtatccggcaggaatggtggcttttttttatattttaaccgtaatctgtaatttcgtttcagactggttcaggatgagctcgctt ggactcctgttgatagatccagtaatgacctcagaactccatctggatttgttcagaacgctcggttgccgccgggcgttttttattggtgag aatccaagcactagcggcgcgccggccggccggtgtgaaataccgcacagatgcgtaaggagaaaataccgcatcaggcgctc ttccgcttcctcgctcactgactcgctgcgctcggtcgttcggctgcggcgagcggtatcagctcactcaaaggcggtaatacggttatc cacagaatcaggggataacgcaggaaagaacatgtgagcaaaaggccagcaaaaggccaggaaccgtaaaaaggccgcgtt gctggcgtttttccataggctccgcccccctgacgagcatcacaaaaatcgacgctcaagtcagaggtggcgaaacccgacaggac tataaagataccaggcgtttccccctggaagctccctcgtgcgctctcctgttccgaccctgccgcttaccggatacctgtccgcctttctc ccttcgggaagcgtggcgctttctcatagctcacgctgtaggtatctcagttcggtgtaggtcgttcgctccaagctgggctgtgtgcacg aaccccccgttcagcccgaccgctgcgccttatccggtaactatcgtcttgagtccaacccggtaagacacgacttatcgccactggc agcagccactggtaacaggattagcagagcgaggtatgtaggcggtgctacagagttcttgaagtggtggcctaactacggctacac tagaaggacagtatttggtatctgcgctctgctgaagccagttaccttcggaaaaagagttggtagctcttgatccggcaaacaaacca ccgctggtagcggtggtttttttgtttgcaagcagcagattacgcgcagaaaaaaaggatctcaagaagatcctttgatcttttctacggg gtctgacgctcagtggaacgaaaactcacgttaagggattttggtcatgagattatcaaaaaggatcttcacctagatccttttaaaggc cggccgcggccgccatcggcattttcttttgcgtttttatttgttaactgttaattgtccttgttcaaggatgctgtctttgacaacagatgttttctt gcctttgatgttcagcaggaagctcggcgcaaacgttgattgtttgtctgcgtagaatcctctgtttgtcatatagcttgtaatcacgacattg tttcctttcgcttgaggtacagcgaagtgtgagtaagtaaaggttacatcgttaggatcaagatccatttttaacacaaggccagttttgttc agcggcttgtatgggccagttaaagaattagaaacataaccaagcatgtaaatatcgttagacgtaatgccgtcaatcgtcattttgatc cgcgggagtcagtgaacaggtaccatttgccgttcattttaaagacgttcgcgcgttcaatttcatctgttactgtgttagatgcaatcagc ggtttcatcactttttttcagtgtgtaatcatcgtttagctcaatcataccgagagcgccgtttgctaactcagccgtgcgttttttatcgctttgca gaagtttttgactttcttgacggaagaatgatgtgcttttgccatagtatgctttgttaaataaagattcttcgccttggtagccatcttcagttcc agtgtttgcttcaaatactaagtatttgtggcctttatcttctacgtagtgaggatctctcagcgtatggttgtcgcctgagctgtagttgccttc atcgatgaactgctgtacattttgatacgttttccgtcaccgtcaaagattgatttataatcctctacaccgttgatgttcaaagagctgtctg atgctgatacgttaacttgtgcagttgtcagtgtttgttgccgtaatgtttaccggagaaatcagtgtagaataaacggattttccgtcaga tgtaaatgtggctgaacctgaccattcttgtgtttggtcttaggatagaatcatttgcatcgaatttgtcgctgtctttaaagacgcggccag cgttttccagctgtcaatagaagtttcgccgacttttgatagaacatgtaaatcgatgtgtcatccgcattttaggatctccggctaatgc aaagacgatgtggtagccgtgatagtttgcgacagtgccgtcagcgttttgtaatggccagctgtcccaaacgtccaggcctttgcaga agagatatttaattgtggacgaatcaaattcagaaacttgatattttcattttttgctgttcagggatttgcagcatatcatggcgtgtaata tgggaaatgccgtatgtttccttatatggcttttggtcgttctttcgcaaacgcttgagttgcgcctcctgccagcagtgcggtagtaaagg ttaatactgttgcttgttttgcaaacttttttgatgttcatcgttcatgtctccttttttatgtactgtgttagcggtctgcttcttccagccctcctgtttga agatggcaagttagttacgcacaataaaaaaagacctaaaatatgtaaggggtgacgccaaagtatacactttgccctttacacatttt aggtcttgcctgctttatcagtaacaaacccgcgcgatttacttttcgacctcattctattagactctcgtttggattgcaactggtctattttcct
```

-continued cttttgtttgatagaaaatcataaaaggatttgcagactacgggcctaaagaactaaaaaatctatctgtttcttttcattctctgtatttttata gtttctgttgcatgggcataaagttgccttttttaatcacaattcagaaaatatcataatatctcatttcactaaataatagtgaacggcaggt atatgtgatgggttaaaaaggatcggcggccgctcgatttaaatc SEQ ID NO: 8 (complete nucleotide sequence of plasmid pSacB_delta_pflD)
tcgagaggcctgacgtcgggcccggtaccacgcgtcatatgactagttcggacctagggatgggatcgagctcttttccttgccgaca aggcggaagctttaggggaaattcccgtaggtgccgtattggtggatgaacggggcaatatcattggtgaaggctggaacctctctatt gtgaactcggatcccaccgccatgccgaaattattgcgttgcgtaacgccgcgcagaaaatccaaaattaccgcctgctcaatacc actttatacgtgactttagaaccctgcaccatgtgcgccggcgcgattttacacagccgaatcaaacgcttggtattcggggcgtccgat tacaaaaccggtgcggtgggttccagatttcatttttttgaggattataaaatgaatcatggggttgagatcacaagcggtgtcttatagga tcaatgcagtcagaagttaagccgcttttttccaaaagcgcagggaacagaaaaaacaacaaaaagctaccgcacttttacaacacc cccggcttaactcctctgaaaaatagtgacaaaaaaaccgtcataatgtttacgacggttttttttatttcttctaatatgtcacattaagcccg tagcctgcaagcaacccccttaacatgctccattaattcttttgtcggcggttttacatcttcaagctcgtatttatcgccgagtacttcccattta tgggcgcctagacggtgataaggtaataattccacttttttcgatattcttcatatctttaatgaaattccccagcatgtgcaaatcttcgtcact atctgtataacccggcactacaacatggcggatccaggtacgctgatttcgatccgctaaatattttgcgaattcgagcactcttttattcg gcacgccaatcaggctttcgtgaacccgttcattcatttctttcaggtcaagcaacacaagatccgtgtcatcaatcaattcatcaataat atgatcatgatgacggacgaaaccgttggtatccaagcaagtattaattccttctttatggcaggctctgaaccagtcccgtacaaattcc gcctgtaaaatagcttcaccgccggaagcggtaactccgccgcccgaggcgttcataaaatggcgataggtcaccacttctttcattaa ttcttcaacggaaatttctttaccgccgtgcaaatcccaggtgtctctgttatggcaatatttacaacgcattaagcagccttgtaaaaataa aataaagcggattcccggcccgtcaactgtcccgcaggtttcaaatgaatgaattcgtcctaaaaccgacataatatgccctttaaataa tcaacaaaatatagcaagaagattatagcaaagaatttcgtfttttttcagagaatagtcaaatcttcgcaaaaaactaccgcacttttatc cgctttaatcagcggg aattaaaacaaaaaaattccgcctattgaggcggaatttattaagcaataagacaaactctcaatttttaatacttc cttcttttctagtattgataagattgaaaccttgcaaggatgacggcggatttgccgtcactctcacccaactaatgtggacgactggtaa accattgcattagaccaatgcaaacaccaccaccgacgatgttacctaaagtaacaggaattaaattttttaattactaaatggtacatat ctaaatttgcaaactgctcggcatttaaacccgttgcctgccagaattccggcgatgcgaaatttgcaattaccatgcccatagggatca taaacatatttgctacgcagtgttcaaagcctgaagcgacaaaayaacccgatcggcaggatcataataaaagctttatccgttagagt yttgccggcataggccatccaaacggcaatacataccataatgttgcaaagaatacctaaacagaaggcttcaayccaggtatgttct attttatgttgtgccgtatttaaaatggttaatccccactgaccgtttgccgccatgatctgaccggaaaaccaaattaatgcaacaataa ataaaccgccgacaaaattaccgaartaaaccacaatccagttacgtaacatctgaattgttgtaattttactctcaaagcgggcaata gtcgataaagttgatgaagtaaatagttcacagccgcaaaccgccaccataattaccccgagagagaacaccaaaccgccgacc agtttagttaatccccaaggcgctcccgcagaggctgtttgagttgttgtataaaaaacgaatgcaagagcaataaacataccggcag agatcgccgataaaaatgaataggcttgtttttttcgtagcttttataaacgccgacgtctaacccggtttgagccatctcggttggcgaagc catccaagccaatttaaaatcttccgatttt cattgagcttt ccttagtaataaaaactactcggaaatgagtagaactgccttaaagcataa atgatagattaaaaaatccaaaattgttgaatattattt taacggggggattataaaagattcataaattagataatagctaatttgagtgat ccatatcaccttttacagatttttt gacctaaatcaaaattacccaaatagagtaataataccattataaagggtgtggatttattcctttggttt acgagataaattgctatttaagctgatttctgataaaaagtgcggtagattttt cccaaaaataaggaaacacaaaatggcagaagaa acaattttcagtaaaattattcgtaaagaaattcccgccgacattatatcaagacgatcttgtcaccgcatttcgcgatattgcgccgca ggcaaaaactcatattttaattattccgaataaattgattccgacagtaaacgacgtaaccgcccatcgtcgacatcgatgctcttctgcg ttaattaacaattgggatcctctagactttgcttccagatgtatgctctcctccggagagtaccgtgactttattttcggcacaaatacaggg gtcgatggataaatacggcgatagtttcctgacggatgatccgtatgtaccggcggaagacaagctgcaaacctgtcagatggagatt gatttaatggcggatgtgctgagagcaccgccccgtgaatccgcagaactgatccgctatgtgtttgcggatgattggcggaataaat aaagccgggcttaatacagattaagcccgtataggg tattattactgaataccaaacagcttacggaggacggaatgttacccattga -continued

```
gacaaccagactgccttctgattattaatattttcactattaatcagaaggaataaccatgaattttacccggattgacctgaatacctgg aatcgcagggaacactttgccctttatcgtcagcagattaaatgcggattcagcctgaccaccaaactcgatataccgctttgcgtacc gcactggcggagacaggttataagttttatccgctgatgatttacctgatctcccgggctgttaatcagtttccggagttccggatggcact gaaagacaatgaacttatttactgggaccagtcagacccggtctttactgtctttcataaagaaaccgaaacattctctgcactgtcctgc cgttatttccggatctcagtgagtttatggcaggttataatgcggtaacggcagaatatcagcatgataccagattgtttccgcagggaa atttaccggagaatcacctgaatatatcatcattaccgtgggtgagttttgacgggatttaacctgaacatcaccggaaatgatgattattt gccccggttttttacgatggcaaagtttcagcaggaaggtgaccgcgtattattacctgtttctgtacaggttcatcatgcagtctgtgatgg ctttcatgcagcacggtttattaatacacttcagctgatgtgtgataacatactgaaataaattaattaattctgtatttaagccaccgtatcc ggcaggaatggtggcttttttttataattttaaccgtaatctgtaatttcgtttcagactggttcaggatgagctcgcttggactcctgttgatag atccagtaatgacctcagaactccatctggatttgttcagaacgctcggttgccgccgggcgttttttattggtgagaatccaagcactag cggcgcgccggccggcccggtgtgaaataccgcacagatgcgtaaggagaaaataccgcatcaggcgctcttccgcttcctcgctc actgactcgctgcgctcggtcgttcggctgcggcgagcggtatcagctcactcaaaggcggtaatacggttatccacagaatcaggg gataacgcaggaaagaacatgtgagcaaaaggccagcaaaaggccaggaaccgtaaaaaggccgcgttgctggcgtttttccat aggctccgcccccctgacgagcatcacaaaaatcgacgctcaagtcagaggtggcgaaacccgacaggactataaagataccag gcgtttccccctggaagctccctcgtgcgctctcctgttccgaccctgccgcttaccggatacctgtccgcctttctcccttcgggaagcgt ggcgctttctcatagctcacgctgtaggtatctcagttcggtgtaggtcgttcgctccaagctgggctgtgtgcacgaaccccccgttcag cccgaccgctgcgccttatccggtaactatcgtcttgagtccaacccggtaagacacgacttatcgccactggcagcagccactggta acaggattagcagagcgaggtatgtaggcggtgctacagagttcttgaagtggtggcctaactacggctacactagaaggacagtat ttggtatctgcgctctgctgaagccagttaccttcggaaaaagagttggtagctcttgatccggcaaacaaaccaccgctggtagcggt ggtttttttgtttgcaagcagcagattacgcgcagaaaaaaaggatctcaagaagatcctttgatcttttctacggggtctgacgctcagtg gaacgaaaactcacgttaagggattttggtcatgagattatcaaaaaggatcttcacctagatccttttaaaggccggccgcggccgcc atcggcattttcttttgcgttttatttgttaactgttaattgtccttgttcaaggatgctgtctttgacaacagatgttttcttgcctttgatgttcagca ggaagctcggcgcaaacgttgattgtttgtctgcgtagaatcctctgtttgtcatatagcttgtaatcacgacattgtttccttcgcttgaggt acagcgaagtgtgagtaagtaaaggttacatcgttaggatcaagatccattttaacacaaggccagttttgttcagcggcttgtatggg ccagttaaagaattagaaacataaccaagcatgtaaatatcgttagacgtaatgccgtcaatcgtcattttgatccgcgggagtcagtg aacaggtaccatttgccgttcattttaaagacgttcgcgcgttcaatttcatctgttactgtgttagatgcaatcagcggtttcatcactttttttca gtgtgtaatcatcgtttagctcaatcataccgagagcgccgtttgctaactcagccgtgcgttttttatcgctttgcagaagttttgactttcttg acggaagaatgatgtgcttttgccatagtatgctttgttaaataaagattcttcgccttggtagccatcttcagttccagtgtttgcttcaaata ctaagtatttgtggcctttatcttctacgtagtgaggatctctcagcgtatggttgtcgcctgagctgtagttgccttcatcgatgaactgctgt acattttgatacgttttccgtcaccgtcaaagattgatttataatcctctacaccgttgatgttcaaagagctgtctgatgctgatacgttaac ttgtgcagttgtcagtgtttgtttgccgtaatgtttaccggagaaatcagtgtagaataaacggattttccgtcagatgtaaatgtggctgaa cctgaccattcttgtgtttggtcttttaggatagaatcatttgcatcgaatttgtcgctgtctttaaagacgcggccagcgttttccagctgtca atagaagtttcgccgacttttgatagaacatgtaaatcgatgtgtcatccgcattttaggatctccggctaatgcaaagacgatgtggta gccgtgatagtttgcgacagtgccgtcagcgttttgtaatggccagctgtcccaaacgtccaggccttttgcagaagagatattttaattg tggacgaatcaaattcagaaacttgatattttcatttttttgctgttcagggatttgcagcatatcatggcgtgtaatatgggaaatgccgtat gtttccttatatggcttttggttcgtttctttcgcaaacgcttgagttgcgcctcctgccagcagtgcggtagtaaaggttaatactgttgcttgtt ttgcaaacttttttgatgttcatcgttcatgtctcctttttttatgtactgtgttagcggtctgcttcttccagccctcctgtttgaagatggcaagttagt tacgcacaataaaaaaagacctaaaatatgtaaggggtgacgccaaagtatacactttgcccttacacattttaggtcttgcctgcttta tcagtaacaaacccgcgcgattttacttttcgacctcattctattagactctcgtttggattgcaactggtctattttcctcttttgtttgatagaaa atcataaaaggatttgcagactacgggcctaaagaactaaaaaatctatctgtttcttttcattctctgtatttttatagtttctgttgcatgggc
```

-continued ataaagttgcctttttaatcacaattcagaaaatatcataatatctcatttcactaaataatagtgaacggcaggtatatgtgatgggttaaa aaggatcggcggccgctcgatttaaatc SEQ ID NO: 9 (complete nucleotide sequence of plasmid pSacB_pykA1)
tcgagcagaagattaagaagaacgaaaatcgtatgtacaatggggcctgcaacagacaaaggcaataatttagaaaaaatcattg ctgccggtgcaaacgttgtacgtatgaacttctcccacggtacgcccgaagatcatatcggtcgtgctgaaaaagtacgtgaaatcgct cataaattaggtaaacacgtagcaatcttaggtgacttacaaggccctaaaatccgtgtttctacttttaaagaaggcaaaattttcttaaa tatcggtgataaattcattttagacgcagagatgcctaaaggtgaaggtaaccaggaagcggttggtttagactataaaacattaccgc aagatgtggttccgggcgatatcttattattagatgacggtcgagttcaattgaaagtattggcaaccgaaggtgcaaaagtattcaccg aagtaacggtcggtggcccactatcaaataataaaggcattaacaaattaggcggcggtttatctgccgatgcattaaccgaaaaag ataaagcggatatcattactgcggcgcgtatcggtgtggattaccttgccgtatctttcccgcgttcaagcgcggatttaaactacgcccg tcaattagcaaaagatgcgggcttggatgcgaaaatcgttgcgaaagtagaacgtgccgaaacagttgaaacggacgaagcaatg gacgatatcatcaatgcggcggacgtaatcatggttgcgcgcggtgacttaggtgttgaaatcggtgatccggaattagtcggtgttcag aaaaaattaatccgtcgttcacgtcagttaaatcgtgttgttattaccgcaactcaaatgatggaatcaatgattagtaatcctatgccgac tcgtgcggaagtaatggacgtagctaacgcagtattggacggtaccgatgcggtaatgctttctgctgaaaccgcggctggtcaatatc cggcggaaactgttgcggcgatggcgaaagttgcgttaggtgcggagaaaatgccaagcattaatgtgtctaaacaccgtatgaacg ttcaattcgagtctattgaagaatctgttgcgatgtctgcaatgtatgcggcaaaccacatgagaggcgtagcggcgattatcacattaa caagtagcggtcgtactgctcgtttaatgtctagactccataggccgctttcctggctttgcttccagatgtatgctctcctccggagagtac cgtgactttattttcggcacaaatacaggggtcgatggataaatacggcgatagtttcctgacggatgatccgtatgtaccggcggaag acaagctgcaaacctgtcagatggagattgatttaatggcggatgtgctgagagcaccgccccgtgaatccgcagaactgatccgct atgtgtttgcggatgattggccggaataaataaagccgggcttaatacagattaagcccgtatagggtattattactgaataccaaaca gcttacggaggacggaatgttacccattgagacaaccagactgccttctgattattaatatttttcactattaatcagaaggaataaccat gaatttttacccggattgacctgaataccctggaatcgcagggaacactttgccctttatcgtcagcagattaaatgcggattcagcctgac caccaaactcgatattaccgctttgcgtaccgcactggcggagacaggttataagttttatccgctgatgatttacctgatctcccgggct gttaatcagtttccggagttccggatggcactgaaagacaatgaacttatttactgggaccagtcagacccggtctttactgtcttttcataa agaaaccgaaacattctctgcactgtcctgccgttattttccggatctcagtgagtttatggcaggttataatgcggtaacggcagaatat cagcatgataccagattgtttccgcagggaaatttaccggagaatcacctgaatatatcatcattaccgtgggtgagttttgacgggattt aacctgaacatcaccggaaatgatgattattttgccccggtttttacgatggcaaagtttcagcaggaaggtgaccgcgtattattacctg tttctgtacaggttcatcatgcagtctgtgatggctttcatgcagcacggttttattaatacacttcagctgatgtgtgataacatactgaaata aattaattaattctgtatttaagccaccgtatccggcaggaatggtggcttttttttatattttaaccgtaatctgtaatttcgtttcagactggttc aggatgagctcgcttggactcctgttgatagatccagtaatgacctcagaactccatctggatttgttcagaacgctcggttgccgccgg gcgttttttattggtgagaatccaagcactagcggcgcgccggccggcccggtgtgaaataccgcacagatgcgtaaggagaaaat accgcatcaggcgctcttccgcttcctcgctcactgactcgctgcgctcggtcgttcggctgcggcgagcggtatcagctcactcaaag gcggtaatacggttatccacagaatcaggggataacgcaggaaagaacatgtgagcaaaaggccagcaaaaggccaggaacc gtaaaaaggccgcgttgctggcgtttttccataggctccgcccccctgacgagcatcacaaaaatcgacgctcaagtcagaggtggc gaaacccgacaggactataaagataccaggcgtttccccctggaagctccctcgtgcgctctcctgttccgaccctgccgcttaccgg atacctgtccgcctttctcccttcgggaagcgtggcgctttctcatagctcacgctgtaggtatctcagttcggtgtaggtcgttcgctccaa gctgggctgtgtgcacgaaccccccgttcagcccgaccgctgcgccttatccggtaactatcgtcttgagtccaacccggtaagacac gacttatcgccactggcagcagccactggtaacaggattagcagagcgaggtatgtaggcggtgctacagagttcttgaagtggtgg cctaactacggctacactagaaggacagtatttggtatctgcgctctgctgaagccagttaccttcggaaaaagagttggtagctcttga tccggcaaacaaaccaccgctggtagcggtggtttttttgtttgcaagcagcagattacgcgcagaaaaaaaggatctcaagaagat cctttgatcttttctacggggtctgacgctcagtggaacgaaaactcacgttaagggattttggtcatgagattatcaaaaaggatcttcac -continued ctagatcctttaaaggccggccgcggccgccatcggcattttcttttgcgttttattgttaactgttaattgtccttgttcaaggatgctgtcttt gacaacagatgttttcttgcctttgatgttcagcaggaagctcggcgcaaacgttgattgtttgtctgcgtagaatcctctgtttgtcatatag cttgtaatcacgacattgtttcctttcgcttgaggtacagcgaagtgtgagtaagtaaaggttacatcgttaggatcaagatccatttttaac acaaggccagttttgttcagcggcttgtatgggccagttaaagaattagaaacataaccaagcatgtaaatatcgttagacgtaatgcc gtcaatcgtcattttgatccgcgggagtcagtgaacaggtaccatttgccgttcatttaaagacgttcgcgcgttcaatttcatctgttactg tgttagatgcaatcagcggtttcatcactttttcagtgtgtaatcatcgtttagctcaatcataccgagagcgccgttgtctaactcagccgt gcgttttttatcgctttgcagaagttttgactttcttgacggaagaatgatgtgcttttgccatagtatgctttgttaaataaagattcttcgcctt ggtagccatcttcagttccagtgtttgcttcaaatactaagtatttgtggcctttatcttctacgtagtgaggatctctcagcgtatggttgtcgc ctgagctgtagttgccttcatcgatgaactgctgtacattttgatacgttttccgtcaccgtcaaagattgattataatcctctacaccgttga tgttcaaagagctgtctgatgctgatacgttaacttgtgcagttgtcagtgtttgtttgccgtaatgtttaccggagaaatcagtgtagaataa acggattttccgtcagatgtaaatgtggctgaacctgaccattcttgtgtttggtcttttaggataagaatcatttgcatcgaatttgtcgctgtct ttaaagacgcggccagcgttttccagctgtcaatagaagtttcgccgacttttgatagaacatgtaaatcgatgtgtcatccgcatttta ggatctccggctaatgcaaagacgatgtggtagccgtgatagtttgcgacagtgccgtcagcgttttgtaatggccagctgtcccaaac gtccaggccttttgcagaagagatatttttaattgtggacgaatcaaattcagaaacttgatattttcatttttttgctgttcagggatttgcag catatcatggcgtgtaatatggaaatgccgtatgtttcttatatggcttttggttcgtttctttcgcaaacgcttgagttgcgcctcctgccag cagtgcggtagtaaaggttaatactgttgcttgttttgcaaactttttgatgttcatcgttcatgtctccttttttatgtactgtgttagcggtctgctt cttccagccctcctgtttgaagatggcaagttagttacgcacaataaaaaagacctaaaatatgtaaggggtgacgccaaagtatac actttgcccttacacattttaggtcttgcctgctttatcagtaacaaaccgcgcgattacttttcgacctcattctattagactctcgtttggat tgcaactggtctattttcctctttgtttgatagaaaatcataaaggatttgcagactacgggcctaaagaactaaaaaatctatctgtttctt ttcattctctgtatttttatagtttctgttgcatgggcataaagttgcctttttaatcacaattcagaaaatatcataatatctcatttcactaaata atagtgaacggcaggtatatgtgatgggttaaaaaggatcggcggccgctcgatttaaatc SEQ ID NO: 10 (complete nucleotide sequence of plasmid pSacB_pykA2)
tcgagcagaagattaagaagaacgaaaatcgtatgtacaatggggcctgcaacagacaaaggcaataatttagaaaaaatcattg ctgccggtgcaaacgttgtacgtatgaacttctcccacggtacgcccgaagatcatatcggtcgtgctgaaaaagtacgtgaaatcgct cataaattaggtaaacacgtagcaatcttaggtgacttacaaggccctaaaatccgtgtttctacttttaaagaaggcaaaattttcttaaa tatcggtgataaattcattttagacgcagagatgcctaaaggtgaaggtaaccaggaagcggttggtttagactataaaacattaccgc aagatgtggttccgggcgatatcttattattagatgacggtcgagttcaattgaaagtattggcaaccgaaggtgcaaaagtattcaccg aagtaacggtcggtggcccactatcaaataataaaggcattaacaaattaggctgcggtttatctgccgatgcattaaccgaaaaaga taaagcggatatcattactgcggcgcgtatcggtgtggattaccttgccgtatctttcccgcgttcaagcgcggatttaaactacgcccgt caattagcaaaagatgcgggcttgatgcgaaaatcgttgcgaaagtagaacgtgccgaaacagttgaaacggacgaagcaatg gacgatatcatcaatgcggcggacgtaatcatggttgcgcgcggtgacttaggtgttgaaatcggtgatccggaattagtcggtgttcag aaaaaattaatccgtcgttcacgtcagttaaatcgtgttgttattaccgcaactcaaatgatggaatcaatgattagtaatcctatgccgac tcgtgcggaagtaatggacgtagctaacgcagtattggacggtaccgatgcggtaatgctttctgctgaaaccgcggctggtcaatatc cggcggaaactgttgcggcgatggcgaaagttgcgttaggtgcggagaaaatgccaagcattaatgtgtctaaacaccgtatgaacg ttcaattcgagtctattgaagaatctgttgcgatgtctgcaatgtatgcggcaaaccacatgagaggcgtagcggcgattatcacattaa caagtagcggtcgtactgctcgtttaatgtctagactccataggccgctttcctggctttgcttccagatgtatgctctcctccggagagtac cgtgactttattttcggcacaaatacaggggtcgatggataaatacggcgatagtttcctgacggatgatccgtatgtaccggcggaag acaagctgcaaacctgtcagatggagattgatttaatggcggatgtgctgagagcaccgccccgtgaatccgcagaactgatccgct atgtgtttgcggatgattggccggaataaataaagccgggcttaatacagattaagcccgtataggggtattattactgaataccaaaca gcttacggaggacggaatgttaccccattgagacaaccagactgccttctgattattaatattttttcactattaatcagaaggaataaccat gaattttacccggattgacctgaatacctggaatcgcagggaacactttgccctttatcgtcagcagattaaatgcggattcagcctgac -continued

```
caccaaactcgatattaccgctttgcgtaccgcactggcggagacaggttataagttttatccgctgatgatttacctgatctcccgggct
gttaatcagtttccggagttccggatggcactgaaagacaatgaacttatttactgggaccagtcagacccggtctttactgtctttcataa
agaaaccgaaacattctctgcactgtcctgccgttattttccggatctcagtgagtttatggcaggttataatgcggtaacggcagaatat
cagcatgataccagattgtttccgcagggaaatttaccggagaatcacctgaatatatcatcattaccgtgggtgagttttgacgggattt
aacctgaacatcaccggaaatgatgattattttgccccggttttttacgatggcaaagtttcagcaggaaggtgaccgcgtattattacctg
tttctgtacaggttcatcatgcagtctgtgatggctttcatgcagcacggtttattaatacacttcagctgatgtgtgataacatactgaaata
aattaattaattctgtatttaagccaccgtatccggcaggaatggtggcttttttttttatattttaaccgtaatctgtaatttcgtttcagactggttc
aggatgagctcgcttggactcctgttgatagatccagtaatgacctcagaactccatctggatttgttcagaacgctcggttgccgccgg
gcgttttttattggtgagaatccaagcactagcggcgcgccggccggcccggtgtgaaataccgcacagatgcgtaaggagaaaat
accgcatcaggcgctcttccgcttcctcgctcactgactcgctgcgctcggtcgttcggctgcggcgagcggtatcagctcactcaaag
gcggtaatacgttatccacagaatcagggggataacgcaggaaagaacatgtgagcaaaaggccagcaaaaggccaggaacc
gtaaaaaggccgcgttgctggcgtttttccataggctccgcccccctgacgagcatcacaaaaatcgacgctcaagtcagaggtggc
gaaacccgacaggactataaagataccaggcgtttccccctggaagctccctcgtgcgctctcctgttccgaccctgccgcttaccgg
atacctgtccgcctttctcccttcgggaagcgtggcgctttctcatagctcacgctgtaggtatctcagttcggtgtaggtcgttcgctccaa
gctgggctgtgtgcacgaaccccccgttcagcccgaccgctgcgccttatccggtaactatcgtcttgagtccaacccggtaagacac
gacttatcgccactggcagcagccactggtaacaggattagcagagcgaggtatgtaggcggtgctacagagttcttgaagtggtgg
cctaactacggctacactagaaggacagtatttggtatctgcgctctgctgaagccagttaccttcggaaaaagagttggtagctcttga
tccggcaaacaaaccaccgctggtagcggtggtttttttgtttgcaagcagcagattacgcgcagaaaaaaaggatctcaagaagat
cctttgatcttttctacggggtctgacgctcagtggaacgaaaactcacgttaagggattttggtcatgagattatcaaaaaggatcttcac
ctagatccttttaaaggccggccgcggccgccatcggcattttcttttgcgttttttatttgttaactgttaattgtccttgttcaaggatgctgtctt
gacaacagatgttttcttgcctttgatgttcagcaggaagctcggcgcaaacgttgattgtttgtctgcgtagaatcctctgtttgtcatatag
cttgtaatcacgacattgtttcctttcgcttgaggtacagcgaagtgtgagtaagtaaaggttacatcgttaggatcaagatccattttaac
acaaggccagttttgttcagcggcttgtatgggccagttaaagaattagaaacataaccaagcatgtaaatatcgttagacgtaatgcc
gtcaatcgtcattttgatccgcgggagtcagtgaacaggtaccatttgccgttcatttaaagacgttcgcgcgttcaatttcatctgttactg
tgttagatgcaatcagcggtttcatcacttttttcagtgtgtaatcatcgtttagctcaatcataccgagagcgccgtttgctaactcagccgt
gcgttttttatcgctttgcagaagttttgacttcttgacggaagaatgatgtgcttttgccatagtatgctttgttaaataaagattcttcgcctt
ggtagccatcttcagttccagtgtttgcttcaaatactaagtatttgtggcctttatcttctacgtagtgaggatctctcagcgtatggttgtcgc
ctgagctgtagttgccttcatcgatgaactgctgtacattttgatacgttttccgtcaccgtcaaagattgatttataatcctctacaccgttga
tgttcaaagagctgtctgatgctgatacgttaacttgtgcagttgtcagtgtttgtttgccgtaatgtttaccggagaaatcagtgtagaataa
acggattttccgtcagatgtaaatgtggctgaacctgaccattcttgtgtttggtcttttaggatagaatcatttgcatcgaatttgtcgctgtct
ttaaagacgcggccagcgttttccagctgtcaatagaagtttcgcgcgactttttgatagaacatgtaaatcgatgtgtcatccgcatttttta
ggatctccggctaatgcaaagacgatgtggtagccgtgatagtttgcgacagtgccgtcagcgttttgtaatggccagctgtcccaaac
gtccaggccttttcagaagagatatttttaattgtggacgaatcaaattcagaaacttgatattttcattttttttgctgttcagggatttgcag
catatcatggcgtgtaatatgggaaatgccgtatgtttccttatatggcttttggttcgtttctttcgcaaacgcttgagttgcgcctcctgccag
cagtgcggtagtaaaggttaatactgttgcttgttttgcaaacttttttgatgttcatcgttcatgtctccttttttatgtactgtgttagcggtctgctt
cttccagccctcctgtttgaagatggcaagttagttacgcacaataaaaaaagacctaaaatatgtaaggggtgacgccaaagtatac
actttgcccttttacacattttaggtcttgcctgctttatcagtaacaaaccgcgcgatttacttttcgacctcattctattagactctcgtttggat
tgcaactggtctattttcctcttttgtttgatagaaaatcataaaaggatttgcagactacgggcctaaagaactaaaaaatctatctgtttctt
ttcattctctgtattttttatagtttctgttgcatgggcataaagttgccttttaatcacaattcagaaaatatcataatatctcatttcactaaata
atagtgaacggcaggtatatgtgatgggttaaaaaggatcggcggccgctcgatttaaatc
```

SEQ ID NO: 11 (complete nucleotide sequence of plasmid pSacB_pykA3)
tcgagagcggatatcattactgcggcgcgtatcggtgtggattaccttgccgtatctttcccgcgttcaagcgcggatttaaactacgccc gtcaattagcaaaagatgcgggcttggatgcgaaaatcgttgcgaaagtagaacgtgccgaaacagttgaaacggacgaagcaat ggacgatatcatcaatgcggcggacgtaatcatggttgcgcgcggtgacttaggtgttgaaatcggtgatccggaattagtcggtgttca gaaaaattaatccgtcgttcacgtcagttaaatcgtgttgttattaccgcaactcaaatgatggaatcaatgattagtaatcctatgccga ctcgtgcggaagtaatggacgtagctaacgcagtattggacggtaccgatgcggtaatgcttctgctgaaaccgcggctggtcaatat ccggcggaaactgttgcggcgatggcgaaagttgcgttaggtgcggagaaaatgccaagcattaatgtgtctaaacaccgtatgaac gttcaattcgagtctattgaagaatctgttgcgatgtctgcaatgtatgcggcaaaccacatgagaggcgtagcggcgattatcacatta acaagtagcggtcgtactgctcgtttaatgtctcgcattagttccggtttaccaatctttgcattgtcacgtaacgaatctacattaaacttatg cgcattatatcgtggtgtgacaccggttcattttgataaagacagccgtacctcagaaggtgcgacagcggcggttcaattattaaaag acgaaggtttcttagtgtctggcgatttagtgttattaactcagggcgacgcaagcagttctagcggtactaaccttttgccgtacattgattg ttgaataataggcaatgaacaaaaaaacgatgatttaagtcatcgtttttttttttgcttttctataaaaattcggaaaaatgcaccgcacta tttgtttaacagatcttttaagcccgccttcattgccgacatctggctttcatcaacgctttgctttcccgctcgtcgatcatataggtgatggt ttcggaaagtgtcattttcatcttttttcgaatatttggaaaggcgtaaccaaaccccatattctaaatcaatagattttttcttcgtggataattttt ccgcgttaaagaaacgtttacgtctggctcgaatcgcctgatctaatttgataatcaacgattcagccatatgattggctatccattcttcaa tttttttcaggataattctggctttctaataaatcatgcactttgctttgctgcaaactgcgttcttcataacgggtaatattctcgccttcacgatttt ttttaattaaatacaaccatttccaatgcgcttcttgattttctaattttgatacttcatggataggttctccatctagactccataggccgctttc ctggctttgcttccagatgtatgctctcctccggagagtaccgtgactttattttcggcacaaatacaggggtcgatggataaatacggcg atagtttcctgacggatgatccgtatgtaccggcggaagacaagctgcaaacctgtcagatggagattgatttaatggcggatgtgctg agagcaccgccccgtgaatccgcagaactgatccgctatgtgtttgcggatgattggccggaataaataaagccgggcttaatacag attaagcccgtatagggtattattactgaataccaaacagcttacggaggacggaatgttacccattgagacaaccagactgccttctg attattaatatttttcactattaatcagaaggaataaccatgaattttaccccgattgacctgaatacctggaatcgcagggaacactttgc cctttatcgtcagcagattaaatgcggattcagcctgaccaccaaactcgatattaccgctttgcgtaccgcactggcggagacaggtt ataagttttatccgctgatgatttacctgatctcccgggctgttaatcagtttccggagttccggatggcactgaaagacaatgaacttattt actgggaccagtcagacccggtctttactgtcttcataaagaaaccgaaacattctctgcactgtcctgccgttattttccggatctcagtg agtttatggcaggttataatgcggtaacggcagaatatcagcatgataccagattgtttccgcagggaaatttaccggagaatcacctg aatatatcatcattaccgtgggtgagttttgacgggatttaacctgaacatcaccggaaatgatgattattttgccccggttttacgatggc aaagtttcagcaggaaggtgaccgcgtattattacctgtttctgtacaggttcatcatgcagtctgtgatggctttcatgcagcacggtttatt aatacacttcagctgatgtgtgataacatactgaaataaattaattaattctgtatttaagccaccgtatccggcaggaatggtggcttttttt ttatattttaaccgtaatctgtaatttcgtttcagactggttcaggatgagctcgcttggactcctgttgatagatccagtaatgacctcagaa ctccatctggatttgttcagaacgctcggttgccgccgggcgttttttattggtgagaatccaagcactagcggcgcgccggccggcccg gtgtgaaataccgcacagatgcgtaaggagaaaataccgcatcaggcgctcttccgcttcctcgctcactgactcgctgcgctcggtc gttcggctgcggcgagcggtatcagctcactcaaaggcggtaatacggttatccacagaatcaggggataacgcaggaaagaaca tgtgagcaaaaggccagcaaaaggccaggaaccgtaaaaaggccgcgttgctggcgtttttccataggctccgcccccctgacga gcatcacaaaaatcgacgctcaagtcagaggtggcgaaacccgacaggactataaagataccaggcgtttccccctggaagctcc ctcgtgcgctctcctgttccgaccctgccgcttaccggatacctgtccgcctttctcccttcgggaagcgtggcgctttctcatagctcacgc tgtaggtatctcagttcggtgtaggtcgttcgctccaagctgggctgtgtgcacgaaccccccgttcagcccgaccgctgcgccttatcc ggtaactatcgtcttgagtccaacccggtaagacacgacttatcgccactggcagcagccactggtaacaggattagcagagcgag gtatgtaggcggtgctacagagttcttgaagtggtggcctaactacggctacactagaaggacagtatttggtatctgcgctctgctgaa gccagttaccttcggaaaaagagttggtagctcttgatccggcaaacaaaccaccgctggtagcggtggtttttttgtttgcaagcagca gattacgcgcagaaaaaaaggatctcaagaagatcctttgatcttttctacggggtctgacgctcagtggaacgaaaactcacgttaa -continued gggattttggtcatgagattatcaaaaaggatcttcacctagatccttttaaaggccggccgcggccgccatcggcattttcttttgcgttttt atttgttaactgttaattgtccttgttcaaggatgctgtctttgacaacagatgttttcttgcctttgatgttcagcaggaagctcggcgcaaac gttgattgtttgtctgcgtagaatcctctgtttgtcatatagcttgtaatcacgacattgtttcctttcgcttgaggtacagcgaagtgtgagtaa gtaaaggttacatcgttaggatcaagatccattttttaacacaaggccagttttgttcagcggcttgtatgggccagttaaagaattagaaa cataaccaagcatgtaaatatcgttagacgtaatgccgtcaatcgtcattttgatccgcgggagtcagtgaacaggtaccatttgccgtt cattttaaagacgttcgcgcgttcaatttcatctgttactgtgttagatgcaatcagcggtttcatcactttttcagtgtgtaatcatcgtttagct caatcataccgagagcgccgtttgctaactcagccgtgcgtttttatcgctttgcagaagttttttgactttcttgacggaagaatgatgtgct tttgccatagtatgctttgttaaataaagattcttcgccttggtagccatcttcagttccagtgtttgcttcaaatactaagtatttgtggcctttat cttctacgtagtgaggatctctcagcgtatggttgtcgcctgagctgtagttgccttcatcgatgaactgctgtacattttgatacgtttttccgt caccgtcaaagattgatttataatcctctacaccgttgatgttcaaagagctgtctgatgctgatacgttaacttgtgcagttgtcagtgtttgt ttgccgtaatgtttaccggagaaatcagtgtagaataaacggattttccgtcagatgtaaatgtggctgaacctgaccattcttgtgtttgg tcttttaggatagaatcatttgcatcgaatttgtcgctgtctttaaagacgcggccagcgttttccagctgtcaatagaagtttcgccgacttt ttgatagaacatgtaaatcgatgtgtcatccgcattttaggatctccggctaatgcaaagacgatgtggtagccgtgatagtttgcgaca gtgccgtcagcgttttgtaatggccagctgtcccaaacgtccaggcctttgcagaagagatatttttaattgtggacgaatcaaattcag aaacttgatatttttcattttttgctgttcagggatttgcagcatatcatggcgtgtaatgggaaatgccgtatgtttccttatatggcttttggt tcgtttcttcgcaaacgcttgagttgcgcctcctgccagcagtgcggtagtaaaggttaatactgttgcttgttttgcaaacttttttgatgttca tcgttcatgtctccttttttatgtactgtgttagcggtctgcttcttccagccctcctgtttgaagatggcaagttagttacgcacaataaaaaaa gacctaaaatatgtaaggggtgacgccaaagtatacactttgccctttacacatttttaggtcttgcctgctttatcagtaacaaacccgcg cgatttacttttcgacctcattctattagactctcgtttggattgcaactggtctattttcctcttttgtttgatagaaaatcataaaaggatttgca gactacgggcctaaagaactaaaaaatctatctgtttcttttcattctctgtattttttatagtttctgttgcatgggcataaagttgcctttttaatc acaattcagaaaatatcataatatctcatttcactaaataatagtgaacggcaggtatatgtgatgggttaaaaaggatcggcggccgc tcgatttaaatc SEQ ID NO: 12 (complete nucleotide sequence of plasmid pSacB_pykA4)
tcgagagcggatatcattactgcggcgcgtatcggtgtggattaccttgccgtatctttcccgcgttcaagcgcggatttaaactacgccc gtcaattagcaaaagatgcgggcttggatgcgaaaatcgttgcgaaagtagaacgtgccgaaacagttgaaacggacgaagcaat ggacgatatcatcaatgcggcggacgtaatcatggttgcgcgcggtgacttaggtgttgaaatcggtgatccggaattagtcggtgttca gaaaaaattaatccgtcgttcacgtcagttaaatcgtgttgttattaccgcaactcaaatgatggaatcaatgattagtaatcctatgccga ctcgtgcggaagtaatggacgtagctaacgcagtattggacggtaccgatgcggtaatgctttctgctgaaaccgcggctggtcaatat ccggcggaaactgttgcggcgatggcgaaagttgcgttaggtgcggagaaaatgccaagcattaatgtgtctaaacaccgtatgaac gttcaattcgagtctattgaagaatctgttgcgatgtctgcaatgtatgcggcaaaccacatgagaggcgtagcggcgattatcacatta acaagtagcggtcgtactgctcgtttaatgtctcgcattagttccggtttaccaatctttgcattgtcacgtaacgaatctactttaaacttata cgcattatatcgtggtgtgacaccggttcattttgataaagacagccgtacctcagaaggtgcgacagcggcggttcaattattaaaag acgaaggtttcttagtgtctggcgatttagtgttattaactcagggcgacgcaagcagttctagcggtactaaccctttgccgtacattgattg ttgaataataggcaatgaacaaaaaaacgatgatttaagtcatcgttttttttttttgcttttctataaaaattcggaaaaatgcaccgcacta tttgtttaacagatcttttaagcccgccttcattgccgacatctggctttcatacaacgctttgctttcccgctcgtcgatcatataggtgatggt ttcggaaagtgtcattttcatcttttttcgaatatttggaaaggcgtaaccaaacccccatattctaaatcaatagatttttttcttcgtggataattttt ccgcgttaaagaaacgtttacgtctggctcgaatcgcctgatctaatttgataatcaacgattcagccatatgattggctatccattcttcaa ttttttcaggataattctggctttctaataaatcatgcactttgcttgctgcaaactgcgttcttcataacgggtaatattctcgccttcacgatttt ttttaattaaatacaaccatttccaatgcgcttcttgattttctaatttttgatacttcatggataggttctccatctagactccataggccgctttc ctggctttgcttccagatgtatgctctcctccggagagtaccgtgactttattttcggcacaaatacagggggtcgatggataaatacggcg atagtttcctgacggatgatccgtatgtaccggcggaagacaagctgcaaacctgtcagatggagattgatttaatggcggatgtgctg -continued

```
agagcaccgccccgtgaatccgcagaactgatccgctatgtgtttgcggatgattggccggaataaataaagccgggcttaatacag attaagcccgtatagggtattattactgaataccaaacagcttacggaggacggaatgttacccattgagacaaccagactgccttctg attattaatatttttcactattaatcagaaggaataaccatgaattttacccggattgacctgaatacctggaatcgcagggaacactttgc cctttatcgtcagcagattaaatgcggattcagcctgaccaccaaactcgatataccgctttgcgtaccgcactggcggagacaggtt ataagttttatccgctgatgatttacctgatctcccgggctgttaatcagtttccggagttccggatggcactgaaagacaatgaacttattt actgggaccagtcagacccggtctttactgtctttcataaagaaaccgaaacattctctgcactgtcctgccgttattttccggatctcagtg agtttatggcaggttataatgcggtaacggcagaatatcagcatgataccagattgtttccgcagggaaatttaccggagaatcacctg aatatatcatcattaccgtgggtgagttttgacgggatttaacctgaacatcaccggaaatgatgattattttgccccggttttttacgatggc aaagtttcagcaggaaggtgaccgcgtattattacctgtttctgtacaggttcatcatgcagtctgtgatggctttcatgcagcacggtttatt aatacacttcagctgatgtgtgataacatactgaaataaattaattaattctgtatttaagccaccgtatccggcaggaatggtggcttttttt ttatattttaaccgtaatctgtaatttcgtttcagactggttcaggatgagctcgcttggactcctgttgatagatccagtaatgacctcagaa ctccatctggatttgttcagaacgctcggttgccgccgggcgttttttattggtgagaatccaagcactagcggcgcgccggccggcccg gtgtgaaataccgcacagatgcgtaaggagaaaataccgcatcaggcgctcttccgcttcctcgctcactgactcgctgcgctcggtc gttcggctgcggcgagcggtatcagctcactcaaaggcggtaatacggttatccacagaatcaggggataacgcaggaaagaaca tgtgagcaaaaggccagcaaaaggccaggaaccgtaaaaaggccgcgttgctggcgtttttccataggctccgcccccctgacga gcatcacaaaaatcgacgctcaagtcagaggtggcgaaacccgacaggactataaagataccaggcgtttccccctggaagctcc ctcgtgcgctctcctgttccgaccctgccgcttaccggatacctgtccgcctttctcccttcgggaagcgtggcgctttctcatagctcacgc tgtaggtatctcagttcggtgtaggtcgttcgctccaagctgggctgtgtgcacgaaccccccgttcagcccgaccgctgcgccttatcc ggtaactatcgtcttgagtccaacccggtaagacacgacttatcgccactggcagcagccactggtaacaggattagcagagcgag gtatgtaggcggtgctacagagttcttgaagtggtggcctaactacggctacactagaaggacagtatttggtatctgcgctctgctgaa gccagttaccttcggaaaaagagttggtagctcttgatccggcaaacaaaccaccgctggtagcggtggtttttttgtttgcaagcagca gattacgcgcagaaaaaaaggatctcaagaagatcctttgatcttttctacggggtctgacgctcagtggaacgaaaactcacgttaa gggattttggtcatgagattatcaaaaaggatcttcacctagatccttttaaaggccggccgcggccgccatcggcattttcttttgcgttttt atttgttaactgttaattgtccttgttcaaggatgctgtctttgacaacagatgttttcttgcctttgatgttcagcaggaagctcggcgcaaac gttgattgtttgtctgcgtagaatcctctgtttgtcatatagcttgtaatcacgacattgtttccttttcgcttgaggtacagcgaagtgtgagtaa gtaaaggttacatcgttaggatcaagatccattttttaacacaaggccagttttgttcagcggcttgtatgggccagttaaagaattagaaa cataaccaagcatgtaaatatcgttagacgtaatgccgtcaatcgtcattttgatccgcgggagtcagtgaacaggtaccatttgccgtt cattttaaagacgttcgcgcgttcaatttcatctgttactgtgttagatgcaatcagcggtttcatcactttttttcagtgtgtaatcatcgtttagct caatcataccgagagcgccgtttgctaactcagccgtgcgttttttatcgctttgcagaagttttgactttcttgacggaagaatgatgtgct tttgccatagtatgctttgttaaataaagattcttcgccttggtagccatcttcagttccagtgtttgcttcaaatactaagtatttgtggcttat cttctacgtagtgaggatctctcagcgtatggttgtcgcctgagctgtagttgccttcatcgatgaactgctgtacattttgatacgttttccgt caccgtcaaagattgatttataatcctctacaccgttgatgttcaaagagctgtctgatgctgatacgttaacttgtgcagttgtcagtgtttgt ttgccgtaatgtttaccggagaaatcagtgtagaataaacggattttccgtcagatgtaaatgtggctgaacctgaccattcttgtgtttgg tctttttaggatagaatcatttgcatcgaatttgtcgctgtctttaaagacgcggccagcgttttttccagctgtcaatagaagtttcgccgacttt ttgatagaacatgtaaatcgatgtgtcatccgcatttttaggatctccggctaatgcaaagacgatgtggtagccgtgatagtttgcgaca gtgccgtcagcgttttgtaatggccagctgtcccaaacgtccaggccttttgcagaagagatattttaattgtggacgaatcaaattcag aaacttgatatttttcattttttgctgttcagggatttgcagcatatcatggcgtgtaatatgggaaatgccgtatgtttccttatatggcttttggt tcgtttctttcgcaaacgcttgagttgcgcctcctgccagcagtgcggtagtaaaggttaatactgttgcttgttttgcaaacttttttgatgttca tcgttcatgtctccttttttatgtactgtgttagcggtctgcttcttccagcccctcctgtttgaagatggcaagttagttacgcacaataaaaaaa gacctaaaatatgtaaggggtgacgccaaagtatacactttgcccttttacacattttaggtcttgcctgctttatcagtaacaaacccgcg
```

-continued cgatttacttttcgacctcattctattagactctcgtttggattgcaactggtctattttcctcttttgtttgatagaaaatcataaaaggatttgca gactacgggcctaaagaactaaaaaatctatctgtttcttttcattctctgtattttttatagtttctgttgcatgggcataaagttgcctttttaatc acaattcagaaaatatcataatatctcatttcactaaataatagtgaacggcaggtatatgtgatgggttaaaaaggatcggcggccgc tcgatttaaatc SEQ ID NO: 13 (complete nucleotid sequence of plasmid pSacB_pykA5)
tcgagcagaagattaagaagaacgaaaatcgtatgtacaatggggcctgcaacagacaaaggcaataatttagaaaaaatcattg ctgccggtgcaaacgttgtacgtatgaacttctcccacggtacgcccgaagatcatatcggtcgtgctgaaaaagtacgtgaaatcgct cataaattaggtaaacacgtagcaatcttaggtgacttacaaggccctaaaatccgtgtttctacttttaaagaaggcaaaattttcttaaa tatcggtgataaattcattttagacgcagagatgcctaaaggtgaaggtaaccaggaagcggttggtttagactataaaacattaccgc aagatgtggttccgggcgatatcttattattagatgacggtcgagttcaattgaaagtattggcaaccgaaggtgcaaaagtattcaccg aagtaacggtcggtggcccactatcaaataataaaggcattaacaaattaggcggcggtttatctggcgatgcgttaaccgaaaaag ataaagcggatatcattactgcggcgcgtatcggtgtggattaccttgccgtatctttcccgcgttcaagcgcggatttaaactacgcccg tcaattagcaaaagatgcgggcttggatgcgaaaatcgttgcgaaagtagaacgtgccgaaacagttgaaacggacgaagcaatg gacgatatcatcaatgcggcggacgtaatcatggttgcgcgcggtgacttaggtgttgaaatcggtgatccggaattagtcggtgttcag aaaaaattaatccgtcgttcacgtcagttaaatcgtgttgttattaccgcaactcaaatgatggaatcaatgattagtaatcctatgccgac tcgtgcggaagtaatggacgtagctaacgcagtattggacggtaccgatgcggtaatgctttctgctgaaaccgcggctggtcaatatc cggcggaaactgttgcggcgatggcgaaagttgcgttaggtgcggagaaaatgccaagcattaatgtgtctaaacaccgtatgaacg ttcaattcgagtctattgaagaatctgttgcgatgtctgcaatgtatgcggcaaaccacatgagaggcgtagcggcgattatcacattaa caagtagcggtcgtactgctcgtttaatgtctagactccataggccgctttcctggctttgcttccagatgtatgctctcctccggagagtac cgtgactttattttcggcacaaatacaggggtcgatggataaatacggcgatagtttcctgacggatgatccgtatgtaccggcggaag acaagctgcaaacctgtcagatggagattgatttaatggcggatgtgctgagagcaccgccccgtgaatccgcagaactgatccgct atgtgtttgcggatgattggccggaataaataaagccgggcttaatacagattaagcccgtatagggtattattactgaataccaaaca gcttacggaggacggaatgttacccattgagacaaccagactgccttctgattattaatattttcactattaatcagaaggaataaccat gaattttacccggattgacctgaatacctggaatcgcagggaacactttgcccttttatcgtcagcagattaaatgcggattcagcctgac caccaaactcgatattaccgctttgcgtaccgcactggcggagacaggttataagttttatccgctgatgatttacctgatctcccgggct gttaatcagtttccggagttccggatggcactgaaagacaatgaacttatttactgggaccagtcagacccggtctttactgtctttcataa agaaaccgaaacattctctgcactgtcctgccgttattttccggatctcagtgagtttatggcaggttataatgcggtaacggcagaatat cagcatgataccagattgtttccgcagggaaatttaccggagaatcacctgaatatatcatcattaccgtgggtgagttttgacgggattt aacctgaacatcaccggaaatgatgattattttgccccggttttacgatggcaaagtttcagcaggaaggtgaccgcgtattattacctg tttctgtacaggttcatcatgcagtctgtgatggctttcatgcagcacggtttattaatacacttcagctgatgtgtgataacatactgaaata aattaattaattctgtatttaagccaccgtatccggcaggaatggtggcttttttttatattttaaccgtaatctgtaatttcgtttcagactggttc aggatgagctcgcttggactcctgttgatagatccagtaatgacctcagaactccatctggatttgttcagaacgctcggttgccgccgg gcgttttttattggtgagaatccaagcactagcggcgcgccggccggcccggtgtgaaataccgcacagatgcgtaaggagaaaat accgcatcaggcgctcttccgcttcctcgctcactgactcgctgcgctcggtcgttcggctgcggcgagcggtatcagctcactcaaag gcggtaatacggttatccacagaatcaggggataacgcaggaaagaacatgtgagcaaaaggccagcaaaaggccaggaacc gtaaaaaggccgcgttgctggcgtttttccataggctccgcccccctgacgagcatcacaaaaatcgacgctcaagtcagaggtggc gaaacccgacaggactataaagataccaggcgtttccccctggaagctccctcgtgcgctctcctgttccgaccctgccgcttaccgg atacctgtccgcctttctcccttcgggaagcgtggcgctttctcatagctcacgctgtaggtatctcagttcggtgtaggtcgttcgctccaa gctgggctgtgtgcacgaaccccccgttcagcccgaccgctgcgccttatccggtaactatcgtcttgagtccaacccggtaagacac gacttatcgccactggcagcagccactggtaacaggattagcagagcgaggtatgtaggcggtgctacagagttcttgaagtggtgg cctaactacggctacactagaaggacagtatttggtatctgcgctctgctgaagccagttaccttcggaaaaagagttggtagctcttga -continued tccggcaaacaaaccaccgctggtagcggtggttttttttgtttgcaagcagcagattacgcgcagaaaaaaggatctcaagaagat cctttgatcttttctacggggtctgacgctcagtggaacgaaaactcacgttaagggattttggtcatgagattatcaaaaaggatcttcac ctagatccttttaaaggccggccgcggccgccatcggcattttcttttgcgttttttattgttaactgttaattgtccttgttcaaggatgctgtctt gacaacagatgttttcttgcctttgatgttcagcaggaagctcggcgcaaacgttgattgtttgtctgcgtagaatcctctgtttgtcatatag cttgtaatcacgacattgtttcctttcgcttgaggtacagcgaagtgtgagtaagtaaaggttacatcgttaggatcaagatccattttttaac acaaggccagttttgttcagcggcttgtatgggccagttaaagaattagaaacataaccaagcatgtaaatatcgttagacgtaatgcc gtcaatcgtcattttgatccgcgggagtcagtgaacaggtaccatttgccgttcattttaaagacgttcgcgcgttcaatttcatctgttactg tgttagatgcaatcagcggtttcatcactttttcagtgtgtaatcatcgtttagctcaatcataccgagagcgccgtttgctaactcagccgt gcgttttttatcgcttgcagaagttttgactttcttgacggaagaatgatgtgcttttgccatagtatgctttgttaaataaagattcttcgcctt ggtagccatcttcagttccagtgtttgcttcaaatactaagtatttgtggcctttatcttctacgtagtgaggatctctcagcgtatggttgtcgc ctgagctgtagttgccttcatcgatgaactgctgtacattttgatacgttttccgtcaccgtcaaagattgattataatcctctacaccgttga tgttcaaagagctgtctgatgctgatacgttaacttgtgcagttgtcagtgtttgtttgccgtaatgtttaccggagaaatcagtgtagaataa acggattttccgtcagatgtaaatgtggctgaacctgaccattcttgtgtttggtcttttaggataagaatcatttgcatcgaatttgtcgctgtct ttaaagacgcggccagcgttttccagctgtcaatagaagtttcgccgacttttttgatagaacatgtaaatcgatgtgtcatccgcatttttta ggatctccggctaatgcaaagacgatgtggtagccgtgatagtttgcgacagtgccgtcagcgttttgtaatggccagctgtcccaaac gtccaggccttttgcagaagagatatttttaattgtggacgaatcaaattcagaaacttgatatttttcattttttgctgttcagggatttgcag catatcatggcgtgtaatatgggaaatgccgtatgtttccttatatggcttttggttcgtttctttcgcaaacgcttgagttgcgcctcctgccag cagtgcggtagtaaaggttaatactgttgcttgttttgcaaacttttttgatgttcatcgttcatgtctccttttttatgtactgtgttagcggtctgctt cttccagccctcctgtttgaagatggcaagttagttacgcacaataaaaaaagacctaaaatatgtaaggggtgacgccaaagtatac actttgcccttttacacattttaggtcttgcctgctttatcagtaacaaaccgcgcgatttacttttcgacctcattctattagactctcgtttggat tgcaactggtctattttcctcttttgtttgatagaaaatcataaaaggatttgcagactacgggcctaaagaactaaaaaatctatctgtttctt ttcattctctgtatttttatagttttctgttgcatgggcataaagttgccttttttaatcacaattcagaaaatatcataatatctcatttcactaaata atagtgaacggcaggtatatgtgatgggttaaaaaggatcggcggccgctcgatttaaatc SEQ ID NO: 14 (complete nucleotide sequence of plasmid pSacB_pykA6)
tcgagcagaagattaagaagaacgaaaatcgtatgtacaatggggcctgcaacagacaaaggcaataatttagaaaaaatcattg ctgccggtgcaaacgttgtacgtatgaacttctcccacggtacgcccgaagatcatatcggtcgtgctgaaaaagtacgtgaaatcgct cataaattaggtaaacacgtagcaatcttaggtgacttacaaggccctaaaatccgtgttttctacttttaaagaaggcaaaattttcttaaa tatcggtgataaattcatttttagacgcagagatgcctaaaggtgaaggtaaccaggaagcggttggtttagactataaaacattaccgc aagatgtggttccgggcgatatcttattattagatgacggtcgagttcaattgaaagtattggcaaccgaaggtgcaaaagtattcaccg aagtaacggtcggtggcccactatcaaataataaaggcattaacaaattaggctgcggttatctgccgatgcgttaaccgaaaaaga taaagcggatatcattactgcggcgcgtatcggtgtggattaccttgccgtatctttcccgcgttcaagcgcggatttaaactacgcccgt caattagcaaaagatgcgggcttggatgcgaaaatcgttgcgaaagtagaacgtgccgaaacagttgaaacggacgaagcaatg gacgatatcatcaatgcggcggacgtaatcatggttgcgcgcggtgacttaggtgttgaaatcggtgatccggaattagtcggtgttcag aaaaaattaatccgtcgttcacgtcagttaaatcgtgttgttattaccgcaactcaaatgatggaatcaatgattagtaatcctatgccgac tcgtgcggaagtaatggacgtagctaacgcagtattggacggtaccgatgcggtaatgctttctgctgaaaccgcggctggtcaatatc cggcggaaactgttgcggcgatggcgaaagttgcgttaggtgcggagaaaatgccaagcattaatgtgtctaaacaccgtatgaacg ttcaattcgagtctattgaagaatctgttgcgatgtctgcaatgtatgcggcaaaccacatgagaggcgtagcggcgattatcacattaa caagtagcggtcgtactgctcgttaatgtctagactccataggccgcttcctggctttgcttccagatgtatgctctcctccggagagtac cgtgactttattttcggcacaaatacaggggtcgatggataaatacggcgatagtttcctgacggatgatccgtatgtaccggcggaag acaagctgcaaacctgtcagatggagattgatttaatggcggatgtgctgagagcaccgccccgtgaatccgcagaactgatccgct atgtgtttgcggatgattggccggaataaataaagcggggcttaatacagattaagcccgtatagggtattattactgaataccaaaca -continued

```
gcttacggaggacggaatgttacccattgagacaaccagactgccttctgattattaatattttttcactattaatcagaaggaataaccat
gaattttacccggattgacctgaatacctggaatcgcagggaacactttgcccttttatcgtcagcagattaaatgcggattcagcctgac
caccaaactcgatattaccgctttgcgtaccgcactggcggagacaggttataagttttatccgctgatgatttacctgatctcccgggct
gttaatcagtttccggagttccggatggcactgaaagacaatgaacttatttactgggaccagtcagacccggtctttactgtcttttcataa
agaaaccgaaacattctctgcactgtcctgccgttattttccggatctcagtgagtttatggcaggttataatgcggtaacggcagaatat
cagcatgataccagattgtttccgcagggaaatttaccggagaatcacctgaatatatcatcattaccgtgggtgagttttgacgggattt
aacctgaacatcaccggaaatgatgattattttgccccggttttttacgatggcaaagtttcagcaggaaggtgaccgcgtattattacctg
tttctgtacaggttcatcatgcagtctgtgatggctttcatgcagcacggtttattaatacacttcagctgatgtgtgataacatactgaaata
aattaattaattctgtatttaagccaccgtatccggcaggaatggtggcttttttttttatattttaaccgtaatctgtaatttcgtttcagactggttc
aggatgagctcgcttggactcctgttgatagatccagtaatgacctcagaactccatctggatttgttcagaacgctcggttgccgccgg
gcgttttttattggtgagaatccaagcactagcggcgcgccggccggcccggtgtgaaataccgcacagatgcgtaaggagaaaat
accgcatcaggcgctcttccgcttcctcgctcactgactcgctgcgctcggtcgttcggctgcggcgagcggtatcagctcactcaaag
gcggtaatacggttatccacagaatcaggggataacgcaggaaagaacatgtgagcaaaaggccagcaaaaggccaggaacc
gtaaaaaggccgcgttgctggcgtttttccataggctccgcccccctgacgagcatcacaaaaatcgacgctcaagtcagaggtggc
gaaacccgacaggactataaagataccaggcgtttccccctggaagctccctcgtgcgctctcctgttccgaccctgccgcttaccgg
atacctgtccgcctttctcccttcgggaagcgtggcgctttctcatagctcacgctgtaggtatctcagttcggtgtaggtcgttcgctccaa
gctgggctgtgtgcacgaaccccccgttcagcccgaccgctgcgccttatccggtaactatcgtcttgagtccaacccggtaagacac
gacttatcgccactggcagcagccactggtaacaggattagcagagcgaggtatgtaggcggtgctacagagttcttgaagtggtgg
cctaactacggctacactagaaggacagtatttggtatctgcgctctgctgaagccagttaccttcggaaaaagagttggtagctcttga
tccggcaaacaaaccaccgctggtagcggtggtttttttgtttgcaagcagcagattacgcgcagaaaaaaaggatctcaagaagat
cctttgatcttttctacggggtctgacgctcagtggaacgaaaactcacgttaagggattttggtcatgagattatcaaaaaggatcttcac
ctagatccttttaaaggccggccgcggccgccatcggcattttcttttgcgttttatttgttaactgttaattgtccttgttcaaggatgctgtcttt
gacaacagatgttttcttgcctttgatgttcagcaggaagctcggcgcaaacgttgattgtttgtctgcgtagaatcctctgtttgtcatatag
cttgtaatcacgacattgtttcctttcgcttgaggtacagcgaagtgtgagtaagtaaaggttacatcgttaggatcaagatccatttttaac
acaaggccagttttgttcagcggcttgtatgggccagttaaagaattagaaacataaccaagcatgtaaatatcgttagacgtaatgcc
gtcaatcgtcatttttgatccgcgggagtcagtgaacaggtaccatttgccgttcattttaaagacgttcgcgcgttcaatttcatctgttactg
tgttagatgcaatcagcggtttcatcacttttttcagtgtgtaatcatcgtttagctcaatcataccgagagcgccgtttgctaactcagccgt
gcgttttttatcgctttgcagaagttttgacttcttgacggaagaatgatgtgcttttgccatagtatgctttgttaaataaagattcttcgcctt
ggtagccatcttcagttccagtgtttgcttcaaatactaagtatttgtggcctttatcttctacgtagtgaggatctctcagcgtatggttgtcgc
ctgagctgtagttgccttcatcgatgaactgctgtacattttgatacgttttccgtcaccgtcaaagattgatttataatcctctacaccgttga
tgttcaaagagctgtctgatgctgatacgttaacttgtgcagttgtcagtgtttgtttgccgtaatgtttaccgagaaatcagtgtagaataa
acggattttccgtcagatgtaaatgtggctgaacctgaccattcttgtgtttggtcttttaggatagaatcatttgcatcgaatttgtcgctgtct
ttaaagacgcggccagcgttttttccagctgtcaatagaagtttcgccgactttttgatagaacatgtaaatcgatgtgtcatccgcatttttta
ggatctccggctaatgcaaagacgatgtggtagccgtgatagtttgcgacagtgccgtcagcgttttgtaatggccagctgtcccaaac
gtccaggccttttgcagaagagatatttttaattgtggacgaatcaaattcagaaacttgatatttttcatttttttgctgttcagggatttgcag
catatcatggcgtgtaatatggaaatgccgtatgtttccttatatggcttttggttcgtttctttcgcaaacgcttgagttgcgcctcctgccag
cagtgcggtagtaaaggttaatactgttgcttgttttgcaaacttttttgatgttcatcgttcatgtctccttttttatgtactgtgttagcggtctgctt
cttccagcccctcctgtttgaagatggcaagttagttacgcacaataaaaaaagacctaaaatatgtaaggggtgacgccaaagtatac
actttgcccttacacatttttaggtcttgcctgctttatcagtaacaaacccgcgcgatttacttttcgacctcattctattagactctcgtttggat
tgcaactggtctattttcctcttttgtttgatagaaaatcataaaaggatttgcagactacgggcctaaagaactaaaaaatctatctgtttctt
```

SEQ ID NO: 15 (nucleotide sequence of the pykA-gene from the DD1 ΔldhA ΔpflA pykA2-strain)
atgtccagaagattaagaagaacgaaaatcgtatgtacaatgggcctgcaacagacaaaggcaataatttagaaaaaatcattgc tgccggtgcaaacgttgtacgtatgaacttctcccacggtacgcccgaagatcatatcggtcgtgctgaaaaagtacgtgaaatcgctc ataaattaggtaaacacgtagcaatcttaggtgacttacaaggccctaaaatccgtgtttctacttttaaagaaggcaaaattttcttaaat atcggtgataaaattcattttagacgcagagatgcctaaaggtgaaggtaaccaggaagcggttggtttagactataaaacattaccgc aagatgtggttccgggcgatatcttattattagatgacggtcgagttcaattgaaagtattggcaaccgaaggtgcaaaagtattcaccg aagtaacggtcggtggcccactatcaaataataaaggcattaacaaattaggcTgcggtttatctgccgatgcattaaccgaaaaag ataaagcggatatcattactgcggcgcgtatcggtgtggattaccttgccgtatctttcccgcgttcaagcgcggatttaaactacgcccg tcaattagcaaaagatgcgggcttggatgcgaaaatcgttgcgaaagtagaacgtgccgaaacagttgaaacggacgaagcaatg gacgatatcatcaatgcggcggacgtaatcatggttgcgcgcggtgacttaggtgttgaaatcggtgatccggaattagtcggtgttcag aaaaaattaatccgtcgttcacgtcagttaaatcgtgttgttattaccgcaactcaaatgatggaatcaatgattagtaatcctatgccgac tcgtgcggaagtaatggacgtagctaacgcagtattggacggtaccgatgcggtaatgctttctgctgaaaccgcggctggtcaatatc cggcggaaactgttgcggcgatggcgaaagttgcgttaggtgcggagaaaatgccaagcattaatgtgtctaaacaccgtatgaacg ttcaattcgagtctattgaagaatctgttgcgatgtctgcaatgtatgcggcaaaccacatgagaggcgtagcggcgattatcacattaa caagtagcggtcgtactgctcgtttaatgtctcgcattagttccggtttaccaatctttgcattgtcacgtaacgaatctacattaaacttatgc gcattatatcgtggtgtgacaccggttcattttgataaagacagccgtacctcagaaggtgcgacagcggcggttcaattattaaaaga cgaaggtttcttagtgtctggcgatttagtgttattaactcagggcgacgcaagcagttctagcggtactaacctttgccgtacattgattgtt gaataa SEQ ID NO: 16 (amino acid sequence of PykA2 from the DD1 ΔldhA ΔpflA pykA2-strain)
MSRRLRRTKIVCTMGPATDKGNNLEKIIAAGANVVRMNFSHGTPEDHIGRAEKVREIAHKLGKH

VAILGDLQGPKIRVSTFKEGKIFLNIGDKFILDAEMPKGEGNQEAVGLDYKTLPQDVVPGDILLLD

DGRVQLKVLATEGAKVFTEVTVGGPLSNNKGINKLGCGLSADALTEKDKADIITAARIGVDYLAV

SFPRSSADLNYARQLAKDAGLDAKIVAKVERAETVETDEAMDDIINAADVIMVARGDLGVEIGDP

ELVGVQKKLIRRSRQLNRVVITATQMMESMISNPMPTRAEVMDVANAVLDGTDAVMLSAETAA

GQYPAETVAAMAKVALGAEKMPSINVSKHRMNVQFESIEESVAMSAMYAANHMRGVAAIITLT

SSGRTARLMSRISSGLPIFALSRNESTLNLCALYRGVTPVHFDKDSRTSEGATAAVQLLKDEGF

LVSGDLVLLTQGDASSSSGTNLCRTLIVE

SEQ ID NO: 17 (nucleotide sequence of the pykA-gene from the DD1 ΔldhA ΔpflD pykA4-strain)
atgtccagaagattaagaagaacgaaaatcgtatgtacaatgggcctgcaacagacaaaggcaataatttagaaaaaatcattgc tgccggtgcaaacgttgtacgtatgaacttctcccacggtacgcccgaagatcatatcggtcgtgctgaaaaagtacgtgaaatcgctc ataaattaggtaaacacgtagcaatcttaggtgacttacaaggccctaaaatccgtgtttctacttttaaagaaggcaaaattttcttaaat atcggtgataaaattcattttagacgcagagatgcctaaaggtgaaggtaaccaggaagcggttggtttagactataaaacattaccgc aagatgtggttccgggcgatatcttattattagatgacggtcgagttcaattgaaagtattggcaaccgaaggtgcaaaagtattcaccg aagtaacggtcggtggcccactatcaaataataaaggcattaacaaattaggcggcggtttatctgccgatgcattaaccgaaaaag ataaagcggatatcattactgcggcgcgtatcggtgtggattaccttgccgtatctttcccgcgttcaagcgcggatttaaactacgcccg tcaattagcaaaagatgcgggcttggatgcgaaaatcgttgcgaaagtagaacgtgccgaaacagttgaaacggacgaagcaatg gacgatatcatcaatgcggcggacgtaatcatggttgcgcgcggtgacttaggtgttgaaatcggtgatccggaattagtcggtgttcag aaaaaattaatccgtcgttcacgtcagttaaatcgtgttgttattaccgcaactcaaatgatggaatcaatgattagtaatcctatgccgac -continued tcgtgcggaagtaatggacgtagctaacgcagtattggacggtaccgatgcggtaatgctttctgctgaaaccgcggctggtcaatatc cggcggaaactgttgcggcgatggcgaaagttgcgttaggtgcggagaaaatgccaagcattaatgtgtctaaacaccgtatgaacg ttcaattcgagtctattgaagaatctgttgcgatgtctgcaatgtatgcggcaaaccacatgagaggcgtagcggcgattatcacattaa caagtagcggtcgtactgctcgtttaatgtctcgcattagttccggtttaccaatctttgcattgtcacgtaacgaatctacTttaaacttatac gcattatatcgtggtgtgacaccggttcattttgataaagacagccgtacctcagaaggtgcgacagcggcggttcaattattaaaaga cgaaggtttcttagtgtctggcgatttagtgttattaactcagggcgacgcaagcagttctagcggtactaacctttgccgtacattgattgtt gaataa SEQ ID NO: 18 (amino acid sequence of PykA4 from the DD1 ΔldhA ΔpflD pykA4-strain)
MSRRLRRTKIVCTMGPATDKGNNLEKIIAAGANVVRMNFSHGTPEDHIGRAEKVREIAHKLGKH

VAILGDLQGPKIRVSTFKEGKIFLNIGDKFILDAEMPKGEGNQEAVGLDYKTLPQDVVPGDILLLD

DGRVQLKVLATEGAKVFTEVTVGGPLSNNKGINKLGGGLSADALTEKDKADIITAARIGVDYLAV

SFPRSSADLNYARQLAKDAGLDAKIVAKVERAETVETDEAMDDIINAADVIMVARGDLGVEIGDP

ELVGVQKKLIRRSRQLNRVVITATQMMESMISNPMPTRAEVMDVANAVLDGTDAVMLSAETAA

GQYPAETVAAMAKVALGAEKMPSINVSKHRMNVQFESIEESVAMSAMYAANHMRGVAAIITLT

SSGRTARLMSRISSGLPIFALSRNESTLNLYALYRGVTPVHFDKDSRTSEGATAAVQLLKDEGF

LVSGDLVLLTQGDASSSSGTNLCRTLIVE

SEQ ID NO: 19 (nucleotide sequence of the pykA-gene from the DD1 ΔldhA ΔpflD pykA5-strain)
atgtccagaagattaagaagaacgaaaatcgtatgtacaatggggcctgcaacagacaaaggcaataatttagaaaaaatcattgc tgccggtgcaaacgttgtacgtatgaacttctcccacggtacgcccgaagatcatatcggtcgtgctgaaaaagtacgtgaaatcgctc ataaattaggtaaacacgtagcaatcttaggtgacttacaaggccctaaaatccgtgtttctacttttaaagaaggcaaaattttcttaaat atcggtgataaaattcattttagacgcagagatgcctaaaggtgaaggtaaccaggaagcggttggtttagactataaaacattaccgc aagatgtggttccgggcgatatcttattattagatgacggtcgagttcaattgaaagtattggcaaccgaaggtgcaaaagtattcaccg aagtaacggtcggtggcccactatcaaataataaaggcattaacaaattaggcggcggttatctctggcgatgcGttaaccgaaaaag ataaagcggatatcattactgcggcgcgtatcggtgtggattaccttgccgtatctttcccgcgttcaagcgcggatttaaactacgcccg tcaattagcaaaagatgcgggcttggatgcgaaaatcgttgcgaaagtagaacgtgccgaaacagttgaaacggacgaagcaatg gacgatatcatcaatgcggcggacgtaatcatggttgcgcgcggtgacttaggtgttgaaatcggtgatccggaattagtcggtgttcag aaaaaattaatccgtcgttcacgtcagttaaatcgtgttgttattaccgcaactcaaatgatggaatcaatgattagtaatcctatgccgac tcgtgcggaagtaatggacgtagctaacgcagtattggacggtaccgatgcggtaatgctttctgctgaaaccgcggctggtcaatatc cggcggaaactgttgcggcgatggcgaaagttgcgttaggtgcggagaaaatgccaagcattaatgtgtctaaacaccgtatgaacg ttcaattcgagtctattgaagaatctgttgcgatgtctgcaatgtatgcggcaaaccacatgagaggcgtagcggcgattatcacattaa caagtagcggtcgtactgctcgtttaatgtctcgcattagttccggtttaccaatctttgcattgtcacgtaacgaatctacattaaacttatgc gcattatatcgtggtgtgacaccggttcattttgataaagacagccgtacctcagaaggtgcgacagcggcggttcaattattaaaaga cgaaggtttcttagtgtctggcgatttagtgttattaactcagggcgacgcaagcagttctagcggtactaacctttgccgtacattgattgtt gaataa SEQ ID NO: 20 (amino acid sequence of PykA5 from the DD1 ΔldhA ΔpflD pykA5-strain)
MSRRLRRTKIVCTMGPATDKGNNLEKIIAAGANVVRMNFSHGTPEDHIGRAEKVREIAHKLGKH

VAILGDLQGPKIRVSTFKEGKIFLNIGDKFILDAEMPKGEGNQEAVGLDYKTLPQDVVPGDILLLD

DGRVQLKVLATEGAKVFTEVTVGGPLSNNKGINKLGGGLSGDALTEKDKADIITAARIGVDYLAV

SFPRSSADLNYARQLAKDAGLDAKIVAKVERAETVETDEAMDDIINAADVIMVARGDLGVEIGDP

ELVGVQKKLIRRSRQLNRVVITATQMMESMISNPMPTRAEVMDVANAVLDGTDAVMLSAETAA

GQYPAETVAAMAKVALGAEKMPSINVSKHRMNVQFESIEESVAMSAMYAANHMRGVAAIITLT

SSGRTARLMSRISSGLPIFALSRNESTLNLCALYRGVTPVHFDKDSRTSEGATAAVQLLKDEGF

LVSGDLVLLTQGDASSSGTNLCRTLIVE

SEQ ID NO: 21 (nucleotide sequence of the pykA-gene from the DD1 ΔldhA ΔpflD pykA6-strain)
atgtccagaagattaagaagaacgaaaatcgtatgtacaatgggcctgcaacagacaaaggcaataatttagaaaaaatcattgc tgccggtgcaaacgttgtacgtatgaacttctcccacggtacgcccgaagatcatatcggtcgtgctgaaaaagtacgtgaaatcgctc ataaattaggtaaacacgtagcaatcttaggtgacttacaaggccctaaaatccgtgtttctacttttaaagaaggcaaaattttcttaaat atcggtgataaattcattttagacgcagagatgcctaaaggtgaaggtaaccaggaagcggttggtttagactataaaacattaccgc aagatgtggttccgggcgatatcttattattagatgacggtcgagttcaattgaaagtattggcaaccgaaggtgcaaaagtattcaccg aagtaacggtcggtggcccactatcaaataataaaggcattaacaaattaggctgcggtttatctgccgatgcGttaaccgaaaaag ataaagcggatatcattactgcggcgcgtatcggtgtggattaccttgccgtatctttcccgcgttcaagcgcggatttaaactacgcccg tcaattagcaaaagatgcgggcttggatgcgaaaatcgttgcgaaagtagaacgtgccgaaacagttgaaacggacgaagcaatg gacgatatcatcaatgcggcggacgtaatcatggttgcgcgcggtgacttaggtgttgaaatcggtgatccggaattagtcggtgttcag aaaaaattaatccgtcgttcacgtcagttaaatcgtgttgttattaccgcaactcaaatgatggaatcaatgattagtaatcctatgccgac tcgtgcggaagtaatggacgtagctaacgcagtattggacggtaccgatgcggtaatgctttctgctgaaaccgcggctggtcaatatc cggcggaaactgttgcggcgatggcgaaagttgcgttaggtgcggagaaaatgccaagcattaatgtgtctaaacaccgtatgaacg ttcaattcgagtctattgaagaatctgttgcgatgtctgcaatgtatgcggcaaaccacatgagaggcgtagcggcgattatcacattaa caagtagcggtcgtactgctcgtttaatgtctcgcattagttccggtttaccaatctttgcattgtcacgtaacgaatctacattaaacttatgc gcattatatcgtggtgtgacaccggttcattttgataaagacagccgtacctcagaaggtgcgacagcggcggttcaattattaaaaga cgaaggtttcttagtgtctggcgatttagtgttattaactcagggcgacgcaagcagttctagcggtactaacctttgccgtacattgattgtt gaataa SEQ ID NO: 22 (amino acid sequence of PykA6 from the DD1 ΔldhA ΔpflD pykA6-strain)
MSRRLRRTKIVCTMGPATDKGNNLEKIIAAGANVVRMNFSHGTPEDHIGRAEKVREIAHKLGKH

VAILGDLQGPKIRVSTFKEGKIFLNIGDKFILDAEMPKGEGNQEAVGLDYKTLPQDVVPGDILLLD

DGRVQLKVLATEGAKVFTEVTVGGPLSNNKGINKLGCGLSADALTEKDKADIITAARIGVDYLAV

SFPRSSADLNYARQLAKDAGLDAKIVAKVERAETVETDEAMDDIINAADVIMVARGDLGVEIGDP

ELVGVQKKLIRRSRQLNRVVITATQMMESMISNPMPTRAEVMDVANAVLDGTDAVMLSAETAA

GQYPAETVAAMAKVALGAEKMPSINVSKHRMNVQFESIEESVAMSAMYAANHMRGVAAIITLT

SSGRTARLMSRISSGLPIFALSRNESTLNLCALYRGVTPVHFDKDSRTSEGATAAVQLLKDEGF

LVSGDLVLLTQGDASSSGTNLCRTLIVE

SEQ ID NO: 23 (sequence of the pykA4_fw primer)
aatgcggcggacgtaatcat

SEQ ID NO: 24 (sequence of the pykA4_rv primer)
tggagaacctatccatgaagtatca

SEQ ID NO: 25 (sequence of the pykA5/6_fw primer)
tggggcctgcaacagacaaa

SEQ ID NO: 26 (sequence of the pykA5/6_rv primer)
aaacgagcagtacgaccgct

SEQ ID NO: 27 (nucleotide sequence of ldhA-gene from strain DD1)
ttgacaaaatcagtatgtttaaataaggagctaactatgaaagttgccgtttacagtactaaaaattatgatcgcaaacatctggatttgg cgaataaaaaatttaattttgagcttcatttctttgattttttacttgatgaacaaaccgcgaaaatggcggagggcgccgatgccgtctgta ttttcgtcaatgatgatgcgagccgcccggtgttaacaaagttggcgcaaatcggagtgaaaattatcgctttacgttgtgccggttttaat aatgtggatttggaggcggcaaaagagctgggattaaaagtcgtacgggtgcctgcgtattcgccggaagccgttgccgagcatgcg atcggattaatgctgactttaaaaccgccgtatccataaggcttatcagcgtacccgcgatgcgaattttctctggaaggattggtcggtttt -continued aatatgttcggcaaaaccgccggagtgattggtacgggaaaaatcggcttggcggctattcgcattttaaaaggcttcggtatggacgtt ctggcgtttgatccttttaaaaatccggcggcggaagcgttgggcgcaaaatatgtcggtttagacgagctttatgcaaaatcccatgtta tcactttgcattgcccggctacggcggataattatcatttattaaatgaagcggcttttaataaaatgcgcgacggtgtaatgattattaata ccagccgcggcgttttaattgacagccgggcggcaatcgaagcgttaaaacggcagaaaatcggcgctctcggtatggatgtttatg aaaatgaacgggatttgttttttcgaggataaatctaacgatgttattacggatgatgtattccgtcgcctttcttcctgtcataatgtgctttttac cggtcatcaggcgttttaacggaagaagcgctgaataatatcgccgatgtgactttatcgaatattcaggcggtttccaaaaatgcaac gtgcgaaaatagcgttgaaggctaa SEQ ID NO: 28 (amino acid sequence of LdhA from strain DD1)
MTKSVCLNKELTMKVAVYSTKNYDRKHLDLANKKFNFELHFFDFLLDEQTAKMAEGADAVCIFV

NDDASRPVLTKLAQIGVKIIALRCAGFNNVDLEAAKELGLKVVRVPAYSPEAVAEHAIGLMLTLN

RRIHKAYQRTRDANFSLEGLVGFNMFGKTAGVIGTGKIGLAAIRILKGFGMDVLAFDPFKNPAAE

ALGAKYVGLDELYAKSHVITLHCPATADNYHLLNEAAFNKMRDGVMIINTSRGVLIDSRAAIEAL

KRQKIGALGMDVYENERDLFFEDKSNDVITDDVFRRLSSCHNVLFTGHQAFLTEEALNNIADVT

LSNIQAVSKNATCENSVEG

SEQ ID NO: 29 (nucleotide sequence of pflA-gene from strain DD1)
atgtcggttttaggacgaattcattcatttgaaacctgcgggacagttgacgggccgggaatccgctttattttattttttacaaggctgcttaa tgcgttgtaaatactgccataatagagacacctgggatttgcacggcggtaaagaaatttccgttgaagaattaatgaaagaagtggtg acctatcgccatttttatgaacgcctcgggcggcggagttaccgcttccggcggtgaagctattttacaggcggaatttgtacgggactgg ttcagagcctgccataaagaaggaattaatacttgcttggataccaacggtttcgtccgtcatcatgatcatatattgatgaattgattgat gacacggatcttgtgttgcttgacctgaaagaaatgaatgaacgggttcacgaaagcctgattggcgtgccgaataaaagagtgctcg aattcgcaaaatatttagcggatcgaaatcagcgtacctggatccgccatgttgtagtgccgggttatacagatagtgacgaagatttgc acatgctggggaatttcattaaagatatgaagaatatcgaaaaagtggaattattaccttatcaccgtctaggcgcccataaatgggaa gtactcggcgataaatacgagcttgaagatgtaaaaccgccgacaaaagaattaatggagcatgttaaggggttgcttgcaggctac gggcttaatgtgacatattag SEQ ID NO: 30 (amino acid sequence of PflA from strain DD1)
MSVLGRIHSFETCGTVDGPGIRFILFLQGCLMRCKYCHNRDTWDLHGGKEISVEELMKEVVTY

RHFMNASGGGVTASGGEAILQAEFVRDWFRACHKEGINTCLDTNGFVRHHDHIIDELIDDTDLV

LLDLKEMNERVHESLIGVPNKRVLEFAKYLADRNQRTWIRHVVVPGYTDSDEDLHMLGNFIKD

MKNIEKVELLPYHRLGAHKWEVLGDKYELEDVKPPTKELMEHVKGLLAGYGLNVTY

SEQ ID NO: 31 (nucleotide sequence of pflD-gene from strain DD1)
atggctgaattaacagaagctcaaaaaaaagcatgggaaggattcgttcccggtgaatggcaaaacggcgtaaatttacgtgactttt atccaaaaaaaactatactccgtatgaaggtgacgaatcattcttagctgatgcgactcctgcaaccagcgagttgtggaacagcgtga tggaaggcatcaaaatcgaaaacaaaactcacgcacctttagatttcgacgaacatactccgtcaactatcacttctcacaagcctgg ttatatcaataaagatttagaaaaaatcgttggtcttcaaacagacgctccgttaaaacgtgcaattatgccgtacggcggtatcaaaat gatcaaaggttcttgcgaagtttacggtcgtaaattagatccgcaagtagaatttatttttcaccgaatatcgtaaaacccataaccaagg cgtattcgacgtttatacgccggatattttacgctgccgtaaatcaggcgtgttaaccggtttaccggatgcttacggtcgtggtcgtattatc ggtgactaccgtcgtttagcggtatacggtattgattacctgatgaaagataaaaaagcccaattcgattcattacaaccgcgtttggaa gcgggcgaagacattcaggcaactatccaattacgtgaagaaattgccgaacaacaccgcgctttaggcaaaatcaaagaaatgg cggcatcttacggttacgacatttccggccctgcgacaaacgcacaggaagcaatccaatggacatattttgcttatctggcagcggtt aaatcacaaaacggtgcggcaatgtcattcggtcgtacgtctacattcttagatatctatatcgaacgtgacttaaaacgcggtttaatca ctgaacaacaggcgcaggaattaatggaccacttagtaatgaaattacgtatggttcgtttcttacgtacgccggaatacgatcaattatt ctcaggcgacccgatgtgggcaaccgaaactatcgccggtatgggcttagacggtcgtccgttggtaactaaaaacagcttccgcgt -continued

```
attacatactttatacactatgggtacttctccggaaccaaacttaactattctttggtccgaacaattacctgaagcgttcaaacgtttctgt gcgaaagtatctattgatacttcctccgtacaatacgaaaatgatgacttaatgcgtcctgacttcaacaacgatgactatgcaatcgcat gctgcgtataccgatggtcgtaggtaaacaaatgcaattcttcggtgcgcgcgcaaacttagctaaaactatgttatacgcaattaac ggcggtatcgatgagaaaaatggtatgcaagtcggtcctaaaactgcgccgattacagacgaagtattgaatttcgataccgtaatcg aacgtatggacagtttcatggactggttggcgactcaatatgtaaccgcattgaacatcatccacttcatgcacgataaatatgcatatg aagcggcattgatggcgttccacgatcgcgacgtattccgtacaatggcttgcggtatcgcgggtcttccgtggctgcggactcattatc cgcaatcaaatatgcgaaagttaaaccgattcgcggcgacatcaaagataaagacggtaatgtcgtggcctcgaatgttgctatcga cttcgaaattgaaggcgaatatccgcaattcggtaacaatgatccgcgtgttgatgatttagcggtagacttagttgaacgtttcatgaaa aaagttcaaaaacacaaaacttaccgcaacgcaactccgacacaatctatcctgactatcacttctaacgtggtatacggtaagaaa accggtaatactccggacggtcgtcgagcaggcgcgccattcggaccgggtgcaaacccaatgcacggtcgtgaccaaaaggt gcggttgcttcacttacttctgtggctaaacttccgttcgcttacgcgaaagacggtatttcatataccttctctatcgtaccgaacgcattag gtaaagatgacgaagcgcaaaaacgcaaccttgccggtttaatggacggttattccatcatgaagcgacagtggaaggcggtcaa cacttgaatgttaacgttcttaaccgtgaaatgttgttagacgcgatggaaaatccggaaaaatacccgcaattaaccattcgtgtttcag gttacgcggttcgtttcaactcattaactaaagagcaacaacaagacgtcatcactcgtacgtttacacaatcaatgtaa
```

SEQ ID NO: 32 (amino acid of PflD from strain DD1)

```
MAELTEAQKKAWEGFVPGEWQNGVNLRDFIQKNYTPYEGDESFLADATPATSELWNSVMEGI

KIENKTHAPLDFDEHTPSTITSHKPGYINKDLEKIVGLQTDAPLKRAIMPYGGIKMIKGSCEVYGR

KLDPQVEFIFTEYRKTHNQGVFDVYTPDILRCRKSGVLTGLPDAYGRGRIIGDYRRLAVYGIDYL

MKDKKAQFDSLQPRLEAGEDIQATIQLREEIAEQHRALGKIKEMAASYGYDISGPATNAQEAIQ

WTYFAYLAAVKSQNGAAMSFGRTSTFLDIYIERDLKRGLITEQQAQELMDHLVMKLRMVRFLRT

PEYDQLFSGDPMWATETIAGMGLDGRPLVTKNSFRVLHTLYTMGTSPEPNLTILWSEQLPEAF

KRFCAKVSIDTSSVQYENDDLMRPDFNNDDYAIACCVSPMVVGKQMQFFGARANLAKTMLYAI

NGGIDEKNGMQVGPKTAPITDEVLNFDTVIERMDSFMDWLATQYVTALNIIHFMHDKYAYEAAL

MAFHDRDVFRTMACGIAGLSVAADSLSAIKYAKVKPIRGDIKDKDGNVVASNVAIDFEIEGEYPQ

FGNNDPRVDDLAVDLVERFMKKVQKHKTYRNATPTQSILTITSNVVYGKKTGNTPDGRRAGAP

FGPGANPMHGRDQKGAVASLTSVAKLPFAYAKDGISYTFSIVPNALGKDDEAQKRNLAGLMDG

YFHHEATVEGGQHLNVNVLNREMLLDAMENPEKYPQLTIRVSGYAVRFNSLTKEQQQDVITRT

FTQSM
```

---

The invention claimed is:

1. A modified microorganism having, compared to its wild-type, a reduced activity of the enzyme that is encoded by the pykA-gene, wherein the activity of the enzyme encoded by the pykA-gene is reduced by introducing at least one mutation into the pykA-gene, wherein the reduction of the activity of the enzyme encoded by the pykA-gene is in the range of 15 to 99%, wherein the wild-type from which the modified microorganism has been derived belongs to the family of Pasteurellaceae, wherein the wildtype refers to the naturally occurring microorganism that has not been genetically modified and wherein the wild-type-pykA-gene comprises a nucleic acid selected from the group consisting of:
   a) a nucleic acid having the nucleotide sequence of SEQ ID NO: 3;
   b) a nucleic acid encoding the amino acid sequence of SEQ ID NO: 4;
   c) a nucleic acid which is at least 90% identical to the nucleic acid of a) or b), the identity being the identity over the total length of the nucleic acid of a) or b); and
   d) a nucleic acid encoding an amino acid sequence which is at least 90% identical to the amino acid sequence encoded by the nucleic acid of a) or b), the identity being the identity over the total length of amino acid sequence encoded by the nucleic acid of a) or b),
   wherein the modified microorganism, compared to the wild-type microorganism in which the activity of the enzyme encoded by the pykA-gene has not been reduced, is characterized by an increased yield of succinic acid and by faster growth when cultivated under anaerobic conditions with at least one assimilable carbon source.

2. The modified microorganism according to claim 1, wherein the wild-type from which the modified microorganism has been derived has a 16 S rDNA of SEQ ID NO: 1 or a sequence, which shows a sequence homology of at least 96% with SEQ ID NO: 1.

3. The modified microorganism according to claim 1, wherein the wild-type from which the modified microorganism has been derived belongs to the genus *Basfia*.

4. The modified microorganism according to claim 3, wherein the wild-type from which the modified microorganism has been derived belongs to the species *Basfia succiniciproducens*.

5. The modified microorganism according to claim 4, wherein the wild-type from which the modified microorganism has been derived is *Basfia succiniciproducens* strain DD1 as deposited under DSM 18541 with the DSMZ, Germany.

6. The modified microorganism according to claim 1, wherein the at least one mutation leads to a modification of the nucleic acid sequence of the pykA-gene, such that the amino acid sequence of the enzyme encoded by the modified gene differs from the amino acid sequence of the enzyme encoded by the wild-type pykA-gene in at least one amino acid.

7. The modified microorganism according to claim 1, wherein the microorganism further comprises:
   A) a deletion of the IdhA-gene or at least a part thereof, a deletion of a regulatory element of the IdhA-gene or at least a part thereof or an introduction of at least one mutation into the IdhA-gene;
   B) a deletion of the pflD-gene or at least a part thereof, a deletion of a regulatory element of the pflD-gene or at least a part thereof or an introduction of at least one mutation into the pflD-gene;
   C) a deletion of the pflA-gene or at least a part thereof, a deletion of a regulatory element of the pflA-gene or at least a part thereof or an introduction of at least one mutation into the pflA-gene;
   D) a deletion of the IdhA-gene or at least a part thereof, a deletion of a regulatory element of the IdhA-gene or at least a part thereof or an introduction of at least one mutation into the IdhA-gene
   and
   a deletion of the pflD-gene or at least a part thereof, a deletion of a regulatory element of the pflD-gene or at least a part thereof or an introduction of at least one mutation into the pflD-gene;
   or
   E) a deletion of the IdhA-gene or at least a part thereof, a deletion of a regulatory element of the IdhA-gene or at least a part thereof or an introduction of at least one mutation into the IdhA-gene
   and
   a deletion of the pflA-gene or at least a part thereof, a deletion of a regulatory element of the pflA-gene or at least a part thereof or an introduction of at least one mutation into the pflA-gene.

8. A method of producing succinic acid comprising:
   I) cultivating the modified microorganism according to claim 1 in a
   culture medium comprising at least one assimilable carbon source to allow the modified microorganism to produce succinic acid, thereby obtaining a fermentation broth comprising succinic acid;
   II) recovering succinic acid from the fermentation broth obtained in process step I).

9. Method according to claim 8, wherein the assimilable carbon source is selected from the group consisting of sucrose, maltose, D-glucose, glycerol, mixtures of glycerol and D-glucose, mixtures of glycerol and sucrose, mixtures of glycerol and D-xylose, mixtures of glycerol and mixtures of maltose and D-glucose and fructose.

10. Method according to claim 8, wherein the process further comprises the process step:

III) conversion of succinic acid contained in the fermentation broth obtained in process step I) or conversion of the recovered succinic acid obtained in process step II) into a secondary organic product being different from succinic acid by at least one chemical reaction.

11. Method according to claim 10, wherein the secondary organic product is selected from the group consisting of succinic acid esters or polymers thereof, tetrahydrofuran (THF), 1,4-butanediol (BDO), gamma-butyrolactone (GBL) and pyrrolidones.

* * * * *

SEQUENCE LISTING

<160> NUMBER OF SEQ ID NOS: 32

<210> SEQ ID NO 1
<211> LENGTH: 1517
<212> TYPE: DNA
<213> ORGANISM: Basfia succiniciproducens
<220> FEATURE:
<221> NAME/KEY: misc_feature
<222> LOCATION: (1)..(1517)
<223> OTHER INFORMATION: 16 S rDNA of strain DD1

<400> SEQUENCE: 1

```
tttgatcctg gctcagattg aacgctggcg gcaggcttaa cacatgcaag tcgaacggta      60
gcgggaggaa agcttgctttt cttttgccgac gagtggcgga cgggtgagta atgcttgggg    120
atctggctta tggaggggga taacgacggg aaactgtcgc taataccgcg taatatcttc     180
ggattaaagg gtgggacttt cgggccaccc gccataagat gagcccaagt gggattaggt     240
```

```
agttggtggg gtaaaggcct accaagccga cgatctctag ctggtctgag aggatgacca    300
gccacactgg aactgagaca cggtccagac tcctacggga ggcagcagtg gggaatattg    360
cacaatgggg ggaaccctga tgcagccatg ccgcgtgaat gaagaaggcc ttcgggttgt    420
aaagttcttt cggtgacgag gaaggtgttt gttttaatag acaagcaat tgacgttaat     480
cacagaagaa gcaccggcta actccgtgcc agcagccgcg gtaatacgga gggtgcgagc    540
gttaatcgga taactgggc gtaaagggca tgcaggcgga cttttaagtg agatgtgaaa     600
gccccgggct taacctggga attgcatttc agactgggag tctagagtac tttagggagg    660
ggtagaattc cacgtgtagc ggtgaaatgc gtagagatgt ggaggaatac cgaaggcgaa    720
ggcagcccct tgggaagata ctgacgctca tatgcgaaag cgtggggagc aaacaggatt    780
agataccctg gtagtccacg cggtaaacgc tgtcgatttg gggattgggc tttaggcctg    840
gtgctcgtag ctaacgtgat aaatcgaccg cctggggagt acggccgcaa ggttaaaact    900
caaatgaatt gacgggggcc cgcacaagcg gtggagcatg tggtttaatt cgatgcaacg    960
cgaagaacct tacctactct tgacatccag agaatcctgt agagatacgg gagtgccttc   1020
gggagctctg agacaggtgc tgcatggctg tcgtcagctc gtgttgtgaa atgttgggtt   1080
aagtcccgca acgagcgcaa cccttatcct ttgttgccag catgtaaaga tgggaactca   1140
aaggagactg ccggtgacaa accggaggaa ggtggggatg acgtcaagtc atcatggccc   1200
ttacgagtag ggctacacac gtgctacaat ggtgcataca gagggcggcg ataccgcgag   1260
gtagagcgaa tctcagaaag tgcatcgtag tccggattgg agtctgcaac tcgactccat   1320
gaagtcggaa tcgctagtaa tcgcaaatca gaatgttgcg gtgaatacgt tcccgggcct   1380
tgtacacacc gcccgtcaca ccatgggagt gggttgtacc agaagtagat agcttaacct   1440
tcgggggggg cgtttaccac ggtatgattc atgactgggg tgaagtcgta acaaggtaac   1500
cgtaggggaa cctgcgg                                                  1517

<210> SEQ ID NO 2
<211> LENGTH: 3008
<212> TYPE: DNA
<213> ORGANISM: Basfia succiniciproducens
<220> FEATURE:
<221> NAME/KEY: misc_feature
<222> LOCATION: (1)..(3008)
<223> OTHER INFORMATION: 23 S rDNA of strain DD1

<400> SEQUENCE: 2
agtaataacg aacgacacag gtataagaat acttgaggtt gtatggttaa gtgactaagc     60
gtacaaggtg gatgccttgg caatcagagg cgaagaagga cgtgctaatc tgcgaaaagc    120
ttgggtgagt tgataagaag cgtctaaccc aagatatccg aatgggggcaa cccagtagat   180
gaagaatcta ctatcaataa ccgaatccat aggttattga ggcaaaccgg gagaactgaa   240
acatctaagt accccgagga aaagaaatca accgagatta cgtcagtagc ggcgagcgaa    300
agcgtaagag ccggcaagtg atagcatgag gattagagga atcggctggg aagccgggcg    360
gcacaggtg atagccccgt acttgaaaat cattgtgtgg tactgagctt gcgagaagta    420
gggcgggaca cgagaaatcc tgtttgaaga aggggggacc atcctccaag gctaaatact    480
cctgattgac cgatagtgaa ccagtactgt gaaggaaagg cgaaaagaac cccggtgagg    540
ggagtgaaat agaaccctgaa accttgtacg tacaagcagt gggagcccgc gagggtgact    600
gcgtaccttt tgtataatgg gtcagcgact tatattatgt agcgaggtta accgaatagg    660
```

-continued

```
ggagccgaag ggaaaccgag tcttaactgg gcgtcgagtt gcatgatata gacccgaaac    720
ccggtgatct agccatgggc aggttgaagg ttgggtaaca ctaactggag gaccgaaccg    780
actaatgttg aaaaattagc ggatgacctg tggctggggg tgaaaggcca atcaaaccgg    840
gagatagctg gttctcccc g aaatctattt aggtagagcc ttatgtgaat accttcgggg    900
gtagagcact gtttcggcta gggggccatc ccggcttacc aacccgatgc aaactgcgaa    960
taccgaagag taatgcatag gagacacacg gcgggtgcta acgttcgtcg tggagaggga   1020
aacaacccag accgccagct aaggtcccaa agtttatatt aagtgggaaa cgaagtggga   1080
aggcttagac agctaggatg ttggcttaga agcagccatc atttaaagaa agcgtaatag   1140
ctcactagtc gagtcggcct gcgcggaaga tgtaacgggg ctcaaatata gcaccgaagc   1200
tgcggcatca ggcgtaagcc tgttgggtag gggagcgtcg tgtaagcgga agaaggtggt   1260
tcgagagggc tgctggacgt atcacgagtg cgaatgctga cataagtaac gataaaacgg   1320
gtgaaaaacc cgttcgccgg aagaccaagg gttcctgtcc aacgttaatc ggggcagggt   1380
gagtcggccc ctaaggcgag gctgaagagc gtagtcgatg ggaaacgggt taatattccc   1440
gtacttgtta taattgcgat gtggggacgg agtaggttag gttatcgacc tgttggaaaa   1500
ggtcgtttaa gttggtaggt ggagcgttta ggcaaatccg gacgcttatc aacaccgaga   1560
gatgatgacg aggcgctaag gtgccgaagt aaccgatacc acacttccag gaaaagccac   1620
taagcgtcag attataataa accgtactat aaaccgacac aggtggtcag gtagagaata   1680
ctcaggcgct tgagagaact cgggtgaagg aactaggcaa aatagcaccg taacttcggg   1740
agaaggtgcg ccggcgtaga ttgtagaggt atacccttga aggttgaacc ggtcgaagtg   1800
acccgctggc tgcaactgtt tattaaaaac acagcactct gcaaacacga aagtggacgt   1860 ataggggtgtg atgcctgccc ggtgctggaa ggttaattga tggcgttatc gcaagagaag   1920
cgcctgatcg aagccccagt aaacggcggc cgtaactata acggtcctaa ggtagcgaaa   1980
ttccttgtcg ggtaagttcc gacctgcacg aatggcataa tgatggccag gctgtctcca   2040
cccgagactc agtgaaattg aaatcgccgt gaagatgcgg tgtacccgcg gctagacgga   2100
aagaccccgt gaacctttac tatagcttga cactgaacct tgaattttga tgtgtaggat   2160
aggtgggagg ctttgaagcg gtaacgccag ttatcgtgga gccatccttg aaataccacc   2220
ctttaacgtt tgatgttcta acgaagtgcc cggaacgggt actcggacag tgtctggtgg   2280
gtagtttgac tggggcggtc tcctcccaaa gagtaacgga ggagcacgaa ggtttgctaa   2340
tgacggtcgg acatcgtcag gttagtgcaa tggtataagc aagcttaact gcgagacgga   2400
caagtcgagc aggtgcgaaa gcaggtcata gtgatccggt ggttctgaat ggaagggcca   2460
tcgctcaacg gataaaaggt actccgggga taacaggctg ataccgccca agagttcata   2520
tcgacggcgg tgtttggcac ctcgatgtcg gctcatcaca tcctgggct gaagtaggtc   2580 ccaagggtat ggctgttcgc catttaaagt ggtacgcgag ctgggtttaa aacgtcgtga   2640
gacagtttgg tccctatctg ccgtgggcgt tggagaattg agaggggctg ctcctagtac   2700
gagaggaccg gagtggacgc atcactggtg ttccggttgt gtcgccagac gcattgccgg   2760
gtagctacat gcggaagaga taagtgctga aagcatctaa gcacgaaact tgcctcgaga   2820
tgagttctcc cagtatttaa tactgtaagg gttgttggag acgacgacgt agataggccg   2880
ggtgtgtaag cgttgcgaga cgttgagcta accggtacta attgcccgag aggcttagcc   2940
atacaacgct caagtgtttt tggtagtgaa agttattacg gaataagtaa gtagtcaggg   3000
aatcggct                                                           3008
```

-continued

<210> SEQ ID NO 3
<211> LENGTH: 1440
<212> TYPE: DNA
<213> ORGANISM: Basfia succiniciproducens
<220> FEATURE:
<221> NAME/KEY: misc_feature
<222> LOCATION: (1)..(1440)
<223> OTHER INFORMATION: nucleotide sequence of pykA-gene from strain DD1

<400> SEQUENCE: 3

| | | | | | |
|---|---|---|---|---|---|
| atgtccagaa | gattaagaag | aacgaaaatc | gtatgtacaa | tggggcctgc | aacagacaaa | 60
| ggcaataatt | tagaaaaaat | cattgctgcc | ggtgcaaacg | ttgtacgtat | gaacttctcc | 120
| cacggtacgc | ccgaagatca | tatcggtcgt | gctgaaaaag | tacgtgaaat | cgctcataaa | 180
| ttaggtaaac | acgtagcaat | cttaggtgac | ttacaaggcc | ctaaaatccg | tgtttctact | 240
| tttaaagaag | gcaaaatttt | cttaaatatc | ggtgataaat | tcattttaga | cgcagagatg | 300
| cctaaaggtg | aaggtaacca | ggaagcggtt | ggtttagact | ataaaacatt | accgcaagat | 360
| gtggttccgg | gcgatatctt | attattagat | gacggtcgag | ttcaattgaa | agtattggca | 420
| accgaaggtg | caaaagtatt | caccgaagta | acggtcggtg | ccccactatc | aaataataaa | 480
| ggcattaaca | aattaggcgg | cggtttatct | gccgatgcat | taaccgaaaa | agataaagcg | 540
| gatatcatta | ctgcggcgcg | tatcggtgtg | gattaccttg | ccgtatcttt | cccgcgttca | 600
| agcgcggatt | taaactacgc | ccgtcaatta | gcaaagatg | cgggcttgga | tgcgaaaatc | 660
| gttgcgaaag | tagaacgtgc | cgaaacagtt | gaaacggacg | aagcaatgga | cgatatcatc | 720
| aatgcggcgg | acgtaatcat | ggttgcgcgc | ggtgacttag | gtgttgaaat | cggtgatccg | 780
| gaattagtcg | gtgttcagaa | aaaattaatc | cgtcgttcac | gtcagttaaa | tcgtgttgtt | 840
| attaccgcaa | ctcaaatgat | ggaatcaatg | attagtaatc | ctatgccgac | tcgtgcggaa | 900
| gtaatggacg | tagctaacgc | agtattggac | ggtaccgatg | cggtaatgct | ttctgctgaa | 960
| accgcggctg | gtcaatatcc | ggcggaaact | gttgcggcga | tggcgaaagt | gcgttaggt | 1020
| gcggagaaaa | tgccaagcat | taatgtgtct | aaacaccgta | tgaacgttca | attcgagtct | 1080
| attgaagaat | ctgttgcgat | gtctgcaatg | tatgcggcaa | accacatgag | aggcgtagcg | 1140
| gcgattatca | cattaacaag | tagccggtcgt | actgctcgtt | taatgtctcg | cattagttcc | 1200
| ggtttaccaa | tctttgcatt | gtcacgtaac | gaatctacat | taaacttatg | cgcattatat | 1260
| cgtggtgtga | caccggttca | ttttgataaa | gacagccgta | cctcagaagg | tgcgacagcg | 1320
| gcggttcaat | tattaaaaga | cgaaggtttc | ttagtgtctg | gcgatttagt | gttattaact | 1380
| cagggcgacg | caagcagttc | tagcggtact | aacctttgcc | gtacattgat | tgttgaataa | 1440

<210> SEQ ID NO 4
<211> LENGTH: 479
<212> TYPE: PRT
<213> ORGANISM: Basfia succiniciproducens
<220> FEATURE:
<221> NAME/KEY: SITE
<222> LOCATION: (1)..(479)
<223> OTHER INFORMATION: amino acid sequence pf PykA from strain DD1

<400> SEQUENCE: 4

Met Ser Arg Arg Leu Arg Arg Thr Lys Ile Val Cys Thr Met Gly Pro
1               5                   10                  15

Ala Thr Asp Lys Gly Asn Asn Leu Glu Lys Ile Ile Ala Ala Gly Ala
            20                  25                  30

Asn Val Val Arg Met Asn Phe Ser His Gly Thr Pro Glu Asp His Ile
          35                  40                  45

Gly Arg Ala Glu Lys Val Arg Glu Ile Ala His Lys Leu Gly Lys His
    50                  55                  60

Val Ala Ile Leu Gly Asp Leu Gln Gly Pro Lys Ile Arg Val Ser Thr
65                  70                  75                  80

Phe Lys Glu Gly Lys Ile Phe Leu Asn Ile Gly Asp Lys Phe Ile Leu
                85                  90                  95

Asp Ala Glu Met Pro Lys Gly Glu Gly Asn Gln Glu Ala Val Gly Leu
               100                 105                 110

Asp Tyr Lys Thr Leu Pro Gln Asp Val Val Pro Gly Asp Ile Leu Leu
           115                 120                 125

Leu Asp Asp Gly Arg Val Gln Leu Lys Val Leu Ala Thr Glu Gly Ala
   130                 135                 140

Lys Val Phe Thr Glu Val Thr Val Gly Gly Pro Leu Ser Asn Asn Lys
145                 150                 155                 160

Gly Ile Asn Lys Leu Gly Gly Leu Ser Ala Asp Ala Leu Thr Glu
                165                 170                 175

Lys Asp Lys Ala Asp Ile Ile Thr Ala Ala Arg Ile Gly Val Asp Tyr
            180                 185                 190

Leu Ala Val Ser Phe Pro Arg Ser Ser Ala Asp Leu Asn Tyr Ala Arg
        195                 200                 205

Gln Leu Ala Lys Asp Ala Gly Leu Asp Ala Lys Ile Val Ala Lys Val
    210                 215                 220

Glu Arg Ala Glu Thr Val Glu Thr Asp Glu Ala Met Asp Asp Ile Ile
225                 230                 235                 240

Asn Ala Ala Asp Val Ile Met Val Ala Arg Gly Asp Leu Gly Val Glu
                245                 250                 255

Ile Gly Asp Pro Glu Leu Val Gly Val Gln Lys Lys Leu Ile Arg Arg
            260                 265                 270

Ser Arg Gln Leu Asn Arg Val Val Ile Thr Ala Thr Gln Met Met Glu
    275                 280                 285

Ser Met Ile Ser Asn Pro Met Pro Thr Arg Ala Glu Val Met Asp Val
    290                 295                 300

Ala Asn Ala Val Leu Asp Gly Thr Asp Ala Val Met Leu Ser Ala Glu
305                 310                 315                 320

Thr Ala Ala Gly Gln Tyr Pro Ala Glu Thr Val Ala Ala Met Ala Lys
                325                 330                 335

Val Ala Leu Gly Ala Glu Lys Met Pro Ser Ile Asn Val Ser Lys His
            340                 345                 350

Arg Met Asn Val Gln Phe Glu Ser Ile Glu Glu Ser Val Ala Met Ser
        355                 360                 365

Ala Met Tyr Ala Ala Asn His Met Arg Gly Val Ala Ala Ile Ile Thr
    370                 375                 380

Leu Thr Ser Ser Gly Arg Thr Ala Arg Leu Met Ser Arg Ile Ser Ser
385                 390                 395                 400

Gly Leu Pro Ile Phe Ala Leu Ser Arg Asn Glu Ser Thr Leu Asn Leu
                405                 410                 415

Cys Ala Leu Tyr Arg Gly Val Thr Pro Val His Phe Asp Lys Asp Ser
            420                 425                 430

Arg Thr Ser Glu Gly Ala Thr Ala Ala Val Gln Leu Leu Lys Asp Glu
        435                 440                 445

```
Gly Phe Leu Val Ser Gly Asp Leu Val Leu Leu Thr Gln Gly Asp Ala
450                 455                 460

Ser Ser Ser Ser Gly Thr Asn Leu Cys Arg Thr Leu Ile Val Glu
465                 470                 475

<210> SEQ ID NO 5
<211> LENGTH: 4285
<212> TYPE: DNA
<213> ORGANISM: artificial sequence
<220> FEATURE:
<223> OTHER INFORMATION: complete nucleotide sequence of plasmid pSacB

<400> SEQUENCE: 5
tcgagaggcc tgacgtcggg cccggtacca cgcgtcatat gactagttcg gacctaggga      60
tatcgtcgac atcgatgctc ttctgcgtta attaacaatt gggatcctct agactccata     120
ggccgctttc ctggctttgc ttccagatgt atgctctcct ccggagagta ccgtgacttt     180
attttcggca caaatacagg ggtcgatgga taaatacggc gatagtttcc tgacggatga     240
tccgtatgta ccggcggaag acaagctgca aacctgtcag atggagattg atttaatggc     300
ggatgtgctg agagcaccgc cccgtgaatc cgcagaactg atccgctatg tgtttgcgga     360
tgattggccg gaataaataa agcccggctt aatacagatt aagcccgtat agggtattat     420
tactgaatac caaacagctt acggaggacg gaatgttacc cattgagaca accagactgc     480
cttctgatta ttaatatttt tcactattaa tcagaaggaa taaccatgaa ttttacccgg     540
attgacctga atacctggaa tcgcagggaa cactttgccc tttatcgtca gcagattaaa     600
tgcggattca gcctgaccac caaactcgat attaccgctt tgcgtaccgc actggcggag     660
acaggttata agttttatcc gctgatgatt tacctgatct cccgggctgt taatcagttt     720
ccggagttcc ggatggcact gaaagacaat gaacttattt actgggacca gtcagacccg     780
gtctttactg tctttcataa agaaaccgaa acattctctg cactgtcctg ccgttatttt     840
ccggatctca gtgagtttat ggcaggttat aatgcggtaa cggcagaata tcagcatgat     900
accagattgt ttccgcaggg aaatttaccg agaatcacc tgaatatatc atcattaccg     960
tgggtgagtt ttgacgggat ttaacctgaa catcaccgga aatgatgatt attttgcccc    1020
ggtttttacg atggcaaagt ttcagcagga aggtgaccgc gtattattac ctgtttctgt    1080
acaggttcat catgcagtct gtgatggctt tcatgcagca cggtttatta atacacttca    1140
gctgatgtgt gataacatac tgaaataaat taattaattc tgtatttaag ccaccgtatc    1200
cggcaggaat ggtggctttt ttttatatt ttaaccgtaa tctgtaattt cgtttcagac    1260
tggttcagga tgagctcgct tggactcctg ttgatagatc cagtaatgac ctcagaactc    1320
catctggatt tgttcagaac gctcggttgc cgccgggcgt tttttattgg tgagaatcca    1380
agcactagcg gcgcgccggc cggcccggtg tgaaataccg cacagatgcg taaggagaaa    1440
ataccgcatc aggcgctctt ccgcttcctc gctcactgac tcgctgcgct cggtcgttcg    1500
gctgcggcga gcggtatcag ctcactcaaa ggcggtaata cggttatcca cagaatcagg    1560
ggataacgca ggaaagaaca tgtgagcaaa aggccagcaa aaggccagga accgtaaaaa    1620
ggccgcgttg ctggcgtttt tccataggct ccgcccccct gacgagcatc acaaaaatcg    1680
acgctcaagt cagaggtggc gaaacccgac aggactataa agataccagg cgtttccccc    1740
tggaagctcc ctcgtgcgct ctcctgttcc gaccctgccg cttaccggat acctgtccgc    1800
ctttctccct tcgggaagcg tggcgctttc tcatagctca cgctgtaggt atctcagttc    1860
ggtgtaggtc gttcgctcca agctgggctg tgtgcacgaa ccccccgttc agcccgaccg    1920
```

```
ctgcgcctta tccggtaact atcgtcttga gtccaacccg gtaagacacg acttatcgcc    1980
actggcagca gccactggta acaggattag cagagcgagg tatgtaggcg gtgctacaga    2040
gttcttgaag tggtggccta actacggcta cactagaagg acagtatttg gtatctgcgc    2100
tctgctgaag ccagttacct tcggaaaaag agttggtagc tcttgatccg gcaaacaaac    2160
caccgctggt agcggtggtt ttttgtttg caagcagcag attacgcgca gaaaaaagg    2220 atctcaagaa gatcctttga tcttttctac ggggtctgac gctcagtgga acgaaaactc    2280
acgttaaggg attttggtca tgagattatc aaaaggatc ttcacctaga tccttttaaa    2340
ggccggccgc ggccgccatc ggcattttct tttgcgtttt tatttgttaa ctgttaattg    2400
tccttgttca aggatgctgt ctttgacaac agatgttttc ttgcctttga tgttcagcag    2460
gaagctcggc gcaaacgttg attgtttgtc tgcgtagaat cctctgtttg tcatatagct    2520
tgtaatcacg acattgtttc ctttcgcttg aggtacagcg aagtgtgagt aagtaaaggt    2580
tacatcgtta ggatcaagat ccattttaa cacaaggcca gttttgttca gcggcttgta    2640
tgggccagtt aaagaattag aaacataacc aagcatgtaa atatcgttag acgtaatgcc    2700
gtcaatcgtc attttgatc cgcgggagtc agtgaacagg taccatttgc cgttcatttt    2760
aaagacgttc gcgcgttcaa tttcatctgt tactgtgtta gatgcaatca gcggtttcat    2820 cactttttc agtgtgtaat catcgtttag ctcaatcata ccgagagcgc cgtttgctaa    2880
ctcagccgtg cgttttttat cgctttgcag aagttttga ctttcttgac ggaagaatga    2940
tgtgcttttg ccatagtatg ctttgttaaa taaagattct tcgccttggt agccatcttc    3000
agttccagtg tttgcttcaa atactaagta tttgtggcct ttatcttcta cgtagtgagg    3060
atctctcagc gtatggttgt cgcctgagct gtagttgcct tcatcgatga actgctgtac    3120
attttgatac gttttccgt caccgtcaaa gattgattta taatcctcta caccgttgat    3180
gttcaaagag ctgtctgatg ctgatacgtt aacttgtgca gttgtcagtg tttgtttgcc    3240
gtaatgttta ccggagaaat cagtgtagaa taaacggatt tttccgtcag atgtaaatgt    3300
ggctgaacct gaccattctt gtgtttggtc ttttaggata gaatcatttg catcgaattt    3360
gtcgctgtct ttaaagacgc ggccagcgtt tttccagctg tcaatagaag tttcgccgac    3420
tttttgatag aacatgtaaa tcgatgtgtc atccgcattt ttaggatctc cggctaatgc    3480
aaagacgatg tggtagccgt gatagtttgc gacagtgccg tcagcgtttt gtaatggcca    3540
gctgtcccaa acgtccaggc cttttgcaga agagatattt ttaattgtgg acgaatcaaa    3600
ttcagaaact tgatattttt catttttttg ctgttcaggg atttgcagca tatcatggcg    3660
tgtaatatgg gaaatgccgt atgtttcctt atatggcttt tggttcgttt ctttcgcaaa    3720
cgcttgagtt gcgcctcctg ccagcagtgc ggtagtaaag gttaatactg ttgcttgttt    3780
tgcaaacttt ttgatgttca tcgttcatgt ctccttttt atgtactgtg ttagcggtct    3840
gcttcttcca gccctcctgt ttgaagatgg caagttagtg acgcacaata aaaaagacc    3900 taaaatatgt aagggtgac gccaaagtat acactttgcc ctttacacat tttaggtctt    3960
gcctgcttta tcagtaacaa acccgcgcga tttacttttc gacctcattc tattagactc    4020
tcgtttggat tgcaactggt ctattttcct cttttgtttg atagaaaatc ataaaggat    4080 ttgcagacta cgggcctaaa gaactaaaaa atctatctgt ttcttttcat tctctgtatt    4140
ttttatagtt tctgttgcat gggcataaag ttgcctttt aatcacaatt cagaaaatat    4200
cataatatct catttcacta aataatagtg aacggcaggt atatgtgatg ggttaaaaag    4260
```

```
gatcggcggc cgctcgattt aaatc                                          4285
```

<210> SEQ ID NO 6
<211> LENGTH: 7074
<212> TYPE: DNA
<213> ORGANISM: artificial sequence
<220> FEATURE:
<223> OTHER INFORMATION: complete nucleotide sequence of plasmid pSacB_
      delta_ldhA

<400> SEQUENCE: 6

```
tcgagaggcc tgacgtcggg cccggtacca cgcgtcatat gactagttcg gacctaggga    60
tgggtcagcc tgaacgaacc gcacttgtat gtaggtagtt ttgaccgccc gaatattcgt   120
tataccttgg tggaaaaatt caaaccgatg gagcaattat acaattttgt ggcggcgcaa   180
aaaggtaaaa gcggtatcgt ctattgcaac agccgtagca aagtggagcg cattgcggaa   240
gccctgaaga aaagaggcat ttccgcagcc gcttatcatg cgggcatgga gccgtcgcag   300
cgggaagcgg tgcaacaggc gtttcaacgg ataatattc aagtggtggt ggcgaccatt   360
gcttttggta tggggatcaa caaatctaat gtgcgttttg tggcgcattt tgatttatct   420
cgcagcattg aggcgtatta tcaggaaacc gggcgcgcgg ggcgggacga cctgccggcg   480
gaagcggtac tgttttacga gccggcggat tatgcctggt tgcataaaat tttattggaa   540
gagccggaaa gcccgcaacg ggatattaaa cggcataagc tggaagccat cggcgaattt   600
gccgaaagcc agacctgccg tcgtttagtg ctgttaaatt atttcggcga aaaccgccaa   660
acgccatgta ataactgtga tatctgcctc gatccgccga aaaaatatga cggattatta   720
gacgcgcaga aaatcctttc gaccatttat cgcaccgggc aacgtttcgg cacgcaatac   780
gtaatcggcg taatgcgcgg tttgcagaat cagaaaataa agaaaatca acatgatgag   840
ttgaaagtct acggaattgg caaagataaa agcaaagaat actggcaatc ggtaattcgt   900
cagctgattc atttgggctt tgtgcaacaa atcatcagcg atttcggcat ggggaccaga   960
ttacagctca ccgaaagcgc gcgtcccgtg ctgcgcggcg aagtgtcttt ggaactggcc  1020
atgccgagat tatcttccat taccatggta caggctccgc aacgcaatgc ggtaaccaac  1080
tacgacaaag atttatttgc ccgcctgcgt ttcctgcgca acagattgc cgacaaagaa  1140
aacattccgc ttatattgt gttcagtgac gcgaccttgc aggaaatgtc gttgtatcag  1200
ccgaccagca aagtggaaat gctgcaaatc aacggtgtcg cgccatcaa atggcagcgc  1260
ttcggacagc ctttttatgg cgattattaa gaacatcagg ctttgcgtaa agcgggtaag  1320
aatccgttgg aattgcaatc ttaaaatttt taacttttg accgcacttt taaggttagc  1380
aaattccaat aaaaagtgcg gtgggttttc gggaattttt aacgcgctga tttcctcgtc  1440
ttttcaattt yttcgyctcc atttgttcgg yggttgccgg atccttctt gactgagatc  1500
cataagagag tagaatagcg ccgcttatat ttttaatagc gtacctaatc gggtacgctt  1560
tttttatgcg gaaaatccat atttttctac cgcactttt ctttaaagat ttatacttaa  1620
gtctgtttga ttcaatttat ttggaggttt tatgcaacac attcaactgg ctcccgattt  1680
aacattcagt cgcttaattc aaggattctg gcggttaaaa agctggcgga aatcgccgca  1740
ggaattgctt acattcgtta agcaaggatt agaattaggc gttgatacgc tggatcatgc  1800
cgcttgttac ggggctttta cttccgaggc ggaattcgga cgggcgctgg cgctggataa  1860
atccttgcgc gcacagctta cttttggtga caaatgcggg attttgtatc ctaatgaaga  1920
attacccgat ataaaatccc atcactatga caacagctac cgccatatta tgtggtcggc  1980
```

```
gcaacgttcc attgaaaaac tgcaatgcga ctatttagat gtattgctga ttcaccgwct    2040
ttctccctgt gcggatcccg aacaaatcgc gcgggctttt gatgaacttt atcaaaccgg    2100
raaagtacgt tatttcgggg tatctaacta tacgccggct aagttcgcca tgttgcaatc    2160
ttatgtgaat cagccgttaa tcactaatca aattgagatt tcgcctcttc atcgtcaggc    2220
ttttgatgac ggtaccctgg attttttact ggaaaaacgt attcaaccga tggcatggtc    2280
gccacttgcc ggcggtcgtt tattcaatca ggatgagaac agtcgggcgg tgcaaaaaac    2340
attactcgaa atcggtgaaa cgaaaggaga acccgttta gatacattgg cttatgcctg    2400
gttattggcg catccggcaa aaattatgcc ggttatgggg tccggtaaaa ttgaacgggt    2460
aaaaagcgcg gcggatgcgt tacgaatttc cttcactgag aagaatgga ttaaggttta    2520 tgttgccgca cagggacggg atattccgta acatcatccg tctaatcctg cgtatctggg    2580
gaaagatgcg tcatcgtaag aggtctataa tattcgtcgt tttgataagg gtgccatatc    2640
cggcacccgt taaaatcaca ttgcgttcgc aacaaaatta ttccttacga atagcattca    2700
cctcttttaa cagatgttga atatccgtat cggcaaaaat atcctctata tttgcggtta    2760
aacggcgccg ccagttagca tattgagtgc tggttcccgg aatattgacg ggttcggtca    2820
taccgagcca gtcttcaggt tggaatcccc atcgtcgaca tcgatgctct tctgcgttaa    2880
ttaacaattg ggatcctcta gactccatag gccgctttcc tggctttgct tccagatgta    2940
tgctctcctc cggagagtac cgtgacttta ttttcggcac aaatacaggg gtcgatggat    3000
aaatacggcg atagtttcct gacggatgat ccgtatgtac cggcggaaga caagctgcaa    3060
acctgtcaga tggagattga tttaatggcg gatgtgctga gagcaccgcc ccgtgaatcc    3120
gcagaactga tccgctatgt gtttgcggat gattggccgg aataaataaa gccgggctta    3180
atacagatta agcccgtata gggtattatt actgaatacc aaacagctta cggaggacgg    3240
aatgttaccc attgagacaa ccagactgcc ttctgattat taatattttt cactattaat    3300
cagaaggaat aaccatgaat tttacccgga ttgacctgaa tacctggaat cgcagggaac    3360
actttgccct ttatcgtcag cagattaaat gcggattcag cctgaccacc aaactcgata    3420
ttaccgcttt gcgtaccgca ctggcggaga caggttataa gttttatccg ctgatgattt    3480
acctgatctc ccgggctgtt aatcagtttc cggagttccg gatggcactg aaagacaatg    3540 aacttatta ctgggaccag tcagacccgg tctttactgt cttttcataaa gaaaccgaaa    3600 cattctctgc actgtcctgc cgttattttc cggatctcag tgagtttatg gcaggttata    3660
atgcggtaac ggcagaatat cagcatgata ccagattgtt tccgcaggga aatttaccgg    3720
agaatcacct gaatatatca tcattaccgt gggtgagttt tgacgggatt taacctgaac    3780
atcaccggaa atgatgatta ttttgccccg gtttttacga tggcaaagtt tcagcaggaa    3840
ggtgaccgcg tattattacc tgtttctgta caggttcatc atgcagtctg tgatggcttt    3900
catgcagcac ggtttattaa tacacttcag ctgatgtgtg ataacatact gaaataaatt    3960
aattaattct gtatttaagc caccgtatcc ggcaggaatg gtggcttttt ttttatttt    4020 taaccgtaat ctgtaatttc gtttcagact ggttcaggat gagctcgctt ggactcctgt    4080
tgatagatcc agtaatgacc tcagaactcc atctggattt gttcagaacg ctcggttgcc    4140
gccgggcgtt ttttattggt gagaatccaa gcactagcgg cgcgccggcc ggcccggtgt    4200
gaaataccgc acagatgcgt aaggagaaaa taccgcatca ggcgctcttc cgcttcctcg    4260
ctcactgact cgctgcgctc ggtcgttcgg ctgcggcgag cggtatcagc tcactcaaag    4320
gcggtaatac ggttatccac agaatcaggg gataacgcag gaaagaacat gtgagcaaaa    4380
```

```
ggccagcaaa aggccaggaa ccgtaaaaag gccgcgttgc tggcgttttt ccataggctc    4440
cgcccccctg acgagcatca caaaaatcga cgctcaagtc agaggtggcg aaacccgaca    4500
ggactataaa gataccaggc gtttccccct ggaagctccc tcgtgcgctc tcctgttccg    4560
accctgccgc ttaccggata cctgtccgcc tttctccctt cgggaagcgt ggcgctttct    4620
catagctcac gctgtaggta tctcagttcg gtgtaggtcg ttcgctccaa gctgggctgt    4680
gtgcacgaac cccccgttca gcccgaccgc tgcgccttat ccggtaacta tcgtcttgag    4740
tccaacccgg taagacacga cttatcgcca ctggcagcag ccactggtaa caggattagc    4800
agagcgaggt atgtaggcgg tgctacagag ttcttgaagt ggtggcctaa ctacggctac    4860
actagaagga cagtatttgg tatctgcgct ctgctgaagc cagttacctt cggaaaaaga    4920
gttggtagct cttgatccgg caaacaaacc accgctggta gcggtggttt ttttgtttgc    4980
aagcagcaga ttacgcgcag aaaaaaagga tctcaagaag atcctttgat cttttctacg    5040
gggtctgacg ctcagtggaa cgaaaactca cgttaaggga ttttggtcat gagattatca    5100
aaaaggatct tcacctagat ccttttaaag gccggccgcg gccgccatcg gcattttctt    5160
ttgcgttttt atttgttaac tgttaattgt ccttgttcaa ggatgctgtc tttgacaaca    5220
gatgttttct tgcctttgat gttcagcagg aagctcggcg caaacgttga ttgtttgtct    5280
gcgtagaatc ctctgtttgt catatagctt gtaatcacga cattgtttcc tttgcttga    5340 ggtacagcga agtgtgagta agtaaaggtt acatcgttag gatcaagatc cattttaac     5400 acaaggccag ttttgttcag cggcttgtat gggccagtta agaattaga acataacca      5460 agcatgtaaa tatcgttaga cgtaatgccg tcaatcgtca ttttgatcc gcgggagtca     5520 gtgaacaggt accatttgcc gttcatttta aagacgttcg cgcgttcaat ttcatctgtt    5580
actgtgttag atgcaatcag cggtttcatc acttttttca gtgtgtaatc atcgtttagc    5640
tcaatcatac cgagagcgcc gtttgctaac tcagccgtgc gttttttatc gctttgcaga    5700 agttttttgac tttcttgacg gaagaatgat gtgcttttgc catagtatgc tttgttaaat    5760
aaagattctt cgccttggta gccatcttca gttccagtgt ttgcttcaaa tactaagtat    5820
ttgtggcctt tatcttctac gtagtgagga tctctcagcg tatggttgtc gcctgagctg    5880
tagttgcctt catcgatgaa ctgctgtaca ttttgatacg ttttttccgtc accgtcaaag    5940 attgattat aatcctctac accgttgatg ttcaaagagc tgtctgatgc tgatacgtta     6000
acttgtgcag ttgtcagtgt ttgtttgccg taatgtttac cggagaaatc agtgtagaat    6060
aaacggattt ttccgtcaga tgtaaatgtg gctgaacctg accattcttg tgtttggtct    6120
tttaggatag aatcatttgc atcgaatttg tcgctgtctt taaagacgcg gccagcgttt    6180
ttccagctgt caatagaagt ttcgccgact ttttgataga acatgtaaat cgatgtgtca    6240
tccgcatttt taggatctcc ggctaatgca agacgatgt ggtagccgtg atagtttgcg     6300
acagtgccgt cagcgttttg taatggccag ctgtcccaaa cgtccaggcc ttttgcagaa    6360
gagatatttt taattgtgga cgaatcaaat tcagaaactt gatatttttc attttttgc     6420 tgttcaggga tttgcagcat atcatggcgt gtaatatggg aaatgccgta tgtttccta     6480 tatggctttt ggttcgtttc tttcgcaaac gcttgagttg cgcctcctgc cagcagtgcg    6540
gtagtaaagg ttaatactgt tgcttgtttt gcaaacttt tgatgttcat cgttcatgtc     6600 tccttttttta tgtactgtgt tagcggtctg cttcttccag ccctcctgtt tgaagatggc    6660
aagttagtta cgcacaataa aaaaagacct aaaatatgta aggggtgacg ccaaagtata    6720
```

| | | | |
|---|---|---|---|
| cactttgccc | tttacacatt | ttaggtcttg | cctgctttat cagtaacaaa cccgcgcgat | 6780 |
| ttacttttcg | acctcattct | attagactct | cgtttggatt gcaactggtc tattttcctc | 6840 |
| ttttgtttga | tagaaaatca | taaaaggatt | tgcagactac gggcctaaag aactaaaaaa | 6900 |
| tctatctgtt | tctttcatt | ctctgtattt | tttatagttt ctgttgcatg gcataaagt | 6960 |
| tgccttttta | atcacaattc | agaaaatatc | ataatatctc atttcactaa ataatagtga | 7020 |
| acggcaggta | tatgtgatgg | gttaaaaagg | atcggcggcc gctcgattta aatc | 7074 |

<210> SEQ ID NO 7
<211> LENGTH: 7183
<212> TYPE: DNA
<213> ORGANISM: artificial sequence
<220> FEATURE:
<223> OTHER INFORMATION: complete nucleotide sequence of plasmid pSacB_delta_pflA

<400> SEQUENCE: 7

| | | | |
|---|---|---|---|
| tcgagtcaat | gcggatttga | cttatgatgt | ggcaaacaac cgatttccga ttattactac | 60 |
| acgtaaaagt | tattggaaag | cggcgattgc | ggagtttctg ggttatatcc gcggctacga | 120 |
| taatgcggcg | gatttccgta | aattaggagc | aaaaacctgg gatgccaacg ctaatgaaaa | 180 |
| tcaggtatgg | ctgaataacc | ctcatcgcaa | aggcaccgac gacatggggc gcgtttacgg | 240 |
| cgtacagggc | agagcctggc | gtaagcctaa | cggcgaaacc gttgatcaat tacgcaaaat | 300 |
| tgtcaacaat | ttaagtcgcg | gcattgatga | tcgcggcgaa attctgacct ttttaaaccc | 360 |
| gggcgaattc | gatctcggtt | gtctgcgccc | ttgtatgtac aatcacacgt tttcttgct | 420 |
| gggcgatacg | ctttatttaa | ccagttatca | acgctcctgt gacgtacctt taggcttgaa | 480 |
| tttcaatcaa | attcaagtat | ttacattctt | agctttaatg gcgcagatta ccggtaaaaa | 540 |
| agccggtcag | gcatatcaca | aaatcgtcaa | tgcgcatatt tacgaagacc agctggaact | 600 |
| aatgcgcgac | gtgcagttaa | aacgcgaacc | gttcccgtcg ccaaaactgg aaattaatcc | 660 |
| ggacattaaa | acccttgaag | atttagaaac | ctgggtaacc atggatgatt tcaacgtcgt | 720 |
| tggttaccaa | tgccacgaac | cgataaaata | tccgttctcg gtataaaccg acaaaagtgc | 780 |
| ggtcaaaaat | ttaatatttt | catctgttat | agaaaatatt tttcaacata aaatctaggg | 840 |
| atgcctgttt | ggcgtccgta | aatacgcaga | aaaatattaa atttttgacc gcactttttt | 900 |
| catctcaatt | aacagcctga | taattcttat | ggatcaacaa attagctttg acgaaaaaat | 960 |
| gatgaatcga | gctctttcc | ttgccgacaa | ggcggaagct ttaggggaaa ttcccgtagg | 1020 |
| tgccgtattg | gtggatgaac | ggggcaatat | cattggtgaa ggctggaacc tctctattgt | 1080 |
| gaactcggat | cccaccgccc | atgccgaaat | tattgcgttg cgtaacgccg cgcagaaaat | 1140 |
| ccaaaattac | cgcctgctca | ataccacttt | atacgtgact ttagaaccct gcaccatgtg | 1200 |
| cgccggcgcg | attttacaca | gccgaatcaa | acgcttggta ttcggggcgt ccgattacaa | 1260 |
| aaccggtgcg | gtgggttcca | gatttcattt | ttttgaggat tataaaatga atcatggggt | 1320 |
| tgagatcaca | agcggtgtct | tacaggatca | atgcagtcag aagttaagcc gcttttccca | 1380 |
| aaagcgcagg | gaacagaaaa | aacaacaaaa | agctaccgca cttttacaac acccccggct | 1440 |
| taactcctct | gaaaaatagt | gacaaaaaaa | ccgtcataat gttacgacg gttttttat | 1500 |
| ttcttaatat | gcccttaaat | aatcaacaaa | atatagcaag aagattatag caaagaattt | 1560 |
| cgttttttc | agagaatagt | caatcttccg | caaaaaacta ccgcactttt atccgcttta | 1620 |
| atcaggggaa | ttaaaacaaa | aaaattccgc | ctattgaggc ggaatttatt aagcaataag | 1680 |

```
acaaactctc aattacattg attgtgtaaa cgtacgagtg atgacgtctt gttgttgctc   1740
tttagttaat gagttgaaac gaaccgcgta acctgaaaca cgaatggtta attgcgggta   1800
tttttccgga ttttccatcg cgtctaacaa catttcacgg ttaagaacgt taacattcaa   1860
gtgttgaccg ccttccactg tcgcttcatg atggaaataa ccgtccatta aaccggcaag   1920
gttgcgtttt tgcgcttcgt catctttacc taatgcgttc ggtacgatag agaaggtata   1980
tgaaataccg tctttcgcgt aagcgaacgg aagtttagcc acagaagtaa gtgaagcaac   2040
cgcacctttt tggtcacgac cgtgcattgg gtttgcaccc ggtccgaatg gcgcgcctgc   2100
tcgacgaccg tccggagtat taccggtttt cttaccgtat accacgttag aagtgatagt   2160
caggatagat tgtgtcggag ttgcgttgcg gtaagttttg tgttttgaa ctttttttcat   2220 gaaacgttca actaagtcta ccgctaaatc atcaacacgc ggatcattgt taccgaattg   2280
cggatattcg ccttcaattt cgaagtcgat agcaacattc gaggccacga cattaccgtc   2340
tttatctttg atgtcgccgc gaatcggttt aactttcgca tatttgattg cggataatga   2400
gtccgcagcc acggaaagac ccgcgatacc gcaagccatt gtacgaaata cgtcgcgatc   2460
gtggaacgcc atcaatgccg cttcatatgc atatttatcg tgcatgaagt ggatgatgtt   2520
caatgcggtt acatattgag tcgccaacca gtccatgaaa ctgtccatac gttcgattac   2580
ggtatcgaaa ttcaatactt cgtctgtaat cggcgcagtt ttaggaccga cttgcatacc   2640 attttttctca tcgataccgc cgttaattgc gtataacata gttttagcta agtttgcgcg   2700
cgcaccgaag aattgcattt gtttacctac gaccatcggt gatacgcagc atgcgattgc   2760
atagtcatcg ttgttgaagt caggacgcat taagtcatca ttttcgtatt gtacggagga   2820
agtatcaata gatactttcg cacagaaacg tttgaacgct tcaggtaatt gttcggacca   2880
aagaatagtt aagtttggtt ccggagaagt acccatagtg tataaagtat gtaatacgcg   2940
gaagctgttt ttagttacca acggacgacc gtctaagccc ataccggcga tagtttcggt   3000
tgccctctag actccatagg ccgctttcct ggctttgctt ccagatgtat gctctcctcc   3060
ggagagtacc gtgactttat tttcggcaca aatacagggg tcgatggata aatacggcga   3120
tagtttcctg acggatgatc cgtatgtacc ggcggaagac aagctgcaaa cctgtcagat   3180
ggagattgat ttaatggcgg atgtgctgag agcaccgccc cgtgaatccg cagaactgat   3240
ccgctatgtg tttgcggatg attggccgga ataaataaag ccgggcttaa tacagattaa   3300
gcccgtatag ggtattatta ctgaatacca aacagcttac ggaggacgga atgttaccca   3360
ttgagacaac cagactgcct tctgattatt aatattttc actattaatc agaaggaata   3420
accatgaatt ttacccggat tgacctgaat acctggaatc gcagggaaca ctttgccctt   3480
tatcgtcagc agattaaatg cggattcagc ctgaccacca aactcgatat taccgctttg   3540
cgtaccgcac tggcggagac aggttataag ttttatccgc tgatgattta cctgatctcc   3600
cgggctgtta atcagtttcc ggagttccgg atggcactga agacaatga acttatttac   3660 tgggaccagt cagacccggt ctttactgtc tttcataaag aaaccgaaac attctctgca   3720
ctgtcctgcc gttatttcc ggatctcagt gagtttatgg caggttataa tgcggtaacg   3780
gcagaatatc agcatgatac cagattgttt ccgcagggaa atttaccgga gaatcacctg   3840
aatatatcat cattaccgtg ggtgagtttt gacgggattt aacctgaaca tcaccggaaa   3900
tgatgattat tttgccccgg tttttacgat ggcaaagttt cagcaggaag gtgaccgcgt   3960
attattacct gtttctgtac aggttcatca tgcagtctgt gatggctttc atgcagcacg   4020
gtttattaat acacttcagc tgatgtgtga taacatactg aaataaatta attaattctg   4080
```

```
tatttaagcc accgtatccg gcaggaatgg tggcttttt tttatatttt aaccgtaatc     4140
tgtaatttcg tttcagactg gttcaggatg agctcgcttg gactcctgtt gatagatcca     4200
gtaatgacct cagaactcca tctggatttg ttcagaacgc tcggttgccg ccgggcgttt     4260
tttattggtg agaatccaag cactagcggc gcgccggccg gcccggtgtg aaataccgca     4320
cagatgcgta aggagaaaat accgcatcag gcgctcttcc gcttcctcgc tcactgactc     4380
gctgcgctcg tcgttcggc tgcggcgagc ggtatcagct cactcaaagg cggtaatacg     4440
gttatccaca gaatcagggg ataacgcagg aagaacatg tgagcaaaag gccagcaaaa      4500
ggccaggaac cgtaaaaagg ccgcgttgct ggcgtttttc cataggctcc gcccccctga     4560
cgagcatcac aaaaatcgac gctcaagtca gaggtggcga acccgacag gactataaag       4620
ataccaggcg tttccccctg gaagctccct cgtgcgctct cctgttccga ccctgccgct     4680
taccggatac ctgtccgcct ttctcccttc gggaagcgtg gcgctttctc atagctcacg     4740
ctgtaggtat ctcagttcgg tgtaggtcgt tcgctccaag ctgggctgtg tgcacgaacc     4800
ccccgttcag cccgaccgct gcgccttatc cggtaactat cgtcttgagt ccaacccggt     4860
aagacacgac ttatcgccac tggcagcagc cactggtaac aggattagca gagcgaggta     4920
tgtaggcggt gctacagagt tcttgaagtg gtggcctaac tacggctaca ctagaaggac     4980
agtatttggt atctgcgctc tgctgaagcc agttaccttc ggaaaaagag ttggtagctc     5040
ttgatccggc aaacaaacca ccgctggtag cggtggtttt tttgtttgca agcagcagat     5100
tacgcgcaga aaaaaaggat ctcaagaaga tcctttgatc ttttctacgg ggtctgacgc     5160
tcagtggaac gaaaactcac gttaagggat tttggtcatg agattatcaa aaaggatctt     5220
cacctagatc cttttaaagg ccggccgcgg ccgccatcgg catttctctt tgcgttttta     5280
tttgttaact gttaattgtc cttgttcaag gatgctgtct ttgacaacag atgttttctt     5340
gcctttgatg ttcagcagga agctcggcgc aaacgttgat tgtttgtctg cgtagaatcc     5400
tctgtttgtc atatagcttg taatcacgac attgtttcct ttcgcttgag gtacagcgaa     5460
gtgtgagtaa gtaaaggtta catcgttagg atcaagatcc atttttaaca caaggccagt     5520
tttgttcagc ggcttgtatg ggccagttaa agaattagaa acataaccaa gcatgtaaat     5580
atcgttagac gtaatgccgt caatcgtcat ttttgatccg cgggagtcag tgaacaggta     5640
ccatttgccg ttcattttaa agacgttcgc gcgttcaatt tcatctgtta ctgtgttaga     5700
tgcaatcagc ggtttcatca cttttttcag tgtgtaatca tcgtttagct caatcatacc     5760
gagagcgccg tttgctaact cagccgtgcg ttttttatcg ctttgcagaa gttttttgact     5820
ttcttgacgg aagaatgatg tgcttttgcc atagtatgct ttgttaaata aagattcttc     5880
gccttggtag ccatcttcag ttccagtgtt tgcttcaaat actaagtatt tgtggccttt     5940
atcttctacg tagtgaggat ctctcagcgt atggttgtcg cctgagctgt agttgccttc     6000
atcgatgaac tgctgtacat tttgatacgt ttttccgtca ccgtcaaaga ttgatttata     6060
atcctctaca ccgttgatgt tcaaagagct gtctgatgct gatacgttaa cttgtgcagt     6120
tgtcagtgtt tgtttgccgt aatgtttacc ggagaaatca gtgtagaata aacggatttt     6180
tccgtcagat gtaaatgtgg ctgaacctga ccattcttgt gtttggtctt ttaggataga     6240
atcatttgca tcgaatttgt cgctgtcttt aaagacgcgg ccagcgtttt tccagctgtc     6300
aatagaagtt tcgccgactt tttgatagaa catgtaaatc gatgtgtcat ccgcatttt      6360
aggatctccg gctaatgcaa agacgatgtg gtagccgtga tagtttgcga cagtgccgtc     6420
```

| | | | |
|---|---|---|---|
| agcgttttgt | aatggccagc tgtcccaaac | gtccaggcct tttgcagaag | agatattttt | 6480 |
| aattgtggac | gaatcaaatt cagaaacttg | atattttca ttttttgct | gttcagggat | 6540 |
| ttgcagcata | tcatggcgtg taatatggga | aatgccgtat gtttccttat | atggcttttg | 6600 |
| gttcgtttct | ttcgcaaacg cttgagttgc | gcctcctgcc agcagtgcgg | tagtaaaggt | 6660 |
| taatactgtt | gcttgttttg caaacttttt | gatgttcatc gttcatgtct | ccttttttat | 6720 |
| gtactgtgtt | agcggtctgc ttcttccagc | cctcctgttt gaagatggca | agttagttac | 6780 |
| gcacaataaa | aaagaccta aaatatgtaa | ggggtgacgc caaagtatac | actttgccct | 6840 |
| ttacacattt | taggtcttgc ctgctttatc | agtaacaaac ccgcgcgatt | tacttttcga | 6900 |
| cctcattcta | ttagactctc gtttggattg | caactggtct attttcctct | tttgtttgat | 6960 |
| agaaaatcat | aaaaggattt gcagactacg | ggcctaaaga actaaaaaat | ctatctgttt | 7020 |
| cttttcattc | tctgtatttt ttatagtttc | tgttgcatgg gcataaagtt | gccttttaa | 7080 |
| tcacaattca | gaaatatca taatatctca | tttcactaaa aatagtgaa | cggcaggtat | 7140 |
| atgtgatggg | ttaaaaagga tcggcggccg | ctcgatttaa atc | | 7183 |

<210> SEQ ID NO 8
<211> LENGTH: 7161
<212> TYPE: DNA
<213> ORGANISM: artificial sequence
<220> FEATURE:
<223> OTHER INFORMATION: complete nucleotide sequence of plasmid pSacB_
delta_pflD

<400> SEQUENCE: 8

| | | | |
|---|---|---|---|
| tcgagaggcc | tgacgtcggg cccggtacca | cgcgtcatat gactagttcg | gacctaggga | 60 |
| tgggatcgag | ctcttttcct tgccgacaag | gcggaagctt taggggaaat | tcccgtaggt | 120 |
| gccgtattgg | tggatgaacg gggcaatatc | attggtgaag gctggaacct | ctctattgtg | 180 |
| aactcggatc | ccaccgccca tgccgaaatt | attgcgttgc gtaacgccgc | gcagaaaatc | 240 |
| caaaattacc | gcctgctcaa taccacttta | tacgtgactt tagaaccctg | caccatgtgc | 300 |
| gccggcgcga | ttttacacag ccgaatcaaa | cgcttggtat cggggcgtc | cgattacaaa | 360 |
| accggtgcgg | tgggttccag atttcatttt | tttgaggatt ataaaatgaa | tcatggggtt | 420 |
| gagatcacaa | gcggtgtctt ataggatcaa | tgcagtcaga agttaagccg | ctttttccaa | 480 |
| aagcgcaggg | aacagaaaaa acaacaaaaa | gctaccgcac ttttacaaca | cccccggctt | 540 |
| aactcctctg | aaaatagtg acaaaaaaac | cgtcataatg tttacgacgg | tttttttatt | 600 |
| tcttctaata | tgtcacatta agcccgtagc | ctgcaagcaa cccttaaca | tgctccatta | 660 |
| attctttgt | cggcggtttt acatcttcaa | gctcgtattt atcgccgagt | acttcccatt | 720 |
| tatgggcgcc | tagacggtga taaggtaata | attccactt ttcgatattc | ttcatatctt | 780 |
| taatgaaatt | ccccagcatg tgcaaatctt | cgtcactatc tgtataaccc | ggcactacaa | 840 |
| catggcggat | ccaggtacgc tgatttcgat | ccgctaaata ttttgcgaat | tcgagcactc | 900 |
| ttttattcgg | cacgccaatc aggctttcgt | gaacccgttc attcatttct | ttcaggtcaa | 960 |
| gcaacacaag | atccgtgtca tcaatcaatt | catcaataat atgatcatga | tgacggacga | 1020 |
| aaccgttggt | atccaagcaa gtattaattc | cttctttatg gcaggctctg | aaccagtccc | 1080 |
| gtacaaattc | cgcctgtaaa atagcttcac | cgccggaagc ggtaactccg | ccgcccgagg | 1140 |
| cgttcataaa | atggcgatag gtcaccactt | ctttcattaa ttcttcaacg | gaatttctt | 1200 |
| taccgccgtg | caaatcccag gtgtctctgt | tatggcaata tttacaacgc | attaagcagc | 1260 |

```
cttgtaaaaa taaaataaag cggattcccg gcccgtcaac tgtcccgcag gtttcaaatg    1320
aatgaattcg tcctaaaacc gacataatat gcccttaaat aatcaacaaa atatagcaag    1380
aagattatag caaagaattt cgttttttc agagaatagt caaatcttcg caaaaaacta    1440
ccgcactttt atccgcttta atcaggggaa ttaaaacaaa aaaattccgc ctattgaggc    1500
ggaatttatt aagcaataag acaaactctc aattttaata cttccttctt ttctagtatt    1560
gataagattg aaaccttgca aggatgacgg cggatttgcc gtcactctca cccaactaat    1620
gtggacgact ggtaaaccat tgcattagac caatgcaaac accaccaccg acgatgttac    1680
ctaaagtaac aggaattaaa ttttaatta ctaaatggta catatctaaa tttgcaaact    1740
gctcggcatt taaacccgtt gcctgccaga attccggcga tgcgaaattt gcaattacca    1800
tgcccatagg gatcataaac atatttgcta cgcagtgttc aaagcctgaa gcgacaaaya    1860
acccgatcgg caggatcata ataaaagctt tatccgttag agtyttgccg gcataggcca    1920
tccaaacggc aatacatacc ataatgttgc aaagaatacc taaacagaag gcttcaayc    1980 aggtatgttc tattttatgt tgtgccgtat ttaaaatggt taatccccac tgaccgtttg    2040
ccgccatgat ctgaccggaa accaaaatta atgcaacaat aaataaaccg ccgacaaaat    2100
taccgaarta aaccacaatc cagttacgta acatctgaat tgttgtaatt ttactctcaa    2160
agcgggcaat agtcgataaa gttgatgaag taaatagttc acagccgcaa accgccacca    2220
taattacccc gagagagaac accaaaccgc cgaccagttt agttaatccc caaggcgctc    2280
ccgcagaggc tgtttgagtt gttgtataaa aaacgaatgc aagagcaata aacataccgg    2340
cagagatcgc cgataaaaat gaataggctt gtttttcgt agctttataa acgccgacgt    2400
ctaacccggt ttgagccatc tcggttggcg aagccatcca agccaattta aaatcttccg    2460
atttcattga gctttcctta gtaataaaac tactcggaaa tgagtagaac tgccttaaag    2520
cataaatgat agattaaaaa atccaaaatt gttgaatatt atttaacggg gggattataa    2580
aagattcata aattagataa tagctaattt gagtgatcca tatcaccttt tacagatttt    2640
ttgacctaaa tcaaaattac ccaaatagag taataatacc attataaagg gtgtggattt    2700
attcctttgg tttacgagat aaattgctat ttaagctgat ttctgataaa aagtgcggta    2760 gattttccc aaaaataagg aaacacaaaa tggcagaaga aacaattttc agtaaaatta    2820
ttcgtaaaga aattcccgcc gacattatat atcaagacga tcttgtcacc gcatttcgcg    2880
atattgcgcc gcaggcaaaa actcatattt taattattcc gaataaattg attccgacag    2940
taaacgacgt aaccgcccat cgtcgacatc gatgctcttc tgcgttaatt aacaattggg    3000
atcctctaga ctttgcttcc agatgtatgc tctcctccgg agagtaccgt gactttattt    3060
tcggcacaaa tacaggggtc gatggataaa tacggcgata gtttcctgac ggatgatccg    3120
tatgtaccgg cggaagacaa gctgcaaacc tgtcagatgg agattgattt aatggcggat    3180
gtgctgagag caccgccccg tgaatccgca gaactgatcc gctatgtgtt tgcggatgat    3240
tggccggaat aaataaagcc gggcttaata cagattaagc ccgtataggg tattattact    3300
gaataccaaa cagcttacgg aggacggaat gttacccatt gagacaacca gactgccttc    3360
tgattattaa tatttttcac tattaatcag aaggaataac catgaatttt acccggattg    3420
acctgaatac ctggaatcgc agggaacact ttgcccttta tcgtcagcag attaaatgcg    3480
gattcagcct gaccaccaaa ctcgatatta ccgctttgcg taccgcactg gcggagacag    3540
gttataagtt ttatccgctg atgatttacc tgatctcccg ggctgttaat cagtttccgg    3600
agttccggat ggcactgaaa gacaatgaac ttatttactg ggaccagtca gacccggtct    3660
```

```
ttactgtctt tcataaagaa accgaaacat tctctgcact gtcctgccgt tattttccgg    3720
atctcagtga gtttatggca ggttataatg cggtaacggc agaatatcag catgatacca    3780
gattgtttcc gcagggaaat ttaccggaga atcacctgaa tatatcatca ttaccgtggg    3840
tgagttttga cgggatttaa cctgaacatc accggaaatg atgattattt tgccccggtt    3900
tttacgatgg caaagtttca gcaggaaggt gaccgcgtat tattacctgt ttctgtacag    3960
gttcatcatg cagtctgtga tggctttcat gcagcacggt ttattaatac acttcagctg    4020
atgtgtgata acatactgaa ataaattaat taattctgta tttaagccac cgtatccggc    4080
aggaatggtg gctttttttt tatattttaa ccgtaatctg taatttcgtt tcagactggt    4140
tcaggatgag ctcgcttgga ctcctgttga tagatccagt aatgacctca gaactccatc    4200
tggatttgtt cagaacgctc ggttgccgcc gggcgttttt tattggtgag aatccaagca    4260
ctagcggcgc gccggccggc ccggtgtgaa ataccgcaca gatgcgtaag gagaaaatac    4320
cgcatcaggc gctcttccgc ttcctcgctc actgactcgc tgcgctcggt cgttcggctg    4380
cggcgagcgg tatcagctca ctcaaaggcg gtaatacggt tatccacaga atcaggggat    4440
aacgcaggaa agaacatgtg agcaaaaggc cagcaaaagg ccaggaaccg taaaaaggcc    4500
gcgttgctgg cgtttttcca taggctccgc cccctgacg agcatcacaa aaatcgacgc    4560
tcaagtcaga ggtggcgaaa cccgacagga ctataaagat accaggcgtt ccccctgga    4620 agctccctcg tgcgctctcc tgttccgacc ctgccgctta ccggatacct gtccgccttt    4680
ctcccttcgg gaagcgtggc gctttctcat agctcacgct gtaggtatct cagttcggtg    4740
taggtcgttc gctccaagct gggctgtgtg cacgaacccc ccgttcagcc cgaccgctgc    4800
gccttatccg gtaactatcg tcttgagtcc aacccggtaa gacacgactt atcgccactg    4860
gcagcagcca ctggtaacag gattagcaga gcgaggtatg taggcggtgc tacagagttc    4920
ttgaagtggt ggcctaacta cggctacact agaaggacag tatttggtat ctgcgctctg    4980
ctgaagccag ttaccttcgg aaaaagagtt ggtagctctt gatccggcaa acaaaccacc    5040
gctggtagcg gtggtttttt tgtttgcaag cagcagatta cgcgcagaaa aaaggatct    5100 caagaagatc ctttgatctt ttctacgggg tctgacgctc agtggaacga aaactcacgt    5160
taagggattt tggtcatgag attatcaaaa aggatcttca cctagatcct tttaaaggcc    5220
ggccgcggcc gccatcggca ttttcttttg cgttttatt tgttaactgt taattgtcct    5280
tgttcaagga tgctgtcttt gacaacagat gttttcttgc ctttgatgtt cagcaggaag    5340
ctcggcgcaa acgttgattg tttgtctgcg tagaatcctc tgtttgtcat atagcttgta    5400
atcacgacat tgtttccttt cgcttgaggt acagcgaagt gtgagtaagt aaaggttaca    5460
tcgttaggat caagatccat ttttaacaca aggccagttt tgttcagcgg cttgtatggg    5520
ccagttaaag aattagaaac ataaccaagc atgtaaatat cgttagacgt aatgccgtca    5580
atcgtcattt tgatccgcg ggagtcagtg aacaggtacc atttgccgtt catttaaag    5640 acgttcgcgc gttcaatttc atctgttact gtgttagatg caatcagcgg tttcatcact    5700
tttttcagtg tgtaatcatc gtttagctca atcataccga gagcgccgtt tgctaactca    5760
gccgtgcgtt tttatcgct ttgcagaagt ttttgacttt cttgacgaa gaatgatgtg    5820 cttttgccat agtatgcttt gttaaataaa gattcttcgc cttggtagcc atcttcagtt    5880
ccagtgtttg cttcaaatac taagtatttg tggcctttat cttctacgta gtgaggatct    5940
ctcagcgtat ggttgtcgcc tgagctgtag ttgccttcat cgatgaactg ctgtacattt    6000
```

```
tgatacgttt ttccgtcacc gtcaaagatt gatttataat cctctacacc gttgatgttc    6060
aaagagctgt ctgatgctga tacgttaact tgtgcagttg tcagtgtttg tttgccgtaa    6120
tgtttaccgg agaaatcagt gtagaataaa cggattttc cgtcagatgt aaatgtggct     6180
gaacctgacc attcttgtgt ttggtctttt aggatagaat catttgcatc gaatttgtcg    6240
ctgtctttaa agacgcggcc agcgtttttc cagctgtcaa tagaagtttc gccgactttt    6300
tgatagaaca tgtaaatcga tgtgtcatcc gcatttttag gatctccggc taatgcaaag    6360
acgatgtggt agccgtgata gtttgcgaca gtgccgtcag cgttttgtaa tggccagctg    6420
tcccaaacgt ccaggccttt tgcagaagag atatttttaa ttgtggacga atcaaattca    6480
gaaacttgat atttttcatt tttttgctgt tcagggattt gcagcatatc atggcgtgta    6540
atatgggaaa tgccgtatgt ttccttatat ggcttttggt tcgtttcttt cgcaaacgct    6600
tgagttgcgc ctcctgccag cagtgcggta gtaaaggtta atactgttgc ttgttttgca    6660 aacttttga tgttcatcgt tcatgtctcc ttttttatgt actgtgttag cggtctgctt     6720
cttccagccc tcctgtttga agatggcaag ttagttacgc acaataaaaa aagacctaaa    6780
atatgtaagg ggtgacgcca aagtatacac tttgcccttt acacatttta ggtcttgcct    6840
gctttatcag taacaaaccc gcgcgattta cttttcgacc tcattctatt agactctcgt    6900
ttggattgca actggtctat tttcctcttt tgtttgatag aaaatcataa aaggatttgc    6960
agactacggg cctaaagaac taaaaaatct atctgtttct tttcattctc tgtatttttt    7020
atagtttctg ttgcatgggc ataaagttgc cttttaatc acaattcaga aaatatcata    7080
atatctcatt tcactaaata atagtgaacg gcaggtatat gtgatgggtt aaaaaggatc    7140
ggcggccgct cgatttaaat c                                              7161

<210> SEQ ID NO 9
<211> LENGTH: 5363
<212> TYPE: DNA
<213> ORGANISM: artificial sequence
<220> FEATURE:
<223> OTHER INFORMATION: complete nucleotide sequence of plasmid pSacB_
      pykA1

<400> SEQUENCE: 9
tcgagcagaa gattaagaag aacgaaaatc gtatgtacaa tggggcctgc aacagacaaa       60
ggcaataatt tagaaaaaat cattgctgcc ggtgcaaacg ttgtacgtat gaacttctcc      120
cacggtacgc ccgaagatca tatcggtcgt gctgaaaaag tacgtgaaat cgctcataaa      180
ttaggtaaac acgtagcaat cttaggtgac ttacaaggcc ctaaaatccg tgtttctact      240
tttaaagaag gcaaaatttt cttaaatatc ggtgataaat tcattttaga cgcagagatg      300
cctaaaggtg aagtaaccca ggaagcggtt ggtttagact ataaacatt accgcaagat       360 gtggttccgg gcgatatctt attattagat gacggtcgag ttcaattgaa agtattggca      420
accgaaggtg caaagtatt caccgaagta acgtcggtg gcccactatc aaataataaa        480
ggcattaaca aattaggcgg cggtttatct gccgatgcat taaccgaaaa agataaagcg      540
gatatcatta ctgcggcgcg tatcggtgtg gattaccttg ccgtatcttt cccgcgttca      600
agcgcggatt taaactacgc ccgtcaatta gcaaagatg cgggcttgga tgcgaaaatc       660
gttgcgaaag tagaacgtgc cgaaacagtt gaaacggacg aagcaatgga cgatatcatc      720
aatgcggcgg acgtaatcat ggttgcgcgc ggtgacttag gtgttgaaat cggtgatccg      780
gaattagtcg gtgttcagaa aaaattaatc cgtcgttcac gtcagttaaa tcgtgttgtt      840
```

```
attaccgcaa ctcaaatgat ggaatcaatg attagtaatc ctatgccgac tcgtgcggaa      900
gtaatggacg tagctaacgc agtattggac ggtaccgatg cggtaatgct ttctgctgaa      960
accgcggctg gtcaatatcc ggcggaaact gttgcggcga tggcgaaagt tgcgttaggt     1020
gcggagaaaa tgccaagcat taatgtgtct aaacaccgta tgaacgttca attcgagtct     1080
attgaagaat ctgttgcgat gtctgcaatg tatgcggcaa accacatgag aggcgtagcg     1140
gcgattatca cattaacaag tagcggtcgt actgctcgtt taatgtctag actccatagg     1200
ccgctttcct ggctttgctt ccagatgtat gctctcctcc ggagagtacc gtgactttat     1260
tttcggcaca aatacagggg tcgatggata aatacggcga tagtttcctg acggatgatc     1320
cgtatgtacc ggcggaagac aagctgcaaa cctgtcagat ggagattgat ttaatggcgg     1380
atgtgctgag agcaccgccc cgtgaatccg cagaactgat ccgctatgtg tttgcggatg     1440
attggccgga ataaataaag ccgggcttaa tacagattaa gcccgtatag ggtattatta     1500
ctgaatacca aacagcttac ggaggacgga atgttaccca ttgagacaac cagactgcct     1560
tctgattatt aatattttc actattaatc agaaggaata accatgaatt ttacccggat     1620
tgacctgaat acctggaatc gcagggaaca cttttgccctt tatcgtcagc agattaaatg     1680
cggattcagc ctgaccacca aactcgatat taccgctttg cgtaccgcac tggcggagac     1740
aggttataag ttttatccgc tgatgattta cctgatctcc cgggctgtta atcagtttcc     1800
ggagttccgg atggcactga agacaatga acttatttac tgggaccagt cagacccggt     1860
ctttactgtc tttcataaag aaaccgaaac attctctgca ctgtcctgcc gttatttttcc    1920
ggatctcagt gagtttatgg caggttataa tgcggtaacg gcagaatatc agcatgatac     1980
cagattgttt ccgcagggaa atttaccgga gaatcacctg aatatatcat cattaccgtg     2040
ggtgagtttt gacgggattt aacctgaaca tcaccgaaaa tgatgattat tttgccccgg     2100
ttttttacgat ggcaaagttt cagcaggaag gtgaccgcgt attattacct gtttctgtac     2160
aggttcatca tgcagtctgt gatggctttc atgcagcacg gtttattaat acacttcagc     2220
tgatgtgtga taacatactg aaataaatta attaattctg tatttaagcc accgtatccg     2280
gcaggaatgg tggcttttt tttatatttt aaccgtaatc tgtaatttcg tttcagactg     2340
gttcaggatg agctcgcttg gactcctgtt gatagatcca gtaatgacct cagaactcca     2400
tctggatttg ttcagaacgc tcggttgccg ccgggcgttt tttattggtg agaatccaag     2460
cactagcggc gcgccggccg gcccggtgtg aaataccgca cagatgcgta aggagaaaat     2520
accgcatcag gcgctcttcc gcttcctcgc tcactgactc gctgcgctcg tcgttcggc      2580
tgcggcgagc ggtatcagct cactcaaagg cggtaatacg gttatccaca gaatcagggg     2640
ataacgcagg aaagaacatg tgagcaaaag gccagcaaaa ggccaggaac cgtaaaaagg     2700
ccgcgttgct ggcgtttttc cataggctcc gcccccctga cgagcatcac aaaaatcgac     2760
gctcaagtca gaggtggcga aacccgacag gactataaag ataccaggcg tttccccctg     2820
gaagctccct cgtgcgctct cctgttccga ccctgccgct taccggatac ctgtccgcct     2880
ttctcccttc gggaagcgtg gcgctttctc atagctcacg ctgtaggtat ctcagttcgg     2940
tgtaggtcgt tcgctccaag ctgggctgtg tgcacgaacc cccgttcag cccgaccgct      3000
gcgccttatc cggtaactat cgtcttgagt ccaacccggt aagacacgac ttatcgccac     3060
tggcagcagc cactggtaac aggattagca gagcgaggta tgtaggcggt gctacagagt     3120
tcttgaagtg gtggcctaac tacggctaca ctagaaggac agtatttggt atctgcgctc     3180
tgctgaagcc agttaccttc ggaaaaagag ttggtagctc ttgatccggc aaacaaacca     3240
```

```
ccgctggtag cggtggtttt tttgtttgca agcagcagat tacgcgcaga aaaaaaggat    3300
ctcaagaaga tcctttgatc ttttctacgg ggtctgacgc tcagtggaac gaaaactcac    3360
gttaagggat tttggtcatg agattatcaa aaaggatctt cacctagatc cttttaaagg    3420
ccggccgcgg ccgccatcgg cattttcttt tgcgttttta tttgttaact gttaattgtc    3480
cttgttcaag gatgctgtct ttgacaacag atgttttctt gcctttgatg ttcagcagga    3540
agctcggcgc aaacgttgat gtttgtctg cgtagaatcc tctgtttgtc atatagcttg    3600
taatcacgac attgttcct ttcgcttgag gtacagcgaa gtgtgagtaa gtaaaggtta    3660
catcgttagg atcaagatcc attttaaca caaggccagt tttgttcagc ggcttgtatg    3720
ggccagttaa agaattagaa acataaccaa gcatgtaaat atcgttagac gtaatgccgt    3780
caatcgtcat ttttgatccg cgggagtcag tgaacaggta ccatttgccg ttcatttaa    3840 agacgttcgc gcgttcaatt tcatctgtta ctgtgttaga tgcaatcagc ggtttcatca    3900 ctttttcag tgtgtaatca tcgtttagct caatcatacc gagagcgccg tttgctaact    3960
cagccgtgcg ttttttatcg ctttgcagaa gttttgact ttcttgacgg aagaatgatg    4020
tgcttttgcc atagtatgct ttgttaaata aagattcttc gccttggtag ccatcttcag    4080
ttccagtgtt tgcttcaaat actaagtatt tgtggccttt atcttctacg tagtgaggat    4140
ctctcagcgt atggttgtcg cctgagctgt agttgcctc atcgatgaac tgctgtacat    4200
tttgatacgt ttttccgtca ccgtcaaaga ttgatttata atcctctaca ccgttgatgt    4260
tcaaagagct gtctgatgct gatacgttaa cttgtgcagt tgtcagtgtt tgtttgccgt    4320
aatgtttacc ggagaaatca gtgtagaata aacggatttt tccgtcagat gtaaatgtgg    4380
ctgaacctga ccattcttgt gtttggtctt ttaggataga atcatttgca tcgaatttgt    4440
cgctgtcttt aaagacgcgg ccagcgtttt tccagctgtc aatagaagtt tcgccgactt    4500
tttgatagaa catgtaaatc gatgtgtcat ccgcatttt aggatctccg gctaatgcaa    4560
agacgatgtg gtagccgtga tagtttgcga cagtgccgtc agcgttttgt aatggccagc    4620
tgtcccaaac gtccaggcct tttgcagaag agatattttt aattgtggac gaatcaaatt    4680
cagaaacttg atattttca ttttttgct gttcagggat ttgcagcata tcatggcgtg    4740
taatatggga aatgccgtat gttccttat atggcttttg gttcgtttct ttcgcaaacg    4800
cttgagttgc gcctcctgcc agcagtgcgg tagtaaaggt taatactgtt gcttgttttg    4860 caaactttt gatgttcatc gttcatgtct cctttttat gtactgtgtt agcggtctgc    4920
ttcttccagc cctcctgttt gaagatggca agttagttac gcacaataaa aaagaccta    4980 aaatatgtaa ggggtgacgc caaagtatac actttgccct ttacacattt taggtcttgc    5040
ctgctttatc agtaacaaac ccgcgcgatt tacttttcga cctcattcta ttagactctc    5100
gtttggattg caactggtct attttcctct tttgtttgat agaaaatcat aaaaggattt    5160
gcagactacg ggcctaaaga actaaaaaat ctatctgttt cttttcattc tctgtatttt    5220
ttatagtttc tgttgcatgg gcataaagtt gcctttttaa tcacaattca gaaaatatca    5280
taatatctca tttcactaaa taatagtgaa cggcaggtat atgtgatggg ttaaaaagga    5340
tcggcggccg ctcgatttaa atc                                           5363
```

<210> SEQ ID NO 10
<211> LENGTH: 5363
<212> TYPE: DNA
<213> ORGANISM: artificial sequence
<220> FEATURE:

<223> OTHER INFORMATION: complete nucleotide sequence of plasmid pSacB_pykA2

<400> SEQUENCE: 10

| | | | | | |
|---|---|---|---|---|---|
| tcgagcagaa | gattaagaag | aacgaaaatc | gtatgtacaa | tggggcctgc | aacagacaaa | 60 |
| ggcaataatt | tagaaaaaat | cattgctgcc | ggtgcaaacg | ttgtacgtat | gaacttctcc | 120 |
| cacggtacgc | ccgaagatca | tatcggtcgt | gctgaaaaag | tacgtgaaat | cgctcataaa | 180 |
| ttaggtaaac | acgtagcaat | cttaggtgac | ttacaaggcc | ctaaaatccg | tgtttctact | 240 |
| tttaaagaag | gcaaaatttt | cttaaatatc | ggtgataaat | tcattttaga | cgcagagatg | 300 |
| cctaaaggtg | aaggtaacca | ggaagcggtt | ggtttagact | ataaaacatt | accgcaagat | 360 |
| gtggttccgg | gcgatatctt | attattagat | gacggtcgag | ttcaattgaa | agtattggca | 420 |
| accgaaggtg | caaaagtatt | caccgaagta | acggtcggtg | gcccactatc | aaataataaa | 480 |
| ggcattaaca | aattaggctg | cggtttatct | gccgatgcat | taaccgaaaa | agataaagcg | 540 |
| gatatcatta | ctgcggcgcg | tatcggtgtg | gattaccttg | ccgtatcttt | cccgcgttca | 600 |
| agcgcggatt | taaactacgc | ccgtcaatta | gcaaaagatg | cgggcttgga | tgcgaaaatc | 660 |
| gttgcgaaag | tagaacgtgc | cgaaacagtt | gaaacggacg | aagcaatgga | cgatatcatc | 720 |
| aatgcggcgg | acgtaatcat | ggttgcgcgc | ggtgacttag | gtgttgaaat | cggtgatccg | 780 |
| gaattagtcg | gtgttcagaa | aaaattaatc | cgtcgttcac | gtcagttaaa | tcgtgttgtt | 840 |
| attaccgcaa | ctcaaatgat | ggaatcaatg | attagtaatc | ctatgccgac | tcgtgcggaa | 900 |
| gtaatggacg | tagctaacgc | agtattggac | ggtaccgatg | cggtaatgct | ttctgctgaa | 960 |
| accgcggctg | gtcaatatcc | ggcggaaact | gttgcggcga | tggcgaaagt | tgcgttaggt | 1020 |
| gcggagaaaa | tgccaagcat | taatgtgtct | aaacaccgta | tgaacgttca | attcgagtct | 1080 |
| attgaagaat | ctgttgcgat | gtctgcaatg | tatgcggcaa | ccacatgag | aggcgtagcg | 1140 |
| gcgattatca | cattaacaag | tagcggtcgt | actgctcgtt | taatgtctag | actccatagg | 1200 |
| ccgcttttcct | ggctttgctt | ccagatgtat | gctctcctcc | ggagagtacc | gtgactttat | 1260 |
| tttcggcaca | aatacagggg | tcgatggata | aatacggcga | tagtttcctg | acggatgatc | 1320 |
| cgtatgtacc | ggcggaagac | aagctgcaaa | cctgtcagat | ggagattgat | ttaatggcgg | 1380 |
| atgtgctgag | agcaccgccc | cgtgaatccg | cagaactgat | ccgctatgtg | tttgcggatg | 1440 |
| attggccgga | ataaataaag | ccgggcttaa | tacagattaa | gcccgtatag | ggtattatta | 1500 |
| ctgaatacca | aacagcttac | ggaggacgga | atgttaccca | ttgagacaac | cagactgcct | 1560 |
| tctgattatt | aatatttttc | actattaatc | agaaggaata | accatgaatt | ttacccggat | 1620 |
| tgacctgaat | acctggaatc | gcagggaaca | ctttgccctt | tatcgtcagc | agattaaatg | 1680 |
| cggattcagc | ctgaccacca | aactcgatat | taccgctttg | cgtaccgcac | tggcggagac | 1740 |
| aggttataag | ttttatccgc | tgatgattta | cctgatctcc | cggctgtta | atcagttttcc | 1800 |
| ggagttccgg | atggcactga | agacaatga | acttatttac | tgggaccagt | cagacccggt | 1860 |
| ctttactgtc | tttcataaag | aaaccgaaac | attctctgca | ctgtcctgcc | gttattttcc | 1920 |
| ggatctcagt | gagtttatgg | caggttataa | tgcggtaacg | gcagaatatc | agcatgatac | 1980 |
| cagattgttt | ccgcagggaa | atttaccgga | gaatcacctg | aatatatcat | cattaccgtg | 2040 |
| ggtgagtttt | gacgggattt | aacctgaaca | tcaccggaaa | tgatgattat | tttgccccgg | 2100 |
| ttttttacgat | ggcaaagttt | cagcaggaag | gtgaccgcgt | attattacct | gtttctgtac | 2160 |
| aggttcatca | tgcagtctgt | gatggctttc | atgcagcacg | gttattaat | acacttcagc | 2220 |

```
tgatgtgtga taacatactg aaataaatta attaattctg tatttaagcc accgtatccg   2280
gcaggaatgg tggcttttt tttatattt aaccgtaatc tgtaatttcg tttcagactg    2340
gttcaggatg agctcgcttg gactcctgtt gatagatcca gtaatgacct cagaactcca   2400
tctggatttg ttcagaacgc tcggttgccg ccgggcgttt tttattggtg agaatccaag   2460
cactagcggc gcgccggccg gcccggtgtg aaataccgca cagatgcgta aggagaaaat   2520
accgcatcag gcgctcttcc gcttcctcgc tcactgactc gctgcgctcg gtcgttcggc   2580
tgcggcgagc ggtatcagct cactcaaagg cggtaatacg ttatccaca gaatcagggg    2640 ataacgcagg aaagaacatg tgagcaaaag gccagcaaaa ggccaggaac cgtaaaaagg   2700
ccgcgttgct ggcgtttttc cataggctcc gcccccctga cgagcatcac aaaaatcgac   2760
gctcaagtca gaggtggcga aacccgacag gactataaag ataccaggcg tttccccctg   2820
gaagctccct cgtgcgctct cctgttccga ccctgccgct taccggatac ctgtccgcct   2880
ttctcccttc gggaagcgtg gcgctttctc atagctcacg ctgtaggtat ctcagttcgg   2940
tgtaggtcgt tcgctccaag ctgggctgtg tgcacgaacc ccccgttcag cccgaccgct   3000
gcgccttatc cggtaactat cgtcttgagt ccaacccggt aagacacgac ttatcgccac   3060
tggcagcagc cactggtaac aggattagca gagcgaggta tgtaggcggt gctacagagt   3120
tcttgaagtg gtggcctaac tacggctaca ctagaaggac agtatttggt atctgcgctc   3180
tgctgaagcc agttaccttc ggaaaaagag ttggtagctc ttgatccggc aaacaaacca   3240
ccgctggtag cggtggtttt tttgtttgca agcagcagat tacgcgcaga aaaaaggat    3300 ctcaagaaga tcctttgatc ttttctacgg gtctgacgc tcagtggaac gaaaactcac    3360
gttaagggat tttggtcatg agattatcaa aaaggatctt cacctagatc cttttaaagg   3420
ccggccgcgg ccgccatcgg catttctctt tgcgttttta tttgttaact gttaattgtc   3480
cttgttcaag gatgctgtct ttgacaacag atgttttctt gcctttgatg ttcagcagga   3540
agctcggcgc aaacgttgat tgtttgtctg cgtagaatcc tctgtttgtc atatagcttg   3600
taatcacgac attgtttcct ttcgcttgag gtacagcgaa gtgtgagtaa gtaaaggtta   3660
catcgttagg atcaagatcc attttttaaca caaggccagt tttgttcagc ggcttgtatg   3720
ggccagttaa agaattagaa acataaccaa gcatgtaaat atcgttagac gtaatgccgt   3780
caatcgtcat ttttgatccg cgggagtcag tgaacaggta ccatttgccg ttcattttaa   3840
agacgttcgc gcgttcaatt tcatctgtta ctgtgttaga tgcaatcagc ggtttcatca   3900
cttttttcag tgtgtaatca tcgtttagct caatcatacc gagagcgccg tttgctaact   3960
cagccgtgcg ttttttatcg ctttgcagaa gtttttgact ttcttgacgg aagaatgatg   4020
tgcttttgcc atagtatgct ttgttaaata aagattcttc gccttggtag ccatcttcag   4080
ttccagtgtt tgcttcaaat actaagtatt tgtggccttt atcttctacg tagtgaggat   4140
ctctcagcgt atggttgtcg cctgagctgt agttgcctttc atcgatgaac tgctgtacat   4200
tttgatacgt ttttccgtca ccgtcaaaga ttgatttata atcctctaca ccgttgatgt   4260
tcaaagagct gtctgatgct gatacgttaa cttgtgcagt tgtcagtgtt tgtttgccgt   4320
aatgtttacc ggagaaatca gtgtagaata acggattttt ccgtcagat gtaaatgtgg    4380 ctgaacctga ccattcttgt gtttggtctt ttaggataga atcatttgca tcgaatttgt   4440
cgctgtcttt aaagacgcgg ccagcgtttt tccagctgtc aatagaagtt tcgccgactt   4500
tttgatagaa catgtaaatc gatgtgtcat ccgcattttt aggatctccg gctaatgcaa   4560
agacgatgtg gtagccgtga tagtttgcga cagtgccgtc agcgttttgt aatggccagc   4620
```

```
tgtcccaaac gtccaggcct tttgcagaag agatatttttt aattgtggac gaatcaaatt    4680
cagaaacttg atattttttca ttttttttgct gttcagggat ttgcagcata tcatggcgtg    4740
taatatggga aatgccgtat gtttccttat atggcttttg gttcgtttct ttcgcaaacg    4800
cttgagttgc gcctcctgcc agcagtgcgg tagtaaaggt taatactgtt gcttgttttg    4860 caaactttttt gatgttcatc gttcatgtct ccttttttat gtactgtgtt agcggtctgc    4920
ttcttccagc cctcctgttt gaagatggca agttagttac gcacaataaa aaagaccta    4980 aaatatgtaa ggggtgacgc caaagtatac actttgccct ttacacattt taggtcttgc    5040
ctgctttatc agtaacaaac ccgcgcgatt tacttttcga cctcattcta ttagactctc    5100
gtttggattg caactggtct atttttcctct tttgtttgat agaaaatcat aaaaggattt    5160
gcagactacg ggcctaaaga actaaaaaat ctatctgttt cttttcattc tctgtatttt    5220
ttatagtttc tgttgcatgg gcataaagtt gccttttttaa tcacaattca gaaaatatca    5280
taatatctca tttcactaaa taatagtgaa cggcaggtat atgtgatggg ttaaaaagga    5340
tcggcggccg ctcgatttaa atc                                              5363

<210> SEQ ID NO 11
<211> LENGTH: 5634
<212> TYPE: DNA
<213> ORGANISM: artificial sequence
<220> FEATURE:
<223> OTHER INFORMATION: complete nucleotide sequence of plasmid pSacB_
      pykA3

<400> SEQUENCE: 11
tcgagagcgg atatcattac tgcggcgcgt atcggtgtgg attaccttgc cgtatctttc      60
ccgcgttcaa gcgcggattt aaactacgcc cgtcaattag caaaagatgc gggcttggat    120
gcgaaaatcg ttgcgaaagt agaacgtgcc gaaacagttg aaacggacga agcaatggac    180
gatatcatca atgcggcgga cgtaatcatg gttgcgcgcg tgacttaggg tgttgaaatc    240
ggtgatccgg aattagtcgg tgttcagaaa aaattaatcc gtcgttcacg tcagttaaat    300
cgtgttgtta ttaccgcaac tcaaatgatg gaatcaatga ttagtaatcc tatgccgact    360
cgtgcggaag taatggacgt agctaacgca gtattggacg gtaccgatgc ggtaatgctt    420
tctgctgaaa ccgcggctgg tcaatatccg gcggaaactg ttgcggcgat ggcgaaagtt    480
gcgttaggtg cggagaaaat gccaagcatt aatgtgtcta acaccgtat gaacgttcaa    540 ttcgagtcta ttgaagaatc tgttgcgatg tctgcaatgt atgcggcaaa ccacatgaga    600
ggcgtagcgg cgattatcac attaacaagt agcggtcgta ctgctcgttt aatgtctcgc    660
attagttccg gtttaccaat cttttgcattg tcacgtaacg aatctacatt aaacttatgc    720
gcattatatc gtggtgtgac accggttcat tttgataaag acagccgtac ctcagaaggt    780
gcgacagcgg cggttcaatt attaaaagac gaaggtttct tagtgtctgg cgatttagtg    840
ttattaactc agggcgacgc aagcagttct agcggtacta cctttgccg tacattgatt    900 gttgaataat aggcaatgaa caaaaaaacg atgatttaag tcatcgtttt tttttttgc    960 ttttctataa aaattcggaa aaatgcaccg cactatttgt ttaacagatc ttttaagccc   1020
gccttcattg ccgacatctg gcttttcatac aacgctttgc tttcccgctc gtcgatcata   1080
taggtgatgg tttcggaaag tgtcatttttc atcttttttcg aatatttgga aaggcgtaac   1140
caaaccccat attctaaatc aatagatttt ttcttcgtgg ataattttttc cgcgttaaag   1200 aaacgtttac gtctggctcg aatcgcctga tctaatttga taatcaacga ttcagccata   1260
```

```
tgattggcta tccattcttc aattttttca ggataattct ggctttctaa taaatcatgc   1320
actttgcttt gctgcaaact gcgttcttca taacgggtaa tattctcgcc ttcacgattt   1380
tttttaatta aatacaacca tttccaatgc gcttcttgat tttctaattt ttgatacttc   1440
atggataggt tctccatcta gactccatag gccgctttcc tggctttgct tccagatgta   1500
tgctctcctc cggagagtac cgtgacttta ttttcggcac aaatacaggg gtcgatggat   1560
aaatacggcg atagtttcct gacggatgat ccgtatgtac cggcggaaga caagctgcaa   1620
acctgtcaga tggagattga tttaatggcg gatgtgctga gagcaccgcc ccgtgaatcc   1680
gcagaactga tccgctatgt gtttgcggat gattggccgg aataaataaa gccgggctta   1740
atacagatta agcccgtata gggtattatt actgaatacc aaacagctta cggaggacgg   1800
aatgttaccc attgagacaa ccagactgcc ttctgattat taatattttt cactattaat   1860
cagaaggaat aaccatgaat tttacccgga ttgacctgaa tacctggaat cgcagggaac   1920
actttgccct ttatcgtcag cagattaaat gcggattcag cctgaccacc aaactcgata   1980
ttaccgcttt gcgtaccgca ctggcggaga caggttataa gttttatccg ctgatgattt   2040
acctgatctc ccgggctgtt aatcagtttc cggagttccg gatggcactg aaagacaatg   2100
aacttattta ctgggaccag tcagacccgg tctttactgt ctttcataaa gaaaccgaaa   2160
cattctctgc actgtcctgc cgttattttc cggatctcag tgagtttatg gcaggttata   2220
atgcggtaac ggcagaatat cagcatgata ccagattgtt tccgcaggga aatttaccgg   2280
agaatcacct gaatatatca tcattaccgt gggtgagttt tgacgggatt taacctgaac   2340
atcaccggaa atgatgatta ttttgccccg gtttttacga tggcaaagtt tcagcaggaa   2400
ggtgaccgcg tattattacc tgtttctgta caggttcatc atgcagtctg tgatggcttt   2460
catgcagcac ggtttattaa tacacttcag ctgatgtgtg ataacatact gaaataaatt   2520
aattaattct gtatttaagc caccgtatcc ggcaggaatg gtggcttttt ttttatattt   2580
taaccgtaat ctgtaatttc gtttcagact ggttcaggat gagctcgctt ggactcctgt   2640
tgatagatcc agtaatgacc tcagaactcc atctggattt gttcagaacg ctcggttgcc   2700
gccgggcgtt ttttattggt gagaatccaa gcactagcgg cgcgcggcc ggcccggtgt    2760 gaaataccgc acagatgcgt aaggagaaaa taccgcatca ggcgctcttc cgcttcctcg   2820
ctcactgact cgctgcgctc ggtcgttcgg ctgcggcgag cggtatcagc tcactcaaag   2880
gcggtaatac ggttatccac agaatcaggg gataacgcag gaaagaacat gtgagcaaaa   2940
ggccagcaaa aggccaggaa ccgtaaaaag gccgcgttgc tggcgttttt ccataggctc   3000
cgcccccctg acgagcatca caaaaatcga cgctcaagtc agaggtggcg aaacccgaca   3060
ggactataaa gataccaggc gtttccccct ggaagctccc tcgtgcgctc tcctgttccg   3120
accctgccgc ttaccggata cctgtccgcc tttctccctt cgggaagcgt ggcgctttct   3180
catagctcac gctgtaggta tctcagttcg gtgtaggtcg ttcgctccaa gctgggctgt   3240
gtgcacgaac cccccgttca gcccgaccgc tgcgccttat ccggtaacta tcgtcttgag   3300
tccaacccgg taagacacga cttatcgcca ctggcagcag ccactggtaa caggattagc   3360
agagcgaggt atgtaggcgg tgctacagag ttcttgaagt ggtggcctaa ctacggctac   3420
actagaagga cagtatttgg tatctgcgct ctgctgaagc cagttacctt cggaaaaaga   3480
gttggtagct cttgatccgg caaacaaacc accgctggta gcggtggttt ttttgtttgc   3540
aagcagcaga ttacgcgcag aaaaaaagga tctcaagaag atcctttgat cttttctacg   3600
```

```
gggtctgacg ctcagtggaa cgaaaactca cgttaaggga ttttggtcat gagattatca    3660
aaaaggatct tcacctagat cctttttaaag gccggccgcg gccgccatcg gcattttctt    3720
ttgcgttttt atttgttaac tgttaattgt ccttgttcaa ggatgctgtc tttgacaaca    3780
gatgttttct tgcctttgat gttcagcagg aagctcggcg caaacgttga ttgtttgtct    3840
gcgtagaatc ctctgtttgt catatagctt gtaatcacga cattgtttcc tttcgcttga    3900
ggtacagcga agtgtgagta agtaaaggtt acatcgttag gatcaagatc catttttaac    3960
acaaggccag ttttgttcag cggcttgtat gggccagtta aagaattaga aacataacca    4020
agcatgtaaa tatcgttaga cgtaatgccg tcaatcgtca ttttgatcc gcgggagtca     4080
gtgaacaggt accatttgcc gttcatttta aagacgttcg cgcgttcaat ttcatctgtt    4140
actgtgttag atgcaatcag cggtttcatc acttttttca gtgtgtaatc atcgtttagc    4200
tcaatcatac cgagagcgcc gtttgctaac tcagccgtgc gttttttatc gctttgcaga    4260
agttttttgac tttcttgacg gaagaatgat gtgcttttgc catagtatgc tttgttaaat    4320
aaagattctt cgccttggta gccatcttca gttccagtgt ttgcttcaaa tactaagtat    4380
ttgtggcctt tatcttctac gtagtgagga tctctcagcg tatggttgtc gcctgagctg    4440
tagttgcctt catcgatgaa ctgctgtaca ttttgatacg ttttttccgtc accgtcaaag   4500
attgatttat aatcctctac accgttgatg ttcaaagagc tgtctgatgc tgatacgtta    4560
acttgtgcag ttgtcagtgt ttgtttgccg taatgtttac cggagaaatc agtgtagaat    4620
aaacggattt ttccgtcaga tgtaaatgtg gctgaacctg accattcttg tgtttggtct    4680
tttaggatag aatcatttgc atcgaatttg tcgctgtctt taaagacgcg gccagcgttt    4740
ttccagctgt caatagaagt ttcgccgact ttttgataga acatgtaaat cgatgtgtca    4800
tccgcatttt taggatctcc ggctaatgca aagacgatgt ggtagccgtg atagtttgcg    4860
acagtgccgt cagcgttttg taatggccag ctgtcccaaa cgtccaggcc ttttgcagaa    4920
gagatatttt taattgtgga cgaatcaaat tcagaaactt gatattttc atttttttgc     4980
tgttcaggga tttgcagcat atcatggcgt gtaatatggg aaatgccgta tgtttcctta    5040
tatggctttt ggttcgtttc tttcgcaaac gcttgagttg cgcctcctgc cagcagtgcg    5100
gtagtaaagg ttaatactgt tgcttgtttt gcaaactttt tgatgttcat cgttcatgtc    5160
tcctttttta tgtactgtgt tagcggtctg cttcttccag ccctcctgtt tgaagatggc    5220
aagttagtta cgcacaataa aaaagacct aaaatatgta aggggtgacg ccaaagtata     5280
cactttgccc tttacacatt ttaggtcttg cctgctttat cagtaacaaa cccgcgcgat    5340
ttactttcg acctcattct attagactct cgtttggatt gcaactggtc tattttcctc     5400
ttttgtttga tagaaaatca taaaggatt tgcagactac gggcctaaag aactaaaaaa     5460
tctatctgtt tcttttcatt ctctgtattt tttatagttt ctgttgcatg gcataaagt    5520
tgcctttttta atcacaattc agaaaatatc ataatatctc atttcactaa ataatagtga   5580
acggcaggta tatgtgatgg gttaaaaagg atcggcggcc gctcgattta aatc          5634
```

<210> SEQ ID NO 12
<211> LENGTH: 5634
<212> TYPE: DNA
<213> ORGANISM: artificial sequence
<220> FEATURE:
<223> OTHER INFORMATION: complete nucleotide sequence of plasmid pSacB_
      pykA4

<400> SEQUENCE: 12

```
tcgagagcgg atatcattac tgcggcgcgt atcggtgtgg attaccttgc cgtatctttc     60
ccgcgttcaa gcgcggattt aaactacgcc cgtcaattag caaaagatgc gggcttggat    120
gcgaaaatcg ttgcgaaagt agaacgtgcc gaaacagttg aaacggacga agcaatggac    180
gatatcatca atgcggcgga cgtaatcatg gttgcgcgcg gtgacttagg tgttgaaatc    240
ggtgatccgg aattagtcgg tgttcagaaa aaattaatcc gtcgttcacg tcagttaaat    300
cgtgttgtta ttaccgcaac tcaaatgatg gaatcaatga ttagtaatcc tatgccgact    360
cgtgcggaag taatggacgt agctaacgca gtattggacg gtaccgatgc ggtaatgctt    420
tctgctgaaa ccgcggctgg tcaatatccg gcggaaactg ttgcggcgat ggcgaaagtt    480
gcgttaggtg cggagaaaat gccaagcatt aatgtgtcta acaccgtat gaacgttcaa    540 ttcgagtcta ttgaagaatc tgttgcgatg tctgcaatgt atgcggcaaa ccacatgaga    600
ggcgtagcgg cgattatcac attaacaagt agcggtcgta ctgctcgttt aatgtctcgc    660
attagttccg gtttaccaat cttttgcattg tcacgtaacg aatctacttt aaacttatac    720
gcattatatc gtggtgtgac accggttcat tttgataaag acagccgtac ctcagaaggt    780
gcgacagcgg cggttcaatt attaaaagac gaaggtttct tagtgtctgg cgatttagtg    840
ttattaactc agggcgacgc aagcagttct agcggtacta acctttgccg tacattgatt    900
gttgaataat aggcaatgaa caaaaaaacg atgatttaag tcatcgtttt tttttttgc    960 ttttctataa aaattcggaa aaatgcaccg cactatttgt ttaacagatc ttttaagccc   1020
gccttcattg ccgacatctg gctttcatac aacgctttgc tttccgctc gtcgatcata   1080 taggtgatgg tttcggaaag tgtcattttc atcttttcg aatatttgga aaggcgtaac   1140
caaaccccat attctaaatc aatagatttt ttcttcgtgg ataatttttc cgcgttaaag   1200
aaacgtttac gtctggctcg aatcgcctga tctaatttga taatcaacga ttcagccata   1260
tgattggcta tccattcttc aatttttttca ggataattct ggctttctaa taaatcatgc   1320
actttgcttt gctgcaaact gcgttcttca taacgggtaa tattctcgcc ttcacgattt   1380
tttttaatta aatacaacca tttccaatgc gcttcttgat tttctaattt ttgatacttc   1440
atggataggt tctccatcta gactccatag gccgctttcc tggctttgct tccagatgta   1500
tgctctcctc cggagagtac cgtgactta ttttcggcac aaatacaggg gtcgatggat   1560
aaatacggcg atagtttcct gacggatgat ccgtatgtac cggcggaaga caagctgcaa   1620
acctgtcaga tggagattga tttaatggcg gatgtgctga gagcaccgcc ccgtgaatcc   1680
gcagaactga tccgctatgt gtttgcggat gattggccgg aataaataaa gccgggctta   1740
atacagatta agcccgtata gggtattatt actgaatacc aaacagctta cggaggacgg   1800
aatgttaccc attgagacaa ccagactgcc ttctgattat taatatttt cactattaat   1860 cagaaggaat aaccatgaat tttacccgga ttgacctgaa tacctggaat cgcagggaac   1920
actttgccct ttatcgtcag cagattaaat gcggattcag cctgaccacc aaactcgata   1980
ttaccgcttt gcgtaccgca ctggcggaga caggttataa gttttatccg ctgatgattt   2040
acctgatctc ccgggctgtt aatcagtttc cggagttccg gatggcactg aaagacaatg   2100
aacttattta ctgggaccag tcagacccgg tctttactgt cttcataaaa gaaaccgaaa   2160
cattctctgc actgtcctgc cgttatttc cggatctcag tgagtttatg gcaggttata   2220
atgcggtaac ggcagaatat cagcatgata ccagattgtt ccgcaggga aatttaccgg   2280 agaatcacct gaatatatca tcattaccgt gggtgagttt tgacgggatt taacctgaac   2340
atcaccggaa atgatgatta ttttgccccg gttttttacga tggcaaagtt tcagcaggaa   2400
```

```
ggtgaccgcg tattattacc tgtttctgta caggttcatc atgcagtctg tgatggcttt     2460
catgcagcac ggtttattaa tacacttcag ctgatgtgtg ataacatact gaaataaatt     2520
aattaattct gtatttaagc caccgtatcc ggcaggaatg gtggctttt ttttatattt      2580 taaccgtaat ctgtaatttc gtttcagact ggttcaggat gagctcgctt ggactcctgt    2640
tgatagatcc agtaatgacc tcagaactcc atctggattt gttcagaacg ctcggttgcc    2700
gccgggcgtt ttttattggt gagaatccaa gcactagcgg cgcgccggcc ggcccggtgt    2760
gaaataccgc acagatgcgt aaggagaaaa taccgcatca ggcgctcttc cgcttcctcg    2820
ctcactgact cgctgcgctc ggtcgttcgg ctgcggcgag cggtatcagc tcactcaaag    2880
gcggtaatac ggttatccac agaatcaggg gataacgcag gaaagaacat gtgagcaaaa    2940
ggccagcaaa aggccaggaa ccgtaaaaag gccgcgttgc tggcgttttt ccataggctc    3000
cgcccccctg acgagcatca caaaaatcga cgctcaagtc agaggtggcg aaacccgaca    3060
ggactataaa gataccaggc gtttccccct ggaagctccc tcgtgcgctc tcctgttccg    3120
accctgccgc ttaccggata cctgtccgcc tttctccctt cgggaagcgt ggcgctttct    3180
catagctcac gctgtaggta tctcagttcg gtgtaggtcg ttcgctccaa gctgggctgt    3240
gtgcacgaac cccccgttca gcccgaccgc tgcgccttat ccggtaacta tcgtcttgag    3300
tccaacccgg taagacacga cttatcgcca ctggcagcag ccactggtaa caggattagc    3360
agagcgaggt atgtaggcgg tgctacagag ttcttgaagt ggtggcctaa ctacggctac    3420
actagaagga cagtatttgg tatctgcgct ctgctgaagc cagttacctt cggaaaaaga    3480
gttggtagct cttgatccgg caaacaaacc accgctggta gcggtggttt ttttgtttgc    3540
aagcagcaga ttacgcgcag aaaaaaagga tctcaagaag atcctttgat cttttctacg    3600
gggtctgacg ctcagtggaa cgaaaactca cgttaaggga ttttggtcat gagattatca    3660
aaaaggatct tcacctagat ccttttaaag ccggccgcg ccgccatcg gcattttctt      3720 ttgcgttttt atttgttaac tgttaattgt ccttgttcaa ggatgctgtc tttgacaaca    3780
gatgttttct tgcctttgat gttcagcagg aagctcggcg caaacgttga ttgtttgtct    3840
gcgtagaatc ctctgtttgt catatagctt gtaatcacga cattgtttcc tttcgcttga    3900
ggtacagcga agtgtgagta agtaaaggtt acatcgttag gatcaagatc cattttaac    3960 acaaggccag ttttgttcag cggcttgtat gggccagtta agaattaga aacataacca     4020 agcatgtaaa tatcgttaga cgtaatgccg tcaatcgtca tttttgatcc gcgggagtca    4080
gtgaacaggt accatttgcc gttcatttta aagacgttcg cgcgttcaat tcatctgtt    4140 actgtgttag atgcaatcag cggtttcatc acttttttca gtgtgtaatc atcgtttagc    4200
tcaatcatac cgagagcgcc gtttgctaac tcagccgtgc gttttttatc gcttgcaga    4260 agttttgac tttcttgacg gaagaatgat gtgcttttgc catagtatgc tttgttaaat    4320
aaagattctt cgccttggta gccatcttca gttccagtgt ttgcttcaaa tactaagtat    4380
ttgtggcctt tatcttctac gtagtgagga tctctcagcg tatggttgtc gcctgagctg    4440
tagttgcctt catcgatgaa ctgctgtaca ttttgatacg ttttccgtc accgtcaaag     4500 attgattat aatcctctac accgttgatg ttcaaagagc tgtctgatgc tgatacgtta    4560
acttgtgcag ttgtcagtgt ttgtttgccg taatgtttac cggagaaatc agtgtagaat    4620
aaacggattt ttccgtcaga tgtaaatgtg gctgaacctg accattcttg tgtttggtct    4680
tttaggatag aatcatttgc atcgaatttg tcgctgtctt taaagacgcg gccagcgttt    4740
```

```
ttccagctgt caatagaagt ttcgccgact ttttgataga acatgtaaat cgatgtgtca    4800
tccgcatttt taggatctcc ggctaatgca aagacgatgt ggtagccgtg atagtttgcg    4860
acagtgccgt cagcgttttg taatggccag ctgtcccaaa cgtccaggcc ttttgcagaa    4920
gagatatttt taattgtgga cgaatcaaat tcagaaactt gatattttc attttttgc     4980 tgttcaggga tttgcagcat atcatggcgt gtaatatggg aaatgccgta tgtttcctta    5040
tatggctttt ggttcgtttc tttcgcaaac gcttgagttg cgcctcctgc cagcagtgcg    5100
gtagtaaagg ttaatactgt tgcttgtttt gcaaactttt tgatgttcat cgttcatgtc    5160
tcctttttta tgtactgtgt tagcggtctg cttcttccag ccctcctgtt tgaagatggc    5220
aagttagtta cgcacaataa aaaaagacct aaaatatgta aggggtgacg ccaaagtata    5280
cactttgccc tttacacatt ttaggtcttg cctgctttat cagtaacaaa cccgcgcgat    5340
ttacttttcg acctcattct attagactct cgtttggatt gcaactggtc tattttcctc    5400
ttttgtttga tagaaaatca taaaggatt tgcagactac gggcctaaag aactaaaaaa    5460
tctatctgtt tcttttcatt ctctgtattt tttatagttt ctgttgcatg gcataaagt     5520 tgccttttta atcacaattc agaaaatatc ataatatctc atttcactaa ataatagtga    5580
acggcaggta tatgtgatgg gttaaaaagg atcggcggcc gctcgattta aatc           5634
```

<210> SEQ ID NO 13
<211> LENGTH: 5363
<212> TYPE: DNA
<213> ORGANISM: artificial sequence
<220> FEATURE:
<223> OTHER INFORMATION: complete nucleotid sequence of plasmid pSacB_pykA5

<400> SEQUENCE: 13

```
tcgagcagaa gattaagaag aacgaaaatc gtatgtacaa tggggcctgc aacagacaaa      60
ggcaataatt tagaaaaaat cattgctgcc ggtgcaaacg ttgtacgtat gaacttctcc     120
cacggtacgc ccgaagatca tatcggtcgt gctgaaaaag tacgtgaaat cgctcataaa     180
ttaggtaaac acgtagcaat cttaggtgac ttacaaggcc ctaaaatccg tgtttctact     240
tttaaagaag gcaaaatttt cttaaatatc ggtgataaat tcattttaga cgcagagatg     300
cctaaaggtg aagtaaccca ggaagcggtt ggtttagact ataaaacatt accgcaagat     360
gtggttccgg gcgatatctt attattagat gacggtcgag ttcaattgaa agtattggca     420
accgaaggtg caaagtatt caccgaagta acggtcggtg gcccactatc aaataataaa      480
ggcattaaca aattaggcgg cggtttatct ggcgatgcgt taaccgaaaa agataaagcg     540
gatatcatta ctgcggcgcg tatcggtgtg gattaccttg ccgtatcttt cccgcgttca    600
agcgcggatt taaactacgc ccgtcaatta gcaaagatg cgggcttgga tgcgaaaatc     660
gttgcgaaag tagaacgtgc cgaaacagtt gaaacggacg aagcaatgga cgatatcatc    720
aatgcggcgg acgtaatcat ggttgcgcgc ggtgacttag tgttgaaat cggtgatccg     780 gaattagtcg gtgttcagaa aaaattaatc cgtcgttcac gtcagttaaa tcgtgttgtt    840
attaccgcaa ctcaaatgat ggaatcaatg attagtaatc ctatgccgac tcgtgcggaa   900
gtaatggaca tagctaacgc agtattggac ggtaccgatg cggtaatgct ttctgctgaa    960
accgcggctg tcaatatcc ggcggaaact gttgcggcga tggcgaaagt tgcgttaggt    1020
gcggagaaaa tgccaagcat taatgtgtct aaacaccgta tgaacgttca attcgagtct    1080
attgaagaat ctgttgcgat gtctgcaatg tatgcggcaa accacatgag aggcgtagcg    1140
```

```
gcgattatca cattaacaag tagcggtcgt actgctcgtt taatgtctag actccatagg    1200
ccgctttcct ggctttgctt ccagatgtat gctctcctcc ggagagtacc gtgactttat    1260
tttcggcaca aatacagggg tcgatggata aatacggcga tagtttcctg acggatgatc    1320
cgtatgtacc ggcggaagac aagctgcaaa cctgtcagat ggagattgat ttaatggcgg    1380
atgtgctgag agcaccgccc cgtgaatccg cagaactgat ccgctatgtg tttgcggatg    1440
attggccgga ataaataaag ccgggcttaa tacagattaa gcccgtatag ggtattatta    1500
ctgaatacca aacagcttac ggaggacgga atgttaccca ttgagacaac cagactgcct    1560
tctgattatt aatattttc actattaatc agaaggaata accatgaatt ttacccggat    1620
tgacctgaat acctggaatc gcagggaaca ctttgcccct tatcgtcagc agattaaatg    1680
cggattcagc ctgaccacca aactcgatat taccgctttg cgtaccgcac tggcggagac    1740
aggttataag ttttatccgc tgatgattta cctgatctcc cgggctgtta atcagtttcc    1800
ggagttccgg atggcactga agacaatga acttatttac tgggaccagt cagacccggt    1860
ctttactgtc tttcataaag aaaccgaaac attctctgca ctgtcctgcc gttattttcc    1920
ggatctcagt gagtttatgg caggttataa tgcggtaacg gcagaatatc agcatgatac    1980
cagattgttt ccgcagggaa atttaccgga gaatcacctg aatatatcat cattaccgtg    2040
ggtgagtttt gacgggattt aacctgaaca tcaccggaaa tgatgattat tttgccccgg    2100 ttttacgat ggcaaagttt cagcaggaag gtgaccgcgt attattacct gtttctgtac    2160
aggttcatca tgcagtctgt gatggctttc atgcagcacg gtttattaat acacttcagc    2220
tgatgtgtga taacatactg aaataaatta attaattctg tatttaagcc accgtatccg    2280
gcaggaatgg tggcttttt tttatatttt aaccgtaatc tgtaatttcg tttcagactg    2340
gttcaggatg agctcgcttg gactcctgtt gatagatcca gtaatgacct cagaactcca    2400
tctggatttg ttcagaacgc tcggttgccg ccgggcgttt tttattggtg agaatccaag    2460
cactagcggc gcgccggccg gcccggtgtg aaataccgca cagatgcgta aggagaaaat    2520
accgcatcag gcgctcttcc gcttcctcgc tcactgactc gctgcgctcg tcgttcggc    2580 tgcggcgagc ggtatcagct cactcaaagg cggtaatacg gttatccaca gaatcagggg    2640
ataacgcagg aaagaacatg tgagcaaaag gccagcaaaa ggccaggaac cgtaaaaagg    2700
ccgcgttgct ggcgtttttc cataggctcc gcccccctga cgagcatcac aaaaatcgac    2760
gctcaagtca gaggtggcga aacccgacag gactataaag ataccaggcg tttccccctg    2820
gaagctccct cgtgcgctct cctgttccga ccctgccgct taccggatac ctgtccgcct    2880
ttctcccttc gggaagcgtg gcgctttctc atagctcacg ctgtaggtat ctcagttcgg    2940
tgtaggtcgt tcgctccaag ctgggctgtg tgcacgaacc ccccgttcag cccgaccgct    3000
gcgccttatc cggtaactat cgtcttgagt ccaacccggt aagacacgac ttatcgccac    3060
tggcagcagc cactggtaac aggattagca gagcgaggta tgtaggcggt gctacagagt    3120
tcttgaagtg gtggcctaac tacggctaca ctagaaggac agtatttggt atctgcgctc    3180
tgctgaagcc agttaccttc ggaaaaagag ttggtagctc ttgatccggc aaacaaacca    3240
ccgctggtag cggtggtttt tttgtttgca agcagcagat tacgcgcaga aaaaaggat    3300 ctcaagaaga tcctttgatc ttttctacgg ggtctgacgc tcagtggaac gaaaactcac    3360
gttaagggat tttggtcatg agattatcaa aaaggatctt cacctagatc cttttaaagg    3420 ccggccgcg ccgccatcgg catttctctt tgcgttttta tttgttaact gttaattgtc    3480
cttgttcaag gatgctgtct ttgacaacag atgttttctt gcctttgatg ttcagcagga    3540
```

```
agctcggcgc aaacgttgat tgtttgtctg cgtagaatcc tctgtttgtc atatagcttg    3600
taatcacgac attgtttcct ttcgcttgag gtacagcgaa gtgtgagtaa gtaaaggtta    3660
catcgttagg atcaagatcc attttaaca caaggccagt tttgttcagc ggcttgtatg     3720
ggccagttaa agaattagaa acataaccaa gcatgtaaat atcgttagac gtaatgccgt    3780
caatcgtcat ttttgatccg cgggagtcag tgaacaggta ccatttgccg ttcattttaa    3840
agacgttcgc gcgttcaatt tcatctgtta ctgtgttaga tgcaatcagc ggtttcatca    3900
cttttttcag tgtgtaatca tcgtttagct caatcatacc gagagcgccg tttgctaact    3960
cagccgtgcg tttttatcg ctttgcagaa gttttgact ttcttgacgg aagaatgatg      4020
tgcttttgcc atagtatgct ttgttaaata aagattcttc gccttggtag ccatcttcag    4080
ttccagtgtt tgcttcaaat actaagtatt tgtggccttt atcttctacg tagtgaggat    4140
ctctcagcgt atggttgtcg cctgagctgt agttgccttc atcgatgaac tgctgtacat    4200
tttgatacgt ttttccgtca ccgtcaaaga ttgatttata atcctctaca ccgttgatgt    4260
tcaaagagct gtctgatgct gatacgttaa cttgtgcagt tgtcagtgtt tgtttgccgt    4320
aatgtttacc ggagaaatca gtgtagaata acggatttt tccgtcagat gtaaatgtgg     4380
ctgaacctga ccattcttgt gtttggtctt ttaggataga atcatttgca tcgaatttgt    4440
cgctgtcttt aaagacgcgg ccagcgtttt tccagctgtc aatagaagtt tcgccgactt    4500
tttgatagaa catgtaaatc gatgtgtcat ccgcattttt aggatctccg gctaatgcaa    4560
agacgatgtg gtagccgtga tagtttgcga cagtgccgtc agcgttttgt aatggccagc    4620
tgtcccaaac gtccaggcct tttgcagaag agatattttt aattgtggac gaatcaaatt    4680
cagaaacttg atatttttca ttttttgct gttcagggat ttgcagcata tcatggcgtg     4740
taatatggga aatgccgtat gtttccttat atggcttttg gttcgtttct ttcgcaaacg    4800
cttgagttgc gcctcctgcc agcagtgcgg tagtaaaggt taatactgtt gcttgttttg    4860
caaacttttt gatgttcatc gttcatgtct ccttttttat gtactgtgtt agcggtctgc    4920
ttcttccagc cctcctgttt gaagatggca agttagttac gcacaataaa aaaagaccta    4980
aaatatgtaa ggggtgacgc caaagtatac actttgcct ttacacattt taggtcttgc     5040
ctgctttatc agtaacaaac ccgcgcgatt tacttttcga cctcattcta ttagactctc    5100
gtttggattg caactggtct attttcctct tttgtttgat agaaaatcat aaaaggattg    5160
gcagactacg ggcctaaaga actaaaaaat ctatctgttt cttttcattc tctgtatttt    5220
ttatagtttc tgttgcatgg gcataaagtt gccttttaa tcacaattca gaaaatatca     5280
taatatctca tttcactaaa taatagtgaa cggcaggtat atgtgatggg ttaaaaagga    5340
tcggcggccg ctcgatttaa atc                                            5363
```

<210> SEQ ID NO 14
<211> LENGTH: 5363
<212> TYPE: DNA
<213> ORGANISM: artificial sequence
<220> FEATURE:
<223> OTHER INFORMATION: complete nucleotide sequence of plasmid pSacB_
      pykA6

<400> SEQUENCE: 14

```
tcgagcagaa gattaagaag aacgaaaatc gtatgtacaa tggggcctgc aacagacaaa      60
ggcaataatt tagaaaaaat cattgctgcc ggtgcaaacg ttgtacgtat gaacttctcc     120
cacggtacgc ccgaagatca tatcggtcgt gctgaaaaag tacgtgaaat cgctcataaa    180
```

```
ttaggtaaac acgtagcaat cttaggtgac ttacaaggcc ctaaaatccg tgtttctact      240
tttaaagaag gcaaaatttt cttaaatatc ggtgataaat tcattttaga cgcagagatg      300
cctaaaggtg aaggtaacca ggaagcggtt ggtttagact ataaaacatt accgcaagat      360
gtggttccgg gcgatatctt attattagat gacggtcgag ttcaattgaa agtattggca      420
accgaaggtg caaaagtatt caccgaagta acggtcggtg gcccactatc aaataataaa      480
ggcattaaca aattaggctg cggtttatct gccgatgcgt taaccgaaaa agataaagcg      540
gatatcatta ctgcggcgcg tatcggtgtg gattaccttg ccgtatcttt cccgcgttca      600
agcgcggatt taaactacgc ccgtcaatta gcaaaagatg cgggcttgga tgcgaaaatc      660
gttgcgaaag tagaacgtgc cgaaacagtt gaaacggacg aagcaatgga cgatatcatc      720
aatgcggcgg acgtaatcat ggttgcgcgc ggtgacttag gtgttgaaat cggtgatccg      780
gaattagtcg gtgttcagaa aaaattaatc cgtcgttcac gtcagttaaa tcgtgttgtt      840
attaccgcaa ctcaaatgat ggaatcaatg attagtaatc ctatgccgac tcgtgcggaa      900
gtaatggacg tagctaacgc agtattggac ggtaccgatg cggtaatgct ttctgctgaa      960
accgcggctg tcaatatcc ggcggaaact gttgcggcga tggcgaaagt tgcgttaggt     1020
gcggagaaaa tgccaagcat taatgtgtct aaacaccgta tgaacgttca attcgagtct     1080
attgaagaat ctgttgcgat gtctgcaatg tatgcggcaa accacatgag aggcgtagcg     1140
gcgattatca cattaacaag tagcggtcgt actgctcgtt taatgtctag actccatagg     1200
ccgctttcct ggctttgctt ccagatgtat gctctcctcc ggagagtacc gtgactttat     1260
tttcggcaca aatacagggg tcgatggata aatacggcga tagtttcctg acggatgatc     1320
cgtatgtacc ggcggaagac aagctgcaaa cctgtcagat ggagattgat ttaatggcgg     1380
atgtgctgag agcaccgccc cgtgaatccg cagaactgat ccgctatgtg tttgcggatg     1440
attggccgga ataaataaag ccgggcttaa tacagattaa gcccgtatag ggtattatta     1500
ctgaatacca aacagcttac ggaggacgga atgttaccca ttgagacaac cagactgcct     1560
tctgattatt aatattttc actattaatc agaaggaata accatgaatt ttacccggat     1620
tgacctgaat acctggaatc gcagggaaca ctttgcccct tatcgtcagc agattaaatg     1680
cggattcagc ctgaccacca aactcgatat taccgctttg cgtaccgcac tggcggagac     1740
aggttataag ttttatccgc tgatgattta cctgatctcc cgggctgtta atcagtttcc     1800
ggagttccgg atggcactga agacaatga acttatttac tgggaccagt cagacccggt     1860
ctttactgtc tttcataaag aaaccgaaac attctctgca ctgtcctgcc gttattttcc     1920
ggatctcagt gagtttatgg caggttataa tgcggtaacg gcagaatatc agcatgatac     1980
cagattgttt ccgcagggaa atttaccgga gaatcacctg aatatatcat cattaccgtg     2040
ggtgagtttt gacgggattt aacctgaaca tcaccggaaa tgatgattat tttgccccgg     2100
tttttacgat ggcaaagttt cagcaggaag gtgaccgcgt attattacct gtttctgtac     2160
aggttcatca tgcagtctgt gatggctttc atgcagcacg gttattaat acacttcagc     2220 tgatgtgtga taacatactg aaataaatta attaattctg tatttaagcc accgtatccg     2280
gcaggaatgg tggctttttt tttatatttt aaccgtaatc tgtaatttcg tttcagactg     2340
gttcaggatg agctcgcttg gactcctgtt gatagatcca gtaatgacct cagaactcca     2400
tctggatttg ttcagaacgc tcggttgccg ccgggcgttt tttattggtg agaatccaag     2460
cactagcggc gcgccggccg gcccggtgtg aaataccgca cagatgcgta aggagaaaat     2520
```

```
accgcatcag gcgctcttcc gcttcctcgc tcactgactc gctgcgctcg gtcgttcggc   2580
tgcggcgagc ggtatcagct cactcaaagg cggtaatacg gttatccaca gaatcagggg   2640
ataacgcagg aaagaacatg tgagcaaaag gccagcaaaa ggccaggaac cgtaaaaagg   2700
ccgcgttgct ggcgtttttc cataggctcc gcccccctga cgagcatcac aaaaatcgac   2760
gctcaagtca gaggtggcga aacccgacag gactataaag ataccaggcg tttccccctg   2820
gaagctccct cgtgcgctct cctgttccga ccctgccgct taccggatac ctgtccgcct   2880
ttctcccttc gggaagcgtg gcgctttctc atagctcacg ctgtaggtat ctcagttcgg   2940
tgtaggtcgt tcgctccaag ctgggctgtg tgcacgaacc ccccgttcag cccgaccgct   3000
gcgccttatc cggtaactat cgtcttgagt ccaacccggt aagacacgac ttatcgccac   3060
tggcagcagc cactggtaac aggattagca gagcgaggta tgtaggcggt gctacagagt   3120
tcttgaagtg gtggcctaac tacggctaca ctagaaggac agtatttggt atctgcgctc   3180
tgctgaagcc agttaccttc ggaaaaagag ttggtagctc ttgatccggc aaacaaacca   3240
ccgctggtag cggtggtttt tttgtttgca agcagcagat tacgcgcaga aaaaaggat   3300
ctcaagaaga tcctttgatc ttttctacgg ggtctgacgc tcagtggaac gaaaactcac   3360
gttaagggat tttggtcatg agattatcaa aaaggatctt cacctagatc cttttaaagg   3420
ccggccgcgg ccgccatcgg cattttcttt tgcgttttta tttgttaact gttaattgtc   3480
cttgttcaag gatgctgtct ttgacaacag atgttttctt gcctttgatg ttcagcagga   3540
agctcggcgc aaacgttgat tgtttgtctg cgtagaatcc tctgtttgtc atatagcttg   3600
taatcacgac attgttttcct ttcgcttgag gtacagcgaa gtgtgagtaa gtaaaggtta   3660
catcgttagg atcaagatcc atttttaaca caaggccagt tttgttcagc ggcttgtatg   3720
ggccagttaa agaattagaa acataaccaa gcatgtaaat atcgttagac gtaatgccgt   3780
caatcgtcat ttttgatccg cgggagtcag tgaacaggta ccatttgccg ttcattttaa   3840
agacgttcgc gcgttcaatt tcatctgtta ctgtgttaga tgcaatcagc ggtttcatca   3900
cttttttcag tgtgtaatca tcgtttagct caatcatacc gagagcgccg tttgctaact   3960
cagccgtgcg tttttatcg cttttgcagaa gttttttgact ttcttgacgg aagaatgatg   4020
tgcttttgcc atagtatgct ttgttaaata aagattcttc gccttggtag ccatcttcag   4080
ttccagtgtt tgcttcaaat actaagtatt tgtggccttt atcttctacg tagtgaggat   4140
ctctcagcgt atggttgtcg cctgagctgt agttgccttc atcgatgaac tgctgtacat   4200
tttgatacgt ttttccgtca ccgtcaaaga ttgatttata atcctctaca ccgttgatgt   4260
tcaaagagct gtctgatgct gatacgttaa cttgtgcagt tgtcagtgtt tgtttgccgt   4320
aatgtttacc ggagaaatca gtgtagaata acggattttt ccgtcagat gtaaatgtgg   4380
ctgaacctga ccattcttgt gtttggtctt ttaggataga atcatttgca tcgaatttgt   4440
cgctgtcttt aaagacgcgg ccagcgtttt tccagctgtc aatagaagtt tcgccgactt   4500
tttgatagaa catgtaaatc gatgtgtcat ccgcattttt aggatctccg gctaatgcaa   4560
agacgatgtg gtagccgtga tagtttgcga cagtgccgtc agcgttttgt aatggccagc   4620
tgtcccaaac gtccaggcct tttgcagaag agatattttt aattgtggac gaatcaaatt   4680
cagaaacttg atatttttca tttttttgct gttcagggat ttgcagcata tcatggcgtg   4740
taatatggga aatgccgtat gttctcttat atggcttttg gttcgtttct ttcgcaaacg   4800
cttgagttgc gcctcctgcc agcagtgcgg tagtaaaggt taatactgtt gcttgttttg   4860
caaacttttt gatgttcatc gttcatgtct ccttttttat gtactgtgtt agcggtctgc   4920
```

```
ttcttccagc cctcctgttt gaagatggca agttagttac gcacaataaa aaaagaccta    4980
aaatatgtaa ggggtgacgc caaagtatac actttgccct ttacacattt taggtcttgc    5040
ctgctttatc agtaacaaac ccgcgcgatt tactttcga cctcattcta ttagactctc     5100
gtttggattg caactggtct attttcctct tttgtttgat agaaaatcat aaaaggattt    5160
gcagactacg ggcctaaaga actaaaaaat ctatctgttt cttttcattc tctgtatttt    5220
ttatagtttc tgttgcatgg gcataaagtt gccttttaa tcacaattca gaaaatatca     5280
taatatctca tttcactaaa taatagtgaa cggcaggtat atgtgatggg ttaaaaagga    5340
tcggcggccg ctcgatttaa atc                                            5363

<210> SEQ ID NO 15
<211> LENGTH: 1440
<212> TYPE: DNA
<213> ORGANISM: Basfia succiniciproducens
<220> FEATURE:
<221> NAME/KEY: misc_feature
<222> LOCATION: (1)..(1440)
<223> OTHER INFORMATION: nucleotide sequence of the pykA-gene from the
      DD1 delta ldhA delta pflA pykA2-strain

<400> SEQUENCE: 15
atgtccagaa gattaagaag aacgaaaatc gtatgtacaa tggggcctgc aacagacaaa     60
ggcaataatt tagaaaaaat cattgctgcc ggtgcaaacg ttgtacgtat gaacttctcc    120
cacggtacgc ccgaagatca tatcggtcgt gctgaaaaag tacgtgaaat cgctcataaa    180
ttaggtaaac acgtagcaat cttaggtgac ttacaaggcc ctaaaatccg tgtttctact    240 tttaagaag gcaaaatttt cttaaatatc ggtgataaat tcattttaga cgcagagatg     300
cctaaaggtg aaggtaacca ggaagcggtt ggtttagact ataaaacatt accgcaagat    360
gtggttccgg gcgatatctt attattagat gacggtcgag ttcaattgaa agtattggca    420
accgaaggtg caaaagtatt caccgaagta acgtcggtg cccactatc aaataataaa      480 ggcattaaca aattaggctg cggtttatct gccgatgcat taaccgaaaa agataaagcg    540
gatatcatta ctgcggcgcg tatcggtgtg gattaccttg ccgtatcttt cccgcgttca    600
agcgcggatt taaactacgc ccgtcaatta gcaaagatg cgggcttgga tgcgaaaatc     660
gttgcgaaag tagaacgtgc cgaaacagtt gaaacggacg aagcaatgga cgatatcatc    720
aatgcggcgg acgtaatcat ggttgcgcgc ggtgacttag tgttgaaat cggtgatccg    780 gaattagtcg tgttcagaa aaaattaatc cgtcgttcac gtcagttaaa tcgtgttgtt    840
attaccgcaa ctcaaatgat ggaatcaatg attagtaatc ctatgccgac tcgtgcggaa    900 gtaatgacg tagctaacgc agtattggac ggtaccgatg cggtaatgct ttctgctgaa     960
accgcggctg gtcaatatcc ggcggaaact gttgcggcga tggcgaaagt tgcgttaggt    1020
gcggagaaaa tgccaagcat taatgtgtct aaacaccgta tgaacgttca attcgagtct    1080
attgaagaat ctgttgcgat gtctgcaatg tatgcggcaa accacatgag aggcgtagcg    1140
gcgattatca cattaacaag tagcggtcgt actgctcgtt taatgtctcg cattagttcc    1200
ggtttaccaa tctttgcatt gtcacgtaac gaatctacat taaacttatg cgcattatat    1260
cgtggtgtga caccggttca ttttgataaa gacagccgta cctcagaagg tgcgacagcg    1320
gcggttcaat tattaaaaga cgaaggtttc ttagtgtctg gcgatttagt gttattaact    1380
cagggcgacg caagcagttc tagcggtact aacctttgcc gtacattgat tgttgaataa    1440
```

<210> SEQ ID NO 16
<211> LENGTH: 479
<212> TYPE: PRT
<213> ORGANISM: Basfia succiniciproducens
<220> FEATURE:
<221> NAME/KEY: SITE
<222> LOCATION: (1)..(479)
<223> OTHER INFORMATION: amino acid sequence of PykA2 from the DD1 delta ldhA delta pflA pykA2-strain

<400> SEQUENCE: 16

```
Met Ser Arg Arg Leu Arg Arg Thr Lys Ile Val Cys Thr Met Gly Pro
1               5                   10                  15

Ala Thr Asp Lys Gly Asn Asn Leu Glu Lys Ile Ile Ala Ala Gly Ala
            20                  25                  30

Asn Val Val Arg Met Asn Phe Ser His Gly Thr Pro Glu Asp His Ile
        35                  40                  45

Gly Arg Ala Glu Lys Val Arg Glu Ile Ala His Lys Leu Gly Lys His
    50                  55                  60

Val Ala Ile Leu Gly Asp Leu Gln Gly Pro Lys Ile Arg Val Ser Thr
65                  70                  75                  80

Phe Lys Glu Gly Lys Ile Phe Leu Asn Ile Gly Asp Lys Phe Ile Leu
                85                  90                  95

Asp Ala Glu Met Pro Lys Gly Glu Gly Asn Gln Glu Ala Val Gly Leu
            100                 105                 110

Asp Tyr Lys Thr Leu Pro Gln Asp Val Val Pro Gly Asp Ile Leu Leu
        115                 120                 125

Leu Asp Asp Gly Arg Val Gln Leu Lys Val Leu Ala Thr Glu Gly Ala
    130                 135                 140

Lys Val Phe Thr Glu Val Thr Val Gly Gly Pro Leu Ser Asn Asn Lys
145                 150                 155                 160

Gly Ile Asn Lys Leu Gly Cys Gly Leu Ser Ala Asp Ala Leu Thr Glu
                165                 170                 175

Lys Asp Lys Ala Asp Ile Ile Thr Ala Ala Arg Ile Gly Val Asp Tyr
            180                 185                 190

Leu Ala Val Ser Phe Pro Arg Ser Ser Ala Asp Leu Asn Tyr Ala Arg
        195                 200                 205

Gln Leu Ala Lys Asp Ala Gly Leu Asp Ala Lys Ile Val Ala Lys Val
    210                 215                 220

Glu Arg Ala Glu Thr Val Glu Thr Asp Glu Ala Met Asp Asp Ile Ile
225                 230                 235                 240

Asn Ala Ala Asp Val Ile Met Val Ala Arg Gly Asp Leu Gly Val Glu
                245                 250                 255

Ile Gly Asp Pro Glu Leu Val Gly Val Gln Lys Lys Leu Ile Arg Arg
            260                 265                 270

Ser Arg Gln Leu Asn Arg Val Val Ile Thr Ala Thr Gln Met Met Glu
        275                 280                 285

Ser Met Ile Ser Asn Pro Met Pro Thr Arg Ala Glu Val Met Asp Val
    290                 295                 300

Ala Asn Ala Val Leu Asp Gly Thr Asp Ala Val Met Leu Ser Ala Glu
305                 310                 315                 320

Thr Ala Ala Gly Gln Tyr Pro Ala Glu Thr Val Ala Ala Met Ala Lys
                325                 330                 335

Val Ala Leu Gly Ala Glu Lys Met Pro Ser Ile Asn Val Ser Lys His
            340                 345                 350

Arg Met Asn Val Gln Phe Glu Ser Ile Glu Glu Ser Val Ala Met Ser
```

Ala Met Tyr Ala Ala Asn His Met Arg Gly Val Ala Ala Ile Ile Thr
370                 375                 380

Leu Thr Ser Ser Gly Arg Thr Ala Arg Leu Met Ser Arg Ile Ser Ser
385                 390                 395                 400

Gly Leu Pro Ile Phe Ala Leu Ser Arg Asn Glu Ser Thr Leu Asn Leu
                405                 410                 415

Cys Ala Leu Tyr Arg Gly Val Thr Pro Val His Phe Asp Lys Asp Ser
                420                 425                 430

Arg Thr Ser Glu Gly Ala Thr Ala Val Gln Leu Leu Lys Asp Glu
                435                 440                 445

Gly Phe Leu Val Ser Gly Asp Leu Val Leu Leu Thr Gln Gly Asp Ala
    450                 455                 460

Ser Ser Ser Ser Gly Thr Asn Leu Cys Arg Thr Leu Ile Val Glu
465                 470                 475

<210> SEQ ID NO 17
<211> LENGTH: 1440
<212> TYPE: DNA
<213> ORGANISM: Basfia succiniciproducens
<220> FEATURE:
<221> NAME/KEY: misc_feature
<222> LOCATION: (1)..(1440)
<223> OTHER INFORMATION: nucleotide sequence of the pykA-gene from the
      DD1 delta ldhA delta pflD pykA4-strain

<400> SEQUENCE: 17

```
atgtccagaa gattaagaag aacgaaaatc gtatgtacaa tggggcctgc aacagacaaa       60
ggcaataatt tagaaaaaat cattgctgcc ggtgcaaacg ttgtacgtat gaacttctcc      120
cacggtacgc ccgaagatca tatcggtcgt gctgaaaaag tacgtgaaat cgctcataaa      180
ttaggtaaac acgtagcaat cttaggtgac ttacaaggcc ctaaaatccg tgtttctact      240 tttaagaag gcaaaatttt cttaaatatc ggtgataaat tcattttaga cgcagagatg       300
cctaaaggtg aaggtaacca ggaagcggtt ggtttagact ataaaacatt accgcaagat      360
gtggttccgg gcgatatctt attattagat gacggtcgag ttcaattgaa agtattggca      420
accgaaggtg caaaagtatt caccgaagta acggtcggtg ccccactatc aaataataaa      480
ggcattaaca aattaggcgg cggtttatct gccgatgcat taaccgaaaa agataaagcg      540
gatatcatta ctgcggcgcg tatcggtgtg gattaccttg ccgtatcttt cccgcgttca      600
agcgcggatt taaactacgc ccgtcaatta gcaaaagatg cgggcttgga tgcgaaaatc      660
gttgcgaaag tagaacgtgc cgaaacagtt gaaacggacg aagcaatgga cgatatcatc      720
aatgcggcgg acgtaatcat ggttgcgcgc ggtgacttag gtgttgaaat cggtgatccg      780
gaattagtcg gtgttcagaa aaaattaatc cgtcgttcac gtcagttaaa tcgtgttgtt      840
attaccgcaa ctcaaatgat ggaatcaatg attagtaatc ctatgccgac tcgtgcggaa      900
gtaatggacg tagctaacgc agtattggac ggtaccgatg cggtaatgct ttctgctgaa      960
accgcggctg gtcaatatcc ggcggaaact gttgcggcga tggcgaaagt tgcgttaggt     1020
gcggagaaaa tgccaagcat taatgtgtct aaacaccgta tgaacgttca attcgagtct     1080
attgaagaat ctgttgcgat gtctgcaatg tatgcggcaa accacatgag aggcgtagcg     1140
gcgattatca cattaacaag tagcggtcgt actgctcgtt taatgtctcg cattagttcc     1200
ggtttaccaa tctttgcatt gtcacgtaac gaatctactt taaacttata cgcattatat     1260
cgtggtgtga caccggttca ttttgataaa gacagccgta cctcagaagg tgcgacagcg     1320
```

```
gcggttcaat tattaaaaga cgaaggtttc ttagtgtctg gcgatttagt gttattaact   1380
cagggcgacg caagcagttc tagcggtact aacctttgcc gtacattgat tgttgaataa   1440
```

<210> SEQ ID NO 18
<211> LENGTH: 479
<212> TYPE: PRT
<213> ORGANISM: Basfia succiniciproducens
<220> FEATURE:
<221> NAME/KEY: SITE
<222> LOCATION: (1)..(479)
<223> OTHER INFORMATION: amino acid sequence of PykA4 from the DD1 delta
      ldhA delta pflD pykA4-strain

<400> SEQUENCE: 18

```
Met Ser Arg Arg Leu Arg Arg Thr Lys Ile Val Cys Thr Met Gly Pro
1               5                   10                  15

Ala Thr Asp Lys Gly Asn Asn Leu Glu Lys Ile Ile Ala Ala Gly Ala
            20                  25                  30

Asn Val Val Arg Met Asn Phe Ser His Gly Thr Pro Glu Asp His Ile
        35                  40                  45

Gly Arg Ala Glu Lys Val Arg Glu Ile Ala His Lys Leu Gly Lys His
    50                  55                  60

Val Ala Ile Leu Gly Asp Leu Gln Gly Pro Lys Ile Arg Val Ser Thr
65                  70                  75                  80

Phe Lys Glu Gly Lys Ile Phe Leu Asn Ile Gly Asp Lys Phe Ile Leu
                85                  90                  95

Asp Ala Glu Met Pro Lys Gly Glu Gly Asn Gln Glu Ala Val Gly Leu
            100                 105                 110

Asp Tyr Lys Thr Leu Pro Gln Asp Val Val Pro Gly Asp Ile Leu Leu
        115                 120                 125

Leu Asp Asp Gly Arg Val Gln Leu Lys Val Leu Ala Thr Glu Gly Ala
    130                 135                 140

Lys Val Phe Thr Glu Val Thr Val Gly Gly Pro Leu Ser Asn Asn Lys
145                 150                 155                 160

Gly Ile Asn Lys Leu Gly Gly Gly Leu Ser Ala Asp Ala Leu Thr Glu
                165                 170                 175

Lys Asp Lys Ala Asp Ile Ile Thr Ala Ala Arg Ile Gly Val Asp Tyr
            180                 185                 190

Leu Ala Val Ser Phe Pro Arg Ser Ser Ala Asp Leu Asn Tyr Ala Arg
        195                 200                 205

Gln Leu Ala Lys Asp Ala Gly Leu Asp Ala Lys Ile Val Ala Lys Val
    210                 215                 220

Glu Arg Ala Glu Thr Val Glu Thr Asp Glu Ala Met Asp Asp Ile Ile
225                 230                 235                 240

Asn Ala Ala Asp Val Ile Met Val Ala Arg Gly Asp Leu Gly Val Glu
                245                 250                 255

Ile Gly Asp Pro Glu Leu Val Gly Val Gln Lys Lys Leu Ile Arg Arg
            260                 265                 270

Ser Arg Gln Leu Asn Arg Val Val Ile Thr Ala Thr Gln Met Met Glu
        275                 280                 285

Ser Met Ile Ser Asn Pro Met Pro Thr Arg Ala Glu Val Met Asp Val
    290                 295                 300

Ala Asn Ala Val Leu Asp Gly Thr Asp Ala Val Met Leu Ser Ala Glu
305                 310                 315                 320

Thr Ala Ala Gly Gln Tyr Pro Ala Glu Thr Val Ala Ala Met Ala Lys
```

```
                    325                 330                 335
Val Ala Leu Gly Ala Glu Lys Met Pro Ser Ile Asn Val Ser Lys His
                340                 345                 350

Arg Met Asn Val Gln Phe Glu Ser Ile Glu Glu Ser Val Ala Met Ser
            355                 360                 365

Ala Met Tyr Ala Ala Asn His Met Arg Gly Val Ala Ala Ile Ile Thr
        370                 375                 380

Leu Thr Ser Ser Gly Arg Thr Ala Arg Leu Met Ser Arg Ile Ser Ser
385                 390                 395                 400

Gly Leu Pro Ile Phe Ala Leu Ser Arg Asn Glu Ser Thr Leu Asn Leu
                405                 410                 415

Tyr Ala Leu Tyr Arg Gly Val Thr Pro Val His Phe Asp Lys Asp Ser
                420                 425                 430

Arg Thr Ser Glu Gly Ala Thr Ala Ala Val Gln Leu Leu Lys Asp Glu
            435                 440                 445

Gly Phe Leu Val Ser Gly Asp Leu Val Leu Leu Thr Gln Gly Asp Ala
        450                 455                 460

Ser Ser Ser Ser Gly Thr Asn Leu Cys Arg Thr Leu Ile Val Glu
465                 470                 475
```

<210> SEQ ID NO 19
<211> LENGTH: 1440
<212> TYPE: DNA
<213> ORGANISM: Basfia succiniciproducens
<220> FEATURE:
<221> NAME/KEY: misc_feature
<222> LOCATION: (1)..(1440)
<223> OTHER INFORMATION: nucleotide sequence of the pykA-gene from the
      DD1 delta ldhA delta pflD pykA5-strain

<400> SEQUENCE: 19

```
atgtccagaa gattaagaag aacgaaaatc gtatgtacaa tggggcctgc aacagacaaa      60
ggcaataatt tagaaaaaat cattgctgcc ggtgcaaacg ttgtacgtat gaacttctcc     120
cacggtacgc ccgaagatca tatcggtcgt gctgaaaaag tacgtgaaat cgctcataaa     180
ttaggtaaac acgtagcaat cttaggtgac ttacaaggcc ctaaaatccg tgtttctact     240
tttaaagaag gcaaaatttt cttaaatatc ggtgataaat tcattttaga cgcagagatg     300
cctaaaggtg aaggtaacca ggaagcggtt ggtttagact ataaaacatt accgcaagat     360
gtggttccgg gcgatatctt attattagat gacggtcgag ttcaattgaa agtattggca     420
accgaaggtg caaagtatt caccgaagta acggtcggtg cccactatc aaataataaa      480 ggcattaaca aattaggcgg cggtttatct ggcgatgcgt taaccgaaaa agataaagcg     540
gatatcatta ctgcggcgcg tatcggtgtg gattaccttg ccgtatcttt cccgcgttca     600
agcgcggatt taaactacgc ccgtcaatta gcaaagatg cgggcttgga tgcgaaaatc     660
gttgcgaaag tagaacgtgc cgaaacagtt gaaacggacg aagcaatgga cgatatcatc     720
aatgcggcgg acgtaatcat ggttgcgcgc ggtgacttag tgttgaaat cggtgatccg     780 gaattagtcg gtgttcagaa aaaattaatc cgtcgttcac gtcagttaaa tcgtgttgtt     840
attaccgcaa ctcaaatgat ggaatcaatg attagtaatc ctatgccgac tcgtgcggaa     900
gtaatggacg tagctaacgc agtattggac ggtaccgatg cggtaatgct ttctgctgaa     960
accgcggctg tcaatatcc ggcggaaact gttgcggcga tggcgaaagt tgcgttaggt    1020
gcggagaaaa tgccaagcat taatgtgtct aaacaccgta tgaacgttca attcgagtct    1080
attgaagaat ctgttgcgat gtctgcaatg tatgcggcaa accacatgag aggcgtagcg    1140
```

-continued

```
gcgattatca cattaacaag tagcggtcgt actgctcgtt taatgtctcg cattagttcc    1200
ggtttaccaa tctttgcatt gtcacgtaac gaatctacat taaacttatg cgcattatat    1260
cgtggtgtga caccggttca ttttgataaa gacagccgta cctcagaagg tgcgacagcg    1320
gcggttcaat tattaaaaga cgaaggtttc ttagtgtctg gcgatttagt gttattaact    1380
cagggcgacg caagcagttc tagcggtact aacctttgcc gtacattgat tgttgaataa    1440
```

<210> SEQ ID NO 20
<211> LENGTH: 479
<212> TYPE: PRT
<213> ORGANISM: Basfia succiniciproducens
<220> FEATURE:
<221> NAME/KEY: SITE
<222> LOCATION: (1)..(479)
<223> OTHER INFORMATION: amino acid sequence of PykA5 from the DD1 delta ldhA delta pflD pykA5-strain

<400> SEQUENCE: 20

```
Met Ser Arg Arg Leu Arg Arg Thr Lys Ile Val Cys Thr Met Gly Pro
1               5                   10                  15

Ala Thr Asp Lys Gly Asn Asn Leu Glu Lys Ile Ile Ala Ala Gly Ala
            20                  25                  30

Asn Val Val Arg Met Asn Phe Ser His Gly Thr Pro Glu Asp His Ile
        35                  40                  45

Gly Arg Ala Glu Lys Val Arg Glu Ile Ala His Lys Leu Gly Lys His
    50                  55                  60

Val Ala Ile Leu Gly Asp Leu Gln Gly Pro Lys Ile Arg Val Ser Thr
65                  70                  75                  80

Phe Lys Glu Gly Lys Ile Phe Leu Asn Ile Gly Asp Lys Phe Ile Leu
                85                  90                  95

Asp Ala Glu Met Pro Lys Gly Glu Gly Asn Gln Glu Ala Val Gly Leu
            100                 105                 110

Asp Tyr Lys Thr Leu Pro Gln Asp Val Val Pro Gly Asp Ile Leu Leu
        115                 120                 125

Leu Asp Asp Gly Arg Val Gln Leu Lys Val Leu Ala Thr Glu Gly Ala
    130                 135                 140

Lys Val Phe Thr Glu Val Thr Val Gly Gly Pro Leu Ser Asn Asn Lys
145                 150                 155                 160

Gly Ile Asn Lys Leu Gly Gly Gly Leu Ser Gly Asp Ala Leu Thr Glu
                165                 170                 175

Lys Asp Lys Ala Asp Ile Ile Thr Ala Ala Arg Ile Gly Val Asp Tyr
            180                 185                 190

Leu Ala Val Ser Phe Pro Arg Ser Ser Ala Asp Leu Asn Tyr Ala Arg
        195                 200                 205

Gln Leu Ala Lys Asp Ala Gly Leu Asp Ala Lys Ile Val Ala Lys Val
    210                 215                 220

Glu Arg Ala Glu Thr Val Glu Thr Asp Glu Ala Met Asp Asp Ile Ile
225                 230                 235                 240

Asn Ala Ala Asp Val Ile Met Val Ala Arg Gly Asp Leu Gly Val Glu
                245                 250                 255

Ile Gly Asp Pro Glu Leu Val Gly Val Gln Lys Lys Leu Ile Arg Arg
            260                 265                 270

Ser Arg Gln Leu Asn Arg Val Val Ile Thr Ala Thr Gln Met Met Glu
        275                 280                 285

Ser Met Ile Ser Asn Pro Met Pro Thr Arg Ala Glu Val Met Asp Val
```

```
            290                 295                 300
Ala Asn Ala Val Leu Asp Gly Thr Asp Ala Val Met Leu Ser Ala Glu
305                 310                 315                 320

Thr Ala Ala Gly Gln Tyr Pro Ala Glu Thr Val Ala Ala Met Ala Lys
            325                 330                 335

Val Ala Leu Gly Ala Glu Lys Met Pro Ser Ile Asn Val Ser Lys His
            340                 345                 350

Arg Met Asn Val Gln Phe Glu Ser Ile Glu Glu Ser Val Ala Met Ser
            355                 360                 365

Ala Met Tyr Ala Ala Asn His Met Arg Gly Val Ala Ala Ile Ile Thr
            370                 375                 380

Leu Thr Ser Ser Gly Arg Thr Ala Arg Leu Met Ser Arg Ile Ser Ser
385                 390                 395                 400

Gly Leu Pro Ile Phe Ala Leu Ser Arg Asn Glu Ser Thr Leu Asn Leu
            405                 410                 415

Cys Ala Leu Tyr Arg Gly Val Thr Pro Val His Phe Asp Lys Asp Ser
            420                 425                 430

Arg Thr Ser Glu Gly Ala Thr Ala Ala Val Gln Leu Leu Lys Asp Glu
            435                 440                 445

Gly Phe Leu Val Ser Gly Asp Leu Val Leu Leu Thr Gln Gly Asp Ala
            450                 455                 460

Ser Ser Ser Ser Gly Thr Asn Leu Cys Arg Thr Leu Ile Val Glu
465                 470                 475
```

<210> SEQ ID NO 21
<211> LENGTH: 1440
<212> TYPE: DNA
<213> ORGANISM: Basfia succiniciproducens
<220> FEATURE:
<221> NAME/KEY: misc_feature
<222> LOCATION: (1)..(1440)
<223> OTHER INFORMATION: nucleotide sequence of the pykA-gene from the
      DD1 delta ldhA delta pflD pykA6-strain

<400> SEQUENCE: 21

```
atgtccagaa gattaagaag aacgaaaatc gtatgtacaa tggggcctgc aacagacaaa      60
ggcaataatt tagaaaaaat cattgctgcc ggtgcaaacg ttgtacgtat gaacttctcc     120
cacggtacgc ccgaagatca tatcggtcgt gctgaaaaag tacgtgaaat cgctcataaa     180
ttaggtaaac acgtagcaat cttaggtgac ttacaaggcc taaaatccg tgtttctact      240 tttaagaag gcaaaatttt cttaaatatc ggtgataaat tcatttaga cgcagagatg       300 cctaaaggtg aaggtaacca ggaagcggtt ggtttagact ataaaacatt accgcaagat     360
gtggttccgg gcgatatctt attattagat gacggtcgag ttcaattgaa agtattggca     420
accgaaggtg caaaagtatt caccgaagta acggtcggtg ccccactatc aaataataaa     480
ggcattaaca aattaggctg cggtttatct gccgatgcgt taaccgaaaa agataaagcg     540
gatatcatta ctgcggcgcg tatcggtgtg gattaccttg ccgtatcttt cccgcgttca     600
agcgcggatt taaactacgc ccgtcaatta gcaaaagatg cgggcttgga tgcgaaaatc     660
gttgcgaaag tagaacgtgc cgaaacagtt gaaacggacg aagcaatgga cgatatcatc     720
aatgcggcgg acgtaatcat ggttgcgcgc ggtgacttag tgttgaaat cggtgatccg     780 gaattagtcg gtgttcagaa aaaattaatc cgtcgttcac gtcagttaaa tcgtgttgtt     840
attaccgcaa ctcaaatgat ggaatcaatg attagtaatc ctatgccgac tcgtgcggaa     900
gtaatggacg tagctaacgc agtattggac ggtaccgatg cggtaatgct ttctgctgaa     960
```

-continued

```
accgcggctg gtcaatatcc ggcggaaact gttgcggcga tggcgaaagt tgcgttaggt    1020
gcggagaaaa tgccaagcat taatgtgtct aaacaccgta tgaacgttca attcgagtct    1080
attgaagaat ctgttgcgat gtctgcaatg tatgcggcaa accacatgag aggcgtagcg    1140
gcgattatca cattaacaag tagcggtcgt actgctcgtt taatgtctcg cattagttcc    1200
ggtttaccaa tctttgcatt gtcacgtaac gaatctacat taaacttatg cgcattatat    1260
cgtggtgtga caccggttca ttttgataaa gacagccgta cctcagaagg tgcgacagcg    1320
gcggttcaat tattaaaaga cgaaggtttc ttagtgtctg gcgatttagt gttattaact    1380
cagggcgacg caagcagttc tagcggtact aacctttgcc gtacattgat tgttgaataa    1440
```

<210> SEQ ID NO 22
<211> LENGTH: 479
<212> TYPE: PRT
<213> ORGANISM: Basfia succiniciproducens
<220> FEATURE:
<221> NAME/KEY: SITE
<222> LOCATION: (1)..(479)
<223> OTHER INFORMATION: amino acid sequence of PykA6 from the DD1 delta
      ldhA delta pflD pykA6-strain

<400> SEQUENCE: 22

```
Met Ser Arg Arg Leu Arg Arg Thr Lys Ile Val Cys Thr Met Gly Pro
1               5                   10                  15

Ala Thr Asp Lys Gly Asn Asn Leu Glu Lys Ile Ile Ala Ala Gly Ala
            20                  25                  30

Asn Val Val Arg Met Asn Phe Ser His Gly Thr Pro Glu Asp His Ile
        35                  40                  45

Gly Arg Ala Glu Lys Val Arg Glu Ile Ala His Lys Leu Gly Lys His
    50                  55                  60

Val Ala Ile Leu Gly Asp Leu Gln Gly Pro Lys Ile Arg Val Ser Thr
65                  70                  75                  80

Phe Lys Glu Gly Lys Ile Phe Leu Asn Ile Gly Asp Lys Phe Ile Leu
                85                  90                  95

Asp Ala Glu Met Pro Lys Gly Glu Gly Asn Gln Glu Ala Val Gly Leu
            100                 105                 110

Asp Tyr Lys Thr Leu Pro Gln Asp Val Val Pro Gly Asp Ile Leu Leu
        115                 120                 125

Leu Asp Asp Gly Arg Val Gln Leu Lys Val Leu Ala Thr Glu Gly Ala
    130                 135                 140

Lys Val Phe Thr Glu Val Thr Val Gly Gly Pro Leu Ser Asn Asn Lys
145                 150                 155                 160

Gly Ile Asn Lys Leu Gly Cys Gly Leu Ser Ala Asp Ala Leu Thr Glu
                165                 170                 175

Lys Asp Lys Ala Asp Ile Ile Thr Ala Ala Arg Ile Gly Val Asp Tyr
            180                 185                 190

Leu Ala Val Ser Phe Pro Arg Ser Ser Ala Asp Leu Asn Tyr Ala Arg
        195                 200                 205

Gln Leu Ala Lys Asp Ala Gly Leu Asp Ala Lys Ile Val Ala Lys Val
    210                 215                 220

Glu Arg Ala Glu Thr Val Glu Thr Asp Glu Ala Met Asp Asp Ile Ile
225                 230                 235                 240

Asn Ala Ala Asp Val Ile Met Val Ala Arg Gly Asp Leu Gly Val Glu
                245                 250                 255

Ile Gly Asp Pro Glu Leu Val Gly Val Gln Lys Lys Leu Ile Arg Arg
```

```
                        260                 265                 270
    Ser Arg Gln Leu Asn Arg Val Val Ile Thr Ala Thr Gln Met Met Glu
            275                 280                 285

Ser Met Ile Ser Asn Pro Met Pro Thr Arg Ala Glu Val Met Asp Val
        290                 295                 300

Ala Asn Ala Val Leu Asp Gly Thr Asp Ala Val Met Leu Ser Ala Glu
    305                 310                 315                 320

Thr Ala Ala Gly Gln Tyr Pro Ala Glu Thr Val Ala Ala Met Ala Lys
                    325                 330                 335

Val Ala Leu Gly Ala Glu Lys Met Pro Ser Ile Asn Val Ser Lys His
                340                 345                 350

Arg Met Asn Val Gln Phe Glu Ser Ile Glu Glu Ser Val Ala Met Ser
                355                 360                 365

Ala Met Tyr Ala Ala Asn His Met Arg Gly Val Ala Ala Ile Ile Thr
        370                 375                 380

Leu Thr Ser Ser Gly Arg Thr Ala Arg Leu Met Ser Arg Ile Ser Ser
    385                 390                 395                 400

Gly Leu Pro Ile Phe Ala Leu Ser Arg Asn Glu Ser Thr Leu Asn Leu
                    405                 410                 415

Cys Ala Leu Tyr Arg Gly Val Thr Pro Val His Phe Asp Lys Asp Ser
                420                 425                 430

Arg Thr Ser Glu Gly Ala Thr Ala Ala Val Gln Leu Leu Lys Asp Glu
                435                 440                 445

Gly Phe Leu Val Ser Gly Asp Leu Val Leu Thr Gln Gly Asp Ala
        450                 455                 460

Ser Ser Ser Ser Gly Thr Asn Leu Cys Arg Thr Leu Ile Val Glu
    465                 470                 475

<210> SEQ ID NO 23
<211> LENGTH: 20
<212> TYPE: DNA
<213> ORGANISM: artificial sequence
<220> FEATURE:
<223> OTHER INFORMATION: sequence of the pykA4_fw primer

<400> SEQUENCE: 23
aatgcggcgg acgtaatcat                                              20

<210> SEQ ID NO 24
<211> LENGTH: 25
<212> TYPE: DNA
<213> ORGANISM: artificial sequence
<220> FEATURE:
<223> OTHER INFORMATION: sequence of the pykA4_rv primer

<400> SEQUENCE: 24
tggagaacct atccatgaag tatca                                        25

<210> SEQ ID NO 25
<211> LENGTH: 20
<212> TYPE: DNA
<213> ORGANISM: artificial sequence
<220> FEATURE:
<223> OTHER INFORMATION: sequence of the pykA5/6_fw primer

<400> SEQUENCE: 25
tggggcctgc aacagacaaa                                              20

<210> SEQ ID NO 26
```

```
<211> LENGTH: 20
<212> TYPE: DNA
<213> ORGANISM: artificial sequence
<220> FEATURE:
<223> OTHER INFORMATION: sequence of the pykA5/6_rv primer

<400> SEQUENCE: 26
aaacgagcag tacgaccgct                                          20

<210> SEQ ID NO 27
<211> LENGTH: 1029
<212> TYPE: DNA
<213> ORGANISM: Basfia succiniciproducens
<220> FEATURE:
<221> NAME/KEY: misc_feature
<222> LOCATION: (1)..(1029)
<223> OTHER INFORMATION: nucleotide sequence of ldhA-gene from strain
      DD1

<400> SEQUENCE: 27
ttgacaaaat cagtatgttt aaataaggag ctaactatga agttgccgt ttacagtact    60 aaaaattatg atcgcaaaca tctggatttg gcgaataaaa aatttaattt tgagcttcat   120
ttctttgatt ttttacttga tgaacaaacc gcgaaaatgg cggagggcgc cgatgccgtc   180
tgtattttcg tcaatgatga tgcgagccgc ccggtgttaa caaagttggc gcaaatcgga   240
gtgaaaatta tcgctttacg ttgtgccggt tttaataatg tggatttgga ggcggcaaaa   300
gagctgggat taaaagtcgt acgggtgcct gcgtattcgc cggaagccgt tgccgagcat   360
gcgatcggat taatgctgac tttaaaccgc cgtatccata aggcttatca gcgtacccgc   420
gatgcgaatt tttctctgga aggattggtc ggttttaata tgttcggcaa aaccgccgga   480
gtgattggta cgggaaaaat cggcttggcg gctattcgca tttttaaagg cttcggtatg   540
gacgttctgg cgtttgatcc ttttaaaaat ccggcggcgg aagcgttggg cgcaaaatat   600
gtcggtttag acgagcttta tgcaaaatcc catgttatca ctttgcattg cccggctacg   660
gcggataatt atcatttatt aaatgaagcg gctttttaata aaatgcgcga cggtgtaatg   720
attattaata ccagccgcgg cgtttttaatt gacagccggg cggcaatcga agcgttaaaa   780
cggcagaaaa tcggcgctct cggtatggat gtttatgaaa atgaacggga tttgtttttc   840
gaggataaat ctaacgatgt tattacggat gatgtattcc gtcgcctttc ttcctgtcat   900
aatgtgcttt taccggtca tcaggcgttt ttaacgaag aagcgctgaa taatatcgcc    960
gatgtgactt tatcgaatat tcaggcggtt tccaaaaatg caacgtgcga aaatagcgtt  1020
gaaggctaa                                                         1029

<210> SEQ ID NO 28
<211> LENGTH: 342
<212> TYPE: PRT
<213> ORGANISM: Basfia succiniciproducens
<220> FEATURE:
<221> NAME/KEY: SITE
<222> LOCATION: (1)..(342)
<223> OTHER INFORMATION: amino acid sequence of LdhA from strain DD1

<400> SEQUENCE: 28

Met Thr Lys Ser Val Cys Leu Asn Lys Glu Leu Thr Met Lys Val Ala
1               5                   10                  15

Val Tyr Ser Thr Lys Asn Tyr Asp Arg Lys His Leu Asp Leu Ala Asn
            20                  25                  30

Lys Lys Phe Asn Phe Glu Leu His Phe Phe Asp Phe Leu Leu Asp Glu
        35                  40                  45
```

Gln Thr Ala Lys Met Ala Glu Gly Ala Asp Ala Val Cys Ile Phe Val
 50                  55                  60

Asn Asp Asp Ala Ser Arg Pro Val Leu Thr Lys Leu Ala Gln Ile Gly
 65                  70                  75                  80

Val Lys Ile Ile Ala Leu Arg Cys Ala Gly Phe Asn Asn Val Asp Leu
                 85                  90                  95

Glu Ala Ala Lys Glu Leu Gly Leu Lys Val Val Arg Val Pro Ala Tyr
            100                 105                 110

Ser Pro Glu Ala Val Ala Glu His Ala Ile Gly Leu Met Leu Thr Leu
        115                 120                 125

Asn Arg Arg Ile His Lys Ala Tyr Gln Arg Thr Arg Asp Ala Asn Phe
130                 135                 140

Ser Leu Glu Gly Leu Val Gly Phe Asn Met Phe Gly Lys Thr Ala Gly
145                 150                 155                 160

Val Ile Gly Thr Gly Lys Ile Gly Leu Ala Ala Ile Arg Ile Leu Lys
                165                 170                 175

Gly Phe Gly Met Asp Val Leu Ala Phe Asp Pro Phe Lys Asn Pro Ala
            180                 185                 190

Ala Glu Ala Leu Gly Ala Lys Tyr Val Gly Leu Asp Glu Leu Tyr Ala
        195                 200                 205

Lys Ser His Val Ile Thr Leu His Cys Pro Ala Thr Ala Asp Asn Tyr
210                 215                 220

His Leu Leu Asn Glu Ala Ala Phe Asn Lys Met Arg Asp Gly Val Met
225                 230                 235                 240

Ile Ile Asn Thr Ser Arg Gly Val Leu Ile Asp Ser Arg Ala Ala Ile
                245                 250                 255

Glu Ala Leu Lys Arg Gln Lys Ile Gly Ala Leu Gly Met Asp Val Tyr
            260                 265                 270

Glu Asn Glu Arg Asp Leu Phe Phe Glu Asp Lys Ser Asn Asp Val Ile
        275                 280                 285

Thr Asp Asp Val Phe Arg Arg Leu Ser Ser Cys His Asn Val Leu Phe
290                 295                 300

Thr Gly His Gln Ala Phe Leu Thr Glu Glu Ala Leu Asn Asn Ile Ala
305                 310                 315                 320

Asp Val Thr Leu Ser Asn Ile Gln Ala Val Ser Lys Asn Ala Thr Cys
                325                 330                 335

Glu Asn Ser Val Glu Gly
            340

<210> SEQ ID NO 29
<211> LENGTH: 741
<212> TYPE: DNA
<213> ORGANISM: Basfia succiniciproducens
<220> FEATURE:
<221> NAME/KEY: misc_feature
<222> LOCATION: (1)..(741)
<223> OTHER INFORMATION: nucleotide sequence of pflA-gene from strain
      DD1

<400> SEQUENCE: 29
atgtcggttt taggacgaat tcattcattt gaaacctgcg ggacagttga cgggccggga    60
atccgcttta tttttatttt acaaggctgc ttaatgcgtt gtaaatactg ccataataga   120
gacacctggg atttgcacgg cggtaaagaa atttccgttg aagaattaat gaaagaagtg   180
gtgacctatc gccattttat gaacgcctcg ggcggcggag ttaccgcttc cggcggtgaa   240

```
gctatttttac aggcggaatt tgtacgggac tggttcagag cctgccataa agaaggaatt    300
aatacttgct tggataccaa cggtttcgtc cgtcatcatg atcatattat tgatgaattg    360
attgatgaca cggatcttgt gttgcttgac ctgaaagaaa tgaatgaacg ggttcacgaa    420
agcctgattg gcgtgccgaa taaaagagtg ctcgaattcg caaaatattt agcggatcga    480
aatcagcgta cctggatccg ccatgttgta gtgccgggtt atacagatag tgacgaagat    540
ttgcacatgc tggggaattt cattaaagat atgaagaata tcgaaaaagt ggaattatta    600
ccttatcacc gtctaggcgc ccataaatgg gaagtactcg gcgataaata cgagcttgaa    660
gatgtaaaac cgccgacaaa agaattaatg gagcatgtta aggggttgct tgcaggctac    720
gggcttaatg tgacatatta g                                              741
```

<210> SEQ ID NO 30
<211> LENGTH: 246
<212> TYPE: PRT
<213> ORGANISM: Basfia succiniciproducens
<220> FEATURE:
<221> NAME/KEY: SITE
<222> LOCATION: (1)..(246)
<223> OTHER INFORMATION: amino acid sequence of PflA from strain DD1

<400> SEQUENCE: 30

```
Met Ser Val Leu Gly Arg Ile His Ser Phe Glu Thr Cys Gly Thr Val
1               5                  10                  15

Asp Gly Pro Gly Ile Arg Phe Ile Phe Leu Gln Gly Cys Leu Met
            20                  25                  30

Arg Cys Lys Tyr Cys His Asn Arg Asp Thr Trp Asp Leu His Gly Gly
        35                  40                  45

Lys Glu Ile Ser Val Glu Glu Leu Met Lys Glu Val Thr Tyr Arg
    50                  55                  60

His Phe Met Asn Ala Ser Gly Gly Val Thr Ala Ser Gly Gly Glu
65                  70                  75                  80

Ala Ile Leu Gln Ala Glu Phe Val Arg Asp Trp Phe Arg Ala Cys His
                85                  90                  95

Lys Glu Gly Ile Asn Thr Cys Leu Asp Thr Asn Gly Phe Val Arg His
            100                 105                 110

His Asp His Ile Ile Asp Glu Leu Ile Asp Thr Asp Leu Val Leu
        115                 120                 125

Leu Asp Leu Lys Glu Met Asn Glu Arg Val His Glu Ser Leu Ile Gly
    130                 135                 140

Val Pro Asn Lys Arg Val Leu Glu Phe Ala Lys Tyr Leu Ala Asp Arg
145                 150                 155                 160

Asn Gln Arg Thr Trp Ile Arg His Val Val Pro Gly Tyr Thr Asp
                165                 170                 175

Ser Asp Glu Asp Leu His Met Leu Gly Asn Phe Ile Lys Asp Met Lys
            180                 185                 190

Asn Ile Glu Lys Val Glu Leu Leu Pro Tyr His Arg Leu Gly Ala His
        195                 200                 205

Lys Trp Glu Val Leu Gly Asp Lys Tyr Glu Leu Glu Asp Val Lys Pro
    210                 215                 220

Pro Thr Lys Glu Leu Met Glu His Val Lys Gly Leu Leu Ala Gly Tyr
225                 230                 235                 240

Gly Leu Asn Val Thr Tyr
                245
```

```
<210> SEQ ID NO 31
<211> LENGTH: 2313
<212> TYPE: DNA
<213> ORGANISM: Basfia succiniciproducens
<220> FEATURE:
<221> NAME/KEY: misc_feature
<222> LOCATION: (1)..(2313)
<223> OTHER INFORMATION: nucleotide sequence of pflD-gene from strain
      DD1

<400> SEQUENCE: 31
```

| | | | | | |
|---|---|---|---|---|---|
| atggctgaat | taacagaagc | tcaaaaaaaa | gcatgggaag | gattcgttcc | cggtgaatgg | 60 |
| caaaacggcg | taaatttacg | tgactttatc | caaaaaaact | atactccgta | tgaaggtgac | 120 |
| gaatcattct | tagctgatgc | gactcctgca | accagcgagt | tgtggaacag | cgtgatggaa | 180 |
| ggcatcaaaa | tcgaaaacaa | aactcacgca | cctttagatt | tcgacgaaca | tactccgtca | 240 |
| actatcactt | ctcacaagcc | tggttatatc | aataaagatt | tagaaaaaat | cgttggtctt | 300 |
| caaacagacg | ctccgttaaa | acgtgcaatt | atgccgtacg | gcggtatcaa | aatgatcaaa | 360 |
| ggttcttgcg | aagtttacgg | tcgtaaatta | gatccgcaag | tagaatttat | tttcaccgaa | 420 |
| tatcgtaaaa | cccataacca | aggcgtattc | gacgtttata | cgccggatat | tttacgctgc | 480 |
| cgtaaatcag | gcgtgttaac | cggtttaccg | gatgcttacg | gtcgtggtcg | tattatcggt | 540 |
| gactaccgtc | gtttagcggt | atacggtatt | gattacctga | tgaaagataa | aaaagcccaa | 600 |
| ttcgattcat | acaaccgcg | tttggaagcg | ggcgaagaca | ttcaggcaac | tatccaatta | 660 |
| cgtgaagaaa | ttgccgaaca | acaccgcgct | ttaggcaaaa | tcaaagaaat | ggcggcatct | 720 |
| tacggttacg | acatttccgg | ccctgcgaca | aacgcacagg | aagcaatcca | atggacatat | 780 |
| tttgcttatc | tggcagcggt | taaatcacaa | aacggtgcgg | caatgtcatt | cggtcgtacg | 840 |
| tctacattct | tagatatcta | tatcgaacgt | gacttaaaac | gcggtttaat | cactgaacaa | 900 |
| caggcgcagg | aattaatgga | ccacttagta | atgaaattac | gtatggttcg | tttcttacgt | 960 |
| acgccggaat | acgatcaatt | attctcaggc | gacccgatgt | gggcaaccga | aactatcgcc | 1020 |
| ggtatgggct | tagacggtcg | tccgttggta | actaaaaaca | gcttccgcgt | attacatact | 1080 |
| ttatacacta | tgggtacttc | tccggaacca | aacttaacta | ttcttggtc | cgaacaatta | 1140 |
| cctgaagcgt | tcaaacgttt | ctgtgcgaaa | gtatctattg | atacttcctc | cgtacaatac | 1200 |
| gaaaatgatg | acttaatgcg | tcctgacttc | aacaacgatg | actatgcaat | cgcatgctgc | 1260 |
| gtatcaccga | tggtcgtagg | taaacaaatg | caattcttcg | gtgcgcgcgc | aaacttagct | 1320 |
| aaaactatgt | tatacgcaat | taacggcggt | atcgatgaga | aaaatggtat | gcaagtcggt | 1380 |
| cctaaaactg | cgccgattac | agacgaagta | ttgaatttcg | ataccgtaat | cgaacgtatg | 1440 |
| gacagtttca | tggactggtt | ggcgactcaa | tatgtaaccg | cattgaacat | catccacttc | 1500 |
| atgcacgata | aatatgcata | tgaagcggca | ttgatggcgt | tccacgatcg | cgacgtattc | 1560 |
| cgtacaatgg | cttgcggtat | cgcgggtctt | tccgtggctg | cggactcatt | atccgcaatc | 1620 |
| aaatatgcga | aagttaaacc | gattcgcggc | gacatcaaag | ataaagacgg | taatgtcgtg | 1680 |
| gcctcgaatg | ttgctatcga | cttcgaaatt | gaaggcgaat | atccgcaatt | cggtaacaat | 1740 |
| gatccgcgtg | ttgatgattt | agcggtagac | ttagttgaac | gtttcatgaa | aaaagttcaa | 1800 |
| aaacacaaaa | cttaccgcaa | cgcaactccg | acacaatcta | tcctgactat | cacttctaac | 1860 |
| gtggtatacg | gtaagaaaac | cggtaatact | ccggacggtc | gtcgagcagg | cgcgccattc | 1920 |
| ggaccgggtg | caaaccccaat | gcacggtcgt | gaccaaaaag | gtgcggttgc | ttcacttact | 1980 |
| tctgtggcta | aacttccgtt | cgcttacgcg | aaagacggta | tttcatatac | cttctctatc | 2040 |

```
gtaccgaacg cattaggtaa agatgacgaa gcgcaaaaac gcaaccttgc cggtttaatg      2100
gacggttatt tccatcatga agcgacagtg gaaggcggtc aacacttgaa tgttaacgtt      2160
cttaaccgtg aaatgttgtt agacgcgatg gaaaatccgg aaaaataccc gcaattaacc      2220
attcgtgttt caggttacgc ggttcgtttc aactcattaa ctaaagagca acaacaagac      2280
gtcatcactc gtacgtttac acaatcaatg taa                                   2313
```

<210> SEQ ID NO 32
<211> LENGTH: 770
<212> TYPE: PRT
<213> ORGANISM: Basfia succiniciproducens
<220> FEATURE:
<221> NAME/KEY: SITE
<222> LOCATION: (1)..(770)
<223> OTHER INFORMATION: amino acid of PflD from strain DD1

<400> SEQUENCE: 32

```
Met Ala Glu Leu Thr Glu Ala Gln Lys Lys Ala Trp Glu Gly Phe Val
1               5                   10                  15

Pro Gly Glu Trp Gln Asn Gly Val Asn Leu Arg Asp Phe Ile Gln Lys
            20                  25                  30

Asn Tyr Thr Pro Tyr Glu Gly Asp Glu Ser Phe Leu Ala Asp Ala Thr
        35                  40                  45

Pro Ala Thr Ser Glu Leu Trp Asn Ser Val Met Glu Gly Ile Lys Ile
    50                  55                  60

Glu Asn Lys Thr His Ala Pro Leu Asp Phe Asp Glu His Thr Pro Ser
65                  70                  75                  80

Thr Ile Thr Ser His Lys Pro Gly Tyr Ile Asn Lys Asp Leu Glu Lys
                85                  90                  95

Ile Val Gly Leu Gln Thr Asp Ala Pro Leu Lys Arg Ala Ile Met Pro
            100                 105                 110

Tyr Gly Gly Ile Lys Met Ile Lys Gly Ser Cys Glu Val Tyr Gly Arg
        115                 120                 125

Lys Leu Asp Pro Gln Val Glu Phe Ile Phe Thr Glu Tyr Arg Lys Thr
    130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Leu Ala Val Tyr Gly Ile Asp Tyr
            180                 185                 190

Leu Met Lys Asp Lys Lys Ala Gln Phe Asp Ser Leu Gln Pro Arg Leu
        195                 200                 205

Glu Ala Gly Glu Asp Ile Gln Ala Thr Ile Gln Leu Arg Glu Glu Ile
    210                 215                 220

Ala Glu Gln His Arg Ala Leu Gly Lys Ile Lys Glu Met Ala Ala Ser
225                 230                 235                 240

Tyr Gly Tyr Asp Ile Ser Gly Pro Ala Thr Asn Ala Gln Glu Ala Ile
                245                 250                 255

Gln Trp Thr Tyr Phe Ala Tyr Leu Ala Ala Val Lys Ser Gln Asn Gly
            260                 265                 270

Ala Ala Met Ser Phe Gly Arg Thr Ser Thr Phe Leu Asp Ile Tyr Ile
        275                 280                 285

Glu Arg Asp Leu Lys Arg Gly Leu Ile Thr Glu Gln Gln Ala Gln Glu
    290                 295                 300
```

```
Leu Met Asp His Leu Val Met Lys Leu Arg Met Val Arg Phe Leu Arg
305                 310                 315                 320

Thr Pro Glu Tyr Asp Gln Leu Phe Ser Gly Asp Pro Met Trp Ala Thr
            325                 330                 335

Glu Thr Ile Ala Gly Met Gly Leu Asp Gly Arg Pro Leu Val Thr Lys
        340                 345                 350

Asn Ser Phe Arg Val Leu His Thr Leu Tyr Thr Met Gly Thr Ser Pro
    355                 360                 365

Glu Pro Asn Leu Thr Ile Leu Trp Ser Glu Gln Leu Pro Glu Ala Phe
370                 375                 380

Lys Arg Phe Cys Ala Lys Val Ser Ile Asp Thr Ser Ser Val Gln Tyr
385                 390                 395                 400

Glu Asn Asp Asp Leu Met Arg Pro Asp Phe Asn Asn Asp Asp Tyr Ala
                405                 410                 415

Ile Ala Cys Cys Val Ser Pro Met Val Val Gly Lys Gln Met Gln Phe
            420                 425                 430

Phe Gly Ala Arg Ala Asn Leu Ala Lys Thr Met Leu Tyr Ala Ile Asn
        435                 440                 445

Gly Gly Ile Asp Glu Lys Asn Gly Met Gln Val Gly Pro Lys Thr Ala
450                 455                 460

Pro Ile Thr Asp Glu Val Leu Asn Phe Asp Thr Val Ile Glu Arg Met
465                 470                 475                 480

Asp Ser Phe Met Asp Trp Leu Ala Thr Gln Tyr Val Thr Ala Leu Asn
                485                 490                 495

Ile Ile His Phe Met His Asp Lys Tyr Ala Tyr Glu Ala Ala Leu Met
            500                 505                 510

Ala Phe His Asp Arg Asp Val Phe Arg Thr Met Ala Cys Gly Ile Ala
        515                 520                 525

Gly Leu Ser Val Ala Ala Asp Ser Leu Ser Ala Ile Lys Tyr Ala Lys
    530                 535                 540

Val Lys Pro Ile Arg Gly Asp Ile Lys Asp Lys Asp Gly Asn Val Val
545                 550                 555                 560

Ala Ser Asn Val Ala Ile Asp Phe Glu Ile Glu Gly Glu Tyr Pro Gln
                565                 570                 575

Phe Gly Asn Asn Asp Pro Arg Val Asp Asp Leu Ala Val Asp Leu Val
            580                 585                 590

Glu Arg Phe Met Lys Lys Val Gln Lys His Lys Thr Tyr Arg Asn Ala
        595                 600                 605

Thr Pro Thr Gln Ser Ile Leu Thr Ile Thr Ser Asn Val Val Tyr Gly
    610                 615                 620

Lys Lys Thr Gly Asn Thr Pro Asp Gly Arg Arg Ala Gly Ala Pro Phe
625                 630                 635                 640

Gly Pro Gly Ala Asn Pro Met His Gly Arg Asp Gln Lys Gly Ala Val
                645                 650                 655

Ala Ser Leu Thr Ser Val Ala Lys Leu Pro Phe Ala Tyr Ala Lys Asp
            660                 665                 670

Gly Ile Ser Tyr Thr Phe Ser Ile Val Pro Asn Ala Leu Gly Lys Asp
        675                 680                 685

Asp Glu Ala Gln Lys Arg Asn Leu Ala Gly Leu Met Asp Gly Tyr Phe
    690                 695                 700

His His Glu Ala Thr Val Glu Gly Gly Gln His Leu Asn Val Asn Val
705                 710                 715                 720
```

```
Leu Asn Arg Glu Met Leu Leu Asp Ala Met Glu Asn Pro Glu Lys Tyr
                725             730             735
Pro Gln Leu Thr Ile Arg Val Ser Gly Tyr Ala Val Arg Phe Asn Ser
            740             745             750
Leu Thr Lys Glu Gln Gln Gln Asp Val Ile Thr Arg Thr Phe Thr Gln
        755             760             765
Ser Met
    770
```